US011851485B2

(12) United States Patent
Amit et al.

(10) Patent No.: US 11,851,485 B2
(45) Date of Patent: Dec. 26, 2023

(54) ENGINEERED ANTI-IL-2 ANTIBODIES

(71) Applicant: Aulos Bioscience, Inc, Larkspur, CA (US)

(72) Inventors: Inbar Amit, Modiin (IL); Itay Levin, Herzeliya (IL); Guy Nimrod, Tel Aviv (IL); Sharon Fischman, Modi'in (IL); Reut Barak Fuchs, Rehovot (IL); Marek Strajbl, Jerusalem (IL); Timothy Wyant, Bellingham, MA (US); Michael Zhenin, Jerusalem (IL); Olga Bluvshtein Yermolaev, Rishon-LeZion (IL); Yehezkel Sasson, Tzur Yigal (IL); Noam Grossman, Mazkeret Batyia (IL); Natalia Levitin, Ashdod (IL); Yanay Ofran, Tel Aviv (IL)

(73) Assignee: AULOS BIOSCIENCE, INC., Larkspur, CA (US)

( * ) Notice: Subject to any disclaimer, the term of this patent is extended or adjusted under 35 U.S.C. 154(b) by 0 days.

(21) Appl. No.: 18/055,975

(22) Filed: Nov. 16, 2022

(65) Prior Publication Data
US 2023/0203152 A1 Jun. 29, 2023

Related U.S. Application Data

(63) Continuation of application No. 17/795,960, filed as application No. PCT/IB2021/051267 on Feb. 15, 2021.

(60) Provisional application No. 63/139,315, filed on Jan. 20, 2021, provisional application No. 62/977,292, filed on Feb. 16, 2020.

(51) Int. Cl.
*C07K 16/24* (2006.01)
*A61P 35/00* (2006.01)
*A61K 39/395* (2006.01)
*A61K 39/00* (2006.01)

(52) U.S. Cl.
CPC .......... *C07K 16/246* (2013.01); *A61K 39/395* (2013.01); *A61P 35/00* (2018.01); *A61K 2039/505* (2013.01); *C07K 2317/24* (2013.01); *C07K 2317/565* (2013.01); *C07K 2317/622* (2013.01); *C07K 2317/74* (2013.01); *C07K 2317/76* (2013.01); *C07K 2317/92* (2013.01)

(58) Field of Classification Search
CPC ............ C07K 16/246; C07K 2317/565; A61K 39/395; A61K 2039/505; A61P 35/00
See application file for complete search history.

(56) References Cited

U.S. PATENT DOCUMENTS

| | | |
|---|---|---|
| 2013/0269056 A1 | 10/2013 | Goldman et al. |
| 2016/0068612 A1 | 3/2016 | Clarke et al. |
| 2016/0272993 A1 | 9/2016 | Abad et al. |
| 2018/0094053 A1* | 4/2018 | Roell ................. C07K 16/246 |
| 2019/0085076 A1 | 3/2019 | Rosenthal et al. |

FOREIGN PATENT DOCUMENTS

| | | |
|---|---|---|
| WO | WO 2014/100014 A1 | 6/2014 |
| WO | WO 2016/005950 A1 | 1/2016 |
| WO | WO 2017/021540 A1 | 2/2017 |
| WO | WO 2017/122130 A1 | 7/2017 |
| WO | WO 2018/064255 A2 | 4/2018 |
| WO | WO 2018/217058 A1 | 11/2018 |
| WO | WO 2019/168791 A2 | 9/2019 |

OTHER PUBLICATIONS

Lo et al. "Effector-attenuating substitutions that maintain antibody stability and reduce toxicity in mice" Journal of Biological Chemistry. Mar. 3, 2017;292(9):3900-8.
Ahmed et al. "Preliminary identification of potential vaccine targets for the COVID-19 coronavirus (SARS-CoV-2) based on SARS-CoV immunological studies" Viruses. Feb. 25, 2020;12(3):254.
Ballesteros-Tato A. "Beyond regulatory T cells: the potentiai role for IL-2 to deplete T-follicular helper cells and treat autoimmune diseases" immunotherapy. Nov. 2014;6(11):1207-20.
Blattman et al. "Therapeutic use of IL-2 to enhance antiviral T-cell responses in vivo" Nature medicine. May 2003;9(5):540-7.
Boyman et al. "Selective stimulation of T cell subsets with antibody-cytokine immune complexes" Science. Mar. 31, 2006;311(5769):1924-7.
Cecere et al. "Regulatory T cells in arterivirus and coronavirus infections: do they protect against disease or enhance it?" Viruses. May 15, 2012;4(5):833-46.
Eton et al. "Phase I trial of subcutaneous recombinant human interleukin-2 in patients with metastatic melanoma" Cancer. Jul. 1, 2002;95(1):127-34.
Hamilton et al. "IL-2 complex treatment can protect naive mice from bacterial and viral infection" The Journal of Immunology. Dec. 1, 2010;185(11):6584-90.
International Search Report for PCT Application No. PCT/IB2021/051267 dated Aug. 5, 2022.
Klatzmann et al. "The promise of low-dose interleukin-2 therapy for autoimmune and inflammatory diseases" Nature Reviews Immunology. May 2015;15(5):283-94.

(Continued)

*Primary Examiner* — Aurora M Fontainhas
*Assistant Examiner* — Jennifer A Benavides
(74) *Attorney, Agent, or Firm* — Mark S. Cohen; PEARL COHEN ZEDEK LATZER BARATZ LLP

(57) ABSTRACT

Described herein are engineered anti-IL-2 antibodies with modified amino acid sequences. The engineered antibodies would confer modified receptor binding specificity to an IL-2-anti-IL2 antibody complex, inhibiting the binding of IL-2 to CD25. The engineered anti-IL-2 antibodies would facilitate expansion of subsets of effector immune cells and decrease undesirable effects caused by IL-2. Thus, the engineered anti-IL-2 antibodies would be useful in treating disease such as cancer and infection.

27 Claims, 62 Drawing Sheets

Specification includes a Sequence Listing.

(56) References Cited

OTHER PUBLICATIONS

Kraft et al. "PC61 (anti-CD25) treatment inhibits influenza A virus-expanded regulatory T cells and severe lung pathology during a subsequent heterologous lymphocytic choriomeningitis virus infection" Journal of virology. Dec. 1, 2013;87(23):12636-47.
Krieg et al. "Improved IL-2 immunotherapy by selective stimulation of IL-2 receptors on lymphocytes and endothelial cells" Proceedings of the National Academy of Sciences. Jun. 29, 2010;107(26):11906-11.
Leu et al. "Overlapping and discrete aspects of the pathology and pathogenesis of the emerging human pathogenic coronaviruses SARS-CoV, MERS-CoV, and 2019-nCoV" Journal of medical virology. May 2020;92(5):491-4.
Liu et al. "Viral dynamics in mild and severe cases of COVID-19" The Lancet infectious diseases. Jun. 1, 2020;20(6):656-7.
Louten J. "Essential human virology" Chapter 6: 93-109, Academic Press; May 28, 2022.
McKinstry et al. "Memory CD4 T cell-derived IL-2 synergizes with viral infection to exacerbate lung inflammation" PLoS pathagens. Aug. 14, 2019;15(8):e1007989.
McNally et al. "CD4+ CD25+ regulatory T cells control CD8+ T-cell effector differentiation by modulating IL-2 homeostasis" Proceedings of the National Academy of Sciences. May 3, 2011;108(18):7529-34.
Melencio et al. "Role of CD4+ CD25+ T regulatory cells in IL-2-induced vascular leak" International immunoiogy. Oct. 1, 2006;18(10):1461-71.
Molloy et al. "Cutting edge: IL-2 immune complexes as a therapy for persistent virus infection" The Journal of Immunology. Apr. 15, 2009;182(8):4512-5.
Ofran et al. "Automated identification of complementarity determining regions (CDRs) reveals peculiar characteristics of CDRs and B cell epitopes" The Journal of Immunology. Nov. 1, 2008;181(9):6230-5.
Rajasagi et al. "IL-2 complex treatment amplifies CD8+ T cell mediated immunity following herpes simplex virus-1 infection" Micobes and infection. Dec. 1, 2016;18(12):735-46.
Schmidt et al. "The CD8 T cell response to respiratory virus infections" Frontiers in immunology. 2018; 9:678.
Shi et al. "COVID-19 infection: The perspectives on immune responses" Cell Death Differ. 2020;27:1451-1454.
Spangler et al. "Antibodies to interleukin-2 elicit selective T cell subset potentiation through distinct conformational mechanisms" Immunity. May 19, 2015;42(5):815-25.
Suzuki, et al. "Iron-regulated outer membrane virulence protein [alpha proteobacterium 1-4, 6-15, 19-21, 23-31 Q-1)" Genbank entry (online). Jul. 26, 2014 [retrieved Jul. 1, 2021]. Retrieved from the Internet: 33-38 [URL: https:www.ncbi.nlm.nih.gov/protein/GAK32620.1J.
Teplyakov et al. "Structural diversity in a human antibody germline library" mAbs Aug. 17, 2016; vol. 8, No. 6, pp. 1045-1063.
Trotta et al. "A human anti-IL-2 antibody that potentiates regulatory T cells by a structure-based mechanism" Nature medicine. Jul. 2018;24(7):1005-14.
Zheng et al. "Study of the lymphocyte change between COVID-19 and non-COVID-19 pneumonia cases suggesting other factors besides uncontrolled inflammation contributed to multi-organ injury" SSRN Electronic Journal. Mar. 30, 2020.

\* cited by examiner

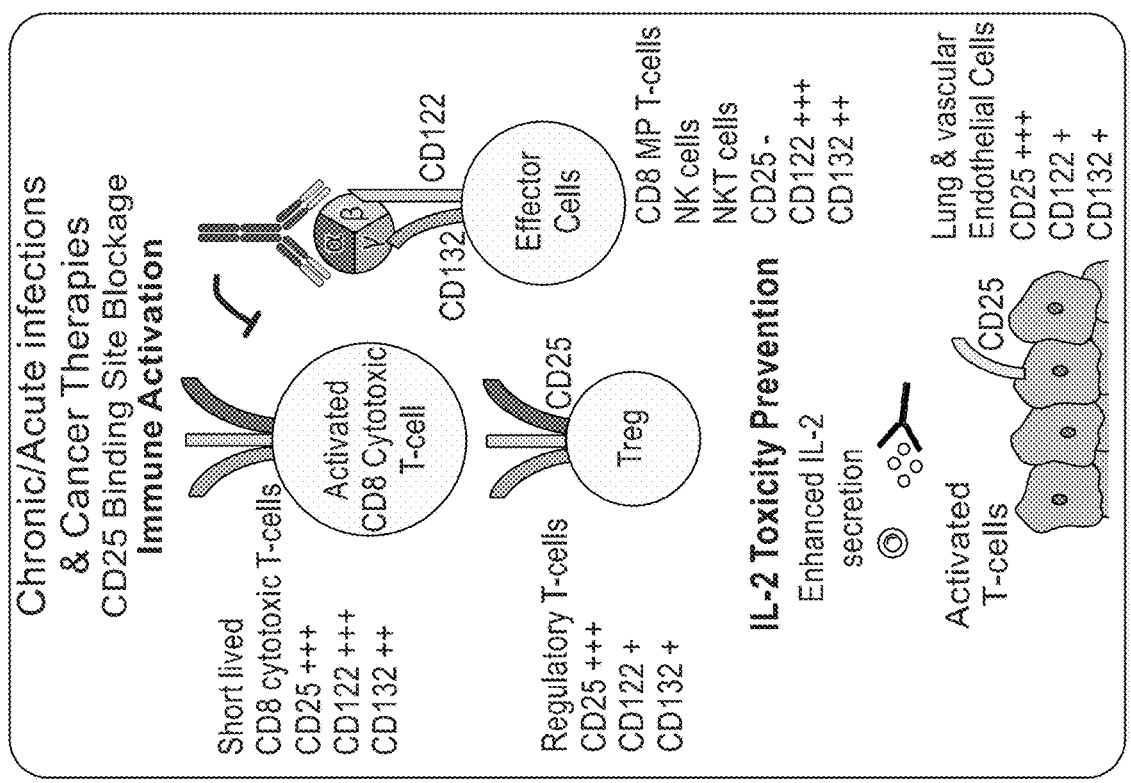
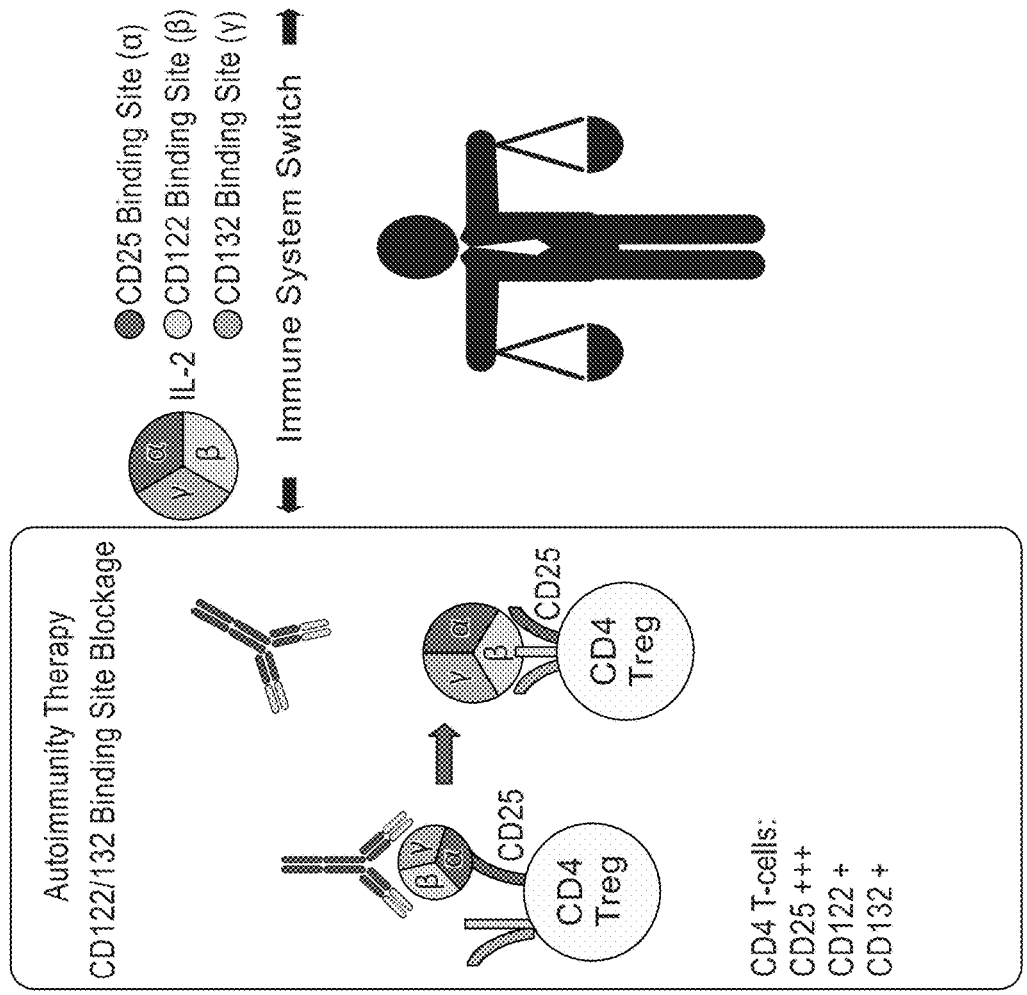
FIG. 2

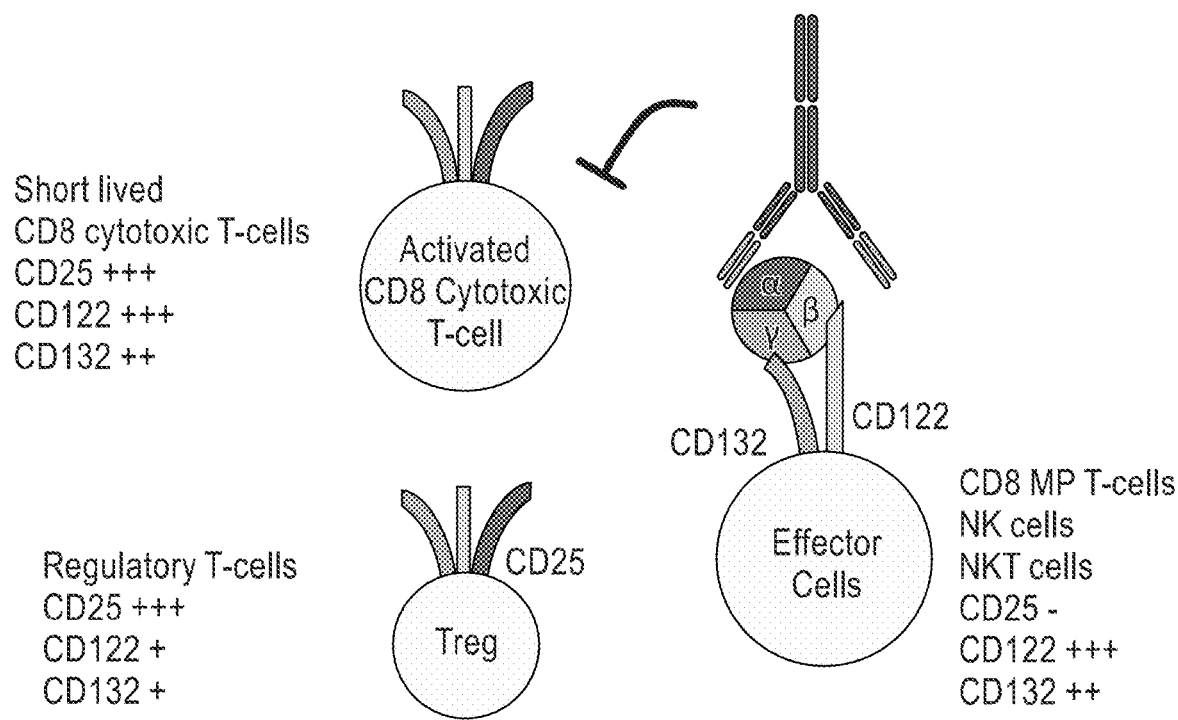
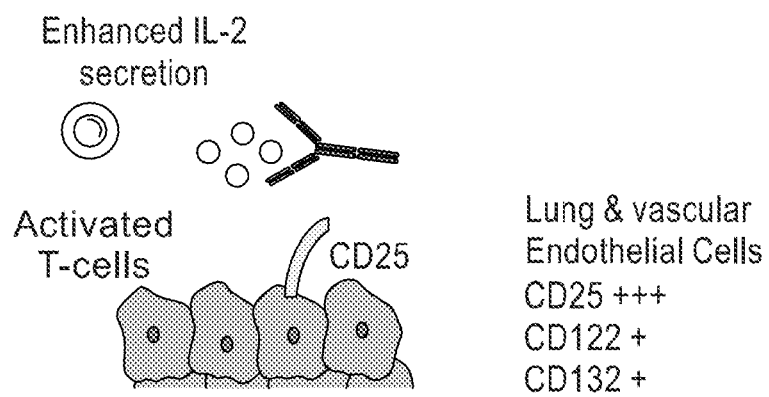
FIG. 3B

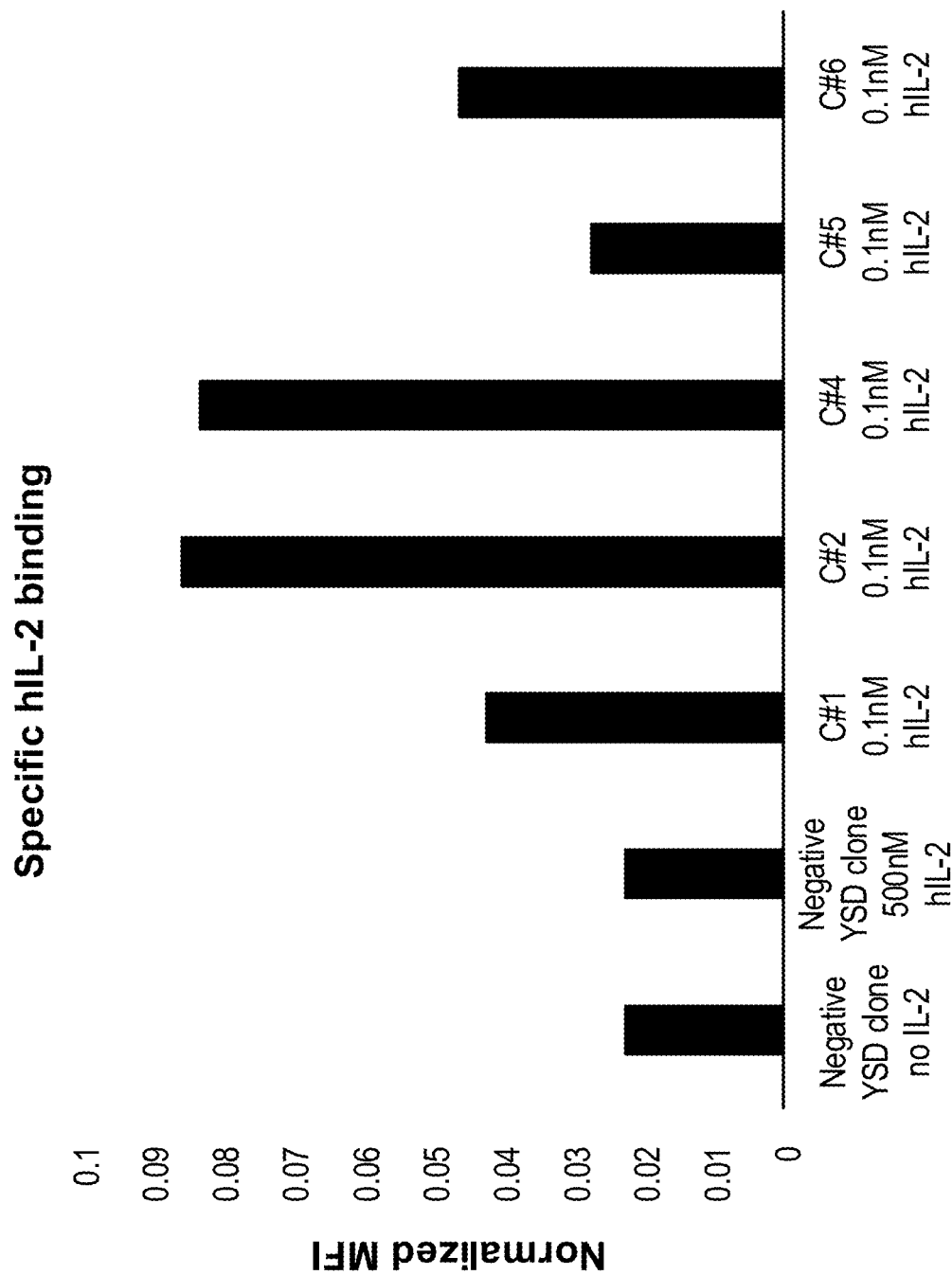

```
                 10         20         30         40         50         60         70         80         90        100        110        120
                 |         |         |         |         |         |         |         |         |         |         |         |
JES6_1_VH  EIQLQQSGPELRRPGSSVKLSCKASGYNITDYLIHWVRHRPEHGLEWIGWIDPEDGETRYAQKFQSKATLTADTSSNAAYMQLSSLTPEDTATYFCARSLDSTYIYPFAYWGQGTLVTVSS
17.021_VH  ........................N...................................................................................................
17.022_VH  ..............................................................................................................................
17.023_VH  ........................................................................................Q.....................................
17.030_VH  ..........................................................................................................D...................
17.035_VH  ........................................................................................N.....................................

JES6_1_VH  = SEQ ID NO:6
17.021_VH  = SEQ ID NO:10
17.022_VH  = SEQ ID NO:12
17.023_VH  = SEQ ID NO:14
17.030_VH  = SEQ ID NO:16
17.035_VH  = SEQ ID NO:18
```

FIG. 11

```
          10         20         30         40         50         60         70         80         90        100        110
          ....|....|....|....|....|....|....|....|....|....|....|....|....|....|....|....|....|....|....|....|....|....|
JES6_1_VL DIVMTQSPFSLAVSEGEMVTINCKSSQSLLSSGNQKNYLAWYQQKPGQSPKLLIYYASTGQSGVPDRFTGSGSGTDFTLTISDVQAEDLADYYCLQHYISPPTFGAGTKLELK
17.021_VL ............................R.............................................................................
17.022_VL ............................R..........................................................Q..................
17.023_VL ............................R...........................................................T..................
17.030_VL ............................R...........................................................T..................
17.035_VL ............................R..................................................M...........................
```

JES6_1_VL = SEQ ID NO:7
17.021_VL = SEQ ID NO:11
17.022_VL = SEQ ID NO:13
17.023_VL = SEQ ID NO:15
17.030_VL = SEQ ID NO:17
17.035_VL = SEQ ID NO:19

FIG. 12

```
              |    10   |    20   |    30   |    40   |    50   |    60   |    70   |    80   |    90   |   100   |   110   |   120
BDG17.014  QVQLVQSGAEVKKPGSSVKVSCKASGYSITDYLIHWVRQAPGQGLEWMGWIDPEDGETNYAQKFQGRVTLTADTSTSTAYMELSSLRSEDTAVYYCARSLDSTPIYPFAYWGQGTLVTVSS
BDG17.038  QVQLVQSGAEVKKPGSSVKVSCKASGYSITDSLIHWVRQAPGQGLEWMGWIDPEDGEINYAQKFQGRVTLTADTSTSTAYMELSSLRSEDTAVYYCARSLDSYPIDPFAYWGQGTLVTVSS
BDG17.043  QVQLVQSGAEVKKPGSSVKVSCKASGYSITDYLIHWVRQAPGQGLEWMGWIDPEDGVTAYAQKFQGRVTLTADTSTSTAYMELSSLRSEDTAVYYCARSLDYDPIYPFAYWGQGTLVTVSS
BDG17.053  QVQLVQSGAEVKKPGSSVKVSCKASGYSITDYLIHWVRQAPGQGLEWMGWIDPEDGVTAYAQKFQGRVTLTADTSTSTAYMELSSLRSEDTAVYYCARSLDYDPIYPFAYWGQGTLVTVSS
BDG17.054  QVQLVQSGAEVKKPGSSVKVSCKASGYSITDDLIHWVRQAPGQGLEWMGWIDPEDGETNYAQKFQGRVTLTADTSTSTAYMELSSLRSEDTAVYYCARSLDSWIVPFAYWGQGTLVTVSS

BDG17.014 = SEQ ID NO: 36
BDG17.038 = SEQ ID NO: 20
BDG17.043 = SEQ ID NO: 22
BDG17.053 = SEQ ID NO: 24
BDG17.054 = SEQ ID NO: 26
```

FIG. 13A

```
         |130      |140       |150       |160       |170       |180       |190       |200       |210       |220       |230
BDG17.014 DIVMTQSPDSLAVSLGERATINCKSSQSLLRSGNQKNYLAWYQQKPGQPPKLLIYYASTGQSGVPDRFSGSGSGTDFTLTISSLQAEDVAVYYCLQHYITPFTFGAGTKVEIK
BDG17.038 DIVMTQSPDSLAVSLGERATINCKSSQSLLRNGNQNYLAWYQQKPGQPPKLLIYYASTGQSGVPDRFSGSGSGTDFTLTISSLQAEDVAVYYCQQHYVTPFTFGAGTKVEIK
BDG17.043 DIVMTQSPDSLAVSLGERATINCKSSQSLLRNGNKNYLAWYQQKPGQPPKLLIYYASTGQSGVPDRFSGSGSGTDFTLTISSLQAEDVAVYYCQQHYVTPFTFGAGTKVEIK
BDG17.053 DIVMTQSPDSLAVSLGERATINCKSSQSLLRNGNQKNYLAWYQQKPGQPPKLLIYYASTGQSGVPDRFSGSGSGTDFTLTISSLQAEDVAVYYCQQHYVTPFTFGAGTKVEIK
BDG17.054 DIVMTQSPDSLAVSLGERATINCKSSQSLLRRGNQNNLAWYQQKPGQPPKLLIYDASTGQSGVPDRFSGSGSGTDFTLTISSLQAEDVAVYYCLQSYITPFTFGAGTKVEIK

BDG17.014 = SEQ ID NO: 37
BDG17.038 = SEQ ID NO: 21
BDG17.043 = SEQ ID NO: 23
BDG17.053 = SEQ ID NO: 25
BDG17.054 = SEQ ID NO: 27
```

FIG. 13B

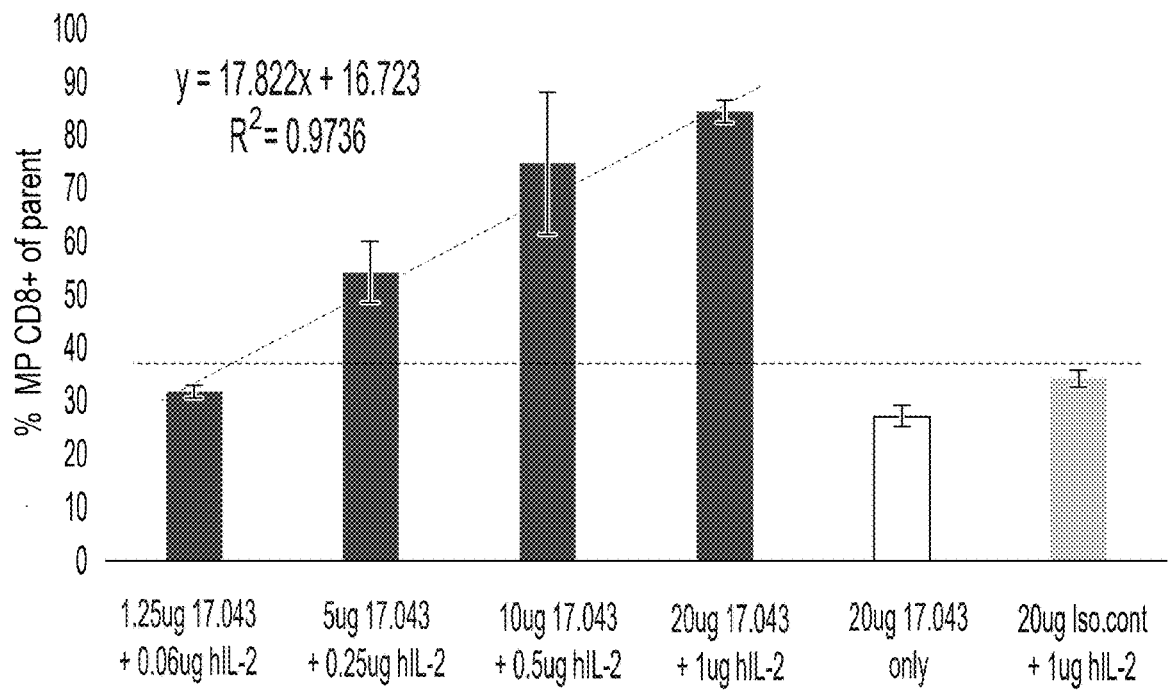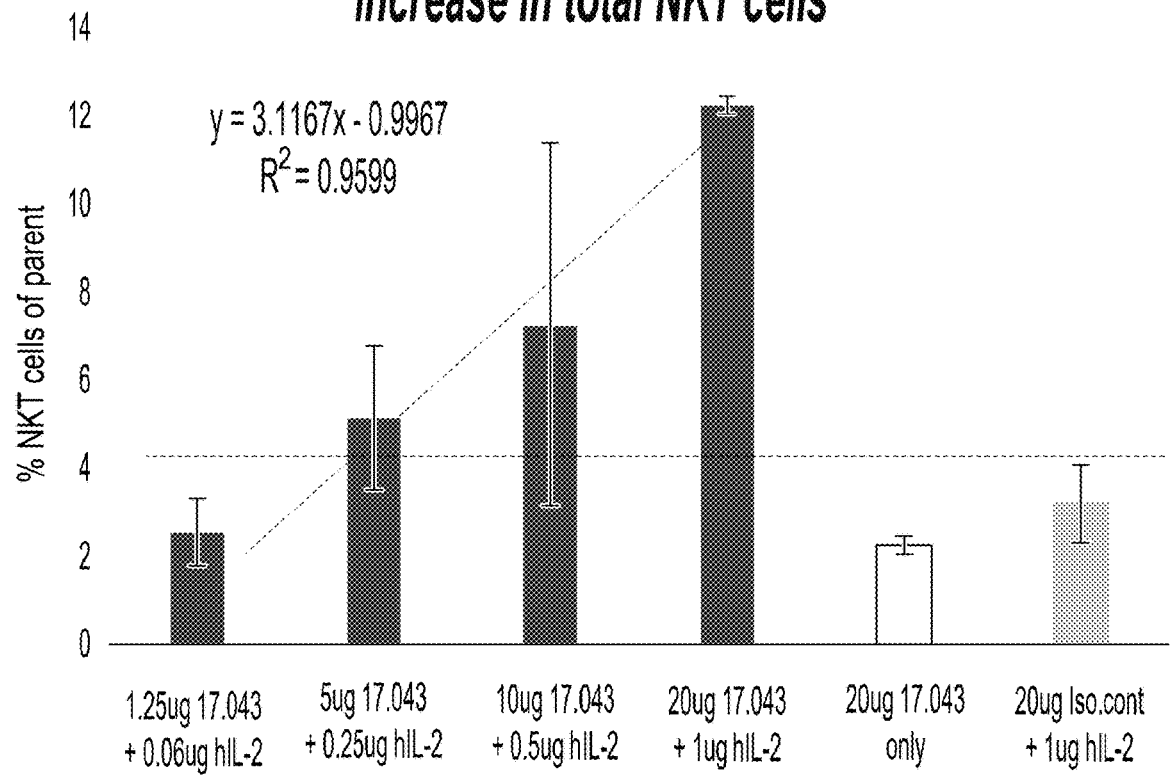
FIG. 19B

| Candidates No. | Appearance | Protein concentration (mg/mL) | Osmolality (mOsmo/kg) | Tg'/°C | DSC Tm onset (°C) | DSC Tm1 (°C) | DSC Tm2 (°C) | DSC Tm3 (°C) | pH |
|---|---|---|---|---|---|---|---|---|---|
| F1 | SY, SO, PF | 31.1 | 313 | -29.80 | 59.88 | 68.09 | 73.83 | 84.07 | 5.5 |
| F2 | SY, SO, PF | 30.8 | 325 | -29.52 | 63.77 | 73.5 | 86.04 | NA | 6.0 |
| F3 | SY, SO, PF | 31.2 | 335 | -29.88 | 63.47 | 73.88 | 85.32 | NA | 5.5 |
| F4 | SY, SO, PF | 30.9 | 349 | -30.11 | 60.11 | 67.4 | 74.04 | 83.03 | 5.5 |

SY (slightly yellow); SO (slightly opalescent liquid); FP (free of visible particle)

FIG. 22A

| Candidates No. | Appearance | | | pH | | | Protein concentration (mg/mL) | | |
|---|---|---|---|---|---|---|---|---|---|
| | T0 | 40°C-1W | 40°C-2W | T0 | 40°C-1W | 40°C-2W | T0 | 40°C-1W | 40°C-2W |
| F1 | SY,SO,FP | SY,SO,FP | SY,SO,PO(5) | 5.5 | 5.5 | 5.6 | 31.1 | 31.3 | 31.2 |
| F2 | SY,SO,FP | SY,SO,FP | SY,SO,FP | 6.0 | 6.0 | 6.1 | 30.8 | 30.9 | 30.8 |
| F3 | SY,SO,FP | SY,SO,FP | SY,SO,FP | 5.5 | 5.5 | 5.4 | 31.2 | 31.1 | 31.2 |
| F4 | SY,SO,FP | SY,SO,FP | SY,SO,FP | 5.5 | 5.5 | 5.6 | 30.9 | 30.9 | 30.9 |

SY (slightly yellow); SO (slightly opalescent liquid); FP (free of visible particle), PO (particle observed)

| Candidates No. | MFI | | | | | | | | | | | |
|---|---|---|---|---|---|---|---|---|---|---|---|---|
| | T0 | | | | 40°C-1W | | | | 40°C-2W | | | |
| | >=2 um | >=5 um | >=10 um | >=25 um | >=2 um | >=5 um | >=10 um | >=25 um | >=2 um | >=5 um | >=10 um | >=25 um |
| F1 | 1532 | 190 | 20 | 4 | 1781 | 187 | 15 | 0 | 3507 | 482 | 58 | 10 |
| F2 | 561 | 76 | 23 | 2 | 3094 | 322 | 32 | 5 | 1717 | 118 | 19 | 0 |
| F3 | 587 | 84 | 22 | 4 | 818 | 115 | 17 | 0 | 1591 | 210 | 32 | 4 |
| F4 | 692 | 66 | 15 | 4 | 1560 | 171 | 10 | 0 | 2958 | 251 | 23 | 0 |

FIG. 22B

| Candidates No. | SEC-UPLC % (MP/HMW/LMW) | | | Caliper-SDS-NR % (Purity) | | | |
|---|---|---|---|---|---|---|---|
| | T0 | 40°C-1W | 40°C-2W | T0 | 40°C-1W | Normalization With T0 STD 40°C-1W | 40°C-2W |
| F1 | 99.1/0.9/ND | 98.2/1.6/0.2 | 95.8(↓3.3)/2.2(↑1.3)/2.0(↑2.0) | 97.6 | 98.0 | 96.9 | 95.4(↓2.2) |
| F2 | 99.1/0.9/ND | 98.0/1.8/0.2 | 95.6(↓3.5)/2.4(↑1.5)/2.0(↑2.0) | 97.6 | 98.1 | 97.0 | 95.8(↓1.8) |
| F3 | 99.1/0.9/ND | 98.0/1.7/0.2 | 95.8(↓3.3)/2.2(↑1.3)/2.1(↑2.1) | 97.6 | 98.2 | 97.1 | 95.4(↓2.2) |
| F4 | 99.1/0.9/ND | 98.2/1.6/0.2 | 95.9(↓3.2)/2.0(↑1.1)/2.1(↑2.1) | 97.7 | 98.4 | 97.3 | 95.8(↓1.9) |
| | NA | | | STD: 98.4 | STD: 99.1 | NA | STD: 98.3 |

| Candidates No. | Caliper-SDS-R % (Purity/LC/HC) | | | cIEF pI | | | cIEF % Acidic/Main/Basic | | |
|---|---|---|---|---|---|---|---|---|---|
| | T0 | 40°C-1W | 40°C-2W | T0 | 40°C-1W | 40°C-2W | T0 | 40°C-1W | 40°C-2W |
| F1 | 99.2/30.4/68.8 | 99.3/31.5/67.8 | 98.4(↓0.8)/29.5/68.8 | 7.5 | 7.6 | 7.5 | 27.0/57.3/15.7 | 31.3/54.8/13.9 | 39.4(↑12.4)/48.2(↓9.1)/12.4(↓3.3) |
| F2 | 99.2/30.3/68.9 | 99.3/31.1/68.2 | 98.8(↓0.4)/29.7/69.1 | 7.6 | 7.6 | 7.5 | 28.3/57.0/14.7 | 32.5/54.5/13.0 | 40.7(↑12.4)/48.6(↓8.4)/10.7(↓4.0) |
| F3 | 98.9/30.6/68.3 | 99.2/30.6/68.6 | 98.3(↓0.6)/29.8/68.4 | 7.6 | 7.6 | 7.6 | 25.8/59.7/14.4 | 37.8/50.1/12.2 | 47.1(↑21.3)/42.1(↓17.6)/10.7(↓3.7) |
| F4 | 99.1/30.5/68.5 | 99.3/31.3/68.0 | 98.8(↓0.4)/29.9/68.9 | 7.6 | 7.6 | 7.6 | 25.5/57.9/16.6 | 32.2/53.9/13.9 | 38.7(↑13.2)/49.0(↓8.9)/12.3(↓4.3) |

FIG. 22C

| Candidates No. | Appearance | | | pH | | Protein concentration (mg/mL) | |
|---|---|---|---|---|---|---|---|
| | T0 | A-1 Days | A-3 Days | T0 | A-3 Days | T0 | A-3 Days |
| F1 | SY,SO,FP | SY,SO,FP | SY,SO,FP | 5.5 | 5.5 | 31.1 | 31.2 |
| F2 | SY,SO,FP | SY,SO,FP | SY,SO,PO+ | 6.0 | 6.1 | 30.8 | 30.8 |
| F3 | SY,SO,FP | SY,SO,FP | SY,SO,PO+ | 5.5 | 5.5 | 31.2 | 31.1 |
| F4 | SY,SO,FP | SY,SO,FP | SY,SO,FP | 5.5 | 5.5 | 30.9 | 31.1 |

■ SY (slightly yellow); SO(slightly opalescent liquid); FP(free of visible particle), PO(particles observed)/+(a few visible particles)
■ Few visible particles were observed in F2/F3 samples for agitation 3 days.

| Candidates No. | MFI | | | | | | | |
|---|---|---|---|---|---|---|---|---|
| | T0 | | | | A-3 Days | | | |
| | >=2 um | >=5 um | >=10 um | >=25 um | >=2 um | >=5 um | >=10 um | >=25 um |
| F1 | 1532 | 190 | 20 | 4 | 2077 | 110 | 12 | 2 |
| F2 | 561 | 76 | 23 | 2 | 644 | 146 | 20 | 7 |
| F3 | 587 | 84 | 22 | 4 | 313 | 55 | 9 | 2 |
| F4 | 692 | 66 | 15 | 4 | 1856 | 77 | 4 | 0 |

FIG. 22D

| Candidates No. | SEC-UPLC % (MP/HMW/LMW) | | Caliper-SDS-NR % (Purity) | | Caliper-SDS-R % (Purity/LC/HC) | | pI | | cIEF % Acidic/Main/Basic | |
|---|---|---|---|---|---|---|---|---|---|---|
| | T0 | A-3 Days | T0 | A-3 Days | T0 | A-3 Days | T0 | A-3 Days | T0 | A-3 Days |
| F1 | 99.1/0.9/ND | 99.0/1.0/ND | 97.6 | 97.7 | 99.2/30.4/68.8 | 99.2/30.9/68.3 | 7.5 | 7.6 | 27.0/57.3/15.7 | 28.3/56.3/15.3 |
| F2 | 99.1/0.9/ND | 99.0/1.0/ND | 97.6 | 97.6 | 99.2/30.3/68.9 | 99.2/31.1/68.1 | 7.6 | 7.6 | 28.3/57.0/14.7 | 27.2/57.4/15.4 |
| F3 | 99.1/0.9/ND | 99.0/1.0/ND | 97.6 | 97.5 | 98.9/30.6/68.3 | 99.0/30.7/68.4 | 7.6 | 7.6 | 25.8/59.7/14.4 | 22.9/61.8/15.3 |
| F4 | 99.1/0.9/ND | 99.1/0.9/ND | 97.7 | 97.5 | 99.1/30.5/68.5 | 99.2/30.8/68.4 | 7.6 | 7.6 | 25.5/57.9/16.6 | 24.5/60.1/15.5 |

FIG. 22E

| Candidates No. | Appearance | | | pH | | Protein concentration (mg/mL) | |
|---|---|---|---|---|---|---|---|
| | T0 | FT-3C | FT-5C | T0 | FT-5C | T0 | FT-5C |
| F1 | SY,SO,FP | SY,SO,FP | SY,SO,FP | 5.5 | 5.6 | 31.1 | 31.3 |
| F2 | SY,SO,FP | SY,SO,FP | SY,SO,FP | 6.0 | 6.1 | 30.8 | 30.9 |
| F3 | SY,SO,FP | SY,SO,FP | SY,SO,FP | 5.5 | 5.6 | 31.2 | 31.1 |
| F4 | SY,SO,FP | SY,SO,FP | SY,SO,FP | 5.5 | 5.6 | 30.9 | 31.0 |

SY (slightly yellow); SO (slightly opalescent liquid); FP (free of visible particle)

| Candidates No. | MFI | | | | | | | |
|---|---|---|---|---|---|---|---|---|
| | T0 | | | | FT-5C | | | |
| | >=2 um | >=5 um | >=10 um | >=25 um | >=2 um | >=5 um | >=10 um | >=25 um |
| F1 | 1532 | 190 | 20 | 4 | 770 | 76 | 4 | 0 |
| F2 | 561 | 76 | 23 | 2 | 469 | 46 | 4 | 0 |
| F3 | 587 | 84 | 22 | 4 | 439 | 30 | 9 | 0 |
| F4 | 692 | 66 | 15 | 4 | 670 | 44 | 14 | 2 |

FIG. 22F

| Candidates No. | SEC-UPLC % (MP/HMW/LMW) | | Caliper-SDS-NR % (Purity) | | Caliper-SDS-R % (Purity/LC/HC) | | pI | | cIEF % Acidic/Main/Basic | |
|---|---|---|---|---|---|---|---|---|---|---|
| | T0 | FT-5C | T0 | FT-5C | T0 | FT-5C | T0 | FT-5C | T0 | FT-5C |
| F1 | 99.1/0.9/ND | 99.1/0.9/ND | 97.6 | 97.7 | 99.2/30.4/68.8 | 99.2/30.4/68.8 | 7.5 | 7.6 | 27.0/57.3/15.7 | 22.3/60.5/17.2 |
| F2 | 99.1/0.9/ND | 99.1/0.9/ND | 97.6 | 97.6 | 99.2/30.3/68.9 | 99.2/30.9/68.4 | 7.6 | 7.6 | 28.3/57.0/14.7 | 20.7/63.5/15.8 |
| F3 | 99.1/0.9/ND | 99.1/0.9/ND | 97.6 | 97.5 | 98.9/30.6/68.3 | 99.2/30.6/68.6 | 7.6 | 7.6 | 25.8/59.7/14.4 | 21.8/62.8/15.4 |
| F4 | 99.1/0.9/ND | 99.1/0.9/ND | 97.7 | 97.6 | 99.1/30.5/68.5 | 99.1/30.3/68.8 | 7.6 | 7.6 | 25.5/57.9/16.6 | 24.4/60.1/15.5 |

FIG. 22G

ENGINEERED ANTI-IL-2 ANTIBODIES

CROSS-REFERENCE TO RELATED APPLICATIONS

This Application is a Continuation Application of U.S. application Ser. No. 17/795,960 filed Jul. 28, 2022, which filed as a National Phase Application of PCT International Application No. PCT/IB2021/051267, International Filing Date Feb. 15, 2021, claiming the benefit of priority of United States Provisional Application Nos. 62/977,292 filed Feb. 16, 2020 and 63/139,315 filed Jan. 20, 2021, which are all hereby incorporated by reference in their entirety.

SEQUENCE LISTING STATEMENT

The instant application contains a Sequence Listing which has been submitted electronically in XML format and is hereby incorporated by reference in its entirety. The XML format copy, created on Nov. 15, 2022, is named P-593094-US1_15NOV22.xml and is 97.8 kilobytes in size.

FIELD OF THE INVENTION

The disclosure relates in general to the field of antibodies. In one embodiment, the present disclosure describes the making and uses of engineered anti-IL-2 antibodies that would confer modified receptor binding specificity to IL-2.

BACKGROUND

Interleukin 2 (IL-2) is a 15.4 kDa type I cytokine with a four helix bundle structure. Since its discovery more than 30 years ago, the importance of IL-2 in regulation of the immune system has been illustrated many times. IL-2 is mostly produced and secreted by CD4+ T cells that are activated by an antigen. To a lesser extent, IL-2 is also produced by CD8+ T cells, natural killer (NK) cells, dendritic cells and mast cells.

IL-2 signaling has two opposite effects. IL-2 can enhance immune response by activation of effector cells and induce their proliferation. Alternatively, IL-2 can tune down immune response by activation and proliferation of CD4+ regulatory T (Treg) cells. To facilitate theses function, IL-2 mediates its effect by binding to two forms of IL-2 receptor: i) trimeric receptors made up of IL-2Rα (CD25), IL-2Rβ (CD122), and a common IL-2Rγ (γc, CD132) chains, or ii) a dimeric receptor that consists of only the IL-2R4 and IL-2Rγ subunits. Both the dimeric and trimeric receptors are able to transmit IL-2 binding signaling via the STAT5 pathway. However, IL-2 binds the αβγ receptor trimer a 100 fold tighter than the βγ receptor dimer. It has been demonstrated that the binding affinity of hIL-2 to the αβγ trimer is approximately 10 pM, whereas the hIL-2 affinity to the βγ dimer is 1 nM.

The difference in affinities to the dimeric and trimeric forms of the IL-2 receptor is one of the key mechanisms in charge of keeping immunological homeostasis in vivo. Activation of the trimeric receptor is associated with FoxP3-mediated transcription in Tregs, which express on its membrane more of the αβγ trimeric IL-2 receptor. In contrast, binding of IL-2 to the βγ dimer is associated with activation of NK cells and memory phenotype (IP) CD8+ cells, which express relatively high levels of the βγ dimer and very low levels the αβγ trimeric IL-2 receptor. Since in normal physiological condition the natural levels of IL-2 are relatively low, it seems the main function of IL-2 is to facilitate immune tolerance by acting as a Treg activating and proliferative factor. On the other hand, once the immune system is activated, IL-2 levels are rising and subsequently IL-2 is able to bind the βγ dimer and facilitate memory phenotype effector T cells (MP) CD8+ and NK cells activation and proliferation.

Since the early 1990's, high dose IL-2 therapy is used to treat melanoma and metastatic renal cell carcinoma with 10%-15% response rate. While efficacious, this approach has not been adopted to other cancers, since IL-2-dependent adverse effects like the potentially lethal Vascular Leak Syndrome (VLS) excludes many patients from being considered for this therapy. The short half-life of administered IL-2 requires very frequent administration, resulting in repeated spikes in the level of circulating IL-2, thereby exacerbating adverse effects. Finally, since wild type IL-2 is not selective it could also enhance a non-desired activation of Treg cells.

It has been discovered that certain antibodies could bind to IL-2 and modulate binding to the βγ dimeric or the αβγ trimeric IL-2 receptors. IL-2 complexed with these antibodies would have relatively longer half-life, and these IL-2 complexes would activate specific subsets of effector or immune cells. For example, the antibody S4B6-mouse IL-2 complex preferentially activates mouse effector cells in vivo, whereas the antibody JES6.1-mouse IL-2 complex preferentially activates mouse T regulatory cells in vivo. The mechanism of the modulation by the JES-6.1 antibody has been elucidated. It has been shown that the JES6.1-mIL-2 complex binds CD25 but not CD122 in vitro.

Increased IL-2 has been implicated to play a role in viral infection. SARS-CoV-2 is a positive stranded RNA virus of the coronaviridae family of respiratory viruses. The virus gains entry into the host by binding angiotensin converting enzyme 2 (ACE2) on lung and gastrointestinal tissues. The course of infection is characterized by a ~7-14 day incubation period followed by symptoms of a dry cough, fever, and shortness of breath. Up to 20% of symptomatic individuals develop severe symptoms and on average 3% of the cases are fatal due to pulmonary failure. Earlier studies with members of the coronavirus family demonstrated that coronavirus infections result in an increase in regulatory T lymphocytes, which likely contributes to delayed viral clearance. More recent studies on COVID-19 patients showed patients in the ICU had higher levels of IL-2, IL-7, IL-10, GSCF, IP10, MCP1, MIP1A, and TNF-α than non-ICU patients, suggesting a role of immunopathology in severe disease. Investigations into direct evidence of alterations in leukocyte homeostasis using the immunological characteristics of peripheral blood leukocytes from SARS-CoV2 infected patients indicate that in COVID-19, similar to some chronic infections, damages to the function of CD4+ T cells promotes excessive activation and possibly subsequent exhaustion of CD8+ T cells. These perturbations of T cell subsets may eventually diminish host antiviral immunity. Therapeutics that either slow viral growth or enhance the immune response to eliminate viral load while reducing some of the associated immune pathologies would therefore be of great benefit.

Immune responses to viruses consist of both the innate and acquired arms of the immune system. The innate system uses toll-like receptors (TLR) and retinoic acid inducible gene I (RIG-I) proteins to sense viral RNA/DNA and induce an initial response. This response includes the production of antiviral cytokines (such as interferon α), chemokines to bring the immune system to the site of the infection and mobilization of the macrophage/dendritic cell arm Natural Killer (NK) cells (innate lymphoid) directly kill virus infected cells in the absence of MHC class-I expression. This can occur even when the virus has interfered with the MHC class I presentation system.

In addition, during an infection response NK cells produce interferon-γ (IFN-γ), thereby increasing the expression of MHC Class I on cells and enhancing the ability of the acquired immune system to respond. The acquired immune system consists of T cells (CD4 and CD8) and B cells. CD4+ T cells recognize viral antigens in the context of MHC-II on antigen presenting cells to both amplify the immune response (through cytokines) and induce B cell class switching and subsequent production of anti-viral antibodies. Activation of CD4 cells, in particular Th1 cells, also releases IFN-γ, thus enhancing the presentation of viral antigens. CD8+ T cells exhibit direct lytic effects to virally infected cells which are presenting viral peptides in the context of MHC-I. The initial induction phase of the immune response typically takes 7-10 days to expand the T cell population and generates the cells required to clear the viruses.

IL-2 is a key mediator in the expansion and activation of T cells and NK cells. IL-2 is commonly thought to play a major role in the secondary signals required for T cell activation. The expression of the dimeric (βγ) and trimeric (αβγ) IL-2 receptor complexes show lineage selectivity in that the trimeric receptor containing CD25 (the α subunit) is found highly expressed on regulatory T cells and a subset of activated short lived cytotoxic effector T cells, whereas the dimeric receptor is found on naive T cells, memory T cells, and NK cells. Consequently, naive T cells, memory T cells, and NK cells can receive signaling via IL-2 binding to the dimeric receptor. Regulatory T cells rely on the high affinity trimeric receptor complex to enhance their functions, which include sequestering IL-2 away from binding to memory and naive T cells, and thereby reducing the function of these populations of cells. IL-2 mechanism of action is described in FIG. 1.

Effector T cell subsets also express the trimeric IL-2 receptor complex. While these cells are highly active, binding of IL-2 to a subset of effector T cells induces activation-induced cell death (AICD). Moreover, CD25 has been shown to be expressed on lung endothelium and on vascular endothelium. This expression was correlated with pulmonary edema and vascular leaking in mouse models using high dose IL-2. It was suggested that the expression of CD25 on lung cells was the reason for pulmonary toxicity of high dose IL-2 therapy. Additionally, while lung endothelial cells express CD25 under steady-state conditions, expression levels of CD25 on these cells increases in vivo upon injection of mice with IL-2. It has been shown that knocking out CD25 on non-immune cells or interfering with the CD25 binding epitope of IL-2 by the use of immune complexes of IL-2 and anti-IL-2 antibody (IL-2/mAb) was able to prevent IL-2-induced pulmonary edema and vascular leak syndrome. It was also demonstrated in mice genetically modified to lack T and B cells, and sub-lethally irradiated to remove the remaining immune cells (NK, monocytes, DC, and granulocytes), addition of high dose IL-2 resulted in significant pulmonary edema, indicating a non-immune component.

There has been much research on the dual role of IL-2 in the ability to clear viral infections of the lung. It has been demonstrated that IL-2 is required for the expansion of CD8+ T cell for viral clearance. It has also been shown that IL-2 can mediate lung edema. For example, it has been demonstrated in a mouse influenza model of influenza viral lung infection that memory CD4+ T cells produce high levels of IL-2 and the presence of this IL-2 worsens disease. Regulatory T cells are important for reducing pathological damage to lung tissue in viral infection. It has been hypothesized and demonstrated that one mechanism to control CD8+ effector cells by Treg is by high affinity consumption of IL-2 via CD25 trimeric receptor on Tregs. This in effect removes IL-2 from the expanding effector cells, and subsequently limits the availability of effector cells and potentially reduces viral clearance. It is likely that Tregs also limit the effects of IL-2 on lung endothelium by sequestering away IL-2 from CD25+ endothelial cells. The outcome may be dependent on the ratio of Teff/Treg. High levels of Teff (effector T cells) may lead to viral clearance but also to excessive levels of IL-2 secreted by the immune activated cells, thus leading to lung edema. In contrast, high Treg expansion may reduce pathology of lung edema but also reduce viral clearance and lead to a prolonged viral infection.

Recent data from COVID-19 patients suggest that higher viral loads lead to poorer outcomes; therefore, reduction in viral clearance would be associated with worse outcomes. In mouse models, the role of Tregs in reducing viral clearance was demonstrated using Influenza A virus (IAV) infection model where mice infected with IAV showed higher levels of Tregs in the lungs, spleens and lymph nodes together with higher levels of viral load in the lungs tissue. This was observed even 6 weeks after the initiation of the infection. It was suggested that Influenza A induces Treg expansion to avoid clearance by the immune response. To evaluate whether boosting immune response would increase clearance of IAV infection in the lungs, investigators used mice previously infected with IAV and subsequently infected the mice with lymphocytic choriomeningitis virus (LCMV) that triggers a vigorous cytotoxic T lymphocytes response. Extensive immune response in IAV-infected lungs also led to pulmonary edema and extensive lung tissue damage. Protection from severe pulmonary edema was achieved by treating IAV bearing mice with anti-CD25 blocking antibody prior to administration of LCMV. These data demonstrate that boosting immune response in a situation where Tregs have slowed viral clearance can induce viral clearance. In addition, it demonstrates that blocking IL-2 binding to CD25+ cells reduces the risk of immune mediated pulmonary edema during viral clearance.

IL-2 given as single agent therapy has been shown to enhance antiviral immune responses. Examining the effect of IL-2 therapy during the expansion, contraction and memory phase of T cells in LCMV-infected mice demonstrated that IL-2 treatment during the expansion phase was detrimental to the survival of rapidly dividing effector T cells that have transiently up-regulated the expression of CD25. These effector T cells were subsequently directed to AICD. In contrast, IL-2 therapy was highly beneficial during the contraction phase and resulted in virus-specific T cells survival and activation. It was observed that IL-2 treatment enhanced activation and proliferation of resting memory T-cells. However, IL-2 therapy has its disadvantages. The half-life of IL-2 is short, thus multiple administrations are required, for example a daily loading dose followed by weekly dosing, leading to the risk of additional related adverse events and increased immunogenicity. In addition, the administration of exogenous high dose IL-2 would be expected to bind to CD25 positive endothelial cells. Indeed, pulmonary edema and vascular leak syndrome are the main severe adverse events for high dose IL-2 therapy in oncology. Developing technologies to overcome these limitations is critical to the use of IL-2 as a therapy.

One of ordinary skill in the art would recognize that the principles discussed above with regard to IL-2 and treating viral infections would equally apply to IL-2 and treating bacterial infections, or treating cancer.

Advances in the field of biomolecular engineering present researchers with unprecedented opportunities to apply molecular design strategies to modify naturally occurring proteins and generate new molecules for targeted disease therapy. In one area, the development of immunotherapeutics such as cytokine-based or antibody-based drugs has been empowered by evolving technologies and insights from protein engineering. Thus, there is a need to develop engineered anti-IL-2 antibodies that would be used to modulate the functions of IL-2 in certain disease states, for example but not limited to viral or bacterial infections, and cancer.

SUMMARY

In one aspect, disclosed herein is an isolated anti-IL-2 antibody comprising a heavy chain variable region (VH) and a light chain variable region (VL), wherein said VH comprises heavy chain complementarity determining regions (HCDRs) HCDR1, HCDR2 and HCDR3, said VL comprises light chain complementarity determining regions (LCDRs) LCDR1, LCDR2 and LCDR3, wherein said CDRs have the amino acid sequences of
  (a) the HCDR1 comprises the amino acid sequence of SEQ ID NO:38, the HCDR2 comprises the amino acid sequence of SEQ ID NO:39, the HCDR3 comprises the amino acid sequence of SEQ ID NO:40, the LCDR1 comprises the amino acid sequence of SEQ ID NO:41, the LCDR2 comprises the amino acid sequence YAS, the LCDR3 comprises the amino acid sequence of SEQ ID NO:43;
  (b) the HCDR1 comprises the amino acid sequence of SEQ ID NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49,
  (c) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55;
  (d) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61; or
  (e) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67.

In a related aspect, the VH and VL have the amino acid sequences of:
  (a) the VH comprises the amino acid sequence of SEQ ID NO:10, the VL comprises the amino acid sequence of SEQ ID NO:11;
  (b) the VH comprises the amino acid sequence of SEQ ID NO:12, the VL comprises the amino acid sequence of SEQ ID NO:13;
  (c) the VH comprises the amino acid sequence of SEQ ID NO:14, the VL comprises the amino acid sequence of SEQ ID NO:15;
  (d) the VH comprises the amino acid sequence of SEQ ID NO:16, the VL comprises the amino acid sequence of SEQ ID NO:17;
  (e) the VH comprises the amino acid sequence of SEQ ID NO:18, the VL comprises the amino acid sequence of SEQ ID NO:19;
  (f) the VH comprises the amino acid sequence of SEQ ID NO:20, the VL comprises the amino acid sequence of SEQ ID NO:21;
  (g) the VH comprises the amino acid sequence of SEQ ID NO:22, the VL comprises the amino acid sequence of SEQ ID NO:23;
  (h) the VH comprises the amino acid sequence of SEQ ID NO:24, the VL comprises the amino acid sequence of SEQ ID NO:25;
  (i) the VH comprises the amino acid sequence of SEQ ID NO:26, the VL comprises the amino acid sequence of SEQ ID NO:27; or
  (j) the VH comprises the amino acid sequence of SEQ ID NO:36, the VL comprises the amino acid sequence of SEQ ID NO:37.

In another related aspect, the antibody comprises an IgG, IgA, IgM, IgE, IgD, a Fv, a scFv, a Fab, a $F(ab')_2$, a minibody, a diabody, a triabody, a nanobody, or a single domain antibody.

In a further related aspect, the antibody comprises a heavy chain comprising a mutation that reduces binding to Fcγ receptor. In still a further related aspect, the antibody comprising a heavy chain sequence and a light chain sequence,
  (a) said heavy chain sequence set forth in SEQ ID NO: 68 and said light chain sequence set forth in SEQ ID NO: 69;
  (b) said heavy chain sequence set forth in SEQ ID NO: 70 and said light chain sequence set forth in SEQ ID NO: 71; or
  (c) said heavy chain sequence set forth in SEQ ID NO: 72 and said light chain sequence set forth in SEQ ID NO: 73.

In a related aspect, disclosed herein is a composition comprising the an anti-IL-2 antibody as described herein and a pharmaceutically acceptable carrier. In further related aspect, the composition is formulated to be at a pH between about pH 5.0-6.0 and comprises a buffer selected from a histidine buffer and a citrate buffer. In still a further related aspect, the composition further comprising at least one of sucrose, methionine, or PS80, or any combination thereof. In yet a further related aspect, the composition further comprises IL-2.

In one aspect, provided herein is an isolated polynucleotide sequence encoding the heavy chain variable region of an anti-IL-2 antibody, wherein the VH amino acid sequences is set forth in the amino acid sequence of SEQ ID NO:10, 12, 14, 16, 18, 20, 22, 24, 26, or 36. In a related aspect, provided herein is a vector comprising the polynucleotide sequence encoding a VH amino acid sequence set forth in the amino acid sequence of SEQ ID NO:10, 12, 14, 16, 18, 20, 22, 24, 26, or 36. In still another related aspect, provided herein is a host cell comprising the vector comprising the polynucleotide sequence encoding a VH amino acid sequence set forth in the amino acid sequence of SEQ ID NO:10, 12, 14, 16, 18, 20, 22, 24, 26, or 36.

In one aspect, provided herein is an isolated polynucleotide sequence encoding the light chain variable region of an anti-IL-2 antibody, wherein the VL amino acid sequences is set forth in the amino acid sequence of SEQ ID NO: 11, 13, 15, 17, 19, 21, 23, 25, 27, or 37. In a related aspect, provided herein is a vector comprising the polynucleotide sequence encoding a VL amino acid sequence set forth in the amino acid sequence of SEQ ID NO: 11, 13, 15, 17, 19, 21, 23, 25, 27, or 37. In still another related aspect, provided herein is a host cell comprising the vector comprising the polynucleotide sequence encoding a VL amino acid sequence set forth in the amino acid sequence of SEQ ID NO: 11, 13, 15, 17, 19, 21, 23, 25, 27, or 37.

In one aspect, provided herein is an isolated polynucleotide sequence encoding an anti-IL-2 scFv, wherein the polynucleotide sequence is set forth in SEQ ID NO: 1, 2, 3, 4, 5, 31, 32, 33, 34, or 35. In a related aspect, provided herein is a vector comprising the polynucleotide sequence encoding the scFv, wherein the polynucleotide sequence is set forth in SEQ ID NO: 1, 2, 3, 4, 5, 31, 32, 33, 34, or 35. In still another related aspect, provided herein is a host cell comprising the vector comprising the polynucleotide sequence encoding the scFv, wherein the polynucleotide sequence is set forth in SEQ ID NO: 1, 2, 3, 4, 5, 31, 32, 33, 34, or 35.

In one aspect, disclosed herein is a method of treating a disease or a condition in a subject, comprising the step of administering to the subject a composition comprising an anti-IL-2 antibody as described in detail herein, wherein said antibody promotes differential growth of subsets of immune cells and decreases undesirable effects caused by IL-2, thereby treating said disease or condition in said subject.

In a related aspect, the composition comprises the anti-IL-2 antibody and IL-2, or the anti-IL-2 antibody complexed with IL-2.

In another related aspect, the disease comprises a viral infection, a bacterial infection, or a cancer. In a further related aspect, the viral infection is caused by SARS CoV-2; norovirus; rotavirus; hepatitis virus A, B, C, D, or E; rabies virus; West Nile virus; enterovirus; echovirus; coxsackievirus; herpes simplex virus (HSV); HSV-2; varicella-zoster virus; mosquito-borne viruses; arbovirus; St. Louis encephalitis virus, California encephalitis virus; lymphocytic choriomeningitis virus; human immunodeficiency virus (HIV); poliovirus; zika virus; rubella virus; cytomegalovirus; human papillomavirus (HPV); enterovirus D68; severe acute respiratory syndrome (SARS) coronavirus; Middle East respiratory syndrome coronavirus; Epstein-Barr virus; influenza virus; respiratory syncytial virus; polyoma viruses including JC virus: BK virus); Ebola virus: Dengue virus; or any combination thereof.

In another related aspect, the condition comprises a weak immune system and said treatment prophylactically boosts the immune system, or said condition comprises IL-2 induced pulmonary edema or IL-2 induced vascular leakage.

In another related aspect, the condition comprises a genetic predisposition that increases likelihood of cancer in said subject. In a further related aspect, the genetic predisposition comprises a change in expression or activity of a gene product, said gene comprising a tumor suppressor gene or a mismatch repair (MMR) gene, or a combination thereof. In another further related aspect, the genetic predisposition comprises a change in expression or activity of a gene product, said gene comprising BRCA1, BRAC2, MLH1, MSH2, MSH6, PMS1, PMS2, TP53, or CHEK2, or a combination thereof.

In another related aspect, the immune cells comprise one or more of naive T cells, memory T cells, $CD8^+$ T cells, NK cells, or Natural Killer T cells.

In yet another related aspect, the undesirable effect caused by IL-2 comprises one or more of activation of regulatory T cells, apoptosis of $CD25^+$ T effector cells, IL-2 induced pulmonary edema, pneumonia, or IL-2-induced vascular leakage.

In a further related aspect, the anti-IL-2 antibody inhibits IL-2 binding to CD25.

In yet another further related aspect, the subject is further treated with one or more immune checkpoint inhibitors targeting one or more immune checkpoints. In still a further related aspect, the subject is treated with said immune checkpoint inhibitors concurrently, before, or after treatment with said anti-IL-2 antibody. In another related aspect, the immune checkpoint comprises PD-1, PDL-1, CTLA-4, TIGIT, TIM-3, B7-H3, CD73, LAG3, CD27, CD70, 4-1BB, GITR, OX40, SIRP-alpha (CD47), CD39, ILDR2, VISTA, BTLA, or VTCN-1.

In one aspect, provided herein is a method of immunizing a subject, wherein said immunization comprises administration of a vaccine comprising an adjuvant, said adjuvant comprising an IL-2 antibody adjuvant, said anti-IL-2 antibody comprising an anti-IL-2 antibody as disclosed herein. In a related aspect, the IL-2 antibody adjuvant comprises the anti-IL-2 antibody and IL-2, or comprises an anti-IL-2 antibody complexed with IL-2. In a further related aspect, the subject has a weakened immune system.

In a related aspect, a method of immunization comprises immunizing a subject suffering from a condition comprises a genetic predisposition that increases likelihood of cancer in said subject. In a further related aspect, the genetic predisposition comprises a change in expression or activity of a gene product, said gene comprising a tumor suppressor gene or a mismatch repair (MMR) gene, or a combination thereof. In another further related aspect, the genetic predisposition comprises a change in expression or activity of a gene product, said gene comprising BRCA1, BRAC2, MLH1, MSH2, MSH6, PMS1, PMS2, TP53, or CHEK2, or a combination thereof.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

The present disclosure of engineered anti-IL-2 antibodies, both as to their generation and method of use, together with objects, features, and advantages thereof, may best be understood by reference to the following detailed description when read with the accompanying drawings in which:

FIG. 2. Presents a schematic representation of anti-IL-2 antibodies-directed immunotherapy.

FIGS. 3A and 3B present a schematic representation of the progression of COVID-19 infection and potential anti-IL-2 therapy as an adjuvant intervention. FIG. 3A is adapted from Shi Y et al., (2020) *COVID-19 infection: the perspec-*

Figure 1:
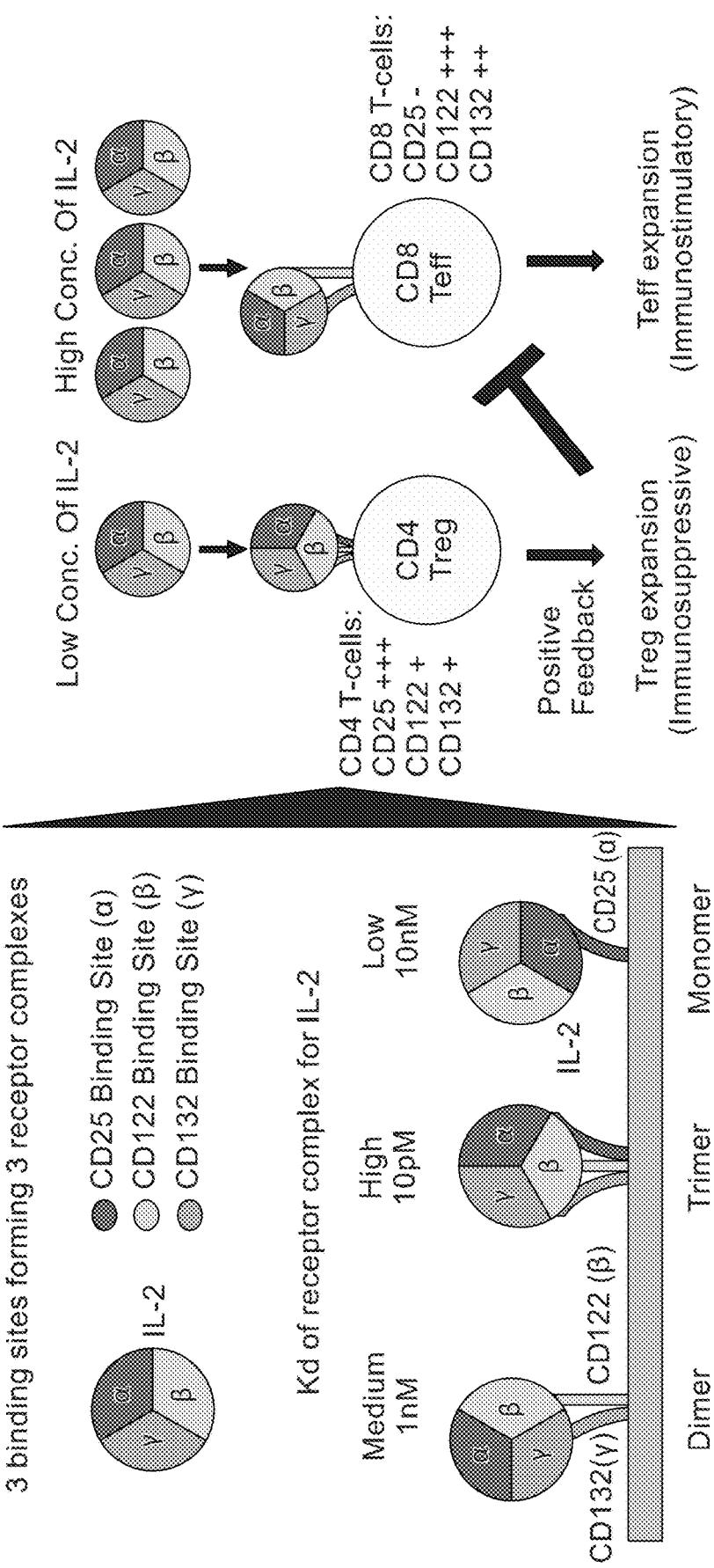
FIG. 1. Presents a schematic representation of IL-2 mechanism of action and its dual role in controlling immune response.

*tives on immune responses.* Cell Death & Differentiation volume 27, pages 1451-1454 (doi:10.1038/s41418-020-0530-3), FIG. 1.

Figure 4A:
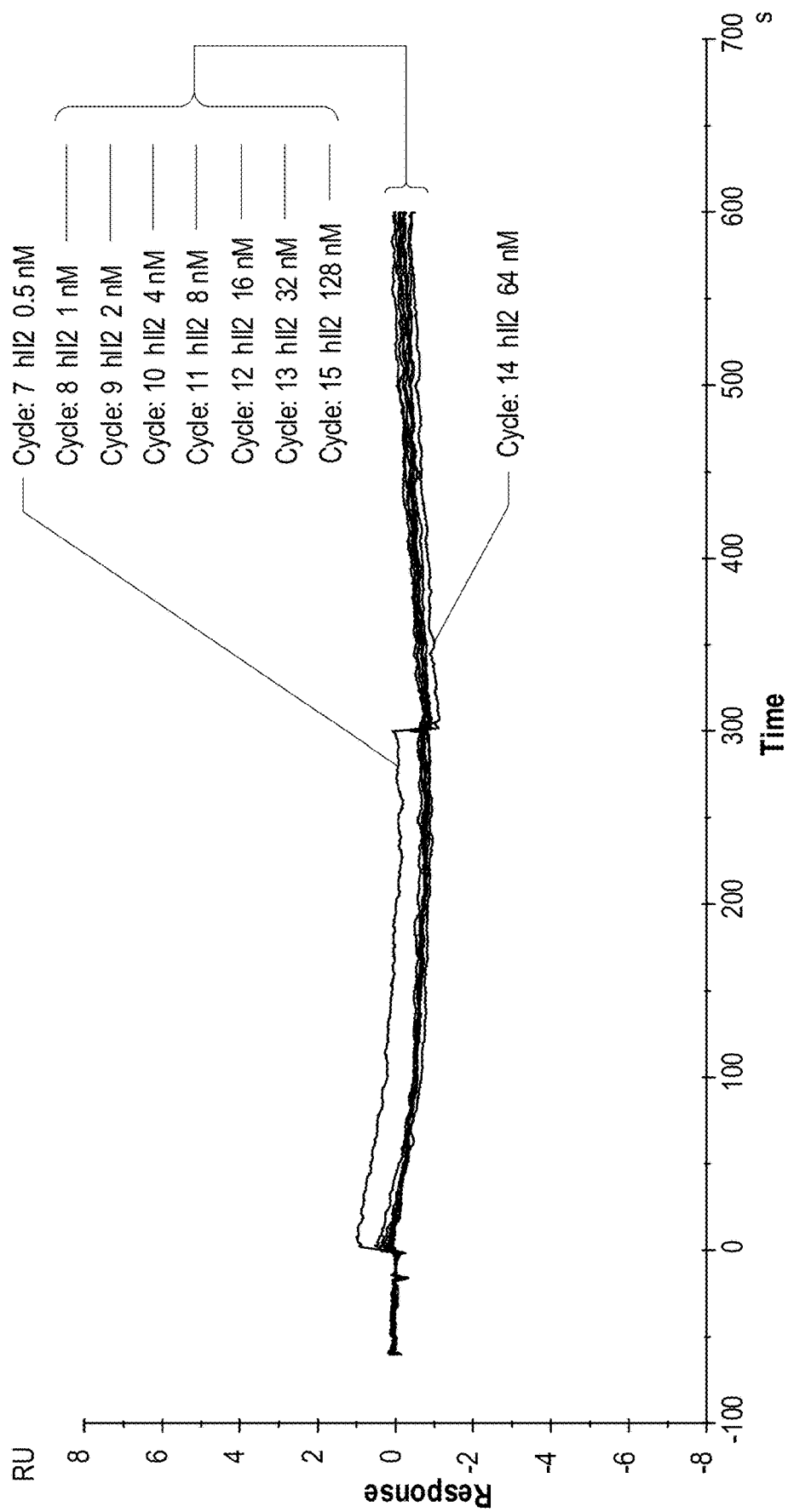
Figure 4B:
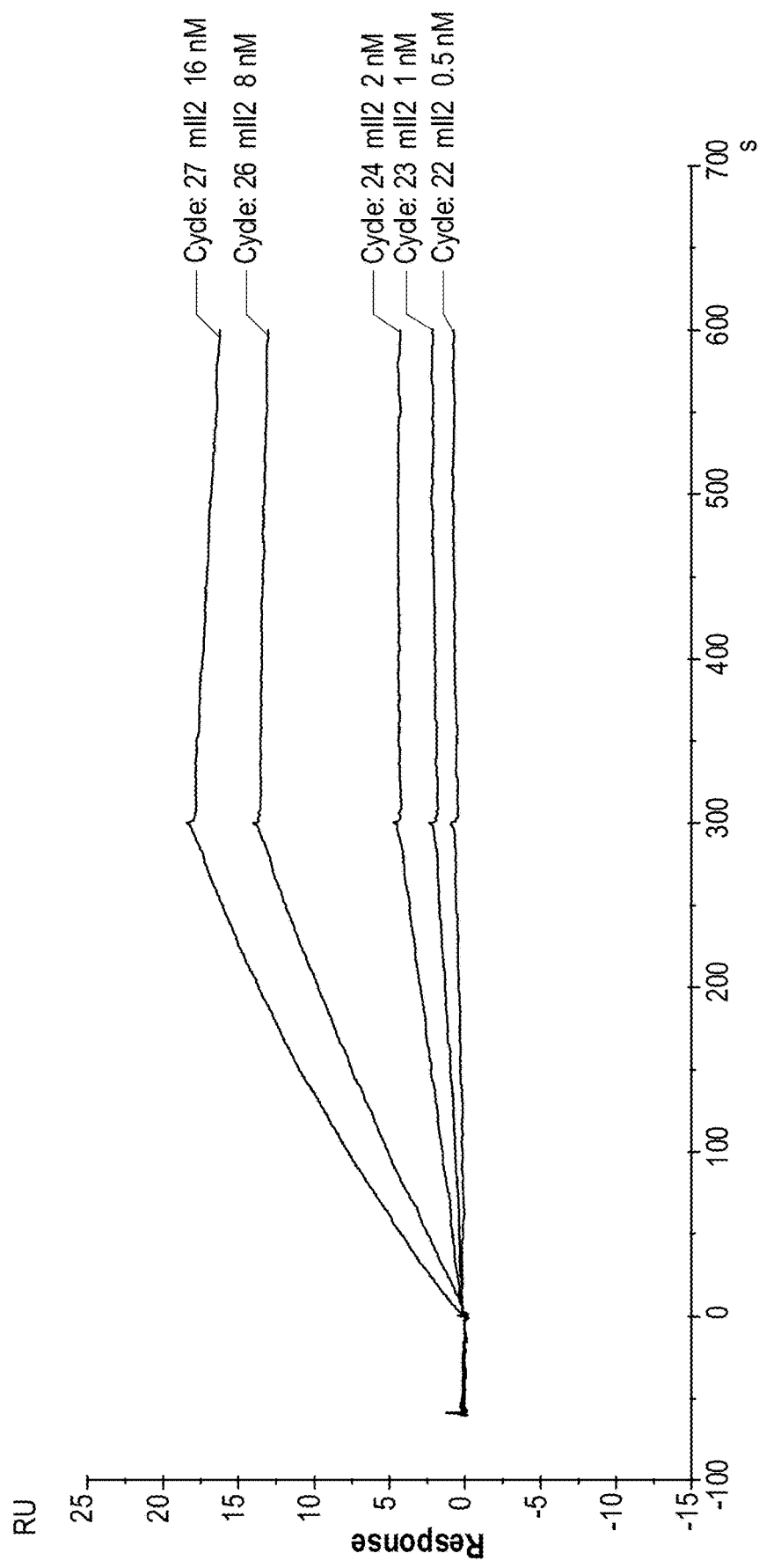
Figure 4C:
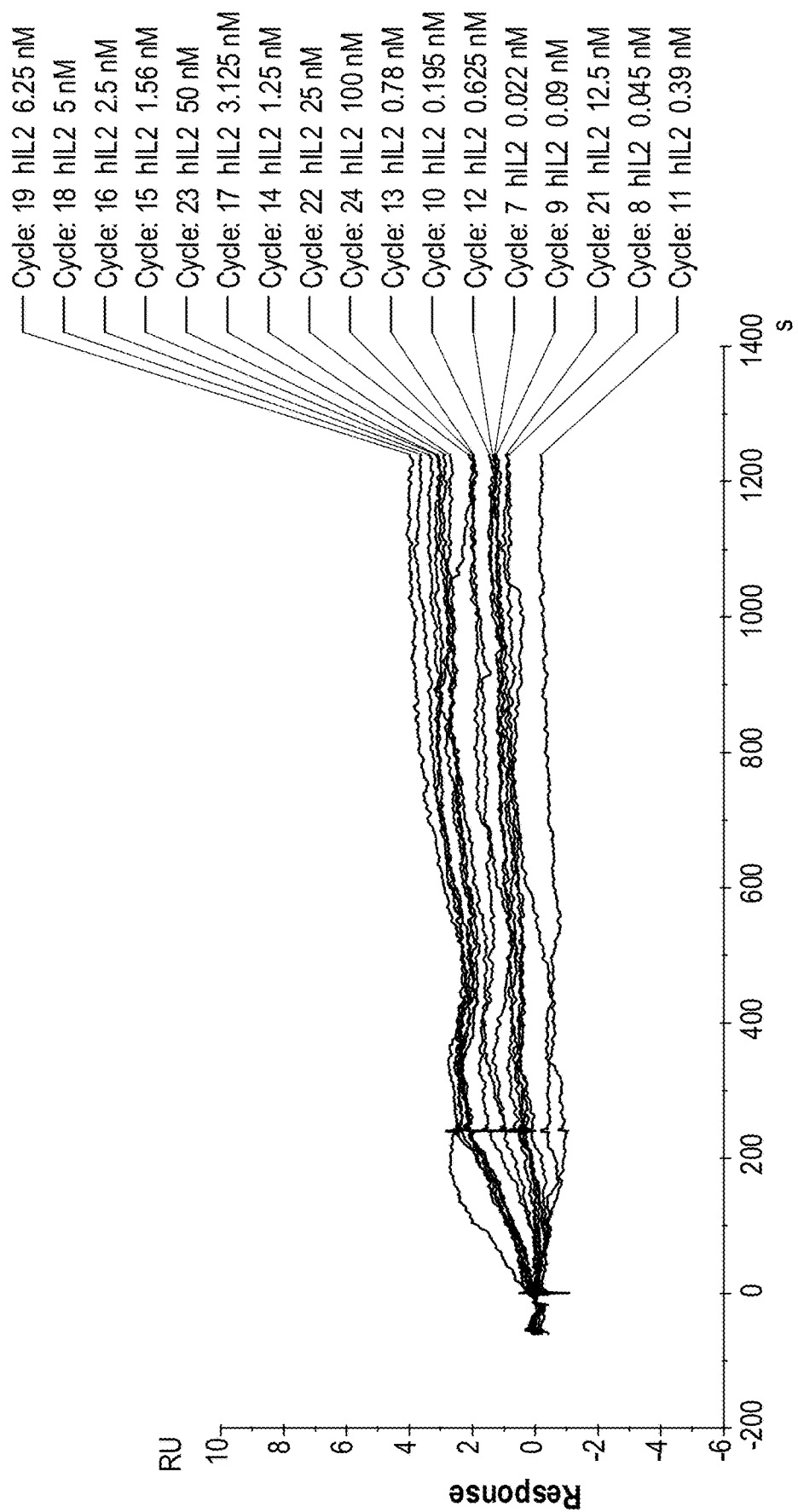
Figure 4D:
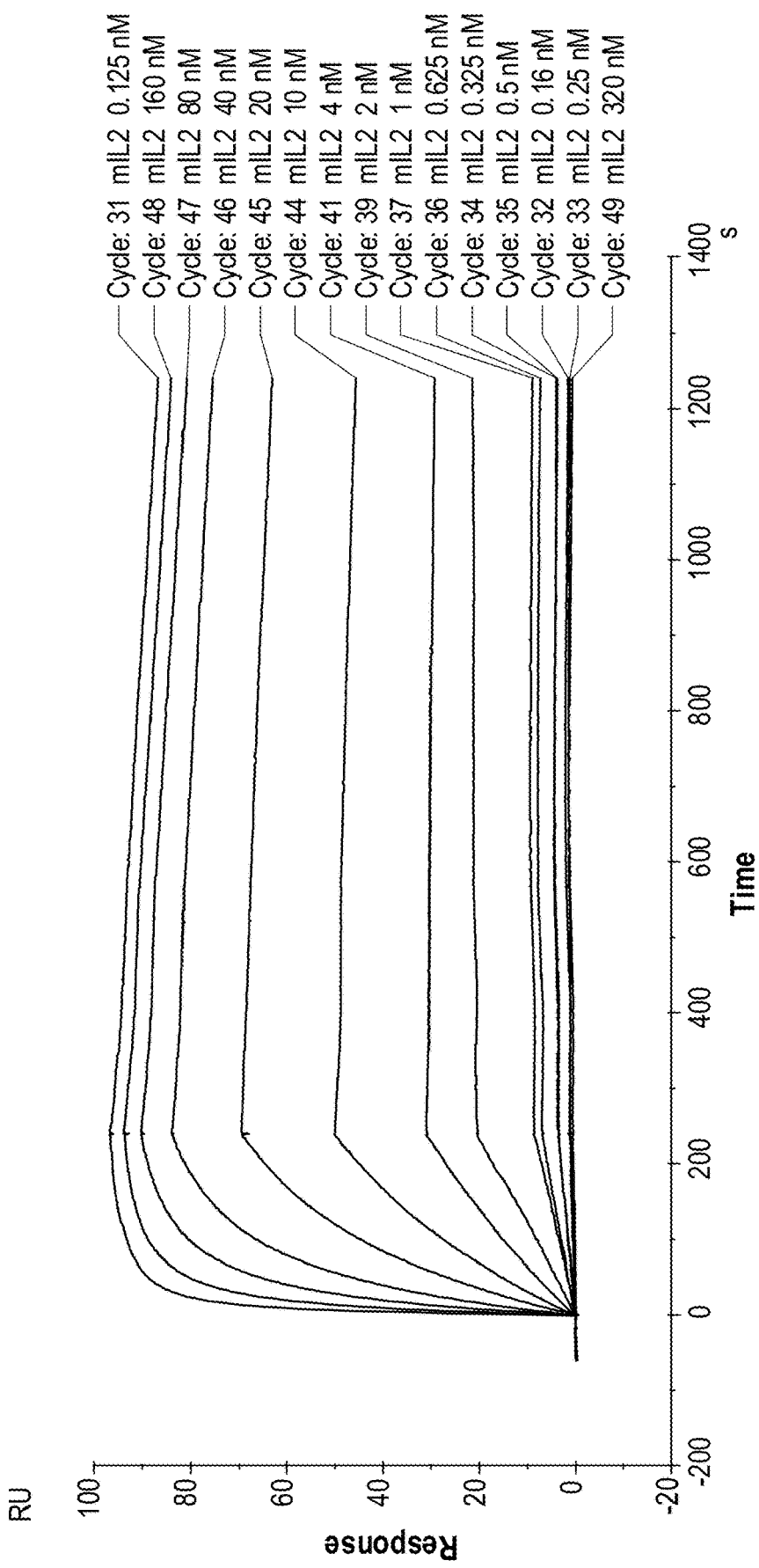

FIGS. 4A-4D present representative SPR sensorgram of JES6.1 antibody binding to human IL-2 (FIG. 4A), mouse IL-2 (FIG. 4B), and of JES6.1RMC antibody binding to human IL-2 (FIG. 4C) and mouse IL-2 (FIG. 4D).

Figure 5A:
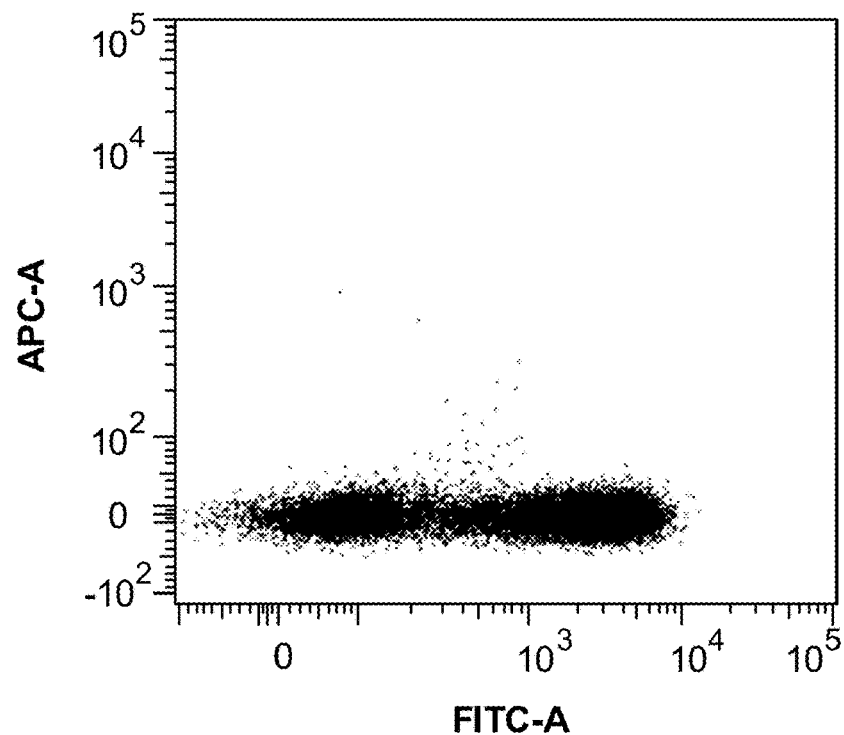
Figure 5B:
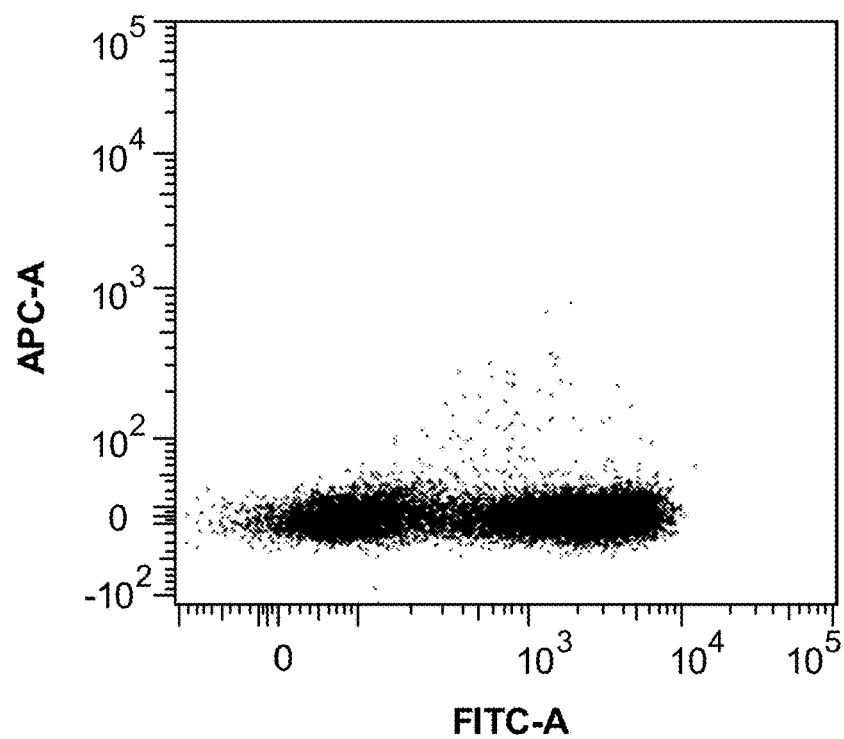
Figure 5C:
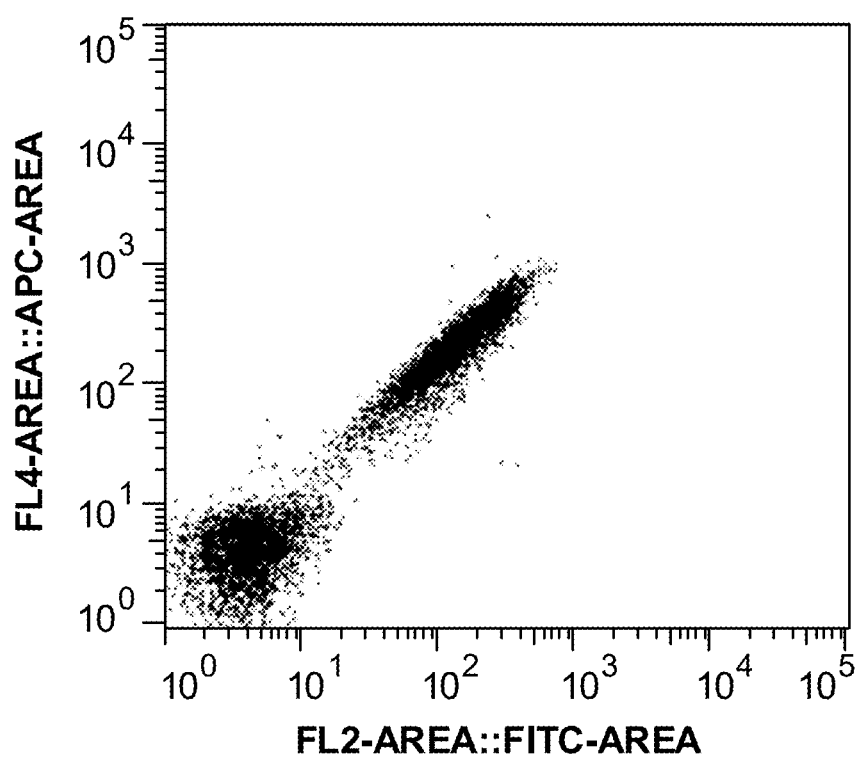

FIGS. 5A-5C present results of IL-2 binding of YSD clones expressing JES6.1 antibody in scFv format. X axis fluorescence levels correspond to scFv expression level of Jes6.1, Y axis fluorescence levels correspond to binding of human or mouse IL-2. FIG. 5A shows negative control without IL-2. FIG. 5B shows JES6.1 YSD clones with 1000 nM human IL-2. FIG. 5C shows YSD expressing mouse IL-2 incubated with 100 nM labeled JES6.1.

FIG. 6A presents binding of isolated yeast-surface display clones to IL-2 (0.1 nM). Mean Fluorescence Intensity (Em 655 nM) was normalized to the yeast surface expression levels. Negative YSD clones were labeled with 500 nM hIL-2.

Figure 6B:
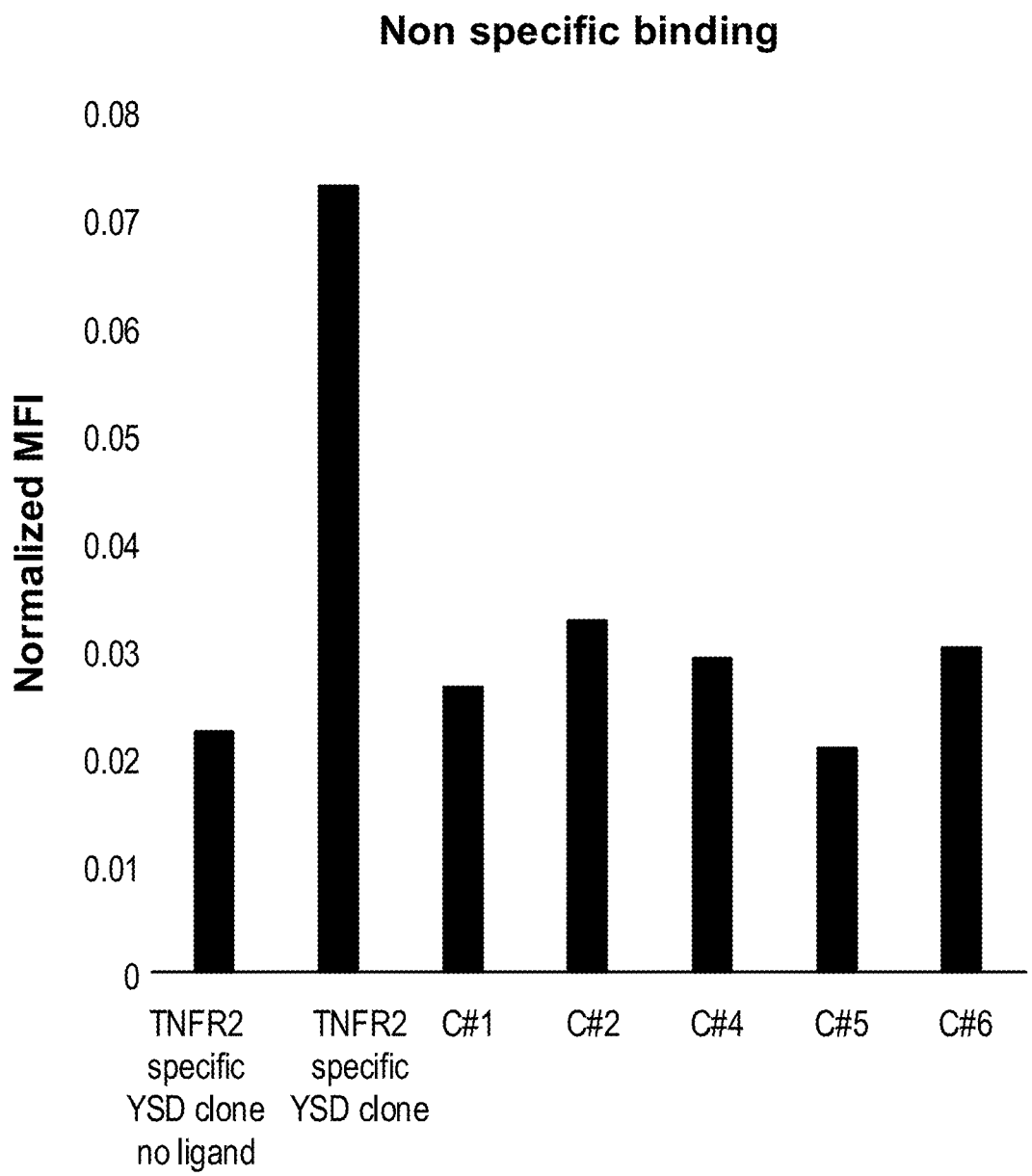

FIG. 6B presents non-specific binding of YSD clones to mixture of OX40/PD-1/TNFR2. The clones were labeled with the 500 nM mixture. TNFR2 binding yeast clone served as positive control.

Figure 7:
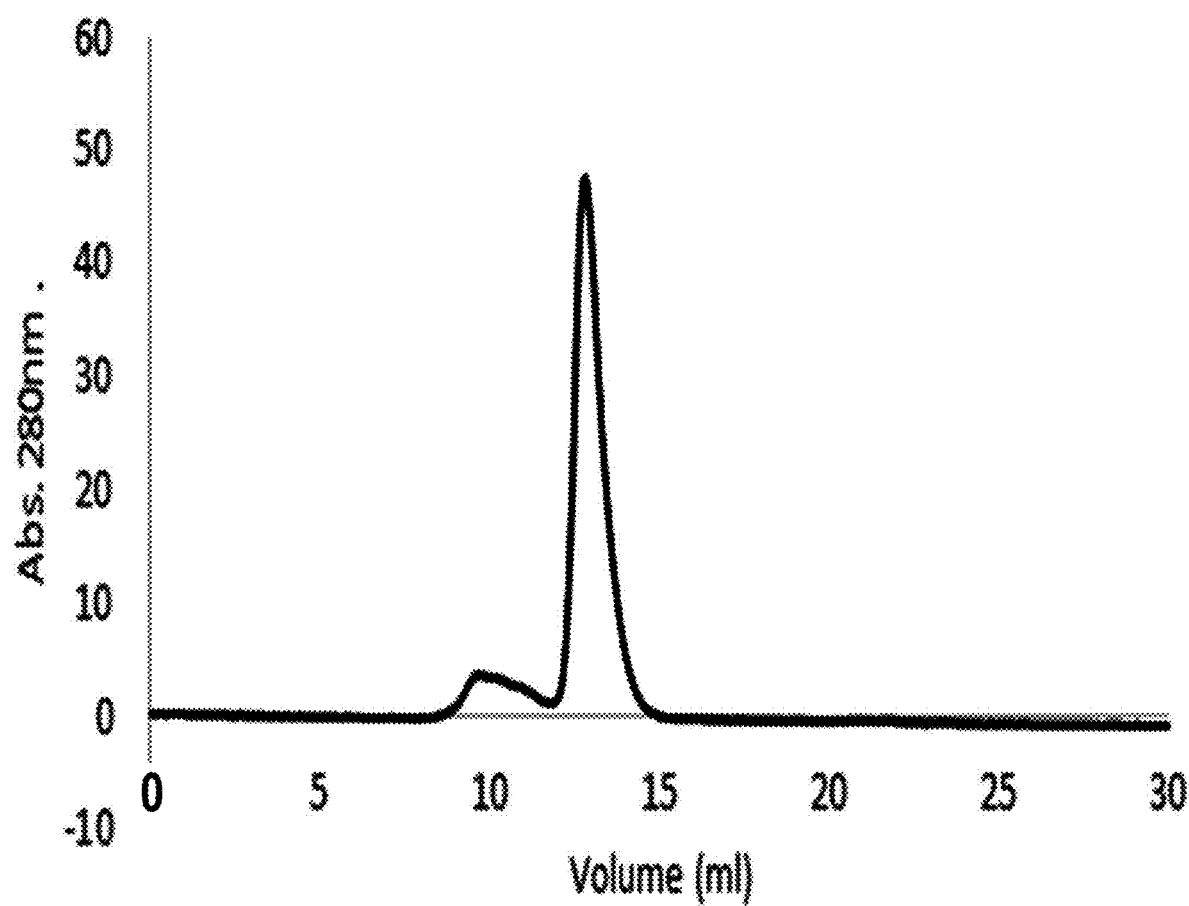

FIG. 7 shows purification of BDG17.023 IgG. The antibody was run on a GE superdex 200 10/300 increase (CV=25 ml) in PBS buffer at 0.5 ml/min. The leading peak (0.38 CV) corresponds to a typical of aggregate, and a second peak (0.51 CV) with retention of approximately 12.9 ml is typical of an ordinary human IgG.

Figure 8A:
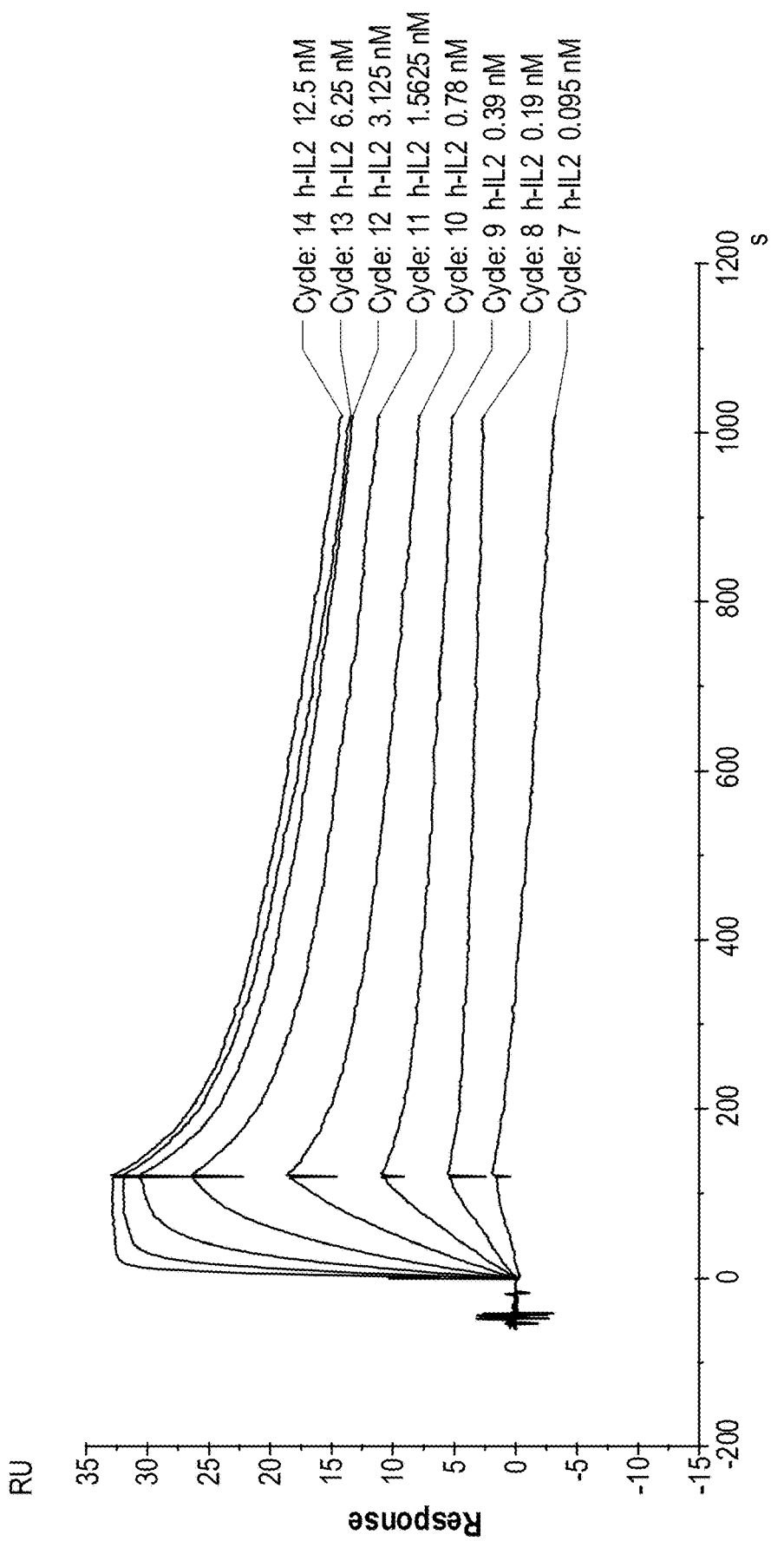
Figure 8B:
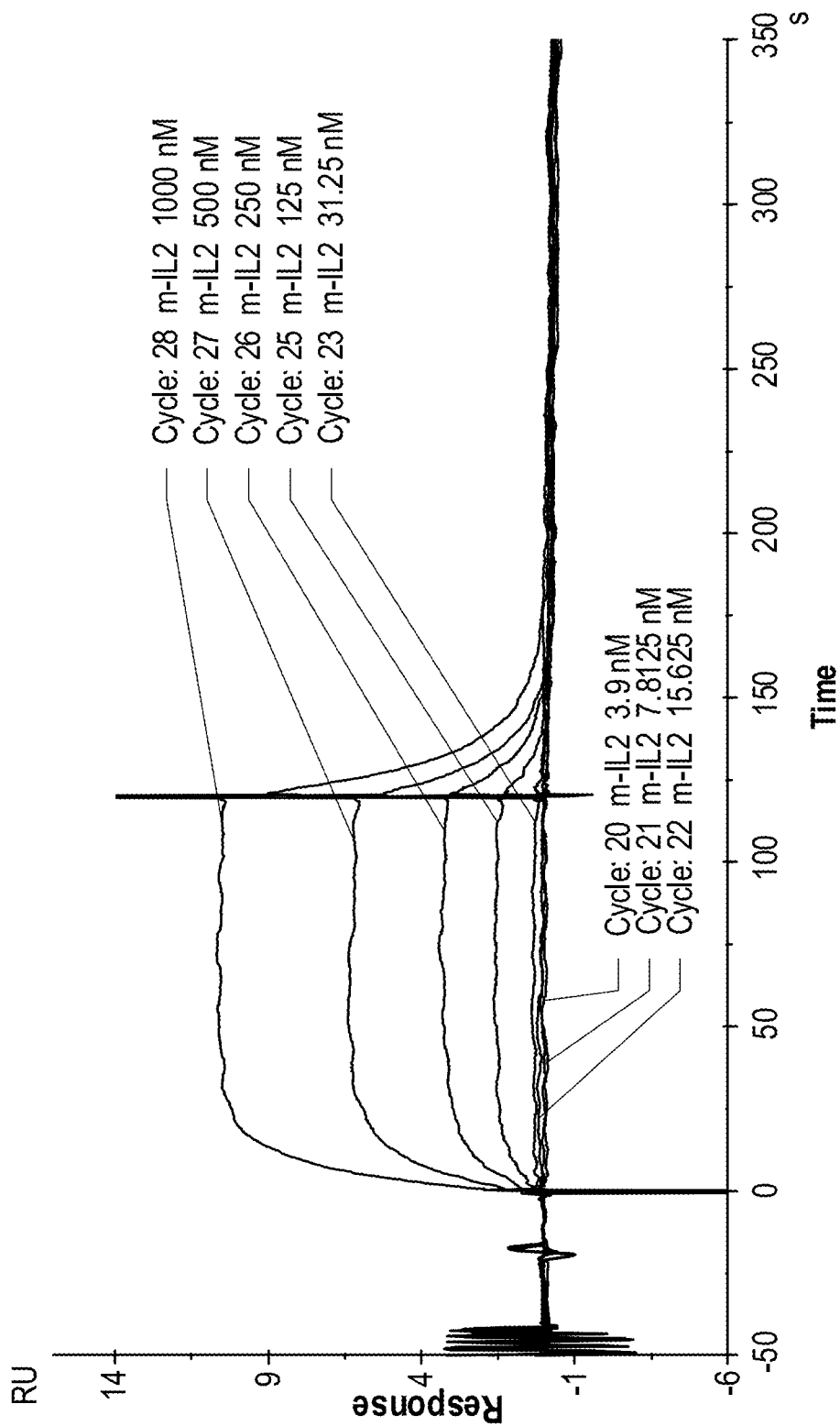

FIGS. 8A-8B present binding kinetic of BDG17.023 IgG to hIL-2 (FIG. 8A) and mIL-2 (FIG. 8B).

Figure 9:
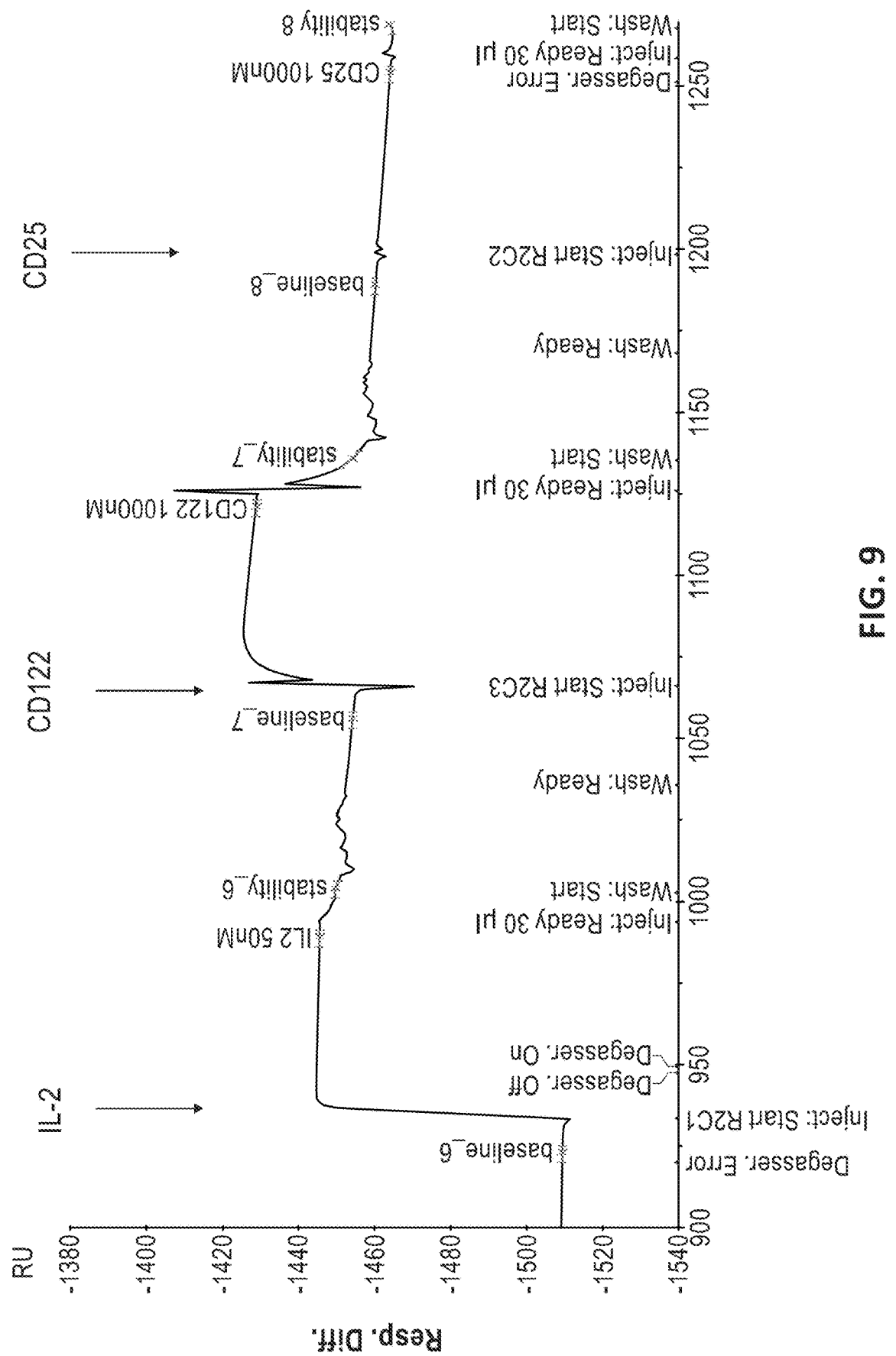

FIG. 9 presents receptor discrimination by BDG17.023-IL-2 complex with traces of SPR response. BDG17.023 was immobilized to the CM5 chip, and hIL-2 (60 RU), CD122 (20 RU) and CD25 (0RU) were streamed as indicated with an arrow.

Figure 10A:
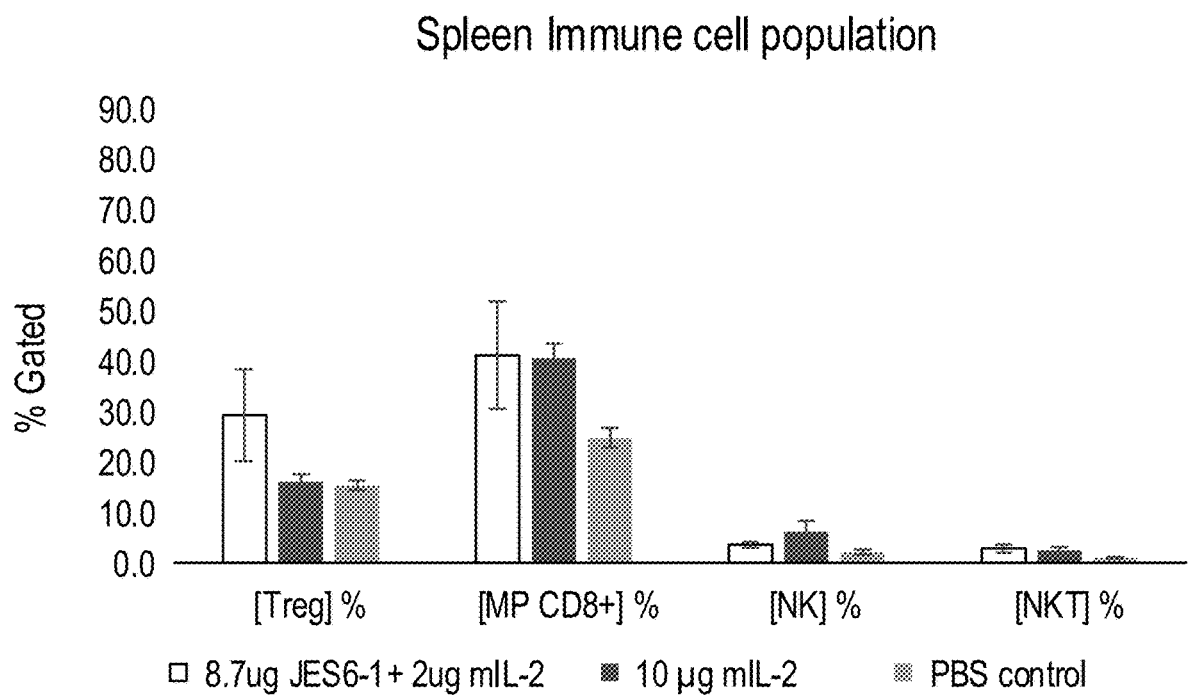
Figure 10B:
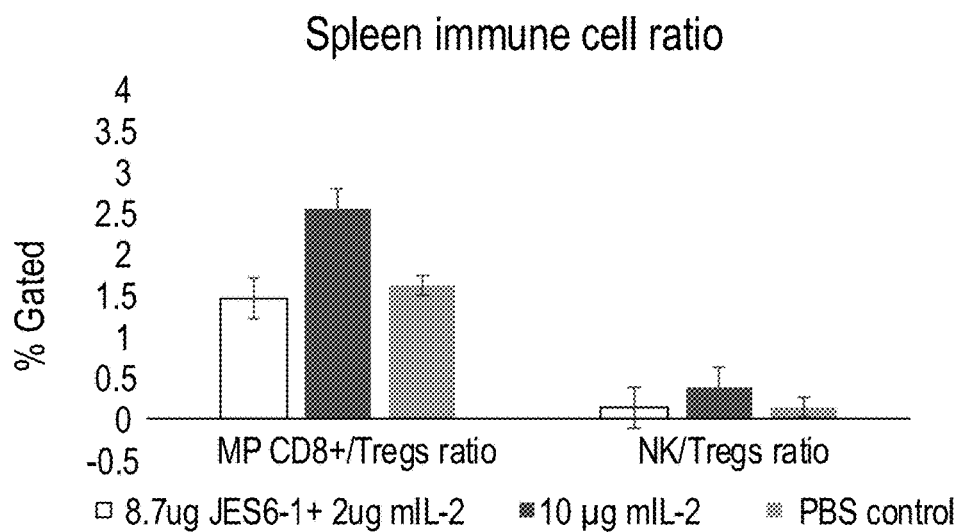
Figure 10C:
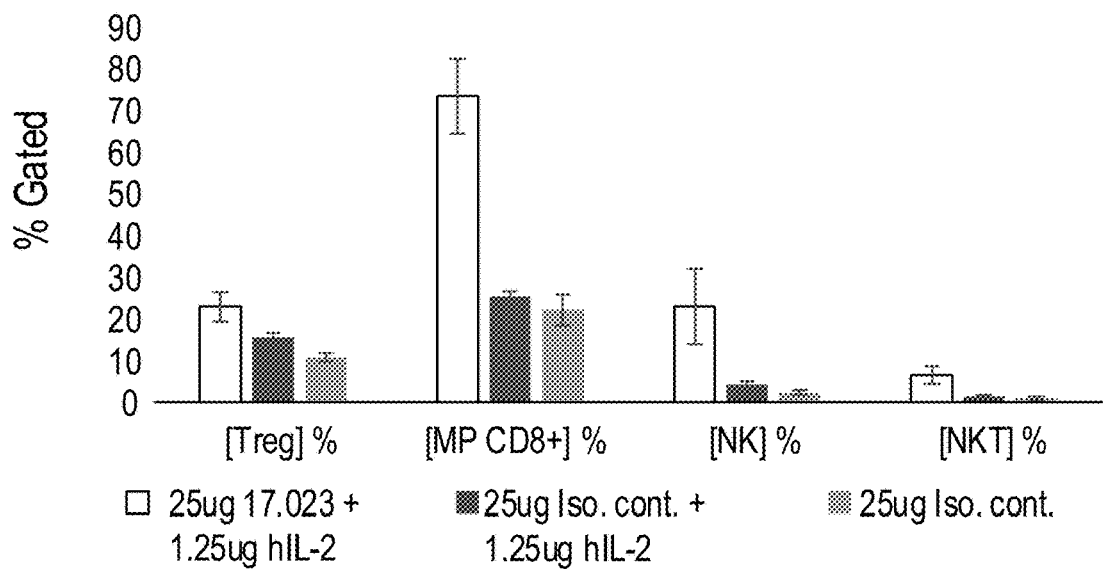
Figure 10D:
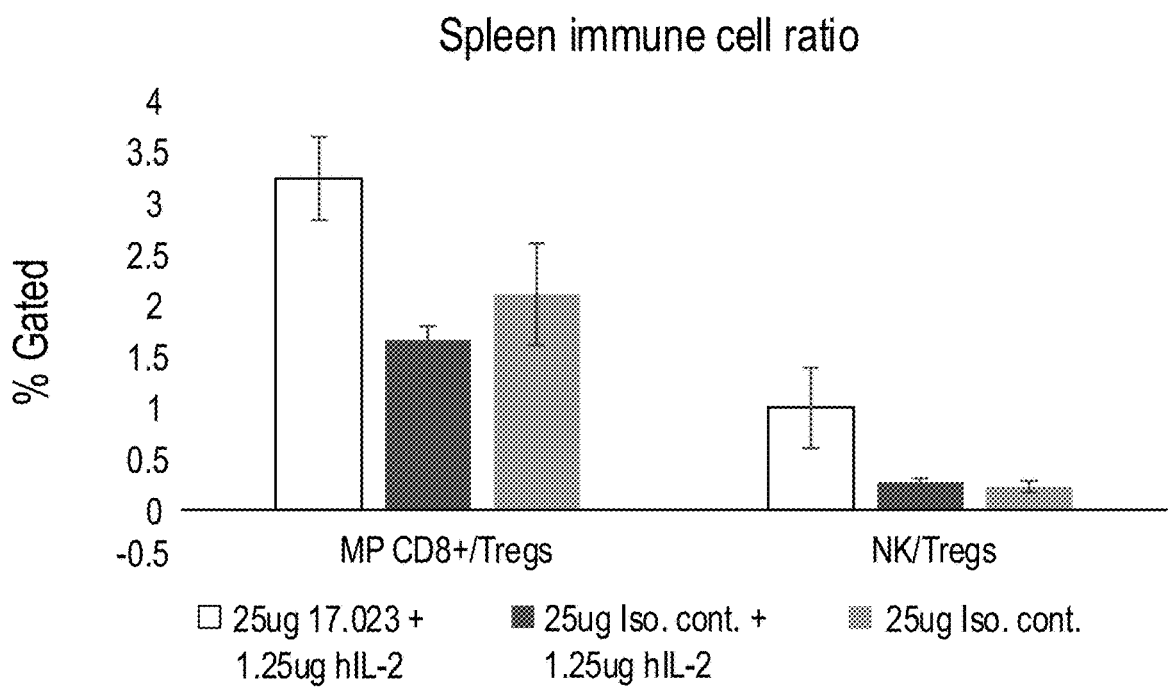
Figure 14A:
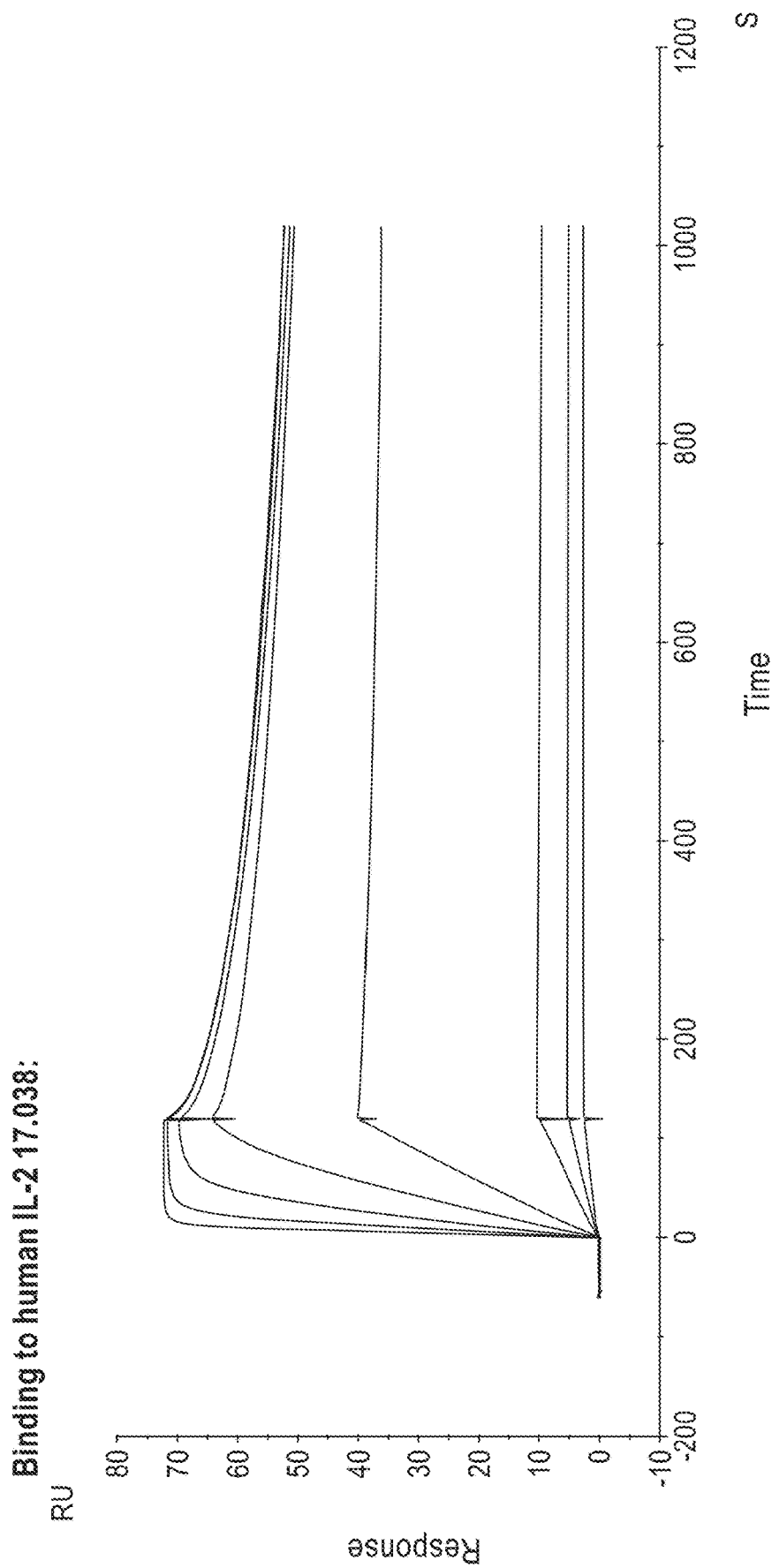
Figure 14B:
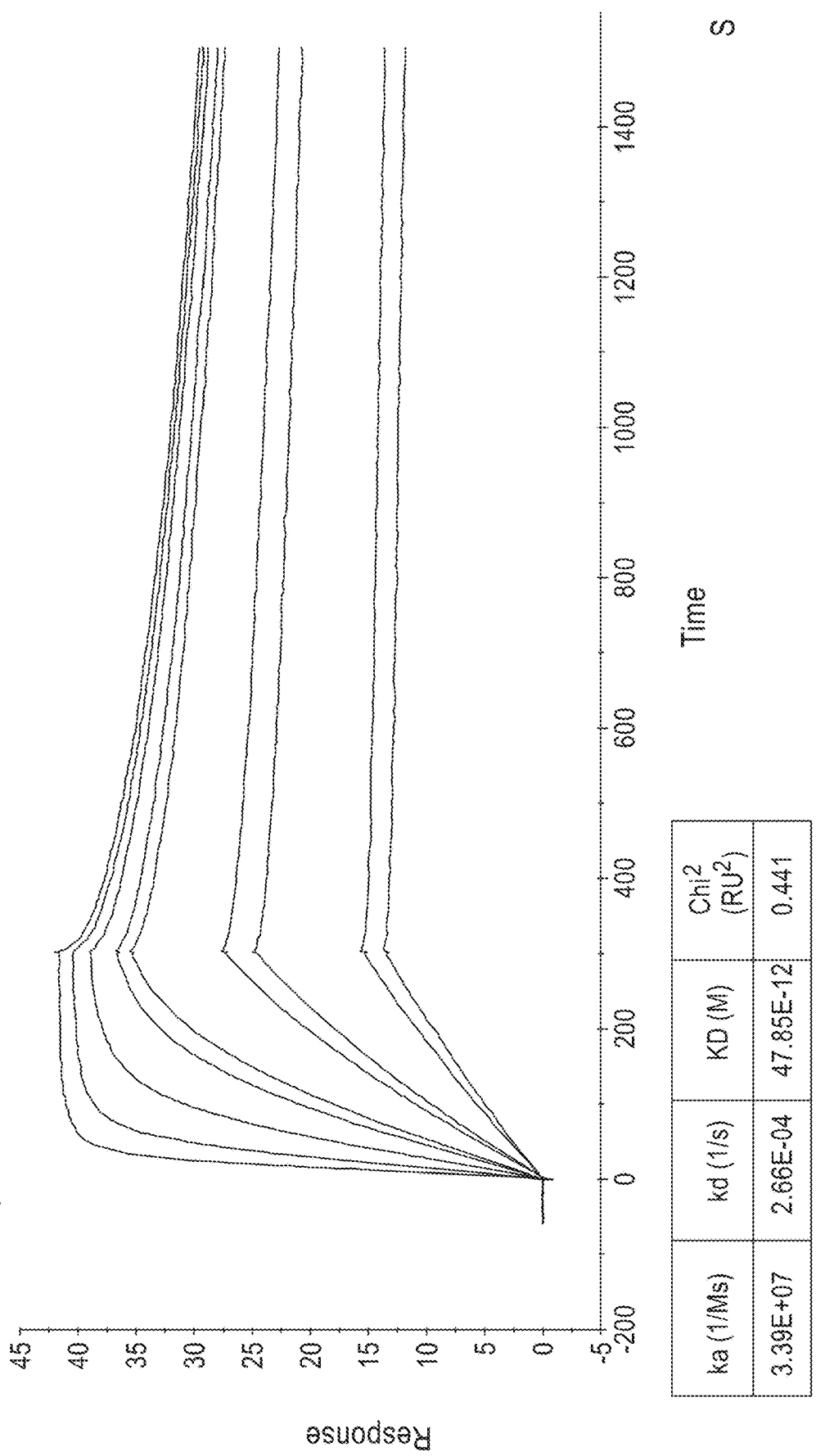
Figure 14C:
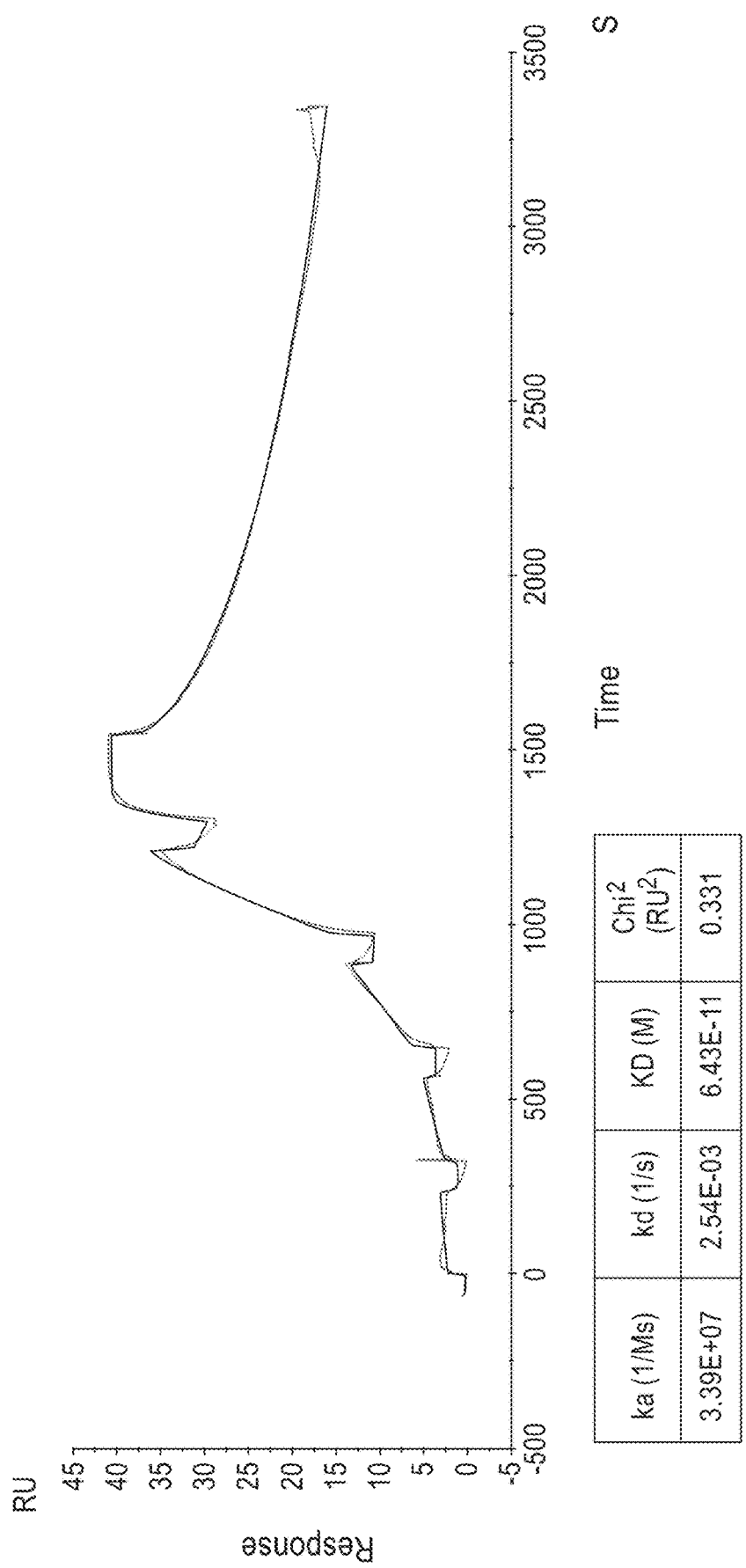
Figure 14D:
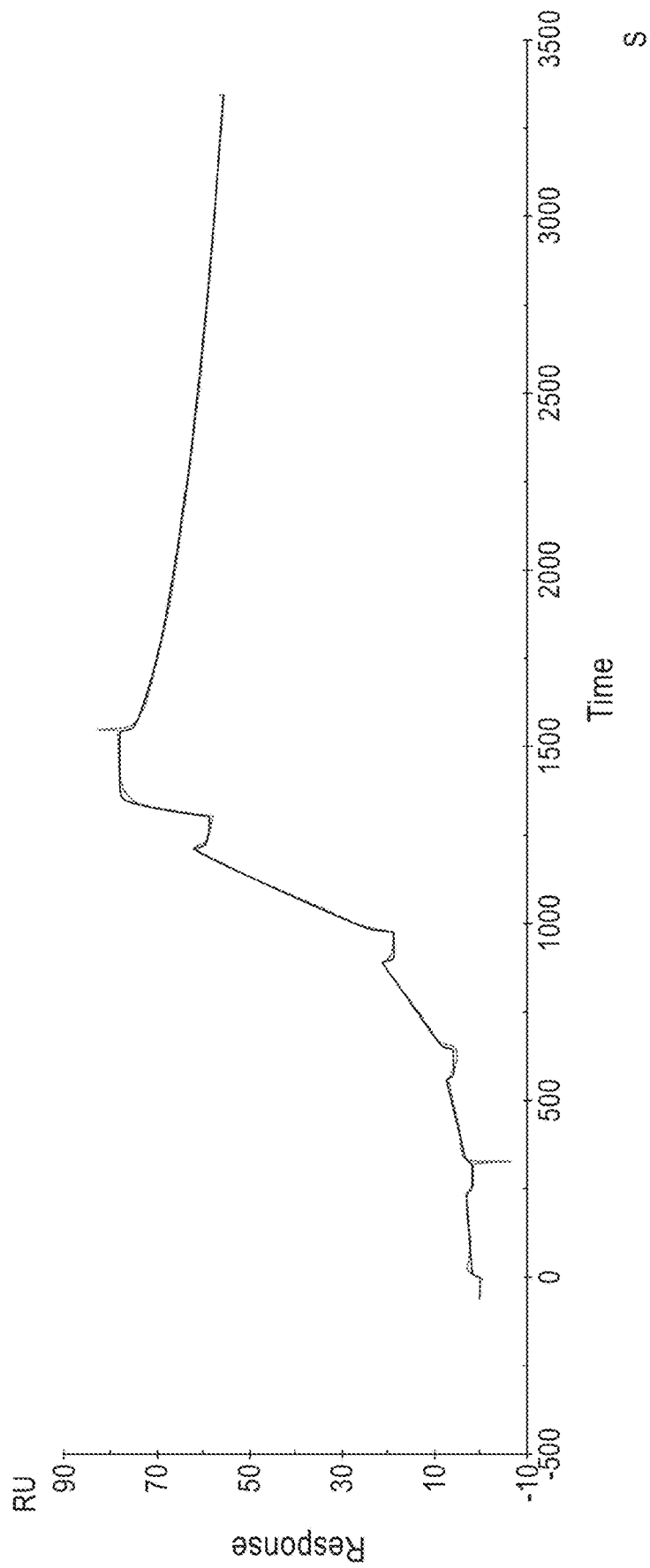
Figure 14E:
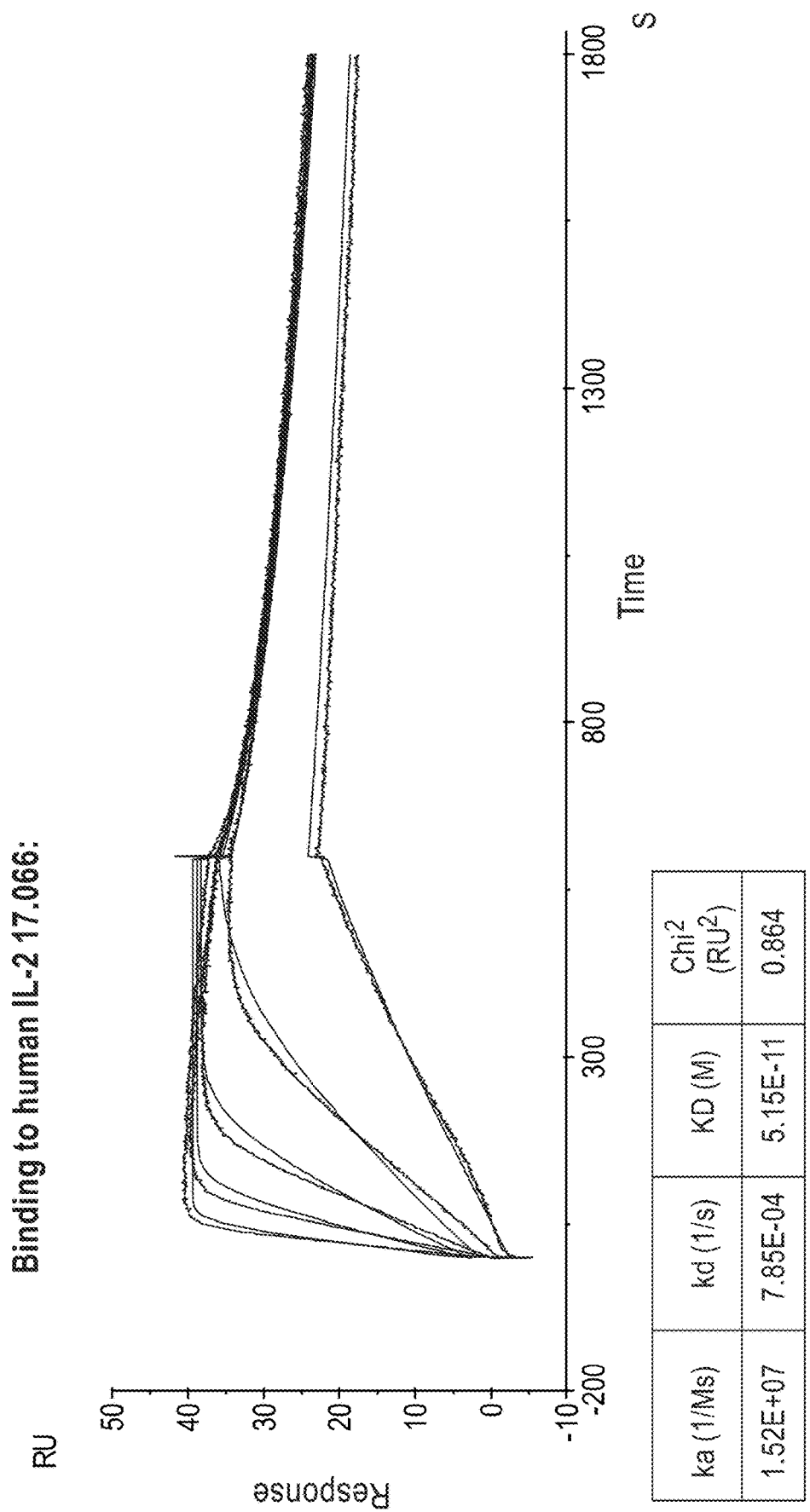
Figure 14F:
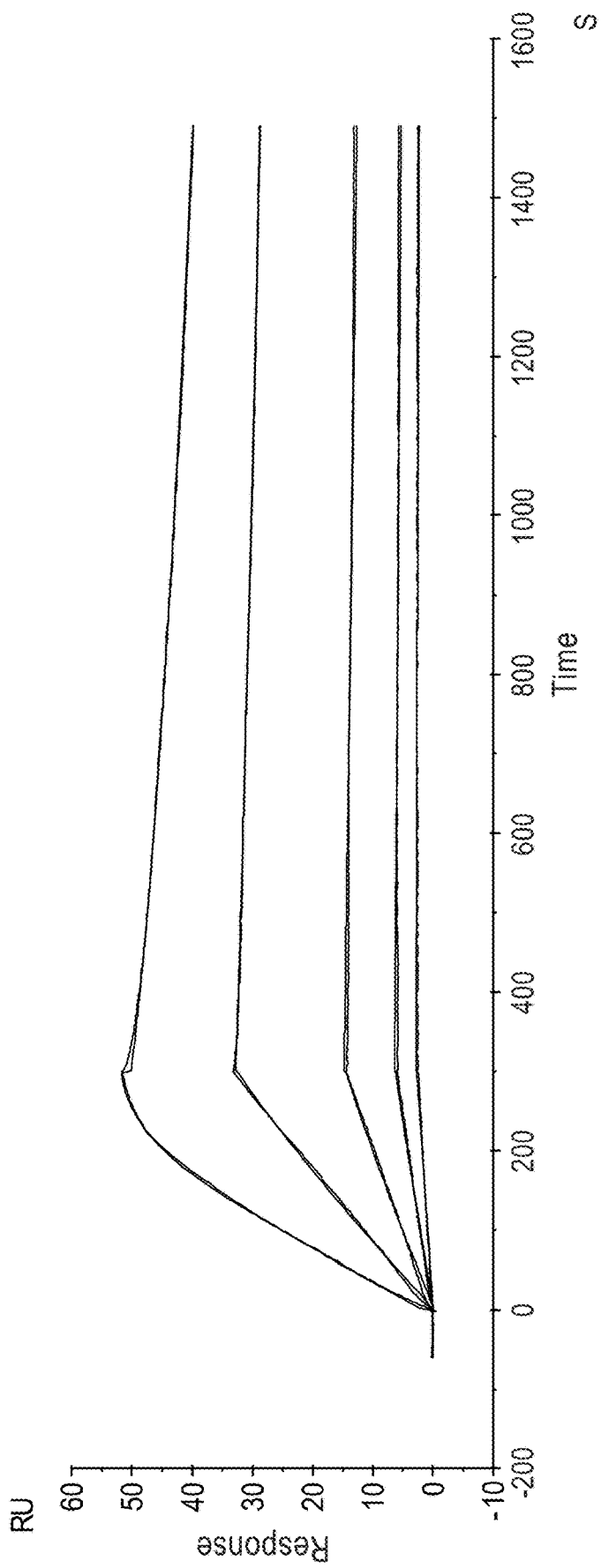
Figure 14G:
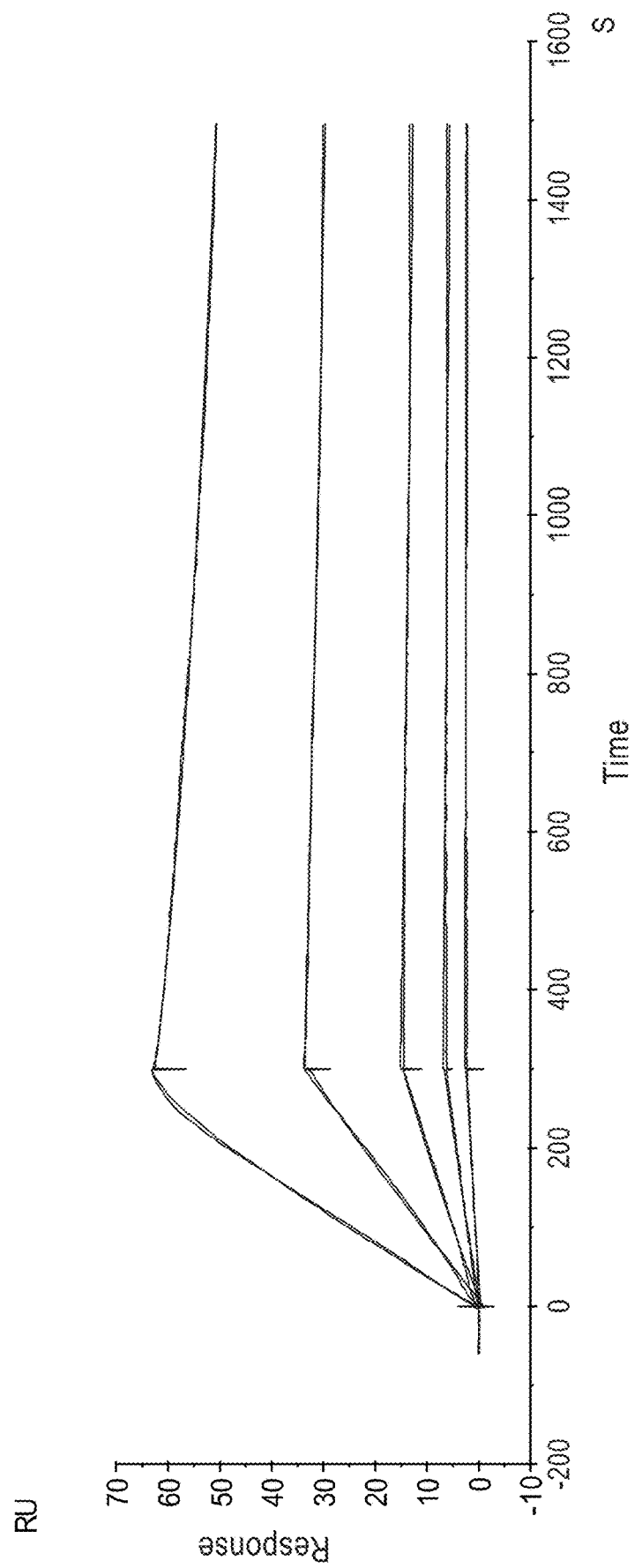

FIGS. 10A-10D present spleen immune cell populations of mice treated with JES6.1-mIL-2 complex and BDG17.023-hIL-2 complex. FIG. 10A shows percentages of immune cell populations from mice treated with JES6.1-mIL-2 complex. FIG. 10B shows memory phenotype effector T cells (MP) CD8+/Tregs ratios of mice treated with JES6.1-mIL-2 complex. FIG. 10C shows percentages of immune cell populations from mice treated with BDG17.023-hIL-2 complex. FIG. 10D shows MP CD8+/Tregs ratios of mice treated with BDG17.023-hIL-2 complex.

FIG. 11 presents the alignment of amino acid sequences of the heavy chain variable region of JES6.1, clone 1 (17.021), clone 2 (17.022), clone 4 (17.023), clone 5 (17.030), and clone 6 (17.035).

FIG. 12 presents the alignment of amino acid sequences of the light chain variable region of JES6.1, clone 1 (17.021), clone 2 (17.022), clone 4 (17.023), clone 5 (17.030), and clone 6 (17.035).

FIGS. 13A and 13B present the alignment of amino acid sequences of the heavy chain variable region (FIG. 13A) and the light chain variable region (FIG. 13B) of the humanized clone 17.014, clone 17.038, clone 17.043, clone 17.053, and clone 17.054. Black triangles denote IMGT CDR positions. Bold/Italic font denotes ABR/CDR positions, respectively.

FIGS. 14A-14G. Binding kinetics of indicated antibodies to human IL-2. Surface plasmon resonance (SPR) sensogram traces of binding kinetics of anti-IL-2 antibody clones BDG17.038 (FIG. 14A), BDG 17.043 (FIG. 14B), BDG17.053 (FIG. 14C), 17.054 (FIG. 14D), BDG17.066 (FIG. 14E), BDG17.067 (FIG. 14F), and BDG17.069 (FIG. 14G), to human IL-2. BDG 17.038, BDG 17.043, BDG 17.066, BDG 17.067 and BDG 17.069 binding kinetics were determined by the multi-cycle method. BDG 17.053 and BDG 17.054 binding kinetics were determined by the single-cycle method.

Figure 15A:
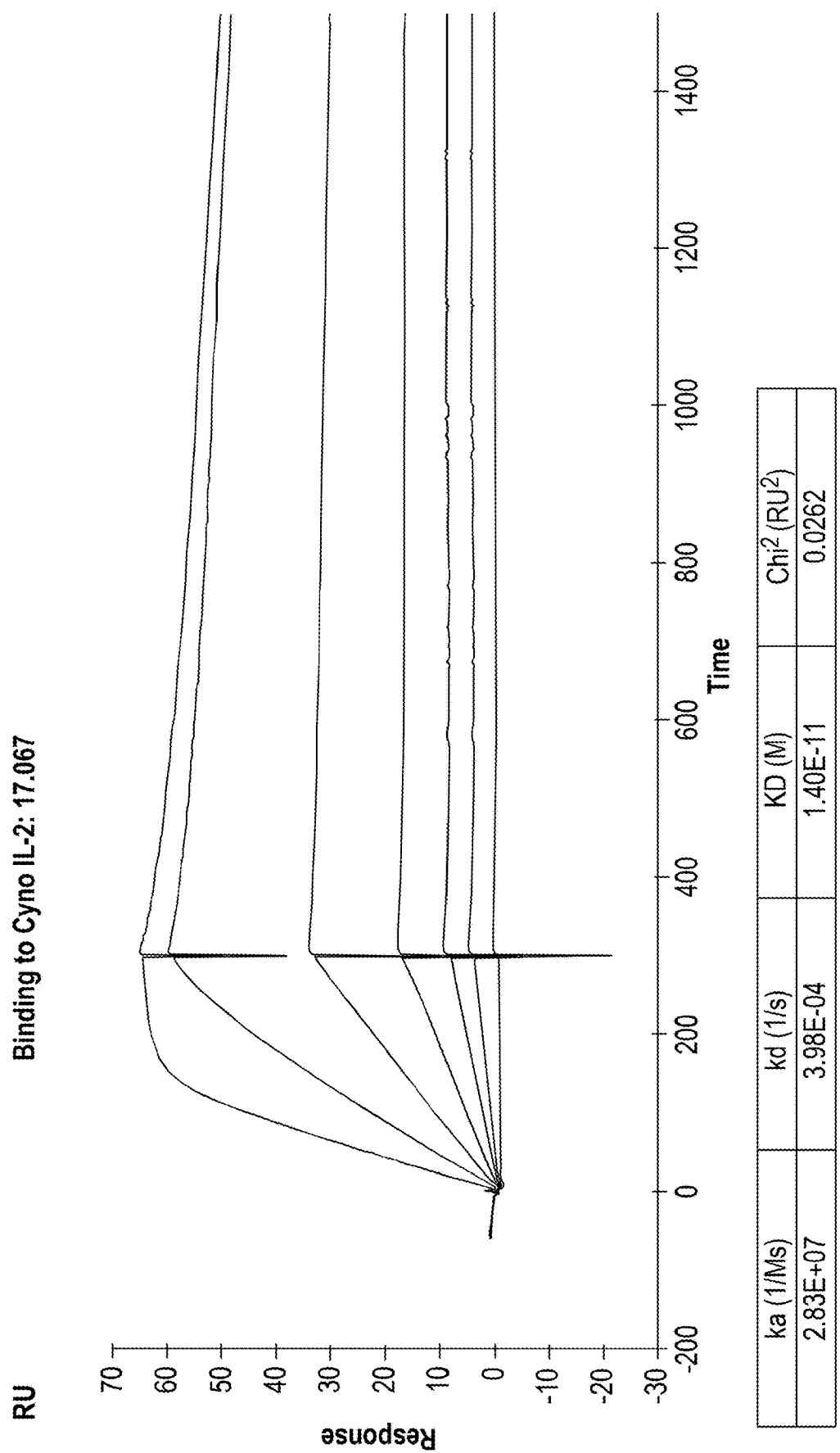
Figure 15B:
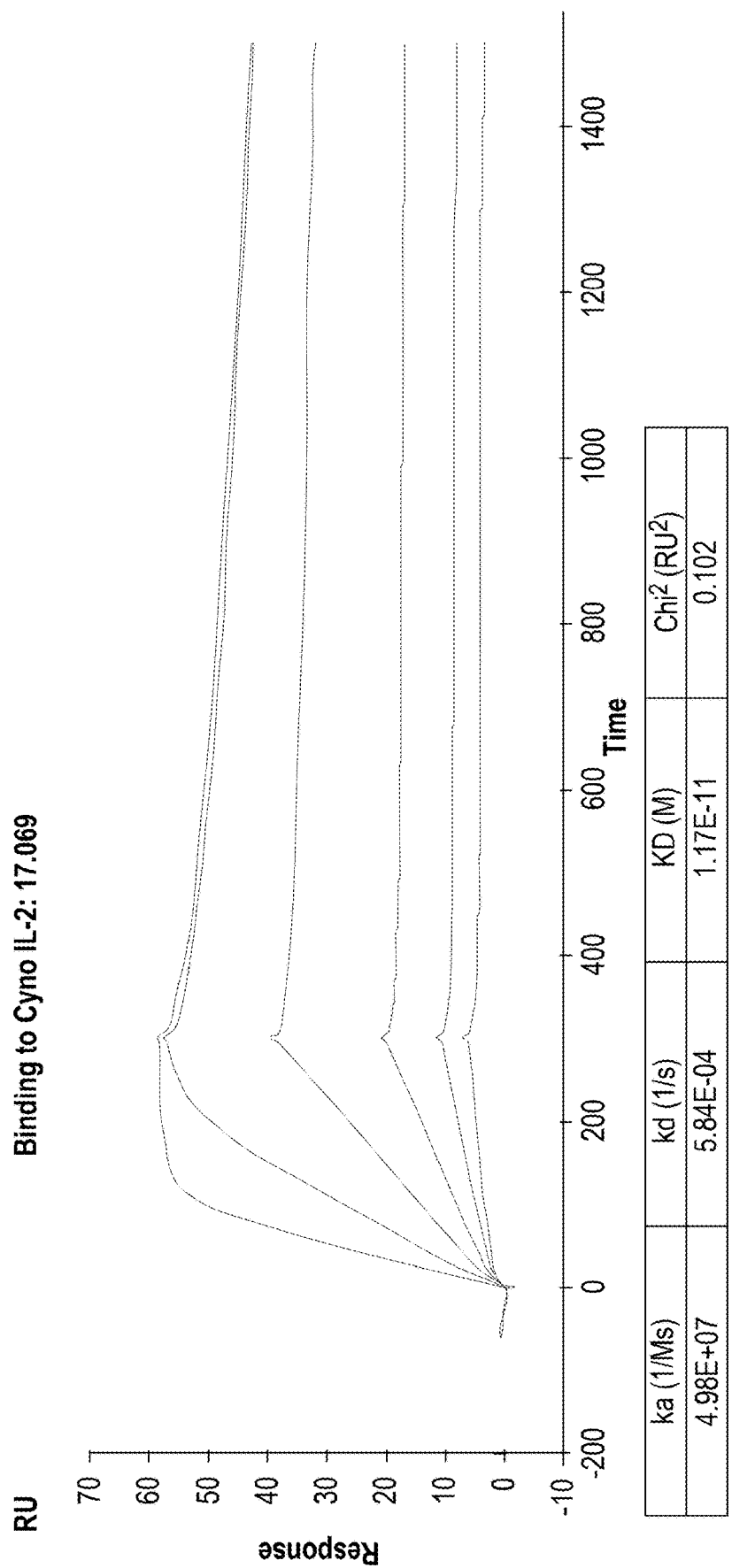

FIGS. 15A-15B. Binding kinetics of indicated antibodies to cynomolgus monkey IL-2. Surface plasmon resonance (SPR) sensogram traces of binding kinetics of anti-IL-2 antibody clones BDG17.067 (FIG. 15A), and BDG17.069 (FIG. 15B), to cynomolgus monkey IL-2.

Figure 16A:
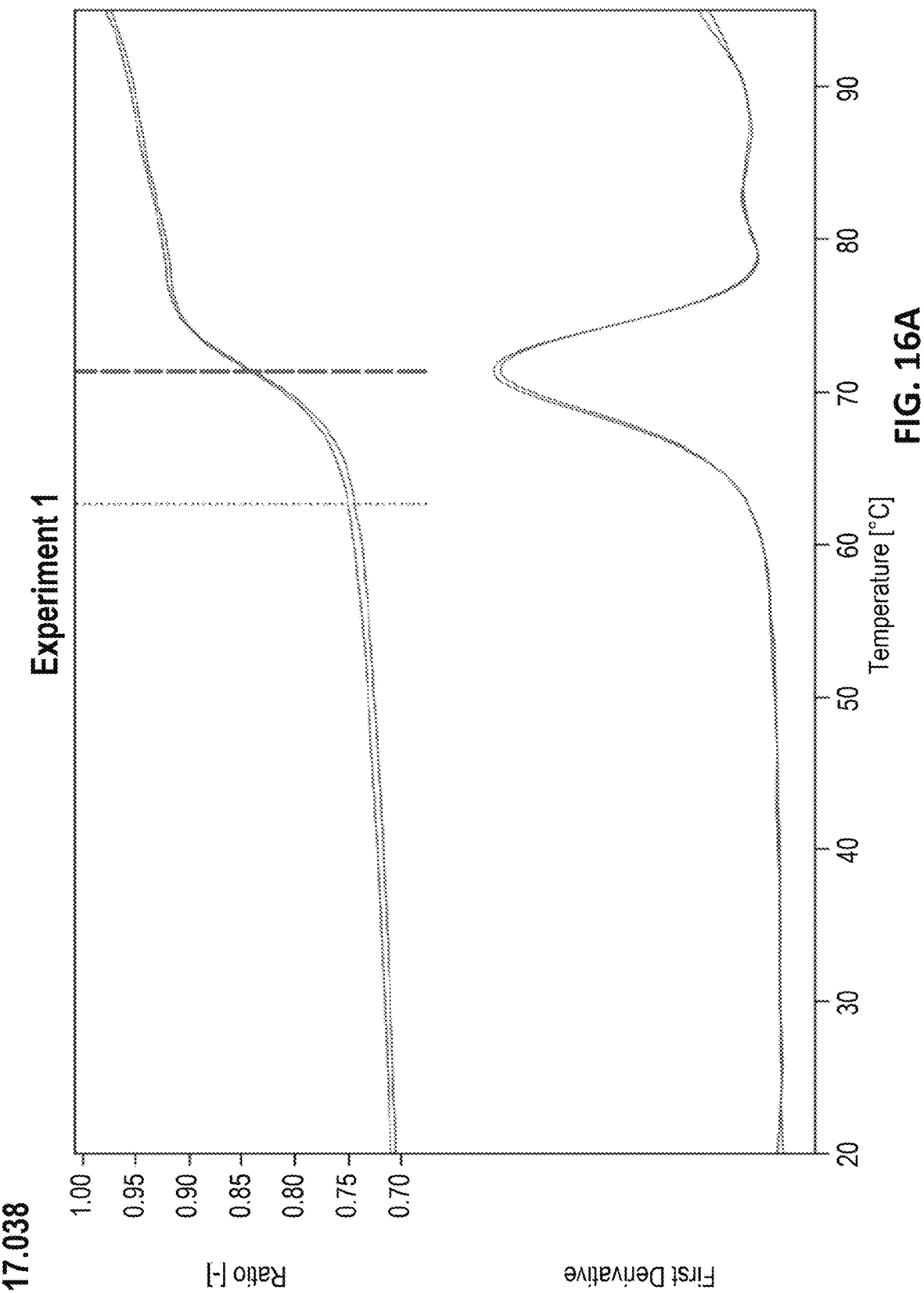
Figure 16B:
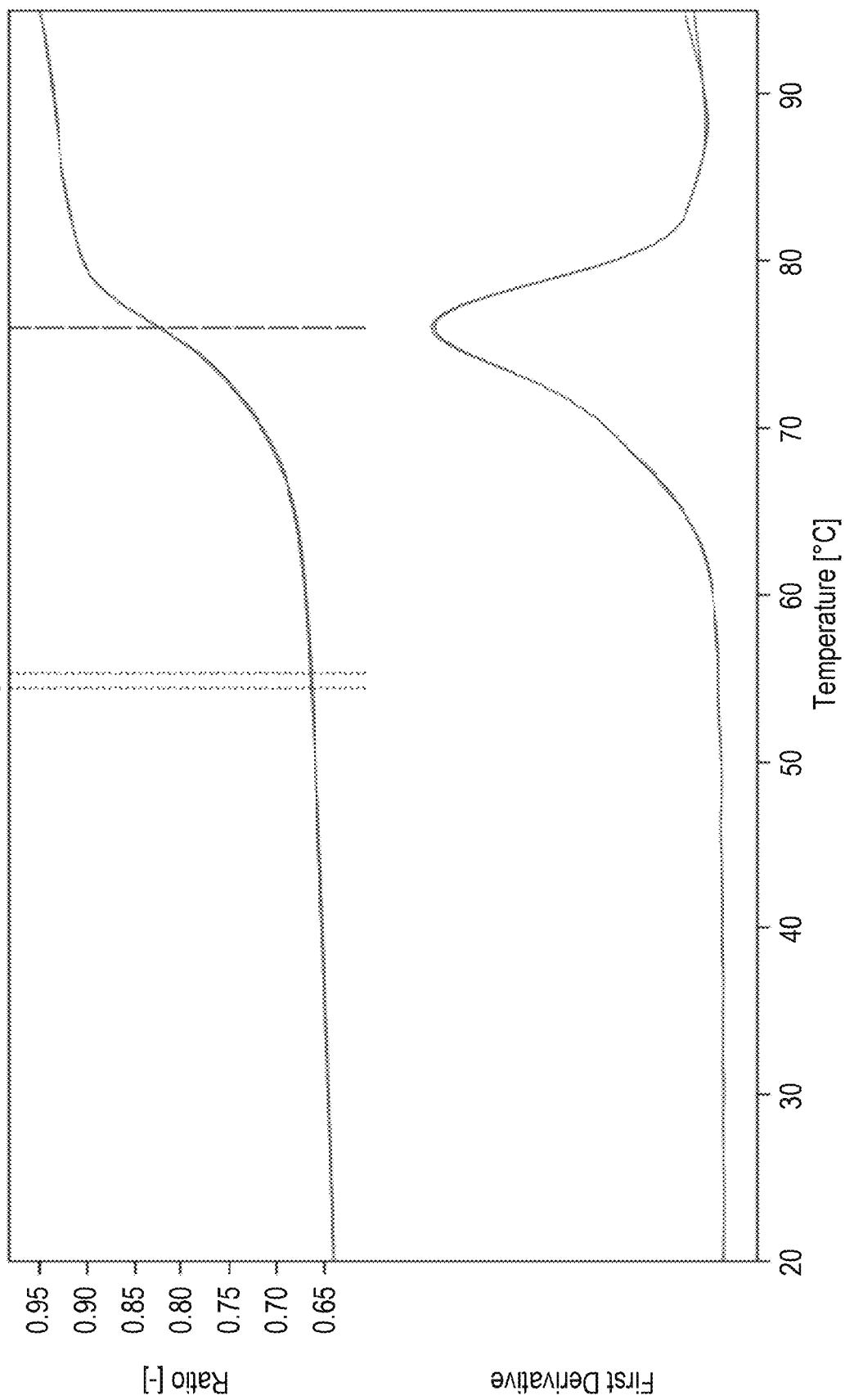
Figure 16C:
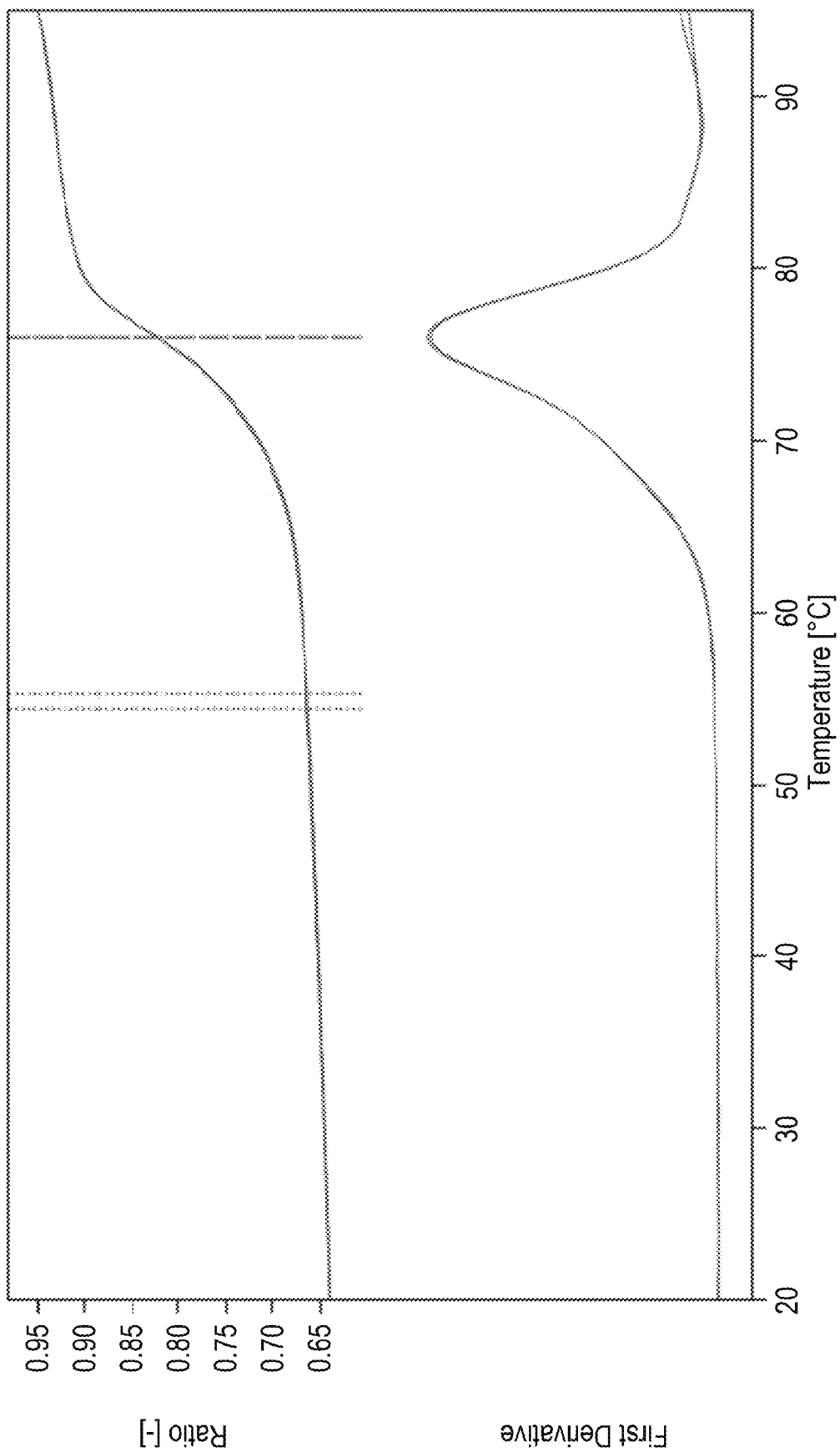
Figure 16D:
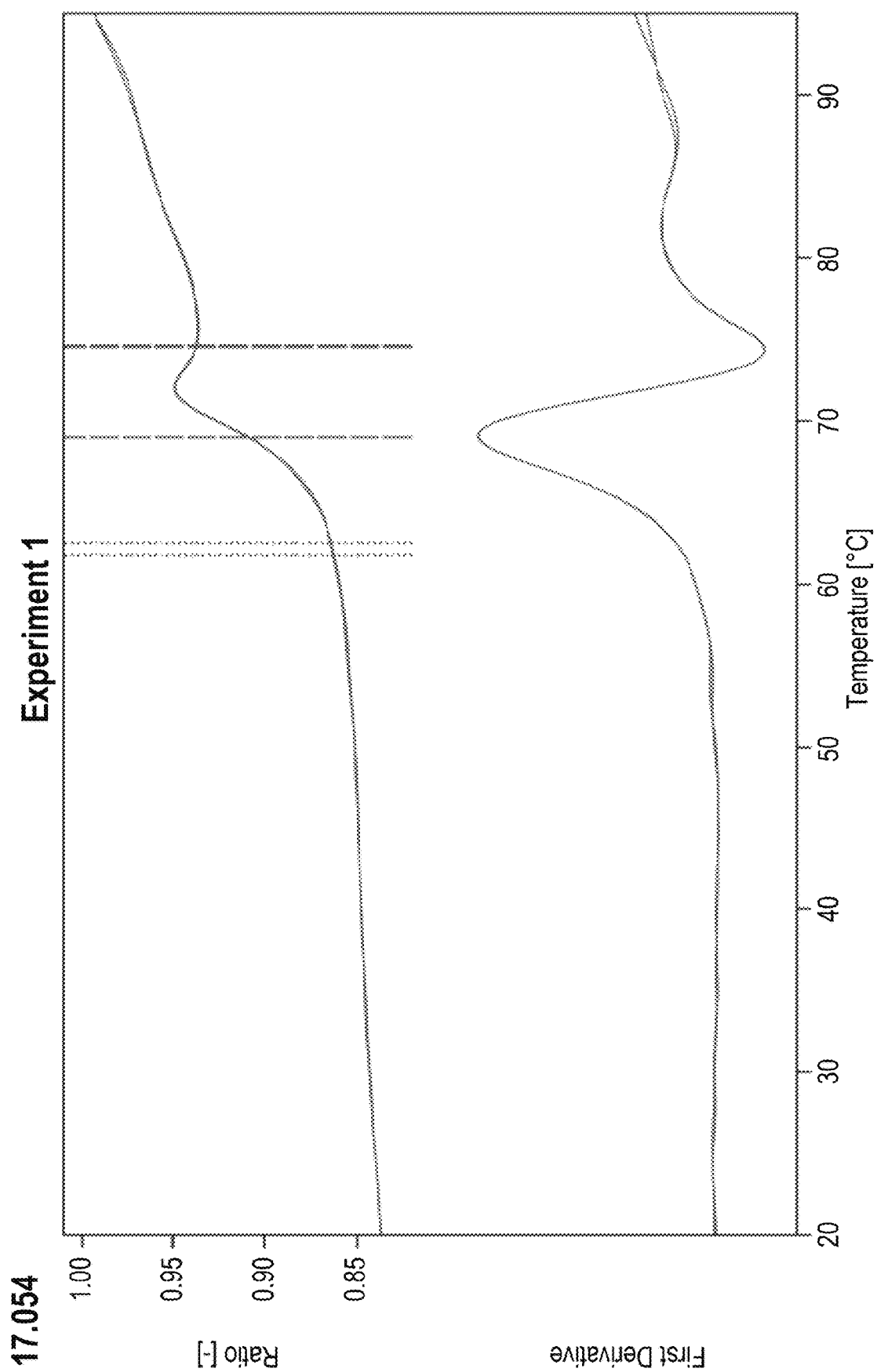
Figure 16E:
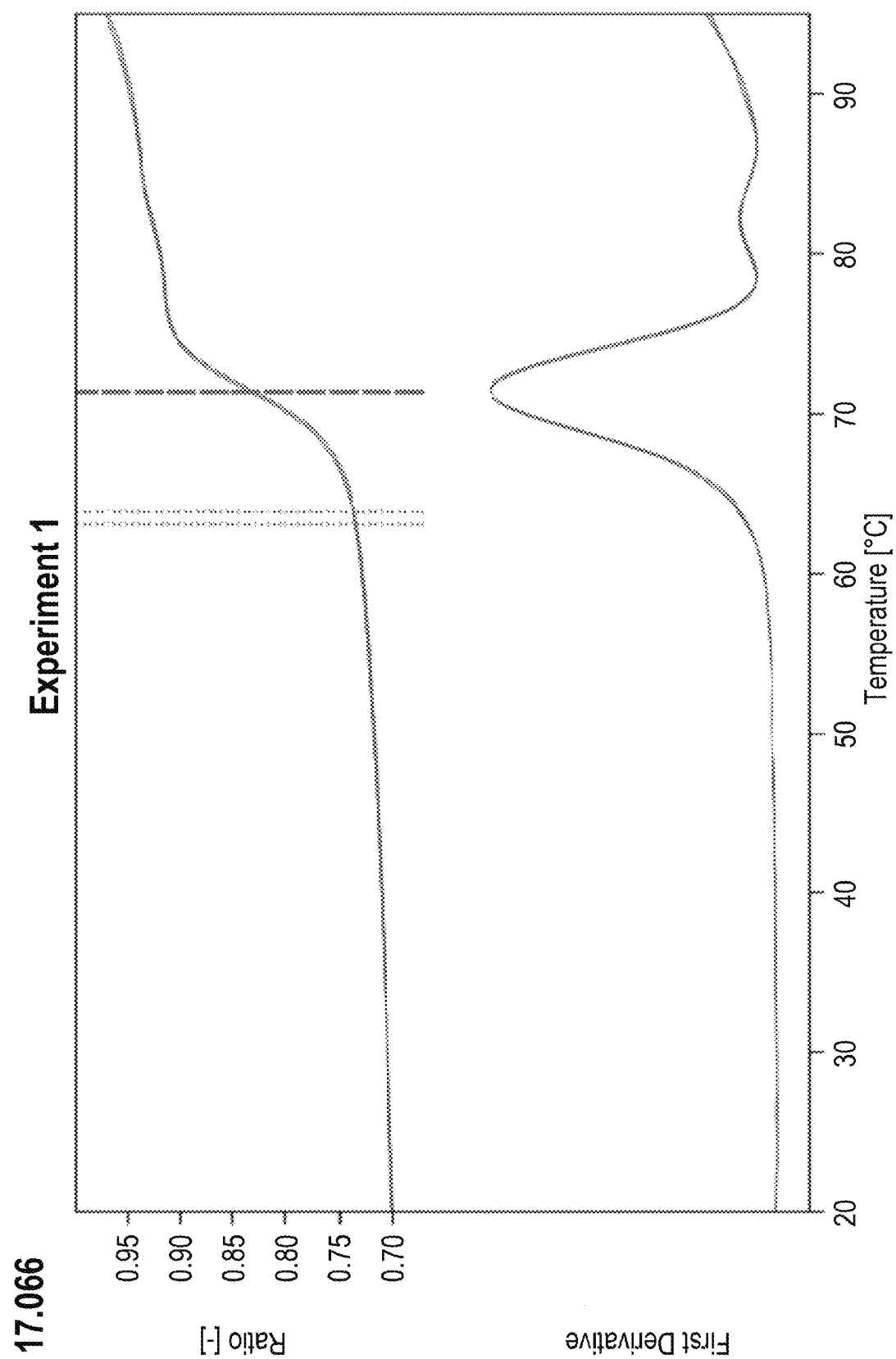
Figure 16F:
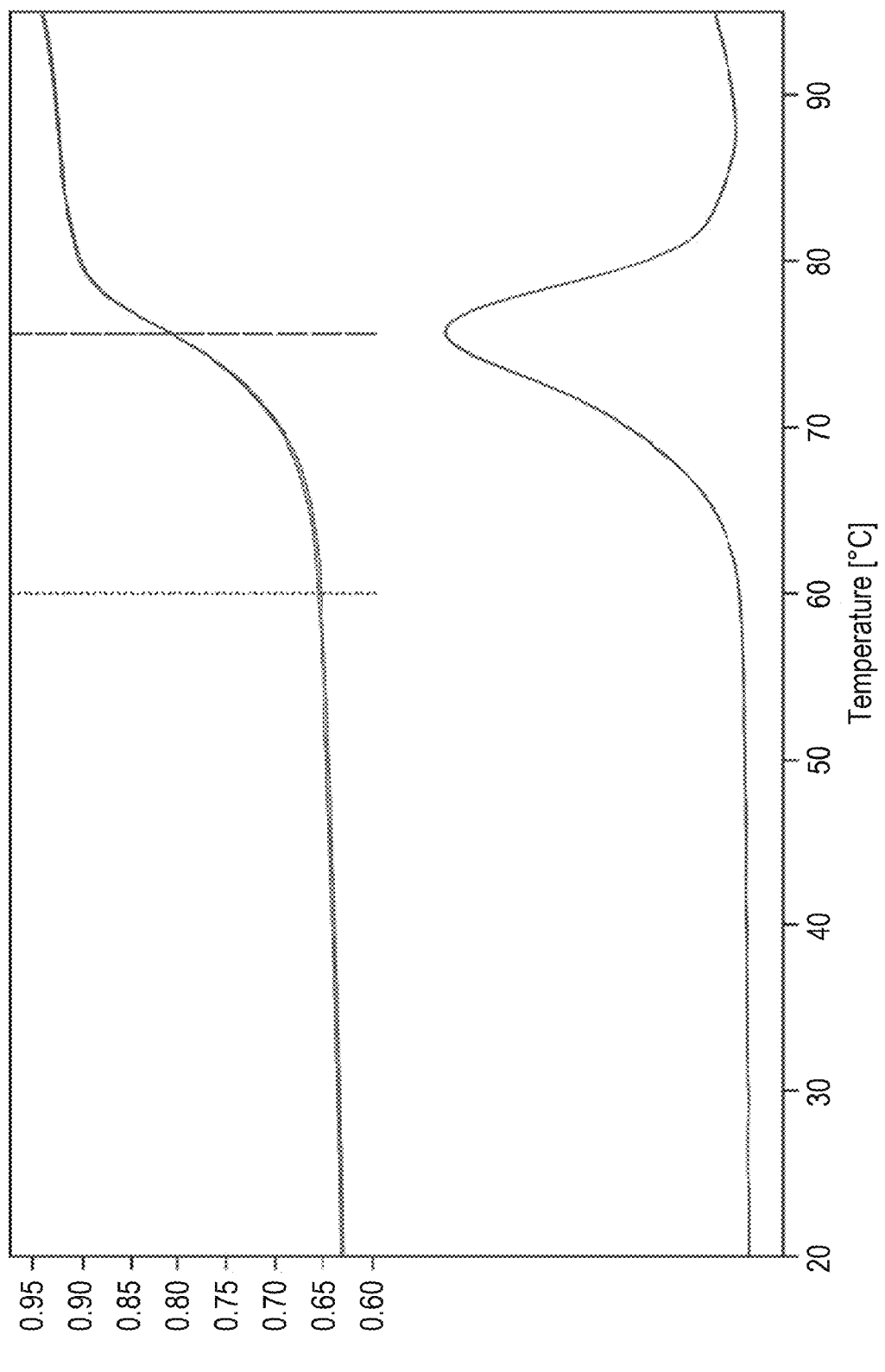
Figure 16G:
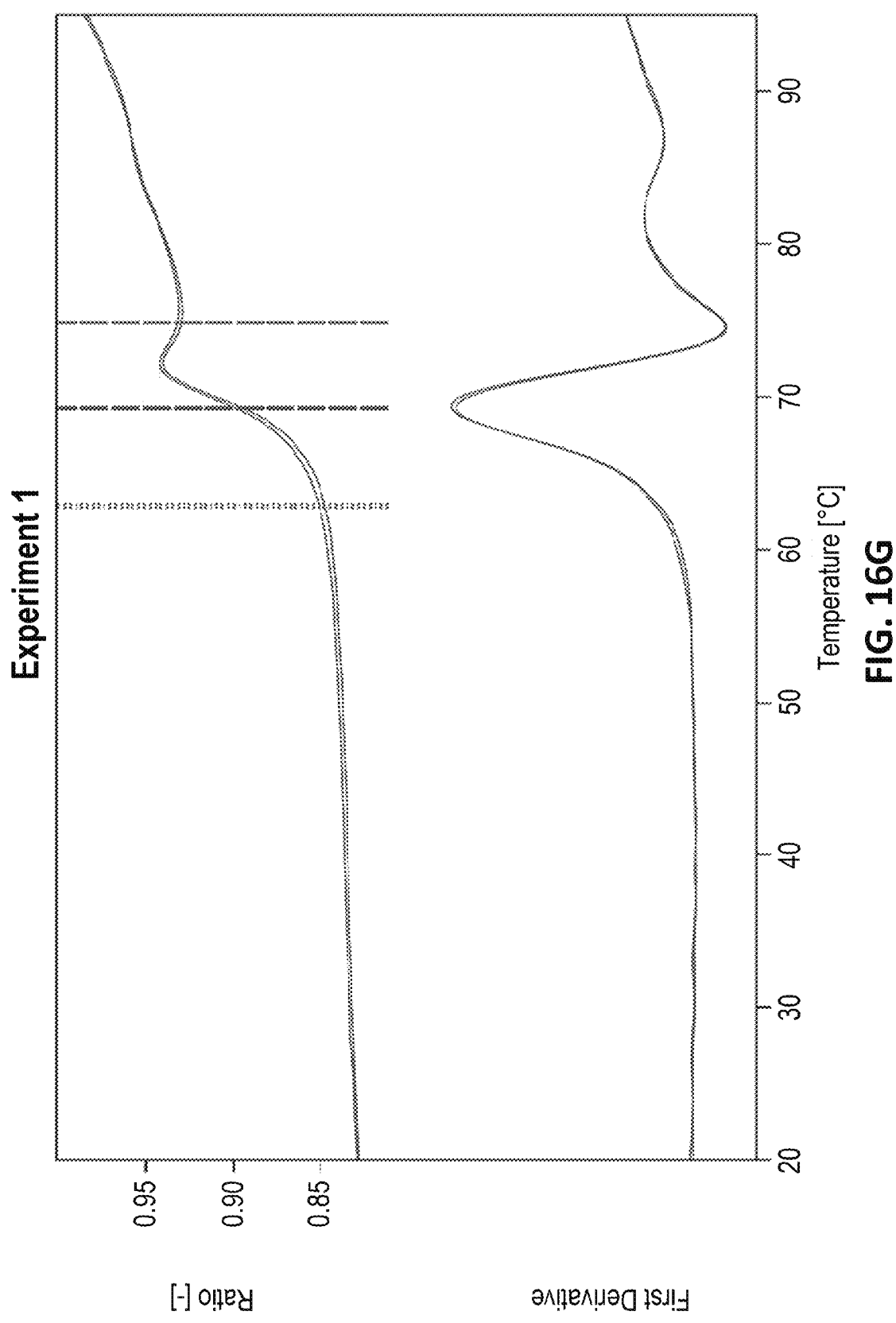

FIGS. 16A-16G. Differential Scanning Fluorimetry (DSF) analysis of the indicated IgGs' melting point. light green dashed line indicates Tonset, and bold green dashed lines indicate Tm1, and where applicable Tm2. Anti-IL-2 clones analyzed are BDG17.038 (FIG. 16A), BDG17.043 (FIG. 16B), BDG 17.053 (FIG. 16C), BDG 17.054 (FIG. 16D), BDG17.066 (FIG. 16E), BDG17.067 (FIG. 16F), and BDG17.069 (FIG. 16G).

Figure 17A:
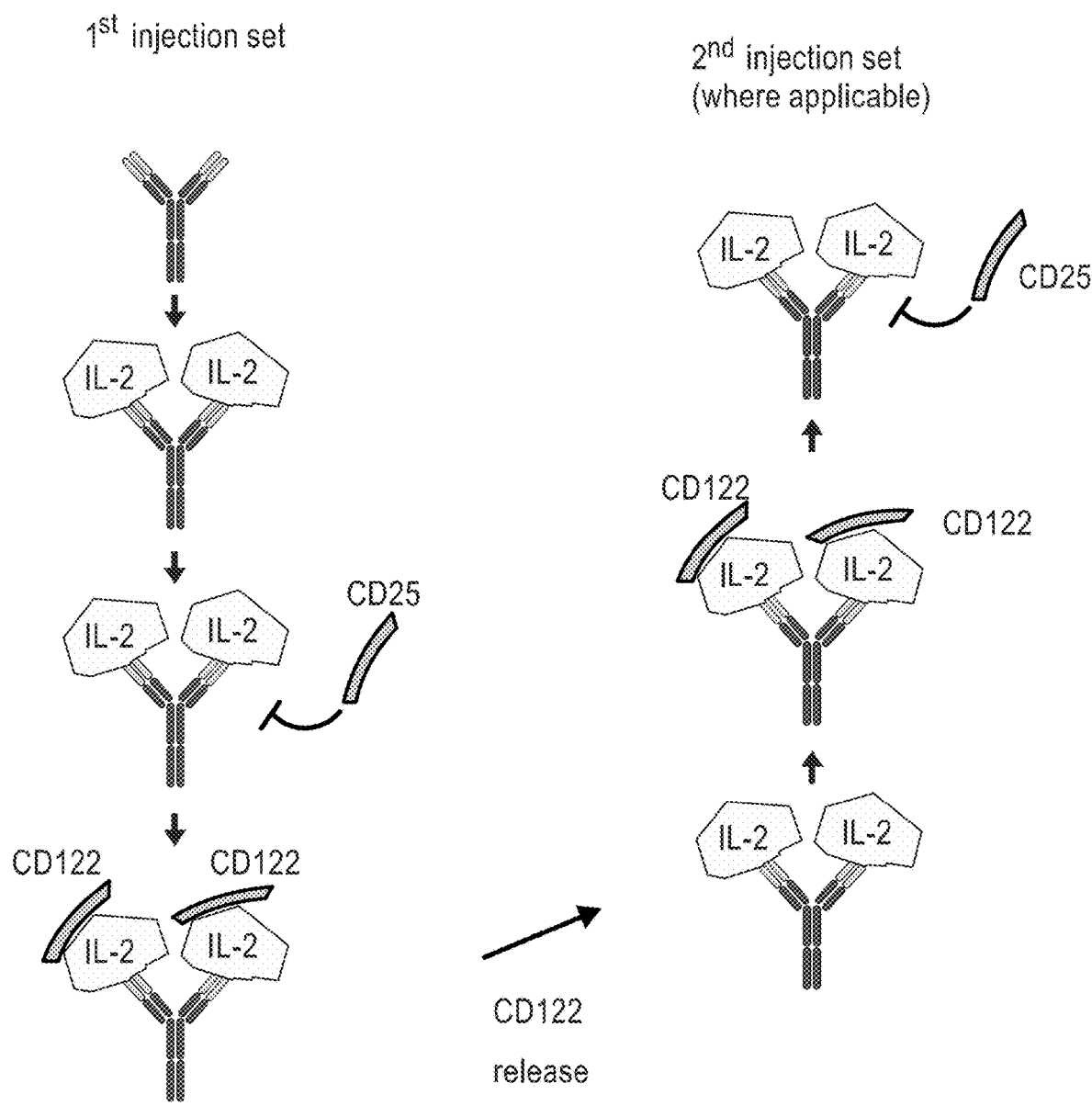
Figure 17B:
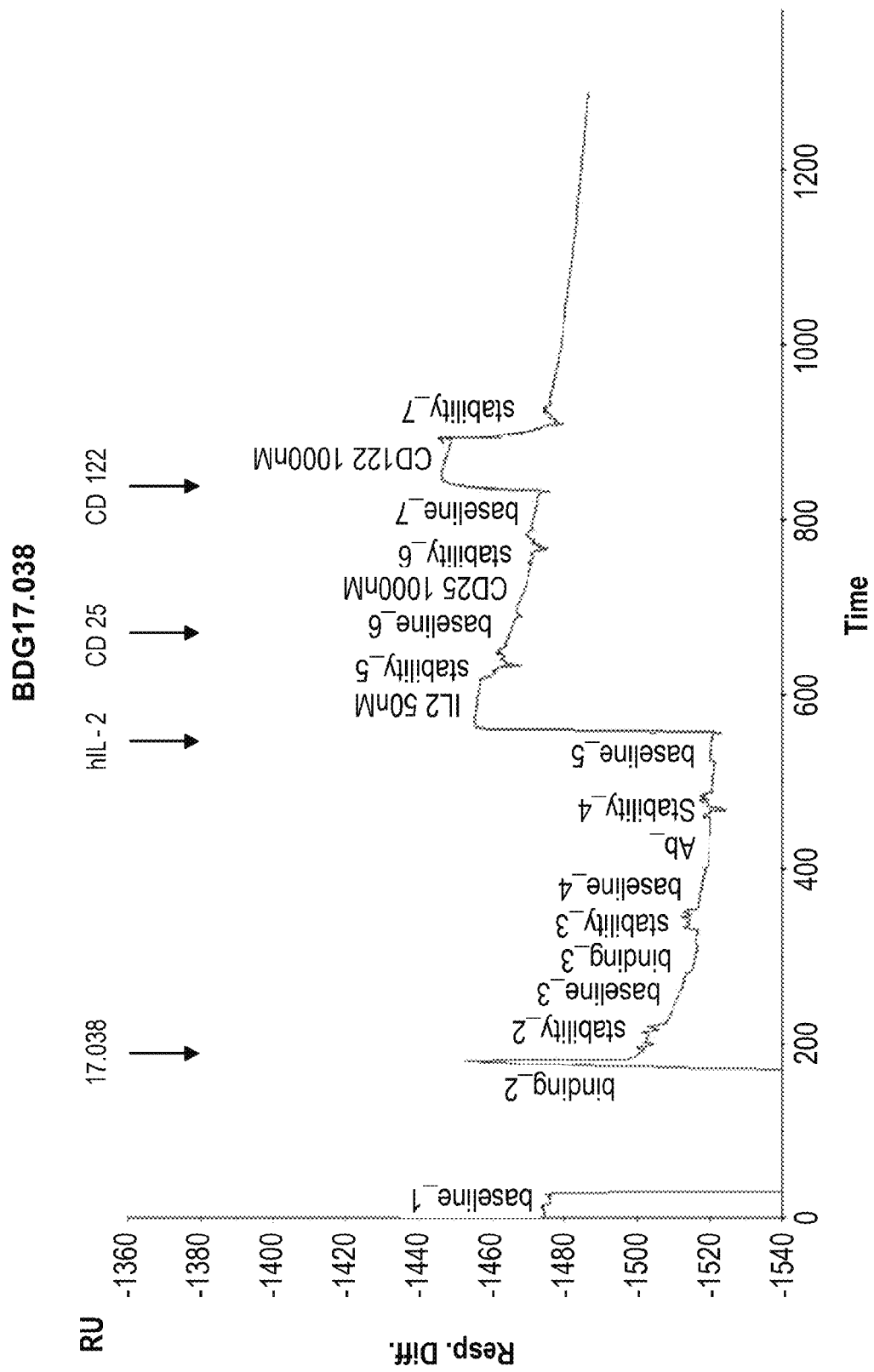
Figure 17C:
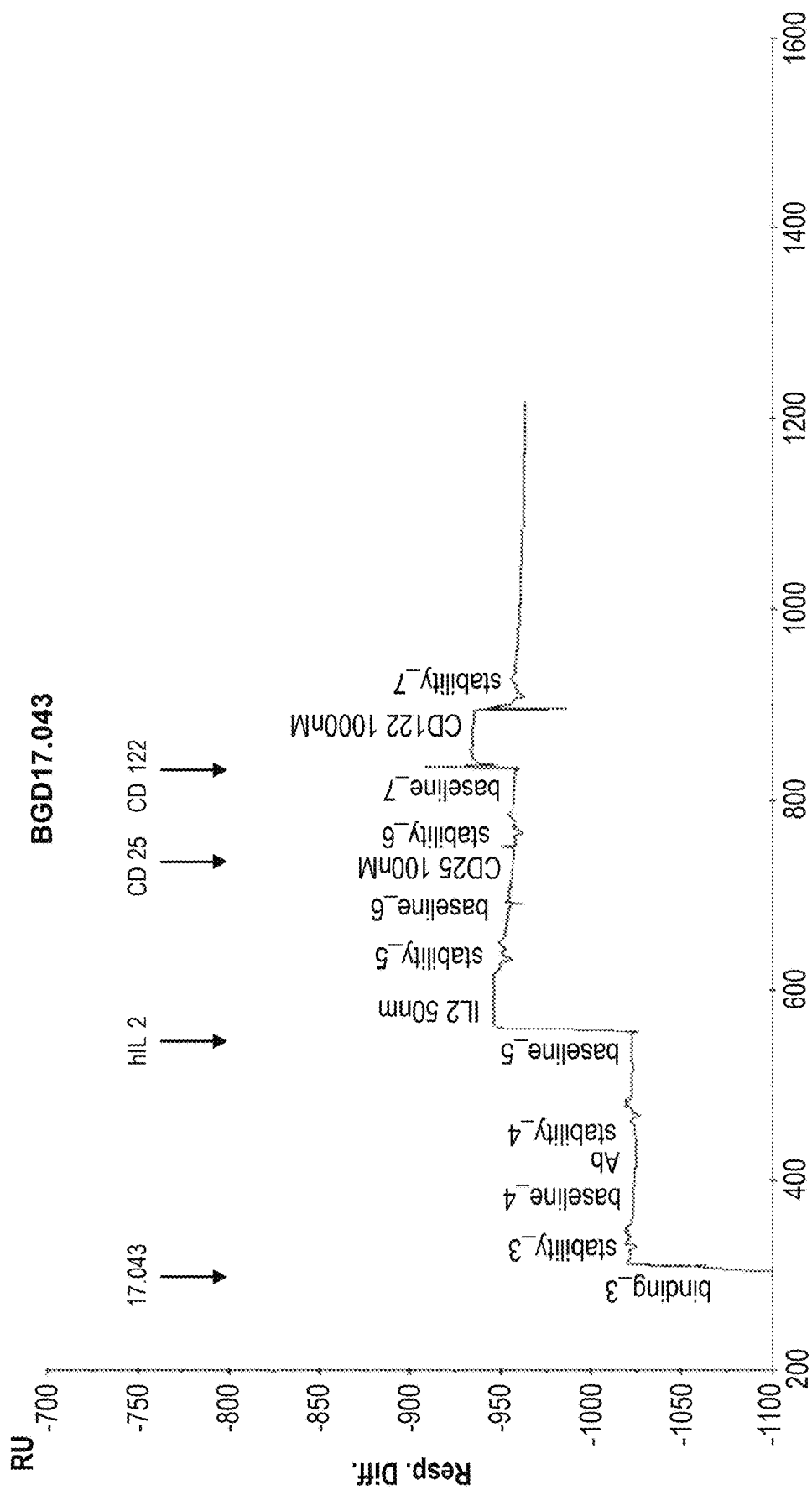
Figure 17D:
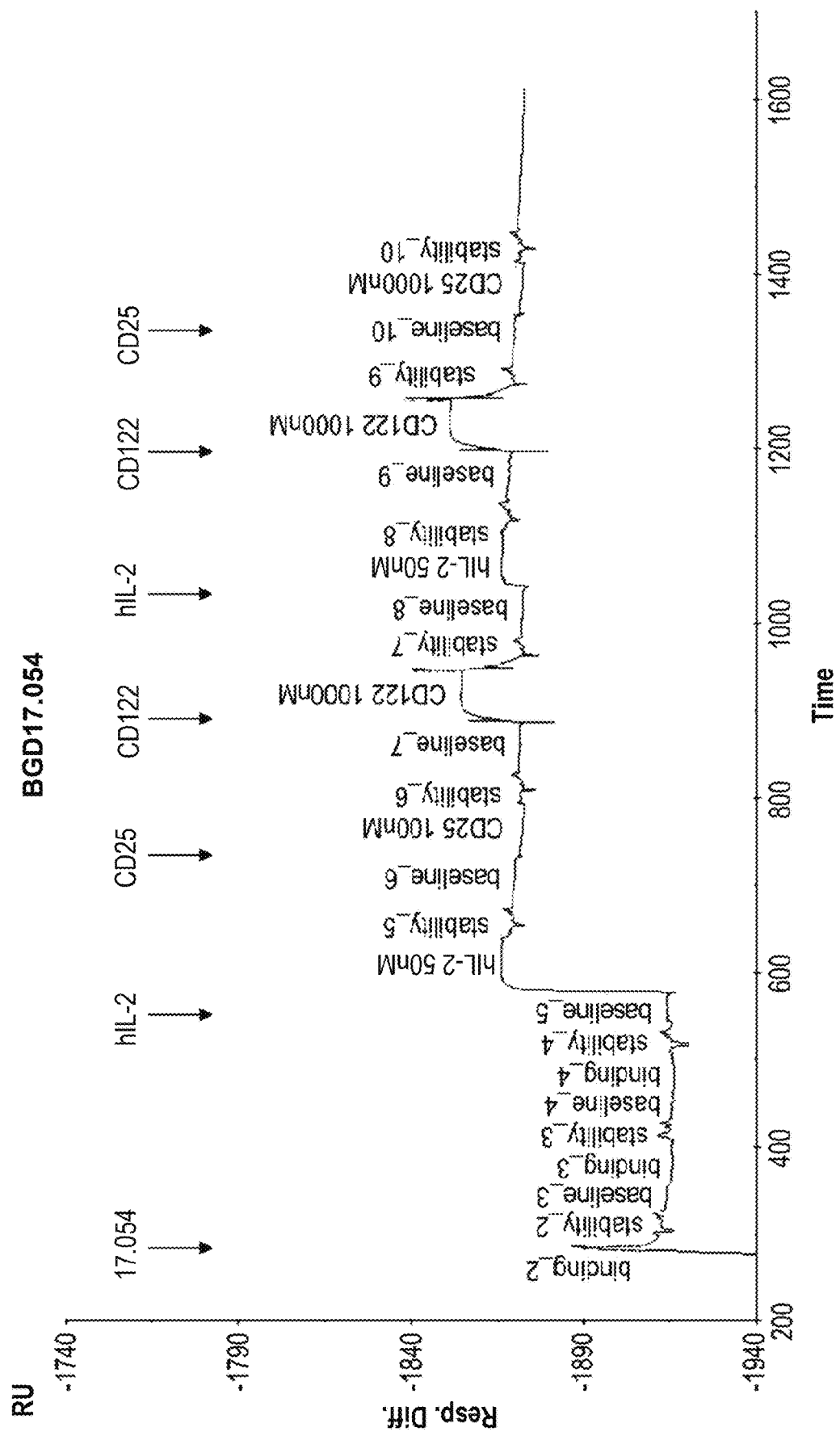
Figure 17E:
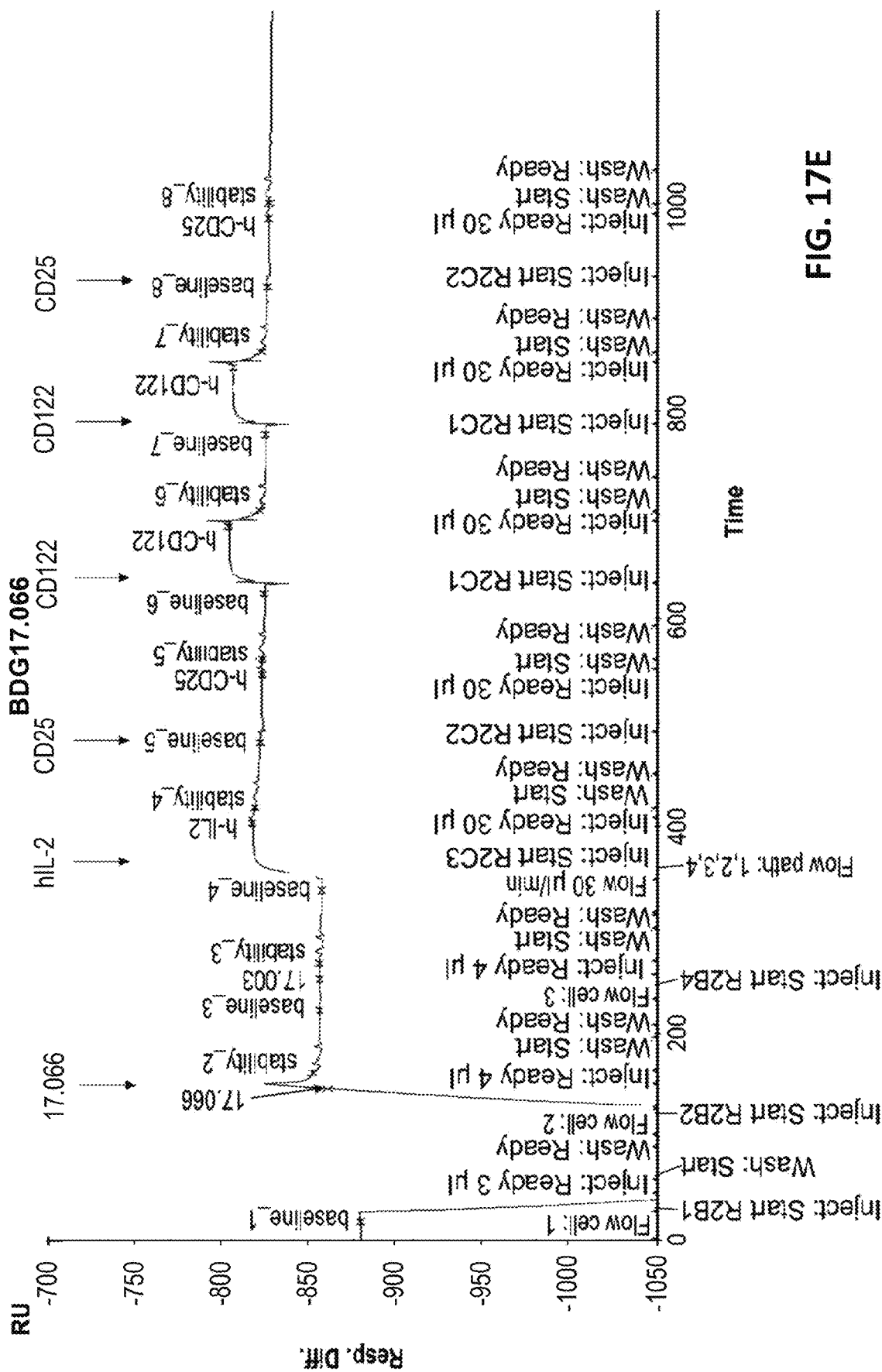
Figure 17F:
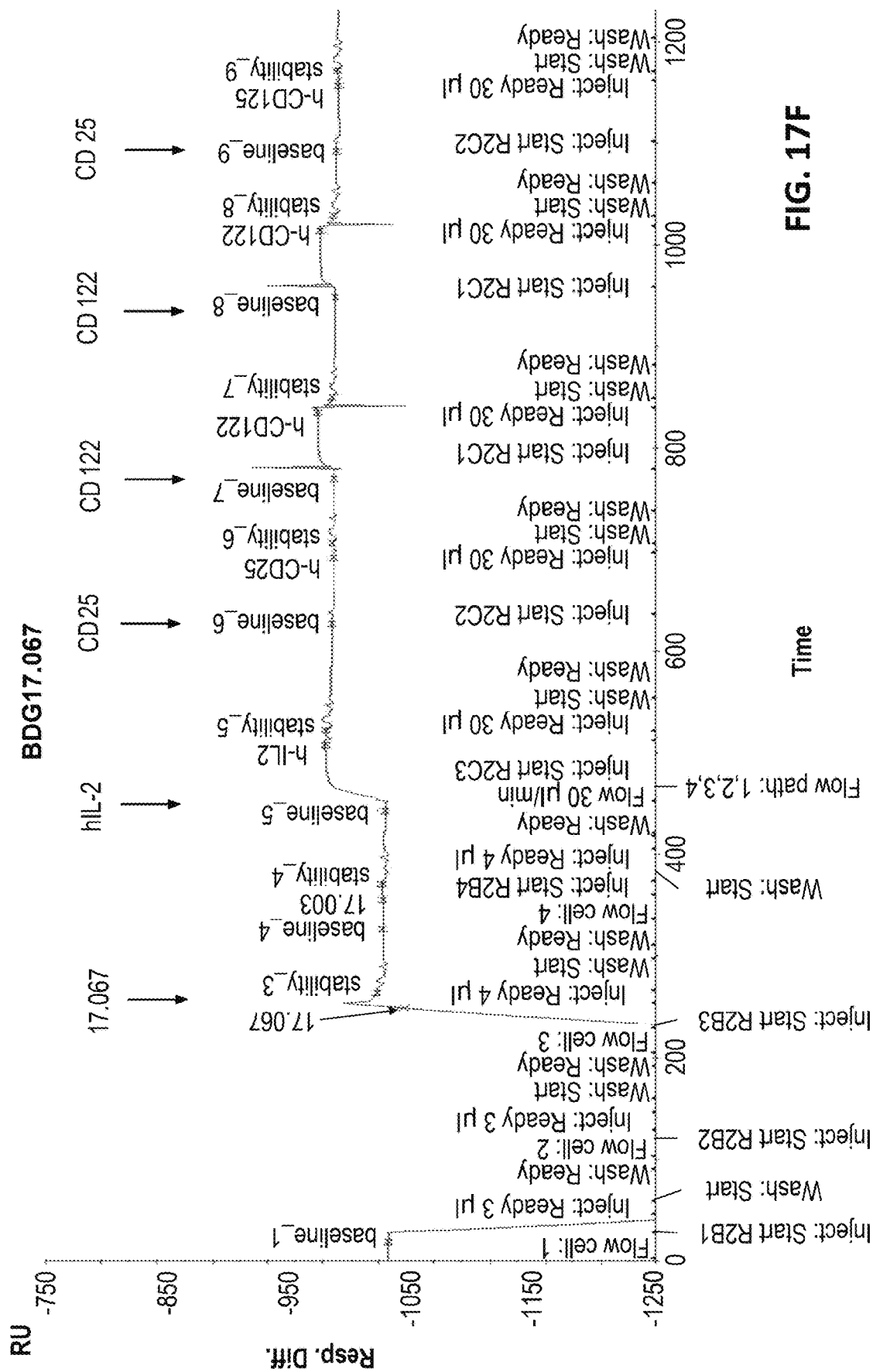
Figure 17G:
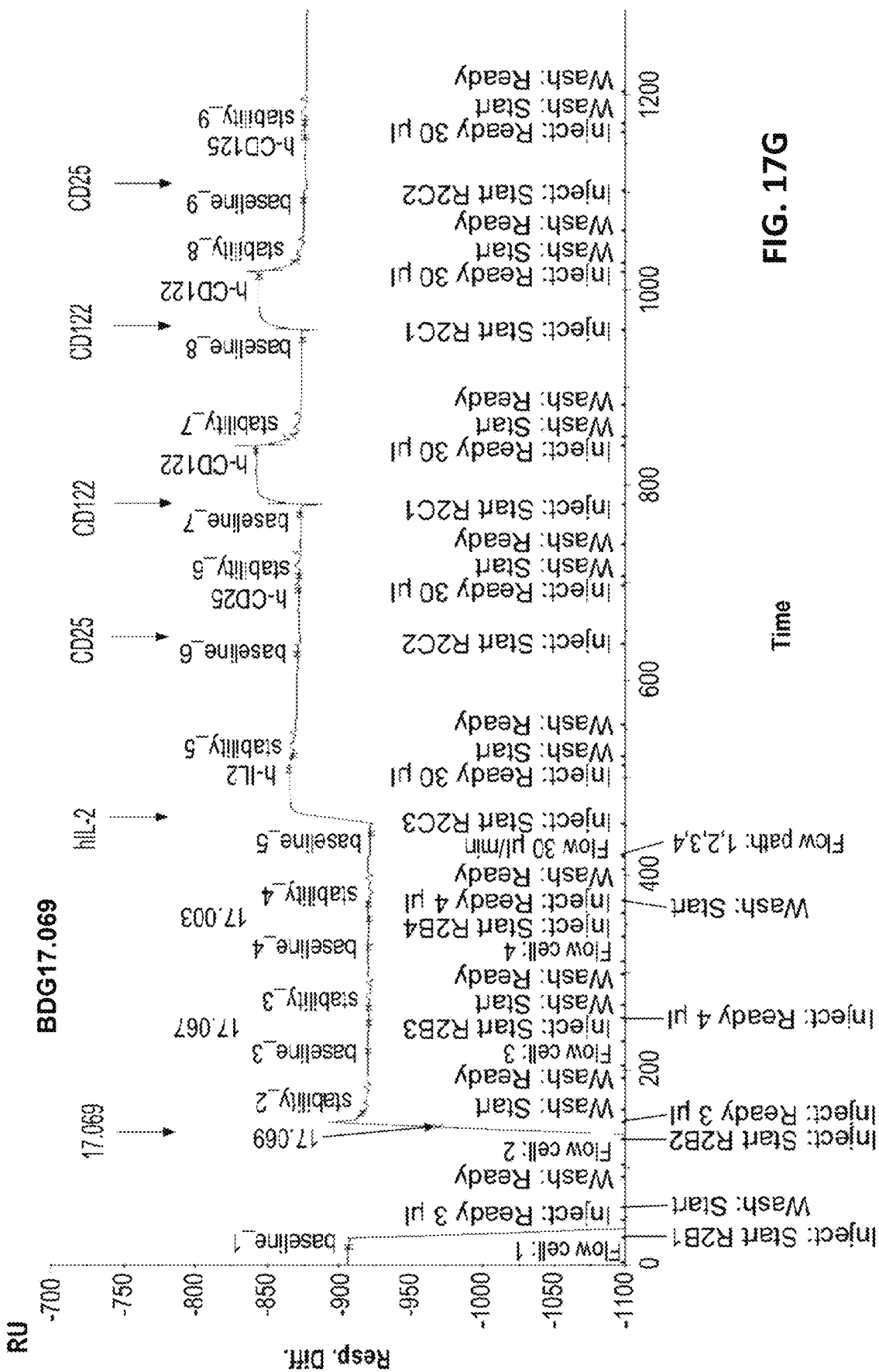

FIGS. 17A-17B. Present receptor discrimination of indicated antibody/IL-2 complex by tracing of SPR response. Antibody was immobilized to the CM5 chip, and hIL-2, CD122, and CD25 were streamed as indicated with an arrow. FIG. 17A presents a schematic order of injection of compounds to SPR chip, that represents sequential anti-IL-2 antibodies complexed with human IL-2 (hIL2), binding to CD122 but not to CD25. FIGS. 17B-17G present the SPR response: BDG17.038 (FIG. 17B), BDG017.043 (FIG. 17C), 17.054 (FIG. 17D), BDG17.066 (FIG. 17E), BDG17.067 (FIG. 17F), and BDG17.069 (FIG. 17G).

Figure 18A:
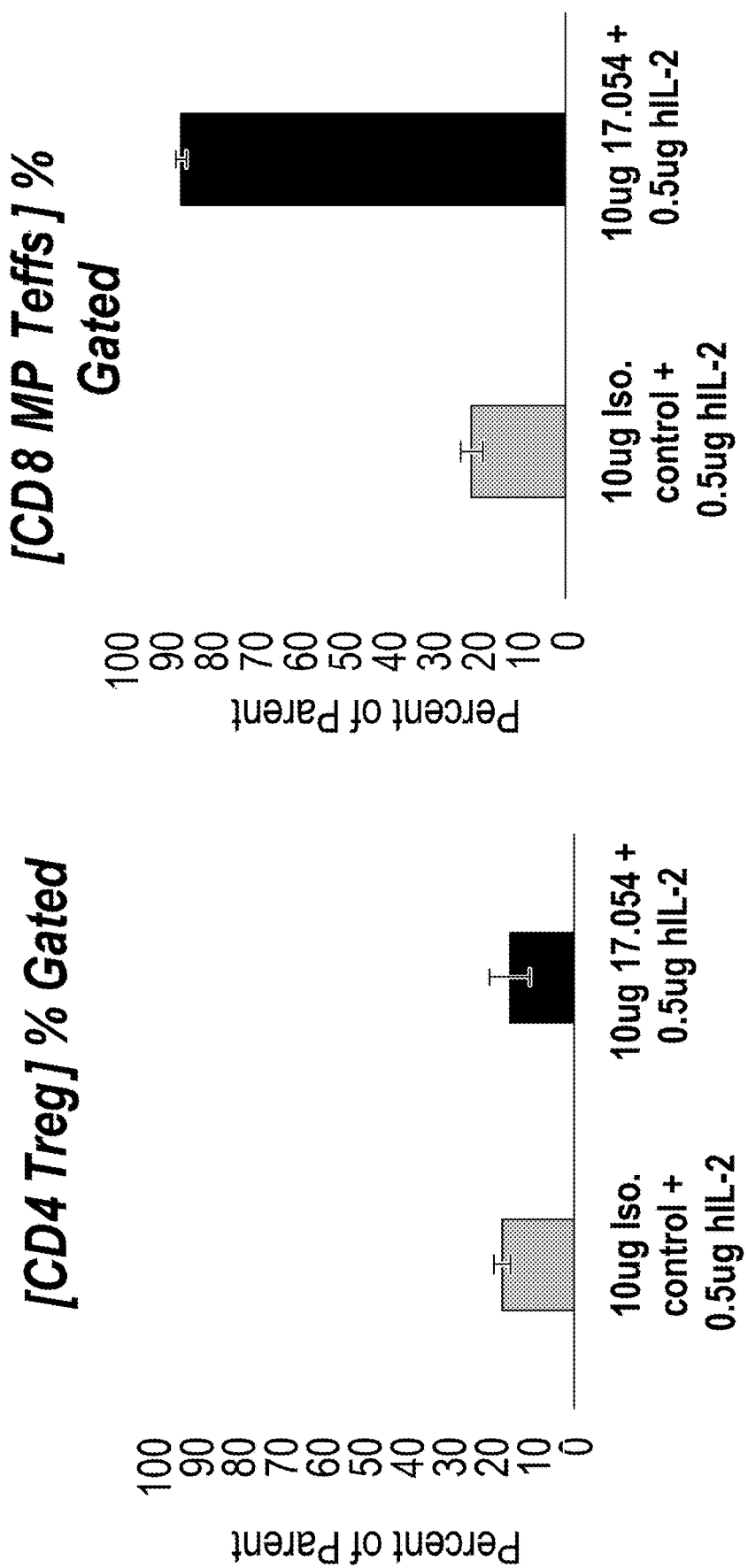
Figure 18A:
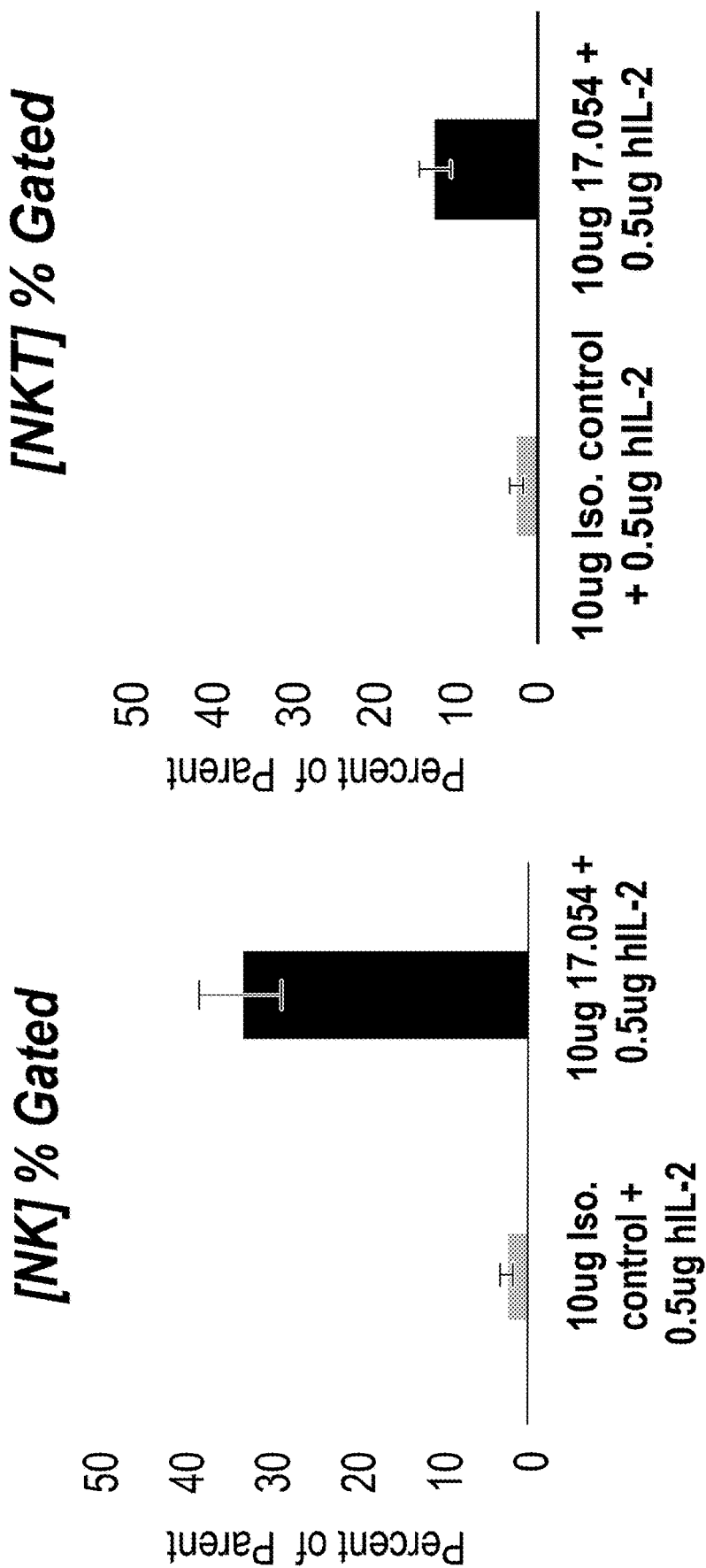
Figure 18B:
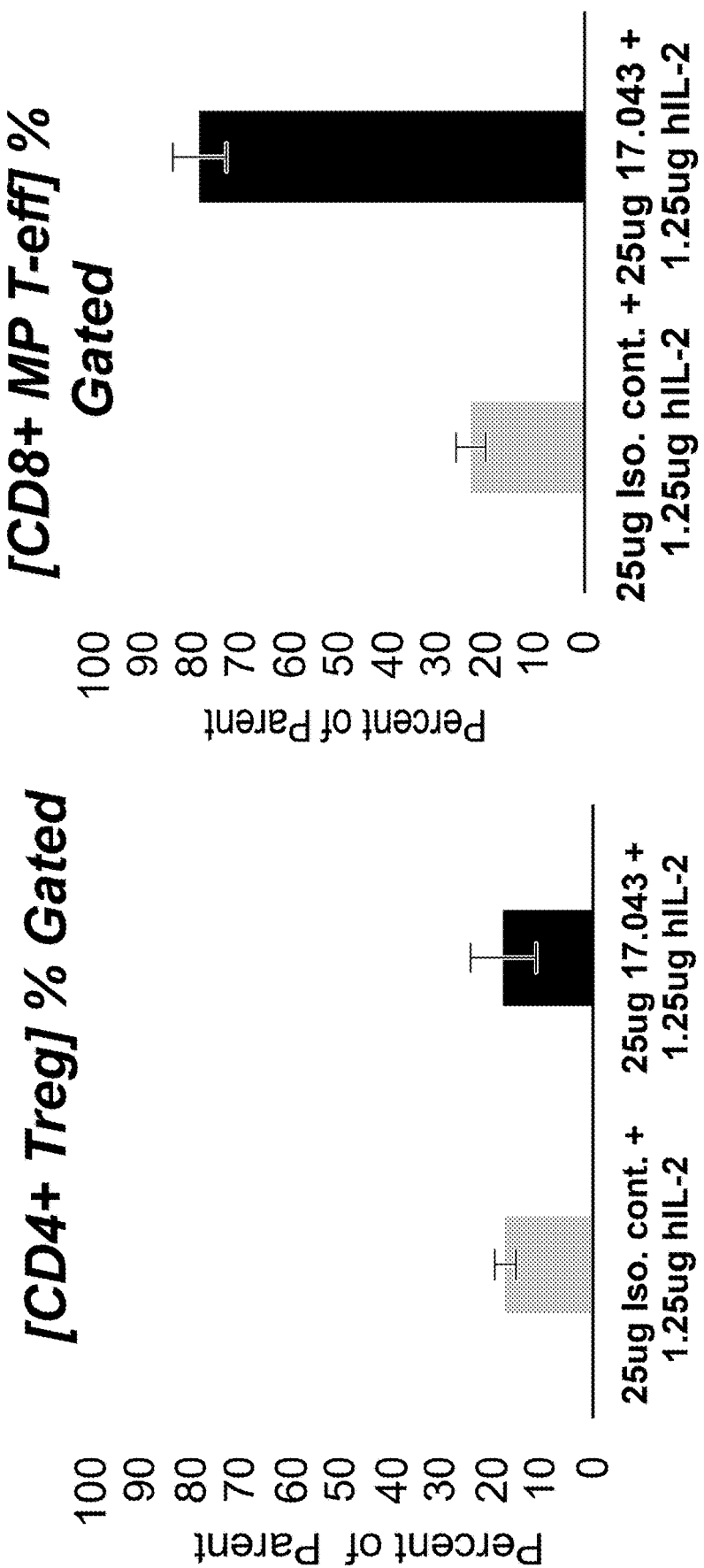
Figure 18B:
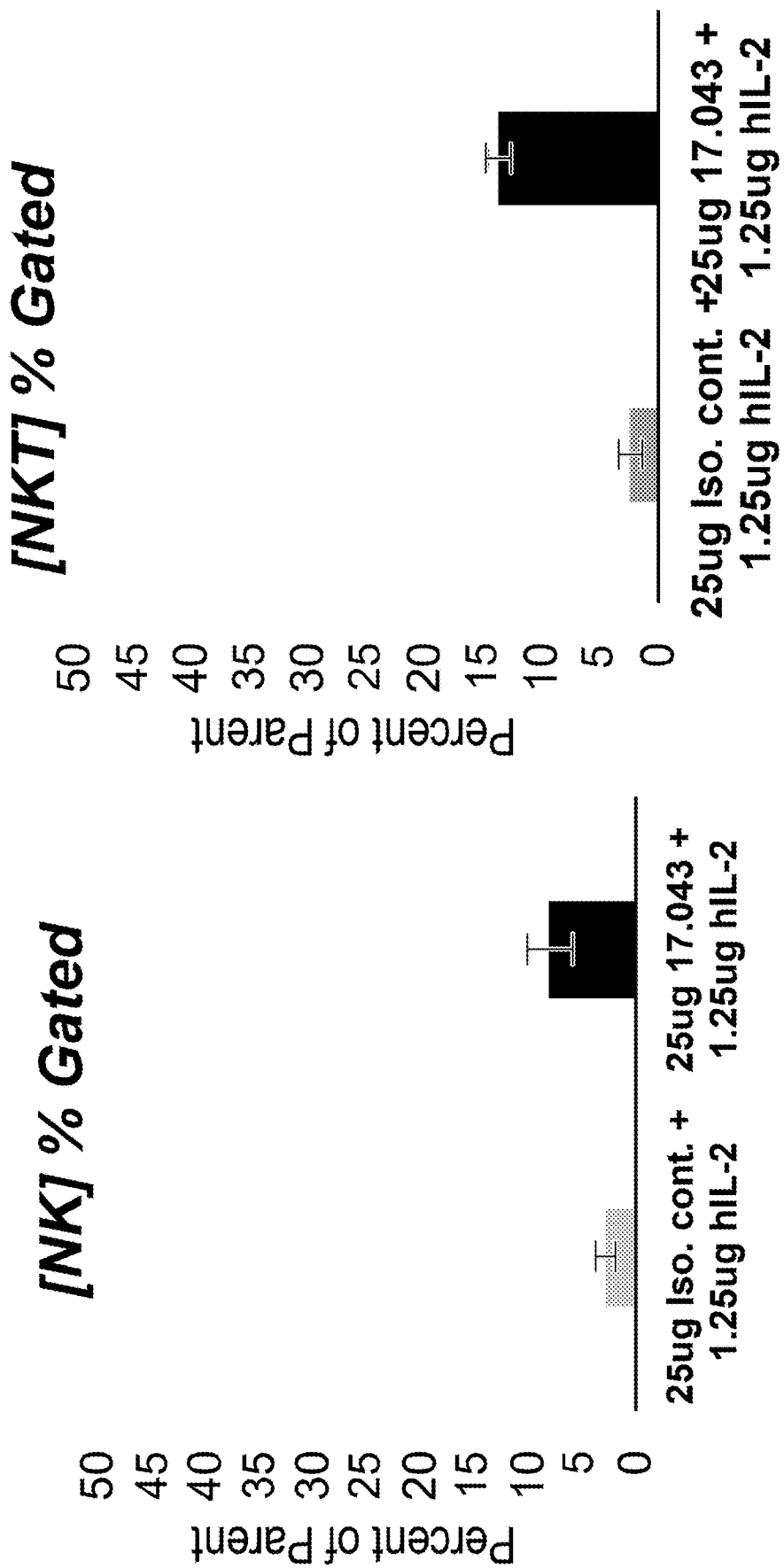

FIGS. 18A and 18B show anti-human IL-2 antibodies (clones 17.043 and 17.054) demonstrate potent immune stimulating effect in vivo. The anti-IL-2 antibody/hIL-2 complexes increase effector cell populations with no observed effect on regulatory T cells. FIG. 18A shows C57BL/6 mice were administered daily with anti-IL-2 antibody (10 ug) pre-complexed with 0.5 ug of hIL-2 for four days. FIG. 18B shows C57BL/6 mice were administered daily with anti-IL-2 antibody (25 ug) pre-complexed with 1.25 ug of hIL-2 for four days. On day 5, splenocytes were isolated and immune cell populations were analyzed by flow cytometry. Presented are mean values for each experimental group (n=6 per group). Lymphocytes were gated according to side-scatter and forward-scatter parameters and subsequent immune cells subpopulations were gated as follows: Tregs (CD45+, CD3+, CD4+, CD25+, FoxP3+), CD8 T cells (CD45+, CD3+, CD8+, CD122+, CD25−), NKT-cells (CD45+, CD3+, CD49b+, NK1.1+), NK cells (CD45+, CD3−, CD49b+, NK1.1+).

Figure 19A:
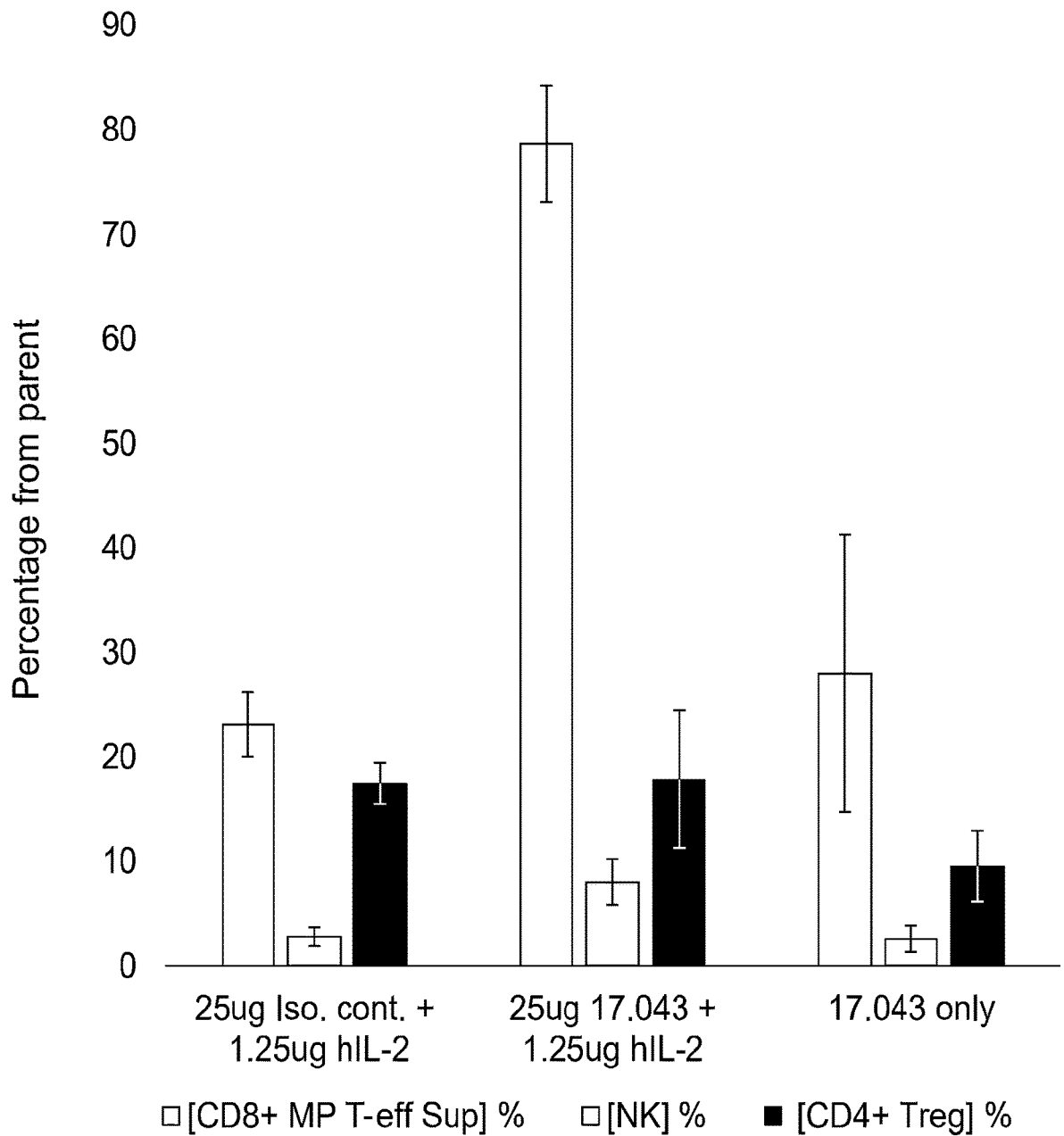

FIGS. 19A and 19B show anti-human IL-2 antibodies (clones 17.043 and 17.054) demonstrate potent dose dependent immune stimulating effect in vivo. FIG. 19A shows C57BL/6 healthy mice were administered daily with anti-IL-2 antibody/hIL-2 complex (25 ug/1.25 ug respectively) for four days. On day 5, splenocytes were isolated and immune cells populations were analyzed by flow cytometry. FIG. 19B shows anti-human IL-2 antibodies demonstrate potent in vivo immune stimulating effect in a dose dependent manner. C57BL/6 healthy mice were administered daily with increasing doses of anti-IL-2 antibody/hIL-2 complex as indicated. On day 5, splenocytes were isolated and immune cells populations were analyzed using flow cytometry. Lymphocytes were gated according to side-scatter and forward-scatter parameters and subsequent immune cells subpopulations were gated as follows. Tregs (CD45+, CD3+, CD4+, CD25+, FoxP3+), CD8 T cells (CD45+, CD3+, CD8+, CD122+, CD25−), NKT-cells (CD45+, CD3+, CD49b+, NK1.1+), NK cells (CD45+, CD3−, CD49b+, NK1.1+).

Figure 20A:
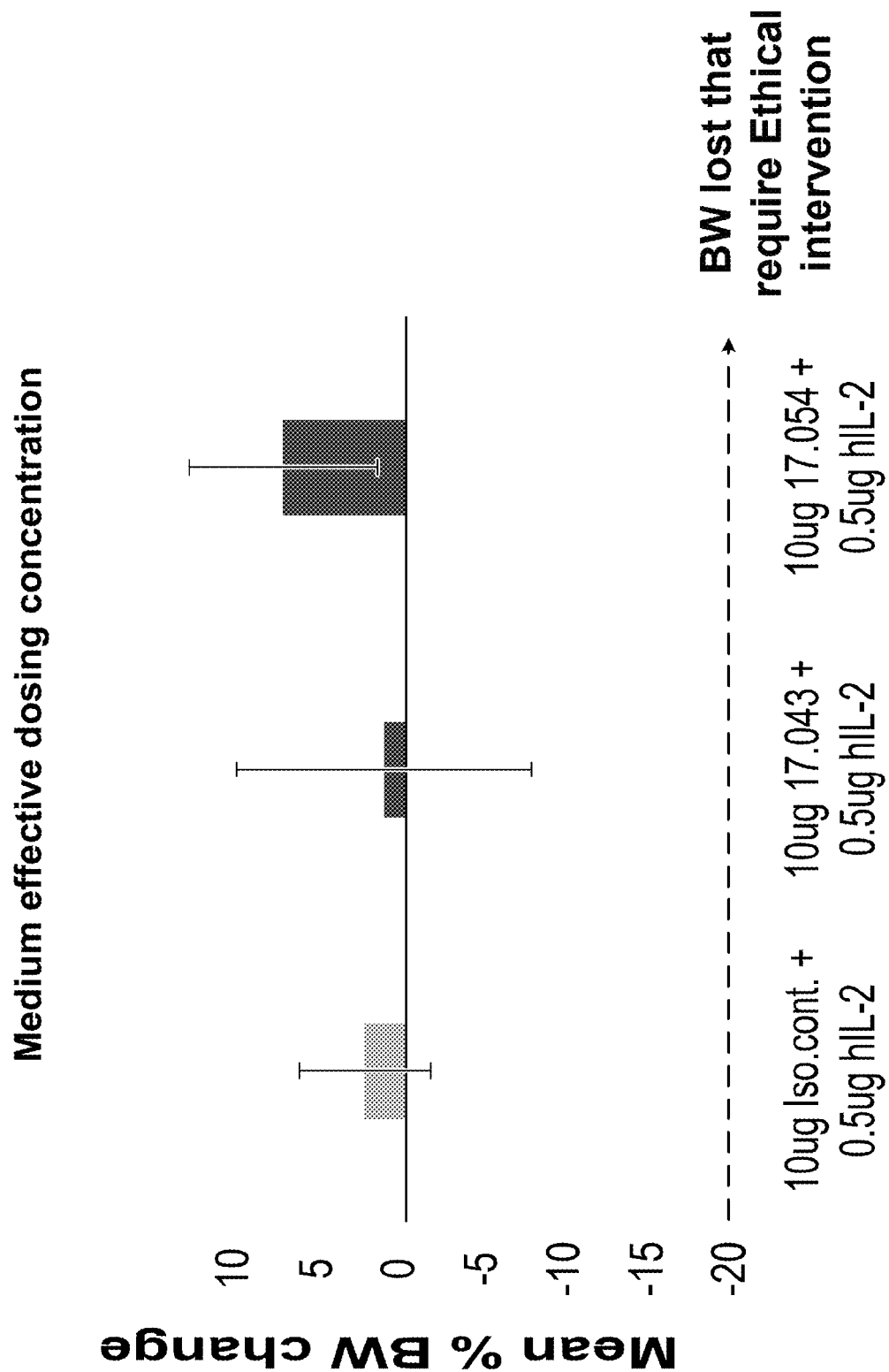
Figure 20B:
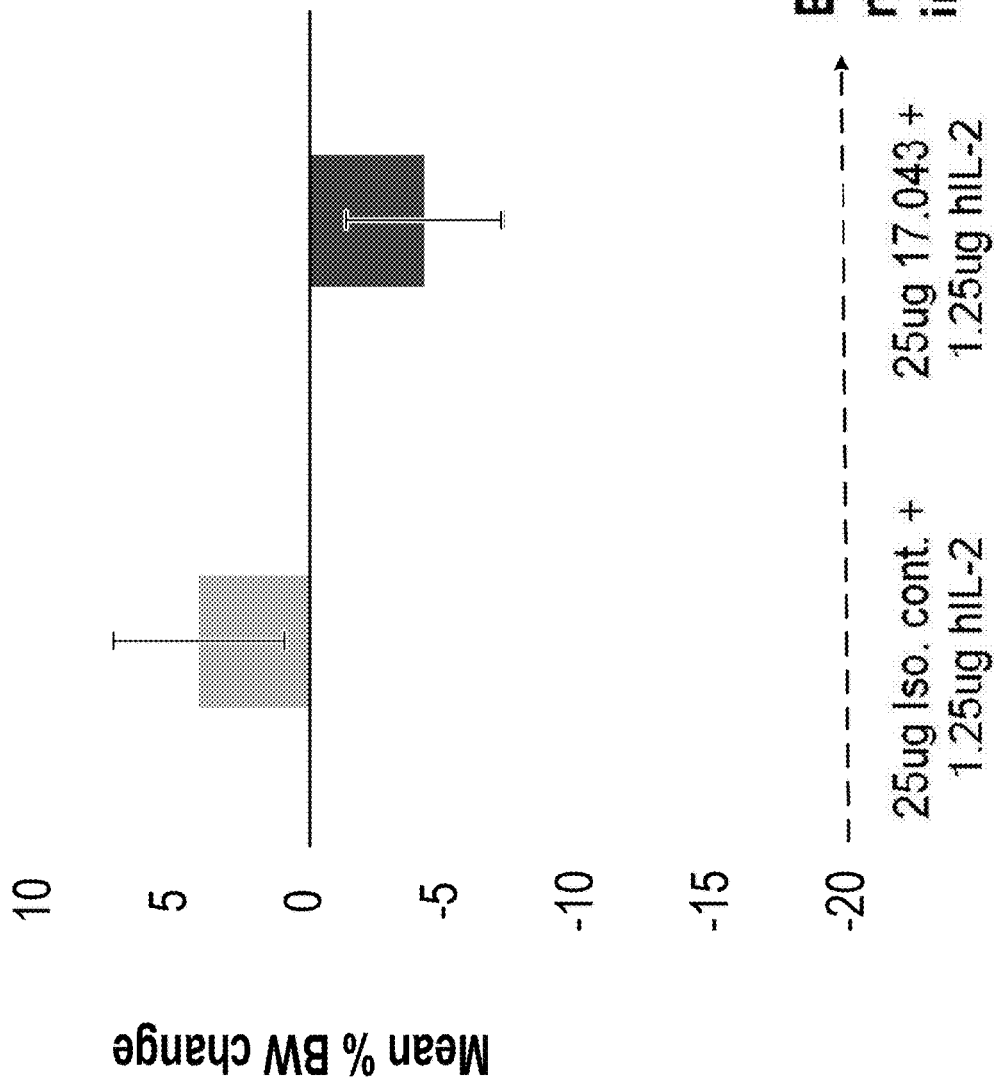

FIGS. 20A and 20B show anti-human IL-2 antibodies (clones 17.043 and 17.054) demonstrate safe dose regimen in vivo. FIG. 20A shows C57BL/6 healthy mice were administered daily with anti-IL-2 antibody/hIL-2 complex (10 ug/0.5 ug respectively) for four days. FIG. 20B shows C57BL/6 healthy mice were administered daily with anti-IL-2 antibody/hIL-2 complex (25 ug/1.25 ug respectively) for four days. At the end of the experiments, mice were weighed, and percent of body weight changes were calculated in respective to the weight of each mouse at the beginning of the study. Presented are mean percent of body weight (BW) change for each experimental group (n=6 per group).

Figure 21A:
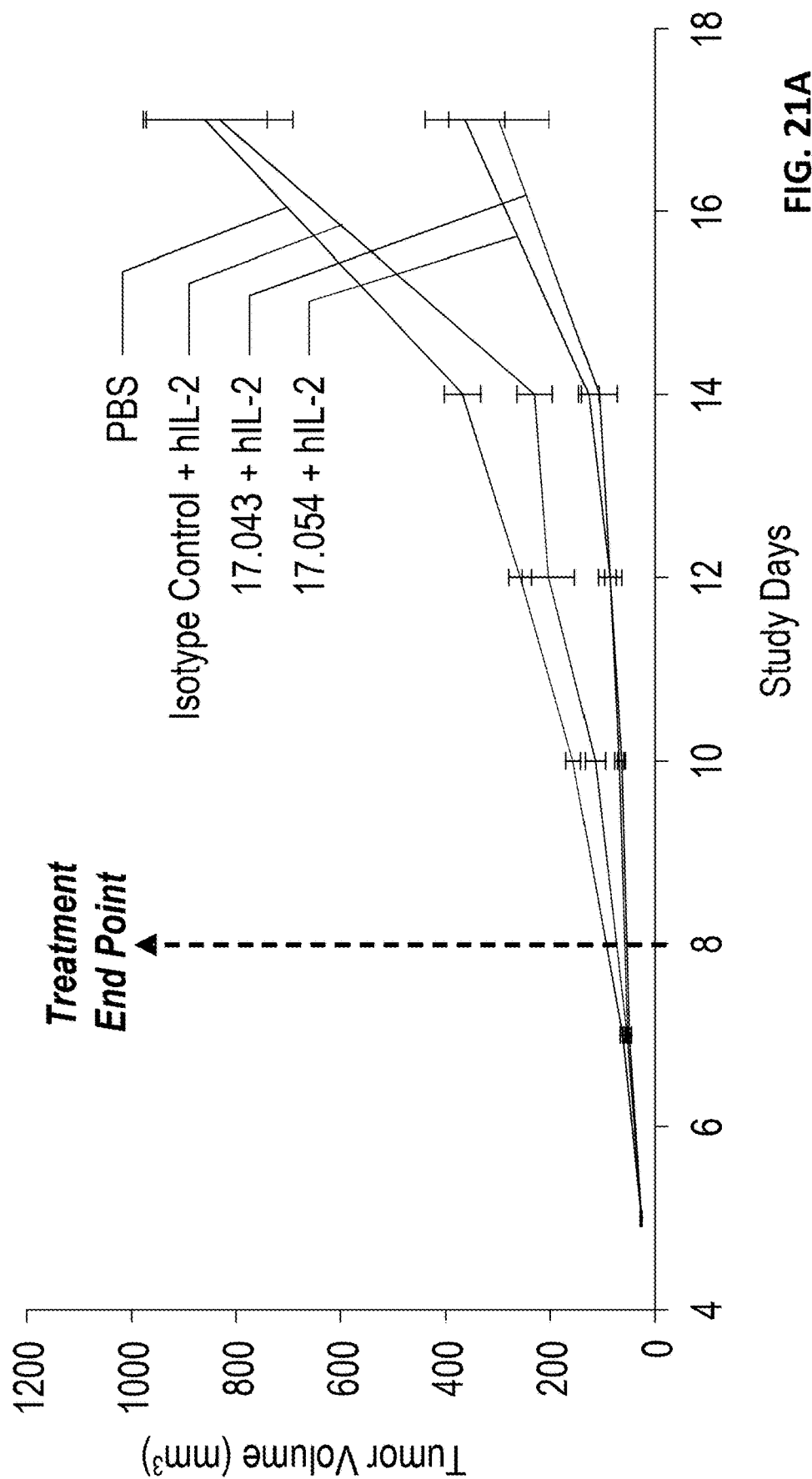
Figure 21B:
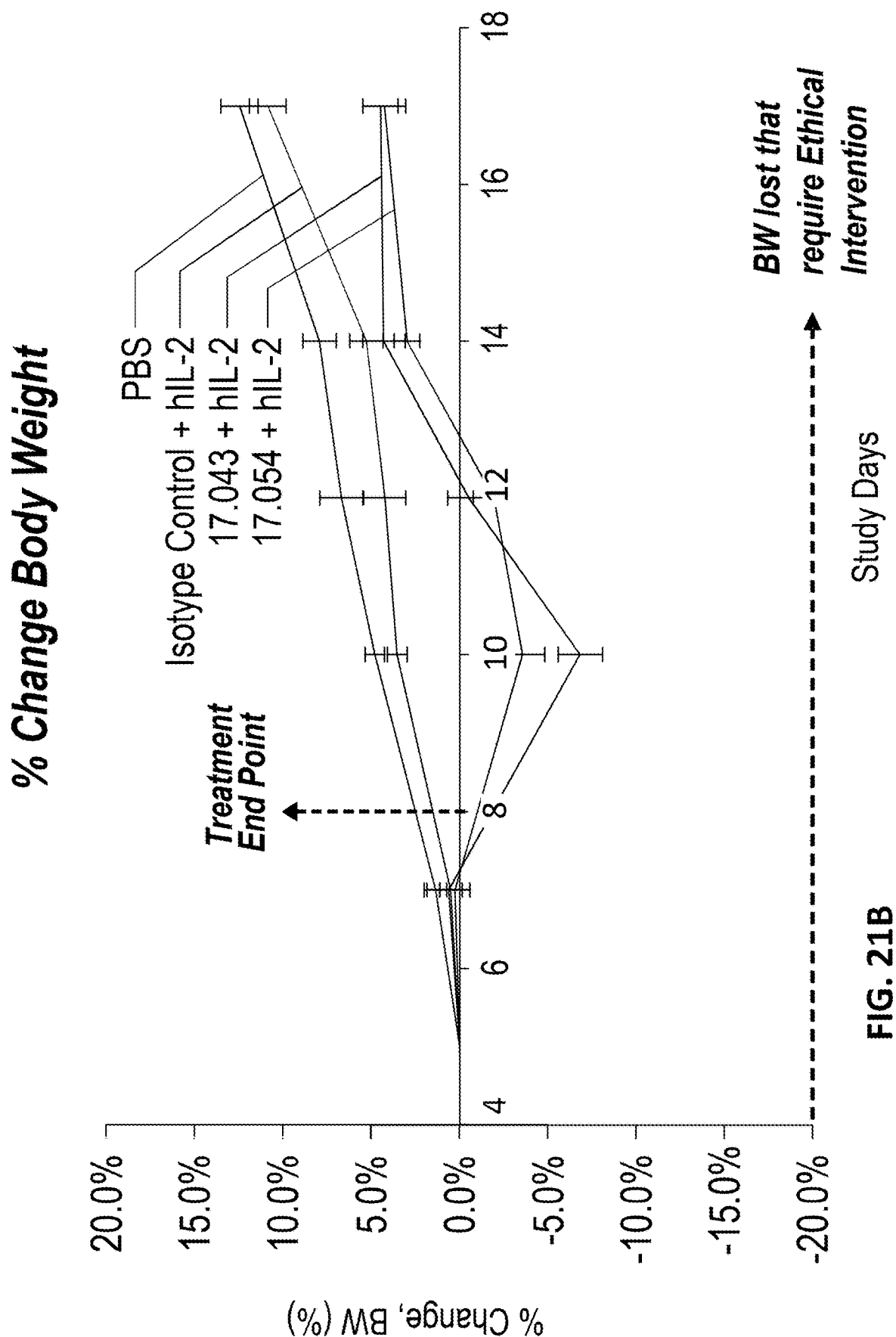

FIGS. 21A and 21B show anti IL-2 antibodies (clones 17.043 and 17.054) inhibit tumor growth in an I/O resistant tumor model with a tolerable safety profile. C57BL/6 healthy mice were inoculated with B16F10 melanoma tumor cells on day 0. On day 5, the mice were randomized to experimental groups (n=10 per group) and administered daily with anti-IL-2 antibody/hIL-2 complex (20 ug/1 ug respectively) or with PBS for four days. FIG. 21A shows changes in tumor volume for each experimental group. FIG. 21B shows changes in body weight for each experimental group. Percent body weight changes were calculated in respective to the weight of each mouse at the beginning of the study.

FIGS. 22A-22G show the results of analyzing the different formulations of anti-IL-2 antibody clone BDG 17.069. FIG. 22A presents the BDG 17.069 parameters at T=0. FIG. 22B presents BDG 17.069 appearance, pH, protein concentration, and sub-visual particle formation at T=0 and after incubation at 40° C. for 1 and 2 weeks. FIG. 22C presents BDG 17.069 SEC, caliper-SDS and capillary isoelectric focusing analysis at T=0 and after incubation at 40° C. for 1- and 2-weeks. FIG. 22D presents BDG 17.069 appearance, pH, protein concentration, and sub-visual particle formation at T=0 and post agitation at 300 rpm for 3 days. FIG. 22E presents BDG 17.069 SEC, caliper-SDS, and capillary isoelectric focusing analysis at T=0 and post agitation at 300 rpm for 3 days. FIG. 22F presents BDG 17.069 appearance, pH, protein concentration, and sub particle formation at T=0 and after five cycles of Freeze/Thaw. FIG. 22G presents BDG 17.069 SEC, caliper-SDS, and capillary isoelectric focusing analysis at T=0 and after five cycles of Freeze/Thaw.

DETAILED DESCRIPTION

The present disclosure provides engineered anti-human IL-2 antibodies that bind human IL-2 with high affinity (e.g., 12.7 pM to 48 pM) to a pre-defined binding epitope. The antibodies bind to IL-2 in a manner that completely prevents CD25 binding yet spares the binding of IL-2 to CD122, thereby modulating immune responses towards immune stimulation by directly activating and expanding effector cells without interacting with CD25-expressing cells (e.g., regulatory T-cells, short lived cytotoxic T-cells, pulmonary endothelial cells and vascular endothelial cells). Thus, the antibody/IL-2 complex would drive a robust immune response to clear viral load or tumor by expanding and activating effector cells such as NK cells, central memory T cells and virus or tumor-specific T-cells while inhibiting IL-2 activation induced cell death of the short lived CD25+ cytotoxic T-cells that are important for viral/tumor clearance. The antibody/IL-2 complex would also decrease immunosuppression caused by the regulatory arm of the immune system. Moreover, the antibody/IL-2 complex would prevent undesired interactions of IL-2 with vascular and pulmonary CD25-expressing cells, thereby preventing severe syndromes of IL-2 induced vascular leakage and IL-2 induced pulmonary edema frequently seen in models of viral lung infections. In some embodiments, the activity of the engineered anti-IL-2 antibodies described herein is dependent on the pre-defined epitope to which they are designed to bind.

A skilled artisan would appreciate that in certain embodiments, the term "anti-IL-2 antibody" as used herein is interchangeable with the term "anti-human-IL-2 antibody", having all the same qualities and meanings. Similarly, as used throughout, in certain embodiments, the term "IL-2" is interchangeable with the term "human IL-2", having all the same qualities and meanings.

In some embodiments, an anti-human IL-2 antibody described herein inhibits binding of IL-2 with an IL-2 receptor alpha (IL-2 Rα, i.e., CD25) subunit and therefore inhibits binding to the trimer IL-2 Rαβγ receptor. In certain embodiments, anti-IL-2 antibodies that inhibit binding of IL-2 with a trimer IL-2 receptor (IL-2 Rαβγ) do not inhibit binding of IL-2 with the dimer IL-2 receptor (IL-2 Rβγ).

FIG. 2 presents a schematic of anti-IL-2 antibodies directed immunotherapy. Targeting IL-2 to different cell populations can be used to either modulate the immune response toward immunosuppression or towards immune activation. The anti-human IL-2 antibodies disclosed herein are designed to bind with high affinity to an IL-2 epitope that blocks IL-2 binding to CD25. As a result, IL-2 is prevented from binding to short-lived CD8+ cytotoxic T cells or regulatory T cells that express high level of CD25 but is redirected to preferentially bind to effector T cells to stimulate enhanced immune response to improve viral or bacterial clearance. Moreover, since IL-2 binding to CD25-expressing endothelial cells is also blocked, IL-2 induced pulmonary edema and vascular leaking would also be prevented.

In one embodiment, the present disclosure provides a method of treating a disease (e.g., viral infection, bacterial infection, or cancer), or a condition (e.g., an undesirable condition caused by IL-2, for example but not limited to lung edema) with an anti-IL-2 antibody designed to enhance T cell immune response and to prevent severe edema symptoms of acute pneumonia induced by IL-2. The anti-IL-2 antibody would bind specifically to human IL-2 with high affinity at a pre-defined epitope that blocks IL-2 binding to the alpha chain of the IL-2 receptors (CD25) while sparing binding to the main signaling beta chain and gamma chain complex of the receptor (CD122/CD132). Consequently, in the presence of such antibody, IL-2 would be directed to immune cells responsible for viral/tumor clearance and away from cells that slow the immune response or cause the edema. The formation of this IL-2/antibody immunocomplex will direct IL-2 to bind and activate exclusively naive and memory T lymphocytes, NK cells, and Natural Killer T lymphocytes while preventing activation of regulatory T cells and apoptosis of short-lived CD25+ cytotoxic T effector cells. Altogether, the end result is an effective immune response, for example, viral or tumor clearance. In addition, this treatment will prevent the toxicity caused by IL-2 binding to endothelial CD25 expressing cells. Thus, in one embodiment, targeting IL-2 with the anti-IL-2 antibodies disclosed herein would be an effective treatment for respiratory diseases caused by viral or bacterial infections. In another embodiment, treatment with the anti-IL-2 antibodies disclosed herein would be effective in preventing the toxicity caused by IL-2 binding to endothelial CD25 expressing cells, e.g., pulmonary edema, or IL-2-induced vascular leakage. More importantly, the enhancement of IL-2 immune stimulation towards general immune activation and expansion of immune effector cells independent of a specific pathogen (e.g., a viral antigen) would be an effective strategy against future viral or bacterial pandemics caused by an unknown pathogen (FIGS. 3A and 3B).

In one embodiment, the method disclosed herein would be useful against infection caused by SARS Co-V2. The SARS Co-V2 binds to angiotensin converting enzyme 2 of lung cells that allow for viral entry and replication. The immune response to viral infections of the lung consists of both the innate and acquired arms of the immune system. As in the cases with many respiratory viruses, clearance of SARS-CoV2 from the lung is expected to be dependent on T cell immune response. The cytokine IL-2 is critical for the expansion of T cells and plays an important role in immune responses to viruses. However, in addition to its pro-stimulatory role IL-2 also induces some adverse side effects like lung edema and vascular leak syndrome through its binding to endothelium expressing the CD25 receptor.

Figure 3A:
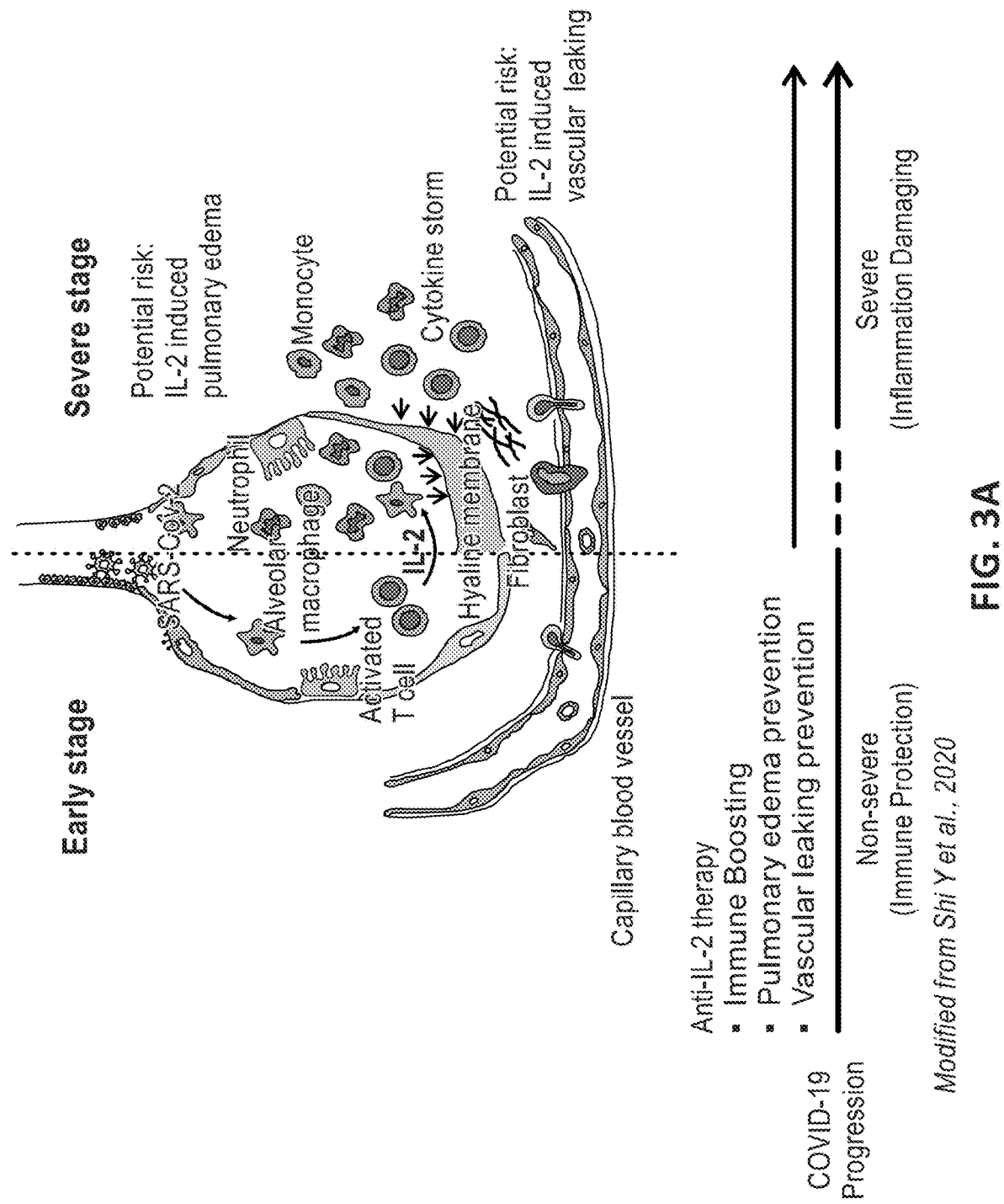

FIGS. 3A and 3B presents a schematic of the progression of COVID-19 infection and potential anti-IL-2 therapy as an adjuvant intervention. FIG. 3A shows the invading SARS Co-V2 causes non-severe symptoms and elicits protective immune responses after an incubation period. Successful elimination of the infection relies on the health status of the infected individual. Individuals with poor immune responses to the virus would have difficulty in clearing the virus while individuals with an over robust immune response may lead to pulmonary edema and other cytokine mediated adverse effects. Therefore, strategies that boost immune response and prevent pulmonary edema are desired. While high concentrations of IL-2 would be beneficial for viral clearance, particularly at the early stage, high levels of IL-2 could lead to IL-2-induced pulmonary edema and vascular leaking through interactions between IL-2 and CD25-expressing endothelial cells. FIG. 3B shows that an anti-human IL-2 antibody designed to bind and block the CD25/IL-2 interaction is predicted to enhance expansion of immune effector cells to improve viral clearance and reduce the negative effects of IL-2 binding to CD25 expressed on endothelial cells, thereby preventing IL-2 induced pulmonary edema and vascular leaking.

FIG. 1 presents a schematic for the mechanism of action of IL-2 and its dual role in controlling immune response. The left panel shows IL-2 consists of three binding epitope sites ($\alpha$, $\beta$, $\gamma$) that interact with different forms of IL2-R (CD25, CD122 and CD132) with different affinities. The right panel shows different IL-2R complexes are expressed on different T cell populations, and their different affinities to IL2 allow immunosuppression under conditions of low local concentrations of IL-2 and immune stimulation when IL-2 local concentration rises.

In the following detailed description, numerous specific details are set forth in order to provide a thorough understanding of the antibodies disclosed herein. However, it will be understood by those skilled in the art that preparation and uses of antibodies disclosed herein may in certain cases be practiced without these specific details. In other instances, well-known methods, procedures, and components have not been described in detail so as not to obscure the disclosure presented herein.

Throughout this application, various references or publications are cited. Disclosures of these references or publications in their entireties are hereby incorporated by reference into this application in order to more fully describe the state of the art to which this invention pertains.

As used herein, the term "antibody" may be used interchangeably with the term "immunoglobulin", having all the same qualities and meanings. An antibody binding domain or an antigen binding site can be a fragment of an antibody or a genetically engineered product of one or more fragments of the antibody, which fragment is involved in specifically binding with a target antigen. By "specifically binding" is meant that the binding is selective for the antigen of interest and can be discriminated from unwanted or nonspecific interactions. For example, an antibody is said to specifically bind an IL-2 epitope when the equilibrium dissociation constant is $\leq 10^{-5}$, $10^{-6}$k, or $10^{-7}$ M. In some embodiments, the equilibrium dissociation constant may be $\leq 10^{-8}$ M or $10^{-9}$ M. In some further embodiments, the equilibrium dissociation constant may be $\leq 10^{-10}$ M, $10^{-11}$ M, or $10^{-12}$M. In some embodiments, the equilibrium dissociation constant may be in the range of $\leq 10^{-5}$ M to $10^{-12}$M.

As used herein, the term "antibody" encompasses an antibody fragment or fragments that retain binding specificity including, but not limited to, IgG, heavy chain variable region (VH), light chain variable region (VL), Fab fragments, F(ab')2 fragments, scFv fragments, Fv fragments, a nanobody, minibodies, diabodies, triabodies, tetrabodies, and single domain antibodies (see, e.g., Hudson and Souriau, Nature Med. 9: 129-134 (2003)). Also encompassed are humanized, primatized, and chimeric antibodies as these terms are generally understood in the art.

As used herein, the term "heavy chain variable region" may be used interchangeably with the term "VH domain" or the term "VH", having all the same meanings and qualities. As used herein, the term "light chain variable region" may be used interchangeably with the term "VL domain" or the term "VL", having all the same meanings and qualities. A skilled artisan would recognize that a "heavy chain variable region" or "VH" with regard to an antibody encompasses the fragment of the heavy chain that contains three complementarity determining regions (CDRs) interposed between flanking stretches known as framework regions. The framework regions are more highly conserved than the CDRs and form a scaffold to support the CDRs. Similarly, a skilled artisan would also recognize that a "light chain variable region" or "VL" with regard to an antibody encompasses the fragment of the light chain that contains three CDRs interposed between framework regions.

As used herein, the term "complementarity determining region" or "CDR" refers to the hypervariable region(s) of a heavy or light chain variable region. Proceeding from the N-terminus, each of a heavy or light chain polypeptide has three CDRs denoted as "CDR1," "CDR2," and "CDR3". Crystallographic analysis of a number of antigen-antibody complexes has demonstrated that the amino acid residues of CDRs form extensive contact with a bound antigen, wherein the most extensive antigen contact is with the heavy chain CDR3. Thus, the CDR regions are primarily responsible for the specificity of an antigen-binding site. In one embodiment, an antigen-binding site includes six CDRs, comprising the CDRs from each of a heavy and a light chain variable region.

As used herein, the term "framework region" or "FR" refers to the four flanking amino acid sequences which frame the CDRs of a heavy or light chain variable region. Some FR residues may contact bound antigen; however, FR residues are primarily responsible for folding the variable region into the antigen-binding site. In some embodiments, the FR residues responsible for folding the variable regions comprise residues directly adjacent to the CDRs. Within FRs, certain amino residues and certain structural features are very highly conserved. In this regard, all variable region sequences contain an internal disulfide loop of around 90 amino acid residues. When a variable region folds into an antigen binding site, the CDRs are displayed as projecting loop motifs that form an antigen-binding surface. It is generally recognized that there are conserved structural regions of FR that influence the folded shape of the CDR loops into certain "canonical" structures regardless of the precise CDR amino acid sequence. Furthermore, certain FR residues are known to participate in non-covalent interdomain contacts which stabilize the interaction of the antibody heavy and light chains.

Wu and Kabat (Tai Te Wu, Elvin A. Kabat. An analysis of the sequences of the variable regions of bence jones proteins and myeloma light chains and their implications for antibody complementarity. Journal of Experimental Medicine, 132, 2, 8 (1970); Kabat E A, Wu T T, Bilofsky H, Reid-Miller M, Perry H. Sequence of proteins of immunological interest. Bethesda: National Institute of Health; 1983. 323 (1983)) pioneered the alignment of antibody peptide sequences, and their contributions in this regard were several-fold: Firstly, through study of sequence similarities between variable domains, they identified correspondent residues that to a greater or lesser extent were homologous across all antibodies in all vertebrate species, inasmuch as they adopted similar three-dimensional structure, played similar functional roles, interacted similarly with neighboring residues, and existed in similar chemical environments. Secondly, they devised a peptide sequence numbering system in which homologous immunoglobulin residues were assigned the same position number. One skilled in the art can unambiguously assign to any variable domain sequence what is now commonly called Kabat numbering without reliance on any experimental data beyond the sequence itself. Thirdly, Kabat and Wu calculated variability for each Kabat-numbered sequence position, by which is meant the finding of few or many possible amino acids when variable domain sequences are aligned. They identified three contiguous regions of high variability embedded within four less variable contiguous regions. Kabat and Wu formally demarcated residues constituting these variable tracts and designated these "complementarity determining regions" (CDRs), referring to chemical complementarity between antibody and antigen. A role in three-dimensional folding of the variable domain, but not in antigen recognition, was ascribed to the remaining less-variable regions, which are now termed "framework regions". Fourth, Kabat and Wu established a public database of antibody peptide and nucleic acid sequences, which continues to be maintained and is well known to those skilled in the art.

Chothia and coworkers (Cyrus Chothia, Arthur M. Lesk. Canonical structures for the hypervariable regions of immunoglobulins. Journal of Molecular Biology, 196, 4, 8 (1987)) found that certain sub portions within Kabat CDRs adopt nearly identical peptide backbone conformations, despite having great diversity at the level of amino acid sequence. These sub portions were designated as L1, L2 and L3 or H1, H2 and H3, where the "L" and the "H" designates the light chain and the heavy chains regions, respectively. These regions may be referred to as Chothia CDRs, which have boundaries that overlap with Kabat CDRs.

More recent studies have shown that virtually all antibody binding residues fall within regions of structural consensus. (Kunik, V. et al., PloS Computational Biology 8(2): e1002388 (February 2012)). In some embodiments, these regions are referred to as antibody binding regions. It was shown that these regions can be identified from the antibody sequence as well. "Paratome", an implementation of a structural approach for the identification of structural consensus in antibodies, was used for this purpose. (Ofran, Y. et al., J. Immunol. 757:6230-6235 (2008)). While residues identified by Paratome cover virtually all the antibody binding sites, the CDRs (as identified by the commonly used CDR identification tools) miss significant portions of them. Antibody binding residues which were identified by Paratome but were not identified by any of the common CDR identification methods are referred to as Paratome-unique residues. Similarly, antibody binding residues that are identified by any of the common CDR identification methods but are not identified by Paratome are referred to as CDR-unique residues. Paratome-unique residues make crucial energetic contribution to antibody-antigen interactions, while CDRs-unique residues have a rather minor contribution. These results allow for better identification of antigen binding sites.

IMGT® is the international ImMunoGeneTics information system®, (See, Nucleic Acids Res. 2015 January; 43 (Database issue): D413-22. doi: 10.1093/nar/gku1056. Epub 2014 Nov. 5 Free article. PMID: 25378316 LIGM:441 and Dev Comp Immunol. 2003 January; 27(1):55-77). IMGT is a unique numbering system for immunoglobulin and T cell receptor variable domains and Ig superfamily V-like domains (Lefranc et al., Dev Comp Immunol. 27: 55-77 (2003)). IMGT® presents a uniform numbering system for these IG and TcR variable domain sequences, based on aligning 5 or more IG and TcR variable region sequences, taking into account and combining the Kabat definition of FRs and CDRs, structural data, and Chothia's characterization of the hypervariable loops. IMGT is considered well known in the art as a universal numbering scheme for antibodies.

In some embodiments, identification of potential variant amino acid positions in the VH and VL domains uses the IMGT system of analysis. In some embodiments, identification of potential variant amino acid positions in the VH and VL domains uses the Paratome system of analysis. In some embodiments, identification of potential variant amino acid positions in the VH and VL domains uses the Kabat system of analysis. In some embodiments, identification of potential variant amino acid positions in the VH and VL domains uses the Clothia system of analysis.

In describing variant amino acid positions present in the VH and VL domains, in some embodiments the IMGT numbering is used. In describing variant amino acid positions present in the VH and VL domains, in some embodiments the Paratome numbering is used. In describing variant amino acid positions present in the VH and VL domains, in some embodiments the Kabat numbering is used. In describing variant amino acid positions present in the VH and VL domains, in some embodiments the Clothia numbering is used.

Antigen binding sequences are conventionally located within the heavy chain and light chain variable regions of an antibody. These heavy and light chain variable regions may, in certain instances, be manipulated to create new binding sites, for example to create antibodies or fragments thereof, that bind to a different antigen or to a different epitope of the same antigen. In some embodiments, as described herein, manipulating the sequences of a heavy chain variable region or the sequences of a light chain variable region, or both, would create a new binding site for a second antigen.

An antibody may exist in various forms or having various domains including, without limitation, a complementarity determining region (CDR), a variable region (Fv), a VH domain, a VL domain, a single chain variable region (scFv), and a Fab fragment.

A person of ordinary skill in the art would appreciate that a scFv is a fusion polypeptide comprising the variable heavy chain (VH) and variable light chain (VL) regions of an immunoglobulin, connected by a short linker peptide, the linker may have, for example, 10 to about 25 amino acids.

A skilled artisan would also appreciate that the term "Fab" with regard to an antibody generally encompasses that portion of the antibody consisting of a single light chain (both variable and constant regions) bound to the variable region and first constant region of a single heavy chain by a disulfide bond, whereas F(ab')$_2$ comprises a fragment of a heavy chain comprising a VH domain and a light chain comprising a VL domain.

In some embodiments, an antibody encompasses whole antibody molecules, including monoclonal and polyclonal antibodies. In some embodiments, an antibody encompasses an antibody fragment or fragments that retain binding specificity including, but not limited to, variable heavy chain (VH) fragments, variable light chain (VL) fragments, Fab fragments, F(ab')$_2$ fragments, scFv fragments, Fv fragments, minibodies, diabodies, triabodies, and tetrabodies.

Engineered Anti-IL-2 Antibodies

In one embodiment, the present disclosure provides engineered anti-IL-2 antibodies resulted from introducing amino acid variations to a parent anti-IL-2 antibody. In one embodiment, the one or more of the amino acid variations are introduced in a CDR region. In another embodiment, the one or more amino acid variations are introduced within a framework (FR) region. In yet another embodiment, the amino acid variations are introduced to both the CDR region and the framework (FR) region. One of ordinary skill in the art would readily employ various standard techniques known in the art to introduce amino acid variations into an anti-IL-2 antibody and then test the resulting modified antibodies for any changes of binding to IL-2. While standard techniques may be used, the resultant binding pattern of the new created antibodies is not predictable and must be analyzed to determine functionality.

In certain embodiments, the present disclosure provides polypeptides comprising the VH and VL domains which could be dimerized under suitable conditions. For example, the VH and VL domains may be combined in a suitable buffer and dimerized through appropriate interactions such as hydrophobic interactions. In another embodiment, the VH and VL domains may be combined in a suitable buffer containing an enzyme and/or a cofactor which can promote dimerization of the VH and VL domains. In another embodiment, the VH and VL domains may be combined in a suitable vehicle that allows them to react with each other in the presence of a suitable reagent and/or catalyst.

In certain embodiments, the VH and VL domains may be contained within longer polypeptide sequences, which may include for example but not limited to, constant regions, hinge regions, linker regions, Fc regions, or disulfide binding regions, or any combination thereof. A constant domain is an immunoglobulin fold unit of the constant part of an immunoglobulin molecule, also referred to as a domain of the constant region (e.g., CH1, CH2, CH3, CH4, Ck, Cl). In some embodiments, the longer polypeptides may comprise multiple copies of one or both of the VH and VL domains generated according to the method disclosed herein; for example, when the polypeptides generated herein are used to forms a diabody or a triabody.

In some embodiments, the Fc region comprises at least one mutation that reduces Fc-gamma binding, i.e., binding to a Fcγ receptor (FcγRs). In some embodiments, reduced binding is abolished binding, which binding to the Fcγ receptor is not detectable. In some embodiments, reduced binding reduces the binding affinity to a Fcγ receptor. In some embodiments, reduced binding reduces the on rate for binding to a Fcγ receptor. In some embodiments, reduced binding reduces the off rate of binding to a Fcγ receptor. In some embodiments, a mutation that reduces the Fc-gamma binding comprises L234A, L235A mutations, also known as LALA mutations. In some embodiments, a mutation that reduces the Fc-gamma binding comprises a P329G mutation in addition to the L234A, L235A mutations. In some embodiments, an antibody described herein comprises a heavy chain comprising a mutation that reduces binding to Fcγ receptor.

In one embodiment, the present disclosure provides an engineered (or modified) anti-IL-2 antibody, wherein the antibody comprises a heavy chain variable region having the sequence of one of SEQ ID NOs:10, 12, 14, 16, 18, 20, 22, 24, 26, or 36. In one embodiment, the engineered antibody can be an IgG, IgA, IgM, IgE, IgD, a Fv, a scFv, a Fab, or a $F(ab')_2$. The IgG can be of the subclass of IgG1, IgG2, IgG3, or IgG4. In another embodiment, the engineered antibody can be part of a minibody, a diabody, a triabody, a nanobody, or a single domain antibody.

In one embodiment, the present disclosure provides an engineered (or modified) anti-IL-2 antibody, wherein the antibody comprises a light chain variable region having the sequence of one of SEQ ID NOs:11, 13, 15, 17, 19, 21, 23, 25, 27, or 37. In one embodiment, the engineered antibody can be an IgG, IgA, IgM, IgE, IgD, a Fv, a scFv, a Fab, or a $F(ab')_2$. The IgG can be of the subclass of IgG1, IgG2, IgG3, or IgG4. In another embodiment, the engineered antibody can be part of a minibody, a diabody, a triabody, a nanobody, or a single domain antibody.

In one embodiment, the present disclosure provides an engineered (or modified) anti-IL-2 antibody, wherein the antibody comprises a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27, or SEQ ID NOs: 36 and 37. In one embodiment, the engineered anti-IL-2 antibody comprises the sequences of SEQ ID NOs:10 and 11. In one embodiment, the engineered anti-IL-2 antibody comprises the sequences of SEQ ID NOs:12 and 13. In one embodiment, the engineered anti-IL-2 antibody comprises the sequences of SEQ ID NOs:14 and 15. In one embodiment, the engineered anti-IL-2 antibody comprises the sequences of SEQ ID NOs:16 and 17. In one embodiment, the engineered anti-IL-2 antibody comprises the sequences of SEQ ID NOs:18 and 19. In one embodiment, the engineered anti-IL-2 antibody comprises the sequences of SEQ ID NOs:20 and 21. In one embodiment, the engineered anti-IL-2 antibody comprises the sequences of SEQ ID NOs:22 and 23. In one embodiment, the engineered anti-IL-2 antibody comprises the sequences of SEQ ID NOs:24 and 25. In one embodiment, the engineered anti-IL-2 antibody comprises the sequences of SEQ ID NOs:26 and 27. In one embodiment, the engineered anti-IL-2 antibody comprises the sequences of SEQ ID NOs:36 and 37.

In some embodiments, an isolated anti-IL-2 antibody comprising a heavy chain variable region (VH) and a light chain variable region (VL), wherein said VH comprises heavy chain complementarity determining regions (HCDRs) HCDR1, HCDR2 and HCDR3, said VL comprises light chain complementarity determining regions (LCDRs) LCDR1, LCDR2 and LCDR3, wherein said CDRs have the amino acid sequences of (a) the HCDR1 comprises the amino acid sequence of SEQ ID NO:38, the HCDR2 comprises the amino acid sequence of SEQ ID NO:39, the HCDR3 comprises the amino acid sequence of SEQ ID NO:40, the LCDR1 comprises the amino acid sequence of SEQ ID NO:41, the LCDR2 comprises the amino acid sequence YAS, the LCDR3 comprises the amino acid sequence of SEQ ID NO:43;

(b) the HCDR1 comprises the amino acid sequence of SEQ ID NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49;

(c) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55;

(d) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61; or (e) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67.

In some embodiments, the VH and VL have the amino acid sequences wherein the VH comprises the amino acid sequence of SEQ ID NO:10, the VL comprises the amino acid sequence of SEQ ID NO: 11; the VH comprises the amino acid sequence of SEQ ID NO:12, the VL comprises the amino acid sequence of SEQ ID NO:13; the VH comprises the amino acid sequence of SEQ ID NO:14, the VL comprises the amino acid sequence of SEQ ID NO:15; the VH comprises the amino acid sequence of SEQ ID NO:16, the VL comprises the amino acid sequence of SEQ ID NO:17; the VH comprises the amino acid sequence of SEQ ID NO:18, the VL comprises the amino acid sequence of SEQ ID NO:19; the VH comprises the amino acid sequence of SEQ ID NO:20, the VL comprises the amino acid sequence of SEQ ID NO:21; the VH comprises the amino acid sequence of SEQ ID NO:22, the VL comprises the amino acid sequence of SEQ ID NO:23; the VH comprises the amino acid sequence of SEQ ID NO:24, the VL comprises the amino acid sequence of SEQ ID NO:25; the VH comprises the amino acid sequence of SEQ ID NO:26, the VL comprises the amino acid sequence of SEQ ID NO:27; or the VH comprises the amino acid sequence of SEQ ID NO:36, the VL comprises the amino acid sequence of SEQ ID NO:37.

In some embodiments, an antibody comprising a heavy chain sequence and a light chain sequence, said heavy chain sequence set forth in SEQ ID NO: 68 and said light chain sequence set forth in SEQ ID NO: 69; said heavy chain sequence set forth in SEQ ID NO: 70 and said light chain sequence set forth in SEQ ID NO: 71, or said heavy chain sequence set forth in SEQ ID NO: 72 and said light chain sequence set forth in SEQ ID NO: 73.

In one embodiment, the engineered antibody can be an IgG, IgA, IgM, IgE, IgD, a Fv, a scFv, a Fab, or a F(ab')$_2$. The IgG can be of the subclass of IgG1, IgG2, IgG3, or IgG4. In another embodiment, the engineered antibody can be part of a minibody, a diabody, a triabody, a nanobody, or a single domain antibody.

In one embodiment, the present disclosure also provides isolated polynucleotide sequence encoding a heavy chain variable region of an anti-IL-2 antibody, wherein the heavy chain variable region comprises the amino acid sequence of one of SEQ ID NOs:10, 12, 14, 16, 18, 20, 22, 24, 26, or 36. In another embodiment, the present disclosure also provides a vector comprising the above-mentioned polynucleotide sequences. In view of the amino acid sequences disclosed herein, one of ordinary skill in the art would readily construct a vector or plasmid to encode for the amino acid sequences. In another embodiment, the present disclosure also provides a host cell comprising the vector provided herein. Depending on the uses and experimental conditions, one of skill in the art would readily employ a suitable host cell to carry and/or express the above-mentioned polynucleotide sequences.

In one embodiment, the present disclosure also provides isolated polynucleotide sequence encoding a light chain variable region of an anti-IL-2 antibody, wherein the light chain variable region comprises the amino acid sequence of one of SEQ ID NOs:11, 13, 15, 17, 19, 21, 23, 25, 27, or 37. In another embodiment, the present disclosure also provides a vector comprising the above-mentioned polynucleotide sequences. In view of the amino acid sequences disclosed herein, one of ordinary skill in the art would readily construct a vector or plasmid to encode for the amino acid sequences. In another embodiment, the present disclosure also provides a host cell comprising the vector provided herein. Depending on the uses and experimental conditions, one of skill in the art would readily employ a suitable host cell to carry and/or express the above-mentioned polynucleotide sequences.

In view of the sequences for the heavy chain variable regions and light chain variable regions disclosed herein, one of ordinary skill in the art would readily employ standard techniques known in the art to construct an anti-IL-2 scFv. In one embodiment, polynucleotide sequences encoding for such anti-IL-2 scFv could have the sequence of one of SEQ ID NOs:1-5 or one of SEQ ID NO: 31-35.

In certain embodiments, an isolated polynucleotide sequence disclosed herein, encoding the heavy chain variable region of an anti-IL-2 antibody, comprises a VH amino acid sequence set forth in the amino acid sequence of any of SEQ ID NO:10, 12, 14, 16, 18, 20, 22, 24, 26, or 36. In some embodiments, a vector comprises the polynucleotide sequence of any of SEQ ID NO:10, 12, 14, 16, 18, 20, 22, 24, 26, or 36. In some embodiments, a host cell comprising the vector comprising the polynucleotide sequence of any of SEQ ID NO:10, 12, 14, 16, 18, 20, 22, 24, 26, or 36.

In certain embodiments, an isolated polynucleotide sequence disclosed herein, encoding the light chain variable region of an anti-IL-2 antibody, comprises a VL amino acid sequence as set forth in the amino acid sequence of any of SEQ ID NO: 11, 13, 15, 17, 19, 21, 23, 25, 27, or 37. In some embodiments, a vector comprises the polynucleotide sequence comprising the amino acid sequence of any of SEQ ID NO: 11, 13, 15, 17, 19, 21, 23, 25, 27, or 37. In some embodiments, a host cell comprises a vector comprising the polynucleotide sequence encoding the amino acid sequence of any of SEQ ID NO: 11, 13, 15, 17, 19, 21, 23, 25, 27, or 37. In some embodiments, an isolated polynucleotide sequence encodes an anti-IL-2 scFv, wherein the polynucleotide sequence is set forth in SEQ ID NO: 1, 2, 3, 4, 5, 31, 32, 33, 34, or 35. In some embodiments, a vector comprises an isolated polynucleotide sequence encodes an anti-IL-2 scFv, wherein the polynucleotide sequence is set forth in SEQ ID NO: 1, 2, 3, 4, 5, 31, 32, 33, 34, or 35. In some embodiments, a host cell comprises a vector comprising an isolated polynucleotide sequence encoding an anti-IL-2 scFv, wherein the polynucleotide sequence is set forth in SEQ ID NO: 1, 2, 3, 4, 5, 31, 32, 33, 34, or 35.

In another embodiment, the present disclosure also provides an isolated anti-IL-2 antibody, wherein the antibody comprises a heavy chain variable region having complementarity determining region (CDR) 1, CDR2 and CDR3. In one embodiment, the CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively. In one embodiment, the antibody can be an IgG, IgA, IgM, IgE, IgD, a Fv, a scFv, a Fab, a F(ab')$_2$, a minibody, a diabody, a triabody, a nanobody, or a single domain antibody. The IgG can be IgG1, IgG2, IgG3, or an IgG4. In one embodiment, the present disclosure also encompasses a composition comprising the above-mentioned antibody and a pharmaceutically acceptable carrier.

In another embodiment, the present disclosure also provides an isolated anti-IL-2 antibody, wherein the antibody comprises a light chain variable region having complementarity determining region (CDR) 1, CDR2 and CDR3. In one embodiment, the CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively. In one embodiment, the antibody can be an IgG, IgA, IgM, IgE, IgD, a Fv, a scFv, a Fab, a F(ab')$_2$, a minibody, a diabody, a triabody, a nanobody, or a single domain antibody. The IgG can be IgG1, IgG2, IgG3, or an IgG4. In one embodiment, the present disclosure also encompasses a composition comprising the above-mentioned antibody and a pharmaceutically acceptable carrier.

In another embodiment, the present disclosure also provides an isolated anti-IL-2 antibody, wherein the antibody comprises a heavy chain variable region having complementarity determining region (CDR) 1, CDR2 and CDR3, and a light chain variable region having CDR1, CDR2 and CDR3. In one embodiment, the heavy chain CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively. In one embodiment, the light chain CDR1, CDR2 and CDR3 comprise amino acid sequences of SEQ ID NOs:41-43 respectively; SEQ ID NOs:47-49 respectively; SEQ ID NOs:53-55 respectively, SEQ ID NOs:59-61 respectively; or SEQ ID NOs:65-67 respectively. In one embodiment, the antibody can be an IgG, IgA, IgM, IgE, IgD, a Fv, a scFv, a Fab, a F(ab')$_2$, a minibody, a diabody, a triabody, a nanobody, or a single domain antibody. The IgG can be IgG1, IgG2, IgG3, or an IgG4. In one embodiment, the present disclosure also encompasses a composition comprising the above-mentioned antibody and a pharmaceutically acceptable carrier.

Pharmaceutical Compositions

In some embodiments, disclosed herein are compositions for therapeutic use. In some embodiments, a composition described herein comprises an anti-IL-2 antibody as disclosed herein and a pharmaceutically acceptable carrier.

As used herein, the terms "composition" and pharmaceutical composition" may in some embodiments, be used interchangeably having all the same qualities and meanings. In some embodiments, disclosed herein is a pharmaceutical composition for the treatment of a condition or disease as described herein.

In some embodiments, disclosed herein are pharmaceutical compositions for use in a combination therapy.

In another embodiment, disclosed herein are compositions for use treating a disease or condition in a subject. In some embodiments, the disease comprises a viral infection, a bacterial infection, or a cancer. In some embodiments the condition comprises an IL-2 induced condition. In some embodiments, the IL-2 induced condition comprises pulmonary edema or vascular leakage.

The VH and/or VL polypeptides disclosed herein can be administered to a subject (e.g., a human or an animal) alone, or in combination with a carrier, i.e., a pharmaceutically acceptable carrier. By pharmaceutically acceptable is meant a material that is not biologically or otherwise undesirable, i.e., the material can be administered to a subject without causing any undesirable biological effects or interacting in a deleterious manner with any of the other components of the pharmaceutical composition in which it is contained. As would be well-known to one of ordinary skill in the art, the carrier is selected to minimize any degradation of the polypeptides disclosed herein and to minimize any adverse side effects in the subject. The pharmaceutical compositions may be prepared by methodology well known in the pharmaceutical art.

The above pharmaceutical compositions comprising the polypeptides disclosed herein can be administered (e.g., to a mammal, a cell, or a tissue) in any suitable manner depending on whether local or systemic treatment is desired. For example, the composition can be administered topically (e.g., ophthalmically, vaginally, rectally, intranasally, transdermally, and the like), orally, by inhalation, or parenterally (including by intravenous drip or subcutaneous, intracavity, intraperitoneal, intradermal, or intramuscular injection). Topical intranasal administration refers to delivery of the compositions into the nose and nasal passages through one or both of the nares. The composition can be delivered by a spraying mechanism or droplet mechanism, or through aerosolization. Delivery can also be directed to any area of the respiratory system (e.g., lungs) via intubation. Alternatively, administration can be intratumoral, e.g., local or intravenous injection.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve preparation of a slow-release or sustained-release system so as to maintain a constant dosage.

In some embodiments, a composition comprises an anti-IL-2 antibody comprising a heavy chain variable region having the sequence of one of SEQ ID NOs:10, 12, 14, 16, 18, 20, 22, 24, 26, or 36. In some embodiments, a composition comprises an anti-IL-2 antibody comprising a light chain variable region having the sequence of one of SEQ ID NOs:11, 13, 15, 17, 19, 21, 23, 25, 27, or 37. In some embodiments, a composition comprises an anti-IL-2 antibody comprising a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27, or SEQ ID NOs: 36 and 37. In some embodiments, a composition comprises an anti-IL-2 antibody comprising a heavy chain variable domain comprising CDR1, CDR2 and CDR3 regions comprising amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively. In some embodiments, a composition comprises an anti-IL-2 antibody comprising a light chain variable domain comprising CDR1, CDR2 and CDR3 regions comprising amino acid sequences of SEQ ID NOs: 41-43 respectively; SEQ ID NOs:47-49 respectively; SEQ ID NOs:53-55 respectively; SEQ ID NOs:59-61 respectively; or SEQ ID NOs:65-67, respectively. In some embodiments, a composition comprises an anti-IL-2 antibody comprising a heavy chain variable domain comprising CDR1, CDR2 and CDR3 regions comprising amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-4, respectively, and a light chain variable domain comprising CDR1, CDR2, and CDR3 regions comprising amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67, respectively.

In some embodiments, a composition comprises an anti-IL-2 antibody comprising any of clones BDG 17.014, BDG 17.023, BDG 17.038, BDG 17.043, BDG 17.053, BDG 17.054, BDG 17.066, BDG 17.067, and BDG 17.069. In some embodiments, a composition comprises an anti-IL-2 antibody comprising anti-IL-2 clone BDG 17.014. In some embodiments, a composition comprises an anti-IL-2 antibody comprising anti-IL-2 clone BDG 17.023. In some embodiments, a composition comprises an anti-IL-2 antibody comprising anti-IL-2 clone BDG 17.038. In some embodiments, a composition comprises an anti-IL-2 antibody comprising anti-IL-2 clone BDG 17.043. In some embodiments, a composition comprises an anti-IL-2 antibody comprising anti-IL-2 clone BDG 17.053. In some embodiments, a composition comprises an anti-IL-2 antibody comprising anti-IL-2 clone BDG 17.054. In some embodiments, a composition comprises an anti-IL-2 antibody comprising anti-IL-2 clone BDG 17.066. In some embodiments, a composition comprises an anti-IL-2 antibody comprising anti-IL-2 clone BDG 17.067. In some embodiments, a composition comprises an anti-IL-2 antibody comprising anti-IL-2 clone BDG 17.069.

In some embodiments, compositions comprise an anti-IL2 antibody and a pharmaceutically acceptable carrier. In some embodiments, compositions comprise an anti-IL2 antibody and IL-2, and a pharmaceutically acceptable carrier. In some embodiments, compositions comprise an anti-IL2 antibody complexed with IL-2, and a pharmaceutically acceptable carrier.

In some embodiments, an anti-IL-2 antibody and IL-2 are comprised in the same composition. In some embodiments, an anti-IL-2 antibody and IL-2 are comprised in different compositions. In some embodiments, administration of a combination of an anti-IL-2 antibody and IL-2, or composition(s) thereof are concurrent. In some embodiments, administration of a combination of an anti-IL-2 antibody and IL-2, or composition(s) thereof comprises administration of an anti-IL-2 antibody or a composition thereof, prior to the IL-2 or a composition thereof. In some embodiments, administration of a combination of an anti-IL-2 antibody and IL-2, or composition(s) thereof comprises administration of an anti-IL-2 antibody or a composition thereof, following administration of the IL-2 or a composition thereof.

A skilled artisan would appreciate that a "pharmaceutical composition" may encompass a preparation of one or more of the active ingredients described herein with other chemical components such as physiologically suitable carriers and excipients. The purpose of a pharmaceutical composition is to facilitate administration of an active agent, for example but not limited to an antibody or a compound, to an organism.

In some embodiments, disclosed herein is a pharmaceutical composition for a therapy use treating a subject with a weakened immune system. In some embodiments, disclosed herein is a pharmaceutical composition for a therapy use treating a subject suffering from a viral infection, a bacterial infection, or a cancer. In some embodiments, disclosed herein is a pharmaceutical composition for use as part of a combination therapy for treating a subject with a weakened immune system. In some embodiments, disclosed herein is a pharmaceutical composition for use as part of a combination therapy for use treating a subject suffering from a viral infection, a bacterial infection, or a cancer.

A skilled artisan would appreciate that the phrases "physiologically acceptable carrier", "pharmaceutically acceptable carrier", "physiologically acceptable excipient", and "pharmaceutically acceptable excipient", may be used interchangeably may encompass a carrier, excipient, or a diluent that does not cause significant irritation to an organism and does not abrogate the biological activity and properties of the administered active ingredient.

A skilled artisan would appreciate that an "excipient" may encompass an inert substance added to a pharmaceutical composition to further facilitate administration of an active ingredient. In some embodiments, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, PA, latest edition, which is incorporated herein by reference.

In some embodiments, the composition as disclosed herein comprises a therapeutic composition. In some embodiments, the composition as disclosed herein comprises a therapeutic efficacy.

Combination Therapies

In some embodiments, an anti-IL-2 antibody or a composition thereof, is used in combination with an immune checkpoint inhibitor. In some embodiments, the term "immune checkpoint inhibitor" may encompass any compound or molecule capable of inhibiting the function of a checkpoint protein. In some embodiments, the term "immune checkpoint inhibitor" may encompass any compound or molecule which targets immune checkpoint proteins. An artisan would appreciate that "immune checkpoints" are key regulators of the immune system that when stimulated can dampen the immune response to an immunologic stimulus. Checkpoint inhibitors can block inhibitory checkpoints, and thereby restore immune system function. In some embodiments, the one or more checkpoint inhibitors comprise immune checkpoint inhibitors.

A skilled artisan would appreciate that the terms "immune checkpoint inhibitors" (ICIs), "checkpoint inhibitors," and the like may be used interchangeably herein having all the same qualities and meanings, wherein an immune checkpoint inhibitor encompasses compounds that inhibit the activity or control mechanism(s) of the immune system. Immune system checkpoints, or immune checkpoints, are inhibitory pathways in the immune system that generally act to maintain self-tolerance or modulate the duration and amplitude of physiological immune responses to minimize collateral tissue damage. Checkpoint inhibitors can inhibit an immune system checkpoint by inhibiting the activity of a protein in the pathway.

Immune checkpoint inhibitor targets include, but are not limited to Programmed cell death protein 1 (PD-1), Programmed death-ligand 1 (PDL-1), Cytotoxic T-lymphocyte protein 4 (CTLA-4), T-cell immunoreceptor with Ig and ITIM domains (TIGIT), Metalloproteinase inhibitor 3 (TIM-3), B7 homolog 3 (B7-H3), cluster of differentiation 73 (CD73), Lymphocyte-activation gene 3 (LAG3), cluster of differentiation 27 (CD27), cluster of differentiation 70 (CD70), Tumor necrosis factor ligand superfamily member 9 (4-1BB), Glucocorticoid-Induced TNFR-Related (GITR), Tumor necrosis factor receptor superfamily member 4 (OX40), cluster of differentiation 47 (SIRP-alpha (CD47)), cluster of differentiation 39 (CD39), Immunoglobulin Like Domain Containing Receptor 2 (ILDR2), V-Domain Ig Suppressor Of T Cell Activation (VISTA), B and T lymphocyte attenuator (BTLA), and V-set domain containing T cell activation inhibitor 1 (VTCN-1). In some embodiments, an anti-IL-2 antibody therapy is used in combination with an immune checkpoint inhibitor, wherein the target of the immune checkpoint inhibitor comprises PD-1, PDL-1, CTLA-4, TIGIT, TIM-3, B7-H3, CD73, LAG3, CD27, CD70, 4-4BB, GITR, OX40, SIRP-alpha (CD47), CD39, ILDR2, VISTA, BTLA, or VTCN-1, or any combination thereof.

Checkpoint inhibitors may include antibodies, or antigen binding fragments thereof, other binding proteins, biologic therapeutics, or small molecules, that bind to and block or inhibit the activity of one or more of PD-1, PDL-1, CTLA-4, TIGIT, TIM-3, B7-H3, CD73, LAG3, CD27, CD70, 4-1BB, GITR, OX40, SIRP-alpha (CD47), CD39, ILDR2, VISTA, BTLA, or VTCN-1. Illustrative checkpoint inhibitors include but are not limited to those listed in Table 1 below.

TABLE 1

Non-Limiting Examples of Checkpoint Inhibitors and the Immune Checkpoint Inhibitor Target.

| Drug name | ICI Target |
| --- | --- |
| Avelumab | anti-PDL1 |
| Atezolizumab | anti-PDL1 |
| Durvalumab | anti-PDL1 |
| Sugemalimab | anti-PDL1 |
| Envafolimab | anti-PDL1 |
| Nivolumab (Optivo)-BMS | anti-PD-1 |
| Pembrolizumab(kytruda) | anti-PD-1 |
| Cemiplimab | anti-PD-1 |
| Camrelizumab | anti-PD-1 |
| Zimberelimab | anti-PD-1 |
| Tislelizumab | anti-PD-1 |
| Sintilimab | anti-PD-1 |
| Teriprizumab | anti-PD-1 |
| Prolgolimab | anti-PD-1 |
| Penpulimab | anti-PD-1 |
| Dostarlimab | anti-PD-1 |
| Genolimzumab | anti-PD-1 |
| Retifanlimab | anti-PD-1 |
| Ipilimumab (Yervoy) | anti-CTLA4 |
| Tiragolumab | anti-TIGIT |
| Domvanalimab | anti-TIGIT |
| Vibostolimab | anti-TIGIT |
| BMS-986207 | anti-TIGIT |
| EOS-448 | anti-TIGIT |
| COM-902 | anti-TIGIT |
| Sabatolimab | anti-TIM3 |
| Cobolimab | anti-TIM3 |
| BMS-986258 | anti-TIM3 |
| INCAGN-02390 | anti-TIM3 |
| S-95018 | anti-TIM3 |
| Omburtamab | anti-B7-H3 |
| MGC-018 | anti-B7-H3 |
| Enoblituzumab | anti-B7-H3 |
| Oleclumab | anti-CD73 |
| BMS-986179 | anti-CD73 |
| NZV-930 | anti-CD73 |
| CPX-006 | anti-CD73 |
| MK-4280 | anti-LAG3 |
| Sym-022 | anti-LAG3 |
| Ieramilimab | anti-LAG3 |
| BI-754111 | anti-LAG3 |
| MK-5890 | anti-CD27 |
| Varlilumab | anti-CD27 |
| Cusatuzumab | anti-CD70 |
| Vorsetuzumab | anti-CD70 |
| Urelumab | anti-4-1BB (agonist) |
| Utomilumab | anti-4-1BB (agonist) |
| ATOR-1017 | anti-4-1BB (agonist) |
| RO-7122290 | anti-4-1BB (agonist) |
| INCAGN-01876 | anti-GITR (agonist) |
| BMS-986156 | anti-GITR (agonist) |
| TRX-518 | anti-GITR (agonist) |
| GWN-323 | anti-GITR (agonist) |
| BMS-986178 | anti-OX40 (agonist) |
| INCAGN-1949 | anti-OX40 (agonist) |
| GSK-3174998 | anti-OX40 (agonist) |
| BGB-A-445 | anti-OX40 (agonist) |
| BI-765063 | anti- SIRP-alpha (CD47) |
| ALX-148 | SIRP-alpha (CD47) |
| IPH-52 | anti-CD39 |
| TTX-030 | anti-CD39 |
| BAY-1905254 | anti-ILDR2 |
| Onvatilimab | anti-VISTA |
| K01401-020 | anti-VISTA |
| JS-004 | anti-BTLA |
| FPA-150 | anti-VTCN1 |

In some embodiments, the checkpoint inhibitor comprises a PD-1 inhibitor. In some embodiments, the checkpoint inhibitor comprises a PDL-1 inhibitor. In some embodiments, the checkpoint inhibitor comprises a CTLA-4 inhibitor. In some embodiments, the checkpoint inhibitor comprises a TIGIT inhibitor. In some embodiments, the checkpoint inhibitor comprises a TIM-3 inhibitor. In some embodiments, the checkpoint inhibitor comprises a B7-H3 inhibitor. In some embodiments, the checkpoint inhibitor comprises a CD73 inhibitor. In some embodiments, the checkpoint inhibitor comprises a LAG3 inhibitor. In some embodiments, the checkpoint inhibitor comprises a CD27 inhibitor. In some embodiments, the checkpoint inhibitor comprises a CD70 inhibitor. In some embodiments, the checkpoint inhibitor comprises a 4-1BB agonist binder. In some embodiments, the checkpoint inhibitor comprises a GITR agonist binder. In some embodiments, the checkpoint inhibitor comprises a OX40 agonist binder. In some embodiments, the checkpoint inhibitor comprises a SIRP-alpha (CD47) inhibitor. In some embodiments, the checkpoint inhibitor comprises a CD39 inhibitor. In some embodiments, the checkpoint inhibitor comprises a ILDR2 inhibitor. In some embodiments, the checkpoint inhibitor comprises a VISTA inhibitor. In some embodiments, the checkpoint inhibitor comprises a BTLA inhibitor. In some embodiments, the checkpoint inhibitor comprises a VTCN-1 inhibitor.

In some embodiments, the checkpoint inhibitor comprises a combination of a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-1BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, a VTCN-1 inhibitor. In some embodiments, the checkpoint inhibitor comprises at least two checkpoint inhibitors selected from of a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-1BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, and a VTCN-1 inhibitor.

In some embodiments, a pharmaceutical composition for use in a combination therapy, as described herein, comprises an effective amount of a checkpoint inhibitor, as described herein, and a pharmaceutically acceptable carrier.

In some embodiments, a composition disclosed herein comprises a checkpoint inhibitor and a pharmaceutically acceptable carrier. In some embodiments, a composition disclosed herein comprises a combination of checkpoint inhibitors, and a pharmaceutically acceptable carrier. In some embodiments, a composition comprises a checkpoint inhibitor comprising a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-1BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, a VTCN-1 inhibitor. In some embodiments, the checkpoint inhibitor comprises at least two checkpoint inhibitors selected from of a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, or a VTCN-1 inhibitor, and a pharmaceutically acceptable carrier. In some embodiments, a composition comprises at least two checkpoint inhibitors selected from a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-1BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, a VTCN-1 inhibitor. In some embodiments, the checkpoint inhibitor comprises at least two checkpoint inhibitors selected from of a PD-1 inhibitor, a PDL-1 inhibitor, a CTLA-4 inhibitor, a TIGIT inhibitor, a TIM-3 inhibitor, a B7-H3 inhibitor, a CD73 inhibitor, a LAG3 inhibitor, a CD27 inhibitor, a CD70 inhibitor, a 4-1BB inhibitor, a GITR inhibitor, a OX40 inhibitor, a SIRP-alpha (CD47) inhibitor, a CD39 inhibitor, a ILDR2 inhibitor, a VISTA inhibitor, a BTLA inhibitor, and a VTCN-1 inhibitor, and a pharmaceutically acceptable carrier.

In certain embodiments, when more than one checkpoint inhibitor is used in a therapeutic method described herein, each checkpoint inhibitor is comprised within a separate composition. In certain embodiments, when more than one checkpoint inhibitor is used in a therapeutic method described herein, checkpoint inhibitor may be comprised within the same composition.

In some embodiments, a combination therapy comprises use of an anti-IL-2 antibody or composition thereof as described herein, and a checkpoint inhibitor or a composition thereof. In some embodiments, a combination therapy comprises use of an anti-IL-2 antibody or composition thereof and IL-2 as described herein, and a checkpoint inhibitor or a composition thereof. In some embodiments, a combination therapy comprises use of an anti-IL-2 antibody or composition thereof complexed with IL-2 as described herein, and a checkpoint inhibitor or a composition thereof.

In some embodiments, a combination therapy comprises use of an anti-IL-2 antibody or composition thereof as described herein, and at least two checkpoint inhibitors or a composition thereof. In some embodiments, a combination therapy comprises use of an anti-IL-2 antibody or composition thereof and IL-2 as described herein, and at least two checkpoint inhibitors or a composition thereof. In some embodiments, a combination therapy comprises use of an anti-IL-2 antibody or composition thereof complexed with IL-2 as described herein, and at least two checkpoint inhibitors or a composition thereof.

In some embodiments, a combination therapy comprises a second composition comprising one or more checkpoint inhibitors, as described herein.

In some embodiments of a combination therapy, an anti-IL-2 antibody and IL-2 are comprised in the same composition as a checkpoint inhibitor. In some embodiments, an anti-IL-2 antibody and IL-2 are comprised in different compositions from each other and from a checkpoint inhibitor.

In some embodiments of a combination therapy, the order of administration of an anti-IL-2 antibody or a composition thereof and a checkpoint inhibitor or a composition thereof, may be in any order. In some embodiments of a combination therapy, the order of administration of an anti-IL-2 antibody or a composition thereof, IL-2 or a composition thereof, and a checkpoint inhibitor or a composition thereof, may be in any order. For example, but not limited to the anti-IL-2 antibody may be administered prior to, concurrent with, or following administration of the checkpoint inhibitor. Similarly, a combination of an anti-IL-2 antibody and IL-2 may be administered prior to, concurrent with, or following administration of the checkpoint inhibitor. In some embodiments, the anti-IL-2 antibody may be administered prior to, concurrent with, or following administration of the at least two checkpoint inhibitors. Similarly, a combination of an anti-IL-2 antibody and IL-2 may be administered prior to, concurrent with, or following administration of the at least two checkpoint inhibitors.

In some embodiments, administration of a combination therapy with a checkpoint inhibitor comprises concurrent administration of an anti-IL-2 antibody or a composition thereof and the checkpoint inhibitor. In some embodiments, administration of a combination therapy with a checkpoint inhibitor comprises concurrent administration of an anti-IL-2 antibody and IL-2, or composition(s) thereof and the checkpoint inhibitor. In some embodiments, administration of a combination therapy with a checkpoint inhibitor comprises prior administration of an anti-IL-2 antibody or a composition thereof before the checkpoint inhibitor. In some embodiments, administration of a combination therapy with a checkpoint inhibitor comprises prior administration of an anti-IL-2 antibody and IL-2, or composition(s) thereof before the checkpoint inhibitor. In some embodiments, administration of a combination therapy with a checkpoint inhibitor comprises later administration of an anti-IL-2 antibody or a composition thereof following administration of the checkpoint inhibitor. In some embodiments, administration of a combination therapy with a checkpoint inhibitor comprises later administration of an anti-IL-2 antibody and IL-2, or composition(s) thereof following the administration of the checkpoint inhibitor.

In some embodiments, a combination therapy comprises use of a checkpoint inhibitor and an anti-IL-2 antibody comprising a heavy chain variable region having the sequence of one of SEQ ID NOs:10, 12, 14, 16, 18, 20, 22, 24, 26, or 36. In some embodiments, a combination therapy comprises use of a checkpoint inhibitor and an anti-IL-2 antibody comprising alight chain variable region having the sequence of one of SEQ ID NOs:11, 13, 15, 17, 19, 21, 23, 25, 27, or 37. In some embodiments, a combination therapy comprises use of a checkpoint inhibitor and an anti-IL-2 antibody comprising a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27, or SEQ ID NOs: 36 and 37. In some embodiments, a combination therapy comprises use of a checkpoint inhibitor and an anti-IL-2 antibody comprising a heavy chain variable domain comprising CDR1, CDR2 and CDR3 regions comprising amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively. In some embodiments, a combination therapy comprises use of a checkpoint inhibitor and an anti-IL-2 antibody comprising a light chain variable domain comprising CDR1, CDR2 and CDR3 regions comprising amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67, respectively. In some embodiments, a combination therapy comprises use of a checkpoint inhibitor and an anti-IL-2 antibody comprising a heavy chain variable domain comprising CDR1, CDR2 and CDR3 regions comprising amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64, respectively, and a light chain variable domain comprising CDR1, CDR2, and CDR3 regions comprising amino acid sequences of SEQ ID NOs:41-43 respectively, SEQ ID NOs:47-49 respectively; SEQ ID NOs:53-55 respectively; SEQ ID NOs:59-61 respectively; or SEQ ID NOs:65-67, respectively.

In some embodiments, a combination therapy comprises use of a checkpoint inhibitor and an anti-IL-2 antibody comprising any of clones BDG 17.014, BDG 17.023, BDG 17.038, BDG 17.043, BDG 17.053, BDG 17.054, BDG 17.066, BDG 17.067, and BDG 17.069. In some embodiments, a combination therapy comprises use of a checkpoint inhibitor and an anti-IL-2 antibody comprising anti-IL-2 clone BDG 17.014. In some embodiments, a combination therapy comprises use of a checkpoint inhibitor and an anti-IL-2 antibody comprising anti-IL-2 clone BDG 17.023. In some embodiments, a combination therapy comprises use of a checkpoint inhibitor and an anti-IL-2 antibody comprising anti-IL-2 clone BDG 17.038. In some embodiments, a combination therapy comprises use of a checkpoint inhibitor and an anti-IL-2 antibody comprising anti-IL-2 clone BDG 17.043. In some embodiments, a combination therapy comprises use of a checkpoint inhibitor and an anti-IL-2 antibody comprising anti-IL-2 clone BDG 17.053. In some embodiments, a combination therapy comprises use of a checkpoint inhibitor and an anti-IL-2 antibody comprising anti-IL-2 clone BDG 17.054. In some embodiments, a combination therapy comprises use of a checkpoint inhibitor and an anti-IL-2 antibody comprising anti-IL-2 clone BDG 17.066. In some embodiments, a combination therapy comprises use of a checkpoint inhibitor and an anti-IL-2 antibody comprising anti-IL-2 clone BDG 17.067. In some embodiments, a combination therapy comprises use of a checkpoint inhibitor and an anti-IL-2 antibody comprising anti-IL-2 clone BDG 17.069.

Formulations

Pharmaceutical compositions disclosed herein comprising anti-IL-2 antibodies, or a combination of anti-IL-2 antibodies and IL-2, or checkpoint inhibitors, can be conveniently provided as sterile liquid preparations, e.g., isotonic aqueous solutions, suspensions, emulsions, dispersions, or viscous compositions, which may be buffered to a selected pH, Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the anti-IL-2 antibodies, or a combination of anti-IL-2 antibodies and IL-2, or checkpoint inhibitors, described herein and utilized in practicing the methods disclosed herein, in the required amount of the appropriate solvent with various amounts of the other ingredients, as desired. Such formulations may be in admixture with a suitable carrier, diluent, or excipient such as sterile water, physiological saline, glucose, dextrose, or the like. The formulations can also be lyophilized. The formulations can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the formulations, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

In certain embodiments, the terms "pharmaceutical composition", "composition", and "formulation" may be used interchangeably having the same meanings and qualities.

The compositions or formulations described herein can be isotonic, i.e., they can have the same osmotic pressure as blood and lacrimal fluid. The desired isotonicity of the compositions as disclosed herein may be accomplished using sodium chloride, or other pharmaceutically acceptable agents such as dextrose, boric acid, sodium tartrate, propylene glycol or other inorganic or organic solutes. Sodium chloride may be preferred particularly for buffers containing sodium ions.

Viscosity of the compositions, if desired, can be maintained at the selected level using a pharmaceutically acceptable thickening agent. Methylcellulose may be preferred because it is readily and economically available and is easy to work with.

Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

In some embodiments, a composition is formulated to beat a pH between about pH 5.0-6.0. In some embodiments, a composition is formulated to be at a pH between about pH 5.0-7.0. In some embodiments, a composition is formulated to be at a pH between about pH 5.0-6.5. In some embodiments, a composition is formulated to be at a pH between about pH 5.0-5.5. In some embodiments, a composition is formulated to be at a pH between about pH 5.5-6.0. In some embodiments, a composition is formulated to be at a pH between about pH 5.5-6.5. In some embodiments, a composition is formulated to be at a pH between about pH 5.0. In some embodiments, a composition is formulated to be at a pH between about pH 5.5. In some embodiments, a composition is formulated to be at a pH between about pH 6.0. In some embodiments, a composition is formulated to be at a pH between about pH 6.5

In some embodiments, a composition is formulated to be at a pH between about pH 5.0-6.0 and comprises a buffer. In seine embodiments, the buffer comprises a pharmaceutically acceptable buffer. In some embodiments, the buffer comprises a histidine buffer or a citrate buffer. In some embodiments, the buffer comprises a histidine buffer. In some embodiments, the buffer comprises a citrate buffer. I In some embodiments, a composition is formulated to be at a pH between about pH 5.0-6.0 and comprises a buffer selected from a histidine buffer and a citrate buffer. In some embodiments, a composition is formulated to be at a pH between about pH 5.0-6.0 and comprises a histidine buffer. In some embodiments, a composition is formulated to be at a pH between about pH 5.0-6.0 and comprises a citrate buffer.

In some embodiments, a composition further comprises at least one of sucrose, methionine, or PS80, or any combination thereof. In some embodiments, a composition further comprises sucrose. In some embodiments, a composition further comprises methionine. In some embodiments, a composition further comprises PS80.

In some embodiments, a composition comprises an anti-IL-2 antibody as disclosed herein and is formulated to be at a pH between about pH 5.0-6.0 and comprises a buffer selected from a histidine buffer and a citrate buffer. In some embodiments, the composition further comprises IL-2.

Those skilled in the art will recognize that the components of the compositions or formulations should be selected to be chemically inert and will not affect the viability or efficacy of the early apoptotic cell populations as described herein, for use in the methods disclosed herein. This will present no problem to those skilled in chemical and pharmaceutical principles, or problems can be readily avoided by reference to standard texts or by simple experiments (not involving undue experimentation), from this disclosure and the documents cited herein.

Methods of Use

In one embodiment, the present disclosure provides a method of producing a heavy chain variable region of an anti-IL-2 antibody, the method comprises the step of culturing host cells under conditions conducive to expressing a vector encoding for the heavy chain variable region, thereby producing the heavy chain variable region of the anti-IL-2 antibody.

In one embodiment, the present disclosure provides a method of producing a light chain variable region of an anti-IL-2 antibody, the method comprises the step of culturing host cells under conditions conducive to expressing a vector encoding for the light chain variable region, thereby producing the light chain variable region of the anti-IL-2 antibody.

The VH and/or VL polypeptides disclosed herein may be used in therapeutic methods. In one embodiment, the polypeptides of the present disclosure can be used as immunotherapeutic agents, for example, for differential activation of immune cells as described herein. The present polypeptides can be administered to a subject directly, or by administering to the subject a nucleic acid sequence encoding the polypeptides, such nucleic acid sequence may be carried by a vector.

The exact amount of the present polypeptides or compositions thereof required to elicit the desired effects will vary from subject to subject, depending on the species, age, gender, weight, and general condition of the subject, the particular polypeptides, the route of administration, and whether other drugs are included in the regimen. Thus, it is not possible to specify an exact amount for every composition. However, an appropriate amount can be determined by one of ordinary skill in the art using routine experimentation. Dosages can vary, and the polypeptides can be administered in one or more (e.g., two or more, three or more, four or more, or five or more) doses daily, for one or more days. Guidance in selecting appropriate doses for antibodies can be readily found in the literature.

In some embodiments of a methods of use of an anti-IL-2 antibody described herein, a subject comprises a mammalian subject. In some embodiments, a subject comprises a human subject. In some embodiments, a subject suffers from immune deficiency problems. Treatment of an immune deficient subject would in some embodiments, comprise a prophylactic treatment.

In one embodiment, the present disclosure provides a method of promoting differential growth of immune cells in a subject, comprising the step of preparing a composition comprising an anti-IL-2 antibody disclosed herein, and administering the composition to the subject, thereby promoting differential growth of immune cells in the subject. In one embodiment, the present disclosure provides a method of promoting differential growth of immune cells in a subject, comprising the step of preparing a composition comprising IL-2 and the anti-IL-2 antibody disclosed herein, and administering the composition to the subject, thereby promoting differential growth of immune cells in the subject. In one embodiment, the subject can be an animal or a human. In one embodiment, the immune cells can be CD8$^+$ cells or NK cells.

In some embodiments, disclosed herein is a method of treating a disease or a condition in a subject, comprising the step of administering to the subject a composition comprising an anti-IL-2 antibody as disclosed herein, wherein said antibody promotes differential growth of subsets of immune cells and decreases undesirable effects caused by IL-2, thereby treating said disease or condition in said subject. In some embodiments, a method of treating a disease disclosed here comprises use of a composition comprising an anti-IL-2 antibody and IL-2, or an anti-IL-2 antibody complexed with IL-2. In some embodiments, a method of treating a disease comprises treating a viral infection, a bacterial infection, or a cancer. In some embodiments, a method of treating a condition comprises treating a weak immune system and the treatment prophylactically boosts the immune system.

In some embodiments of a method of treating a disease or a condition, the condition comprises a genetic predisposition that increases likelihood of cancer in said subject. In some embodiments, the genetic predisposition comprises a change in expression or activity of a gene product. In some embodiments, a genetic predisposition that increases the likelihood of cancer comprises a mutation in a tumor suppressor gene or a mismatch repair (MMR) gene, or a combination thereof.

Many hereditary cancers are known in the art non-limiting examples include but are not limited to Hereditary Breast and Ovarian Cancer (HBOC) syndrome, Lynch syndrome (hereditary non-polyposis colorectal cancer), and Li-Fraumeni syndrome.

In some embodiments, the genetic predisposition increases the likelihood of HBOC. HBOC is associated with mutations in the BRAC1 and BRAC2 genes. HBOC is associated with a number of different cancers not just breast cancer, including but not limited to fallopian tube cancer, primary peritoneal cancer, male breast cancer, pancreatic cancer, and prostate cancer. In some embodiments, the genetic predisposition increases the likelihood of any of breast cancer, ovarian cancer, fallopian tube cancer, primary peritoneal cancer, male breast cancer, pancreatic cancer, or prostate cancer, or a combination thereof.

In some embodiments, the genetic predisposition increases the likelihood of hereditary non-polyposis colorectal cancer (HNPCC). HNPCC is associated with mutation in genes including but not limited to MLH1, MSH2, MSH6, PMS1, and PMS2. HNPCC is associated with high risk of developing endometrial cancer, as well as cancers of the ovary, stomach, small intestine, pancreas, kidney, brain, ureters, and bile duct. In some embodiments, the genetic predisposition increases the likelihood of any of hereditary non-polyposis colorectal cancer, cancer of the ovary, stomach cancer, cancer of the small intestine, pancreatic cancer, kidney cancer, brain cancer, cancer of ureters, and cancer of a bile duct.

In some embodiments, the genetic predisposition increases the likelihood of Li-Fraumeni syndrome. Li-Fraumeni syndrome in genes including but not limited to TP53 and CHEK2, or a combination thereof. Li-Fraumeni syndrome is associated with cancers, including sarcoma, osteosarcoma, soft-tissue sarcomas, leukemia, brain (central nervous system) cancers, cancer of the adrenal cortex and breast cancer, or combinations thereof. In some embodiments, the genetic predisposition increases the likelihood of any of a sarcoma, osteosarcoma, soft-tissue sarcomas, leukemia, brain (central nervous system) cancers, cancer of the adrenal cortex and breast cancer, or combinations thereof.

In some embodiments, a condition being treated in a subject, comprises treating a subject with a genetic predisposition comprising a change in expression or activity of a gene product, said gene comprising Breast Cancer gene 1 (BRCA1), Breast Cancer gene 2 (BRAC2), MutL Homolog 1 (MLH1), mutS homolog 2 (MSH2), MutS Homolog 6 (MSH6), PMS1 homolog 1, mismatch repair system component (PMS1), PMS1 homolog 2, mismatch repair system component (PMS2), tumor protein p53 (TP53), or checkpoint kinase 2 (CHEK2), or a combination thereof.

As described herein, a complex of IL-2 and the anti-IL-2 antibodies disclosed exhibited pronounced effect in inducing proliferation of memory phenotype effector T cells (MP) CD8$^+$ cells and NK cells, while there was much smaller effect on CD4$^+$ Tregs. Thus, the engineered anti-IL-2 antibodies disclosed herein would be useful in adjusting immune cell populations and inducing differential expansion of certain immune effector cells. In one embodiment, such differential expansion of immune effect cells would result in robust activation of the immune system and could be useful for treatment of tumors. In some embodiments, treatment comprising treating a solid tumor. In some embodiments, treatment comprises treating a non-solid tumor. In some embodiments, treating comprising treating solid and or non-solid tumors, such as but not limited to melanoma, renal cell carcinoma, small cell lung cancer or other cancer conditions. In another embodiment, the method disclosed herein would be useful for treatment of viral infection or bacterial infection. In another embodiment, the method disclosed herein would be useful for treating or preventing a condition caused by IL-2 binding to endothelial CD25 expressing cells, e.g., pulmonary edema, or IL-2-induced vascular leakage.

In some embodiments of a methods of treating a disease or condition, the immune cells showing differential growth comprise one or more of naive T cells, memory T cells, CD8+ T cells, NK cells, or Natural Killer T cells. In some embodiments of a methods of treating a disease or condition, the undesirable effect caused by IL-2 comprises one or more of activation of regulatory T cells, apoptosis of CD25+ T effector cells, IL-2 induced pulmonary edema, IL-2 induced pneumonia, or IL-2-induced vascular leakage. In some embodiments of a method of treating a disease or condition, an anti-IL-2 antibody disclosed herein inhibits IL-2 binding to CD25.

In some embodiments, treatment of cancer comprises maintenance treatments. In some embodiments, maintenance treatments are administered to maintain the absence of a cancer or tumor. In some embodiments, maintenance treatments are administered to maintain lack of metastasis of a cancer or tumor. In some embodiments, maintenance treatments are administered to inhibit metastasis of a cancer or tumor. In some embodiments, maintenance treatments are administered to maintain lack of growth of a cancer or tumor. In some embodiments, maintenance treatments are administered to inhibit growth of a cancer or tumor.

In some embodiments, treatment of cancer comprises prophylactic treatment, for example but not limited to a subject harboring a genetic marker or markers with a high risk of developing cancer. In some embodiments, the genetic marker comprises a mutation in the BRCA1 gene.

In some embodiments of methods of promoting differential growth of immune cells in a subject, comprising the step of preparing and administering a composition comprising an anti-IL-2 antibody disclosed herein.

In some embodiments of methods of promoting differential growth of immune cells in a subject, comprising the step of preparing and administering a composition comprising IL-2 and an anti-IL-2 antibody disclosed herein, the administration of a combination of an anti-IL-2 antibody and IL-2, or composition(s) thereof are concurrent. In some embodiments of methods of promoting differential growth of immune cells in a subject, comprising the step of preparing and administering a composition comprising IL-2 and an anti-IL-2 antibody, the administration of an anti-IL-2 antibody and IL-2, or composition(s) thereof comprises administration of an anti-IL-2 antibody or a composition thereof, prior to the IL-2 or a composition thereof. In some embodiments of methods of promoting differential growth of immune cells in a subject, comprising the step of preparing and administering a composition comprising IL-2 and an anti-IL-2 antibody, the administration of an anti-IL-2 antibody and IL-2, or composition(s) thereof comprises administration of an anti-IL-2 antibody or a composition thereof, following administration of the IL-2 or a composition thereof.

In some embodiments, the present disclosure provides a method of treating a subject with a disease or a condition through induction of differential growth of immune cells. In one embodiment, the disease can be viral infection, bacterial infection, or cancer. In one embodiment, the condition can be IL-2 induced pulmonary edema, or IL-2-induced vascular leakage. The method comprises the step of:
 (a) preparing a composition comprising an anti-IL-2 antibody as disclosed herein; and
 (b) administering the composition from (a) to the subject, thereby treating the subject through differential growth of immune cells in the subject. In certain embodiments, any of the engineered anti-IL-2 antibodies disclosed herein may be used in the method of treatment as described.

In some embodiments, the present disclosure provides a method of treating a subject with a disease or a condition through induction of differential growth of immune cells. In one embodiment, the disease can be viral infection, bacterial infection, or cancer. In one embodiment, the condition can be IL-2 induced pulmonary edema, or IL-2-induced vascular leakage. The method comprises the step of:
 (a) preparing a composition comprising IL-2 and an anti-IL-2 antibody as disclosed herein; and
 (b) administering the composition from (a) to the subject, thereby treating the subject through differential growth of immune cells in the subject. In addition to facilitate expansion of subsets of immune effector cells, the antibody/IL-2 complex would also decrease undesirable effects caused by IL-2 (e.g., IL-2 induced pulmonary edema, or IL-2-induced vascular leakage). In one embodiment, the subject can be an animal or a human. In certain embodiments, any of the engineered anti-IL-2 antibodies disclosed herein may be used in the method of treatment as described.

In one embodiment, the present disclosure provides a method of treating a disease or a condition in a subject (e.g., an animal or a human), comprising the step of administering to the subject a composition comprising anti-IL-2 antibodies, wherein the antibodies facilitate expansion of subsets of immune cells and decrease undesirable effects caused by IL-2, thereby treating the disease or condition in the subject. In some embodiments of a method of treating a disease or a condition in a subject, comprising the step of preparing and administering a composition comprising an anti-IL-2 antibody disclosed herein, and administering the composition comprising the anti-IL-2 antibody. In one embodiment, the composition comprises IL-2 and the anti-IL-2 antibodies as disclosed herein, or the composition comprises anti-IL-2 antibodies that are complexed with IL-2.

In some embodiments of a method of treating a disease or a condition in a subject, comprising the step of preparing and administering a composition comprising IL-2 and an anti-IL-2 antibody disclosed herein, the administration of a combination of an anti-IL-2 antibody and IL-2, or composition(s) thereof are concurrent. In some embodiments of a method of treating a disease or a condition in a subject, comprising the step of preparing and administering a composition comprising IL-2 and an anti-IL-2 antibody, the administration of an anti-IL-2 antibody and IL-2, or composition(s) thereof comprises administration of an anti-IL-2 antibody or a composition thereof, prior to the IL-2 or a composition thereof. In some embodiments of a method of treating a disease or a condition in a subject, comprising the step of preparing and administering a composition comprising IL-2 and an anti-IL-2 antibody, the administration of an anti-IL-2 antibody and IL-2, or composition(s) thereof comprises administration of an anti-IL-2 antibody or a composition thereof, following administration of the IL-2 or a composition thereof.

In one embodiment, the method of treatment would be effective for treating condition such as IL-2 induced pulmonary edema, or IL-2-induced vascular leakage. In another embodiment, the method of treatment would be effective for treating pulmonary edema (mild or chronic) resulted from viral or bacterial infections.

In one embodiment, the disease can be viral infection, bacterial infection, cancer, autoimmune disease or immune disorder. In one embodiment, the disease can be upper respiratory viral infections, early-stage lung infections, or late-stage lung infections. A number of diseases and cancer are known to be caused by viruses. Examples of disease-causing viruses include, but are not limited to, norovirus; rotavirus; hepatitis virus A, B, C, D, or E; rabies virus, West Nile virus, enterovirus, echovirus, coxsackievirus, herpes simplex virus (HSV), HSV-2, varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enterovirus D68, severe acute respiratory syndrome (SARS) coronavirus, Middle East respiratory syndrome coronavirus, SARS coronavirus 2, Epstein-Barr virus, influenza virus, respiratory syncytial virus, polyoma viruses (such as JC virus, BK virus), Ebola virus, Dengue virus, or any combination thereof. In one embodiment, the viral infection is caused by SARS CoV-2. In another embodiment, the cancer can be, but is not limited to, melanoma or renal cell carcinoma.

In one embodiment, the immune cells that are expanded by treatment with the anti-IL-2 antibodies comprise one or more of naive T cells, memory T cells, $CD8^+$ T cells, NK cells, and Natural Killer T cells. In one embodiment, treatment with the anti-IL-2 antibodies would decrease one or more undesirable effects caused by IL-2 such as activation of regulatory T cells, apoptosis of CD25+ T effector cells, pulmonary edema, pneumonia, and IL-2-induced vascular leakage.

In one embodiment, the anti-IL-2 antibodies administered in the above method are engineered or modified anti-IL-2 antibodies that can inhibit IL-2 binding to CD25. In some embodiments, the engineered or modified anti-IL-2 antibodies comprise a heavy chain variable region having the sequence of one of SEQ ID NOs:10, 12, 14, 16, 18, 20, 22, 24, 26, or 36. In some embodiments, the engineered or modified anti-IL-2 antibodies comprise a light chain variable region having the sequence of one of SEQ ID NOs:11, 13, 15, 17, 19, 21, 23, 25, 27, or 37. In some embodiments, the engineered or modified anti-IL-2 antibodies comprise a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs: 36 and 37.

In another embodiment, the engineered or modified anti-IL-2 antibodies comprise a heavy chain variable region having complementarity determining region (CDR) 1, CDR2 and CDR3. In one embodiment, the heavy chain CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively.

In another embodiment, the engineered or modified anti-IL-2 antibodies comprise a light chain variable region having complementarity determining region (CDR) 1, CDR2 and CDR3. In one embodiment, the light chain CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively.

In some embodiments, the engineered anti-IL-2 antibody can be an IgG, IgA, IgM, IgE, IgD, a Fv, a scFv, a Fab, or a F(ab')$_2$. The IgG can be of the subclass of IgG1, IgG2, IgG3, or IgG4. In some embodiments, the engineered antibody can be part of a minibody, a diabody, a triabody, a nanobody, or a single domain antibody.

In some embodiments, a polynucleotide sequence encoding an engineered anti-IL-2 antibody is used in a method of treating a subject with a disease or condition as described herein, wherein the polynucleotide encodes an antibody comprising a heavy chain variable region having the amino acid sequence of one of SEQ ID NOs:10, 12, 14, 16, 18, 20, 22, 24, 26, or 36 In some embodiments, a polynucleotide sequence encoding an engineered anti-IL-2 antibody is used in a method of treating a subject with a disease or condition as described herein, wherein the polynucleotide encodes an antibody comprising a light chain variable region having the amino acid sequence of one of SEQ ID NOs:11, 13, 15, 17, 19, 21, 23, 25, 27, or 37. In some embodiments, a polynucleotide sequence encoding an engineered anti-IL-2 antibody is used in a method of treating a subject with a disease or condition as described herein, wherein the polynucleotide encodes an antibody comprising a heavy chain variable region and a light chain variable region having the amino acid sequences of one of: SEQ ID NOs:10 and 11; SEQ ID NOs:12 and 13. SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs: 36 and 37.

In some embodiments of a method of using a polynucleotide to treat a disease or condition as described above, the polynucleotide encodes an engineered anti-IL-2 antibody that can be an IgG, IgA, IgM, IgE, IgD, a Fv, a scFv, a Fab, or a F(ab')$_2$. The IgG can be of the subclass of IgG1, IgG2, IgG3, or IgG4. In some embodiments, the polynucleotide encodes an engineered antibody which is part of a minibody, a diabody, a triabody, a nanobody, or a single domain antibody.

In some embodiments a polynucleotide sequence encoding an engineered anti-IL-2 antibody is used in a method of treating a subject with a disease or condition as described herein, wherein the polynucleotide sequence comprises the sequence of one of SEQ ID NOs: 1, 2, 3, 4, 5, 31, 32, 33, 34, or 35.

In some embodiments of a method of treating a disease or condition as described herein, the immune effector cells that are activated by the treatment are CD8+ cells or NK cells. In one embodiment, the anti-IL-2 antibodies disclosed herein, or a complex of IL-2 and the anti-IL-2 antibodies disclosed herein, exhibits pronounced effect in inducing proliferation of MP CD8+ cells and NK cells, while there was much smaller effect on CD4+ Tregs. In certain embodiments, there is no effect on CD4+Tregs.

In certain embodiments, methods of use of an anti-IL-2 antibody disclosed herein provide a pro-stimulatory effect. A skilled artisan would appreciate that use of the anti-IL-2 antibodies described and exemplified herein e.g., Example 1, clearly demonstrate a pro-stimulatory effect as opposed to an anti-stimulatory or pro-regulatory effect.

In some embodiments, use of an engineered or modified anti-IL-2 antibody comprising a heavy chain variable region having the sequence of one of SEQ ID NOs:10, 12, 14, 16, 18, 20, 22, 24, 26, or 36, provides a pro-stimulatory immune effect in a subject in need thereof. In some embodiments, use of an engineered or modified anti-IL-2 antibody comprising a light chain variable region having the sequence of one of SEQ ID NOs:11, 13, 15, 17, 19, 21, 23, 25, 27, or 37, provides a pro-stimulatory immune effect in a subject in need thereof. In some embodiments, use of an engineered or modified anti-IL-2 antibody comprising a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs: 36 and 37, provides a pro-stimulatory immune effect in a subject in need thereof. In some embodiments, said use comprises the anti-IL-2 antibody. In some embodiments, said use comprises the anti-IL-2 antibody and an IL-2. In some embodiments, use comprises a complex of an anti-IL-2 antibody with an IL-2.

In some embodiments, use of an engineered or modified anti-IL-2 antibody comprising a heavy chain variable region having the sequence of one of SEQ ID NOs:10, 12, 14, 16, 18, 20, 22, 24, 26, or 36, provides a pro-stimulatory immune effect in a subject in need thereof as opposed to an anti-stimulatory or pro-regulatory effect. In some embodiments, use of an engineered or modified anti-IL-2 antibody comprising a light chain variable region having the sequence of one of SEQ ID NOs:11, 13, 15, 17, 19, 21, 23, 25, 27, or 37, provides a pro-stimulatory immune effect in a subject in need thereof as opposed to an anti-stimulatory or pro-regulatory effect. In some embodiments, use of an engineered or modified anti-IL-2 antibody comprising a heavy chain variable region and a light chain variable region having the sequences of one of: SEQ ID NOs:10 and 11; SEQ ID NOs:12 and 13, SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs: 36 and 37, provides a pro-stimulatory immune effect in a subject in need thereof as opposed to an anti-stimulatory or pro-regulatory effect. In some embodiments, said use comprises the anti-IL-2 antibody. In some embodiments, said use comprises the anti-IL-2 antibody and an IL-2. In some embodiments, use comprises a complex of an anti-IL-2 antibody with an IL-2.

In some embodiments, use of an anti-IL-2 antibody comprising a heavy chain variable region comprising heavy chain CDR1, CDR2 and CDR3 as set forth in amino acid sequences SEQ ID NOs:38-40 respectively; SEQ ID NOs: 4-46 respectively, SEQ ID NOs:50-52 respectively; SEQ ID NOs:56-58 respectively; or SEQ ID NOs:62-64 respectively, provides a pro-stimulatory immune effect in a subject in need thereof. In some embodiments, use of an anti-IL-2 antibody comprising a light chain comprising light chain CDR1, CDR2 and CDR3 as set forth in amino acid sequences SEQ ID NOs:41-43 respectively; SEQ ID NOs: 47-49 respectively; SEQ ID NOs:53-55 respectively; SEQ ID NOs:59-61 respectively; or SEQ ID NOs:65-67 respectively, provides a pro-stimulatory immune effect in a subject in need thereof. In some embodiments, use of an anti-IL-2 antibody comprising a heavy chain variable region comprising heavy chain CDR1, CDR2 and CDR3 as set forth in amino acid sequences SEQ ID NOs:38-40 respectively; SEQ ID NOs:44-46 respectively; SEQ ID NOs:50-52 respectively; SEQ ID NOs:56-58 respectively; or SEQ ID NOs: 6264 respectively, and a light chain comprising light chain CDR1, CDR2 and CDR3 as set forth in amino acid sequences SEQ ID NOs:41-43 respectively; SEQ ID NOs: 4749 respectively; SEQ ID NOs:53-55 respectively; SEQ ID NOs:59-61 respectively; or SEQ ID NOs:65-67 respectively, provides a pro-stimulatory immune effect in a subject in need thereof. In some embodiments, said use comprises the anti-IL-2 antibody. In some embodiments, said use comprises the anti-IL-2 antibody and an IL-2. In some embodiments, use comprises a complex of an anti-IL-2 antibody with an IL-2.

In some embodiments, use of an anti-IL-2 antibody comprising a heavy chain variable region comprising heavy chain CDR1, CDR2 and CDR3 as set forth in amino acid sequences SEQ ID NOs:38-40 respectively; SEQ ID NOs: 44-46 respectively; SEQ ID NOs:50-52 respectively; SEQ ID NOs:56-58 respectively; or SEQ ID NOs:62-64 respectively, provides a pro-stimulatory immune effect in a subject in need thereof as opposed to an anti-stimulatory or pro-regulatory effect. In some embodiments, use of an anti-IL-2 antibody comprising a light chain comprising light chain CDR1, CDR2 and CDR3 as set forth in amino acid sequences SEQ ID NOs:41-43 respectively; SEQ ID NOs: 47-49 respectively; SEQ ID NOs:53-55 respectively; SEQ ID NOs:59-61 respectively; or SEQ ID NOs:65-67 respectively, provides a pro-stimulatory immune effect in a subject in need thereof as opposed to an anti-stimulatory or pro-regulatory effect. In some embodiments, use of an anti-IL-2 antibody comprising a heavy chain variable region comprising heavy chain CDR1, CDR2 and CDR3 as set forth in amino acid sequences SEQ ID NOs:38-40 respectively; SEQ ID NOs:44-46 respectively; SEQ ID NOs:50-52 respectively; SEQ ID NOs: 62-64 respectively, and a light chain comprising light chain CDR1, CDR2 and CDR3 as set forth in amino acid sequences SEQ ID NOs:41-43 respectively; SEQ ID NOs: 47-49 respectively; SEQ ID NOs:53-55 respectively; SEQ ID NOs:59-61 respectively; or SEQ ID NOs:65-67 respectively, provides a pro-stimulatory immune effect in a subject in need thereof, as opposed to an anti-stimulatory or pro-regulatory effect. In some embodiments, said use comprises the anti-IL-2 antibody. In some embodiments, said use comprises the anti-IL-2 antibody and an IL-2. In some embodiments, use comprises a complex of an anti-IL-2 antibody with an IL-2.

Thus, the engineered anti-IL-2 antibodies disclosed herein would be useful in adjusting immune cell populations and inducing differential expansion of certain immune effector cells in a method of treating a disease such as viral infection, bacterial infection, or cancer, or treating a condition such as IL-2 induced pulmonary edema, or IL-2-induced vascular leakage.

In some embodiments, disclosed herein is a method of immunizing of a subject, wherein said immunization comprises administration of a vaccine comprising an adjuvant, said adjuvant comprising an IL-2 antibody adjuvant. In some embodiments, an IL-2 antibody adjuvant comprises the anti-IL-2 antibody and IL-2 or comprises an anti-IL-2 antibody complexed with IL-2. In some embodiments, an IL-2 antibody adjuvant comprises the anti-IL-2 antibody and IL-2. In some embodiments, an IL-2 antibody adjuvant comprises an anti-IL-2 antibody complexed with IL-2. In some embodiments, an IL-2 antibody adjuvant comprises an anti-IL-2 antibody.

In some embodiments, the subject being immunized is a mammalian subject. In some embodiments, the subject being immunized is a human. In some embodiments, the subject being immunized has a weakened immune system.

In some embodiments of a method of immunization, the anti-IL-2 antibody comprise a heavy chain variable region having the sequence of one of SEQ ID NOs: 10, 12, 14, 16, 18, 20, 22, 24, 26, or 36. In some embodiments of a method of immunization, the anti-IL-2 antibody comprise a light chain variable region having the sequence of one of SEQ ID NOs: 11, 13, 15, 17, 19, 21, 23, 25, 27, or 37. In some embodiments of a method of immunization, the anti-IL-2 antibody comprise an anti-IL-2 antibody comprising a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs:36 and 37.

In some embodiments of a method of immunization, the anti-IL-2 antibody comprises an anti-IL-2 antibody comprising a heavy chain variable region comprising complementarity determining region (CDR) 1, CDR2 and CDR3, said CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively. In some embodiments of a method of immunization, the anti-IL-2 antibody comprises and anti-IL-2 antibody comprising a light chain variable region comprising complementarity determining region (CDR) 1, CDR2 and CDR3, said CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively. In some embodiments of a method of immunization, the anti-IL-2 antibody comprises an anti-IL-2 antibody comprise a heavy chain variable region and a light chain variable region, each of said heavy chain variable region and light chain variable region comprises complementarity determining region (CDR) 1, CDR2 and CDR3, wherein said heavy chain CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively, wherein said light chain CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively.

In some embodiments of a method of immunizing a subject, an immunization comprises administration of a vaccine comprising an adjuvant, said adjuvant comprising an IL-2 antibody adjuvant, said anti-IL-2 antibody comprising an anti-IL-2 antibody as disclosed herein. In certain embodiments, an IL-2 antibody adjuvant comprises the anti-IL-2 antibody and IL-2 or comprises an anti-IL-2 antibody complexed with IL-2. In some embodiments, of a method of immunizing a subject, a subject has a weakened immune system.

In some embodiments, a subject for immunization with a vaccine comprising an IL-2 antibody adjuvant comprises a subject suffering from a condition comprising a genetic predisposition that increases likelihood of cancer in said subject. In some embodiments, the genetic predisposition comprises a change in expression or activity of a gene product. In some embodiments, a genetic predisposition that increases the likelihood of cancer comprises a mutation in a tumor suppressor gene or a mismatch repair (MMR) gene, or a combination thereof. Many hereditary cancers are known in the art non-limiting examples include but are not limited to Hereditary Breast and Ovarian Cancer (HBOC) syndrome, Lynch syndrome (hereditary non-polyposis colorectal cancer), and Li-Fraumeni syndrome.

In some embodiments, a subject treated by a method disclosed herein for treating a disease or condition is further treated with one or more immune checkpoint inhibitors targeting one or more immune checkpoints. In some embodiments, a subject is treated with said immune checkpoint inhibitors concurrently, before, or after treatment with said anti-IL-2 antibody. In some embodiments of a method of treating disclosed herein, an immune checkpoint comprises PD-1, PDL-1, CTLA-4, TIGIT, TIM-3, B7-H3, CD73, LAG3, CD27, CD70, 4-1BB, GITR, OX40, SIRP-alpha (CD47), CD39, ILDR2, VISTA, BTLA, or VTCN-1, or a combination thereof.

As discussed above, in some embodiments, a therapeutic method of treatment as disclosed herein, further comprises an additional active agent comprising a checkpoint inhibitor. One skilled in the art would appreciate that a combination therapy comprising an anti-IL-2 antibody therapy in the presence or absence of IL-2, and additionally comprising a checkpoint inhibitor may utilize any of the therapeutic compositions or formulations comprising an anti-IL-2 antibody+/−IL-2, and a checkpoint inhibitor as provided herein. In some embodiments, at least two checkpoint inhibitors are used in a combination therapy.

Embodiments of this application include.

An isolated anti-IL-2 antibody, wherein the antibody comprises a heavy chain variable region comprising the sequence of one of SEQ ID NOs:10, 12, 14, 16, 18, 20, 22, 24, 26, or 36.

An antibody including an antibody comprising an IgG, IgA, IgM, IgE, IgD, a Fv, a scFv, a Fab, a F(ab')2, a minibody, a diabody, a triabody, a nanobody, or a single domain antibody.

An IgG comprising
(a) an IgG1, IgG2, IgG3, or an IgG4;
(b) a heavy chain comprising a mutation that that reduces binding to a Fcγ receptor (FcγRs); or
(c), a lambda or kappa light chain; or
(d) any combination of (a)-(c) thereof.

A composition comprising the isolated anti-IL-2 antibody and a pharmaceutically acceptable carrier.

An isolated anti-IL-2 antibody, wherein the antibody comprises a light chain variable region comprising the sequence of one of SEQ ID NOs:11, 13, 15, 17, 19, 21, 23, 25, 27, or 37.

An isolated anti-IL-2 antibody, wherein the antibody comprises a heavy chain variable region and a light chain variable region having the sequences of one of: SEQ ID NOs:10 and 11; SEQ ID NOs:12 and 13; SEQ ID NOs:14 and 15; SEQ ID NOs:16 and 17; SEQ ID NOs:18 and 19; SEQ ID NOs:20 and 21; SEQ ID NOs:22 and 23; SEQ ID NOs:24 and 25; SEQ ID NOs:26 and 27; or SEQ ID NOs:36 and 37.

An isolated anti-IL-2 antibody, wherein the antibody comprises a heavy chain variable region having complementarity determining region 1 (CDR1), CDR2 and CDR3, said CDR1, CDR2 and CDR3 comprise amino acid sequences of SEQ ID NOs:38-40 respectively, SEQ ID NOs:44-46 respectively; SEQ ID NOs:50-52 respectively; SEQ ID NOs:56-58 respectively; or SEQ ID NOs:62-64 respectively.

An isolated anti-IL-2 antibody, wherein the antibody comprises a light chain variable region having complementarity determining region 1 (CDR1), CDR2 and CDR3, said CDR1, CDR2 and CDR3 comprise amino acid sequences of SEQ ID NOs:4143 respectively; SEQ ID NOs:47-49 respectively; SEQ ID NOs:53-55 respectively; SEQ ID NOs:59-61 respectively; or SEQ ID NOs:65-67 respectively.

An isolated anti-IL-2 antibody, wherein the antibody comprises a heavy chain variable region comprising complementarity determining region 1 (CDR1), CDR2 and CDR3, said CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively, and a light chain variable region having complementarity determining region 1 (CDR1), CDR2 and CDR3, said CDR1, CDR2 and CDR3 comprise amino acid sequences of SEQ ID NOs:4143 respectively; SEQ ID NOs:47-49 respectively; SEQ ID NOs:53-55 respectively; SEQ ID NOs:59-61 respectively; or SEQ ID NOs:65-67 respectively.

An isolated polynucleotide sequence encoding a heavy chain variable region of an anti-IL-2 antibody, wherein the heavy chain variable region comprises the amino acid sequence of one of SEQ ID NOs:10, 12, 14, 16, 18, 20, 22, 24, 26, or 36.

A vector comprising a polynucleotide sequence described herein. A host cell comprising a vector described herein.

An isolated polynucleotide sequence encoding a light chain variable region of an anti-IL-2 antibody, wherein the light chain variable region comprises the amino acid sequence of one of SEQ ID NOs:11, 13, 15, 17, 19, 21, 23, 25, 27, or 37.

An isolated polynucleotide sequence encoding a heavy chain variable region of an anti-IL-2 antibody, wherein the heavy chain variable region comprises the amino acid sequence of one of SEQ ID NOs:10, 12, 14, 16, 18, 20, 22, 24, 26, or 36, and encoding a light chain variable region of an anti-IL-2 antibody, wherein the light chain variable region comprises the amino acid sequence of one of SEQ ID NOs:11, 13, 15, 17, 19, 21, 23, 25, 27, or 37.

An isolated polynucleotide sequence encoding a scFv, said polynucleotide sequence comprises the sequence of one of SEQ ID NOs: 1, 2, 3, 4, 5, 31, 32, 33, 34, or 35.

A method of producing a heavy chain variable region of an anti-IL-2 antibody, said method comprises the step of culturing a host cell comprising a vector disclosed herein, under conditions conducive to expressing said vector in said host cell, thereby producing the heavy chain variable region of the anti-IL-2 antibody.

A method of producing a light chain variable region of an anti-IL-2 antibody, said method comprises the step of culturing a host cell under conditions conducive to expressing said vector in said host cell, thereby producing the light chain variable region of the anti-IL-2 antibody.

A method of producing an anti-IL-2 antibody comprising a heavy chain variable region and a light chain variable region of an anti-IL-2 antibody, said method comprises the step of culturing a host cell under conditions conducive to expressing said vector in said host cell, thereby producing the heavy chain variable region and the light chain variable region of the anti-IL-2 antibody.

A method of promoting differential growth of immune cells in a subject, comprising the step of administering a composition comprising an anti-IL-2 antibody, thereby promoting differential growth of immune cells in the subject. In some embodiments, the composition comprises the anti-IL-2 antibody and IL-2, or the anti-IL-2 antibody complexed with IL-2.

A method of treating a subject with cancer through induction of differential growth of immune cells, comprising the step of administering a composition comprising an anti-IL-2 antibody, thereby treating a subject with cancer.

A method of treating a disease or a condition in a subject, comprising the step of administering to the subject a composition comprising an anti-IL-2 antibody wherein said antibody facilitates expansion of subsets of immune cells and decreases undesirable effects caused by IL-2, thereby treating said disease or condition in said subject.

In some embodiments, the disease comprises a viral infection, a bacterial infection, or a cancer. In some embodiments, the viral infection is caused by SARS CoV-2; norovirus; rotavirus; hepatitis virus A, B, C, D, or E; rabies virus; West Nile virus; enterovirus; echovirus; coxsackievirus; herpes simplex virus (HSV); HSV-2; varicella-zoster virus; mosquito-borne viruses; arbovirus; St. Louis encephalitis virus; California encephalitis virus; lymphocytic choriomeningitis virus; human immunodeficiency virus (HIV); poliovirus; zika virus; rubella virus; cytomegalovirus; human papillomavirus (HPV); enterovirus D68; severe acute respiratory syndrome (SARS) coronavirus; Middle East respiratory syndrome coronavirus; Epstein-Barr virus; influenza virus; respiratory syncytial virus; polyoma viruses including JC virus; BK virus); Ebola virus; Dengue virus; or any combination thereof. In some embodiments, the condition comprises a weak immune system and said treatment prophylactically boosts the immune system.

In some embodiments, the condition comprises IL-2 induced pulmonary edema.

In some embodiments of a method disclosed herein, the immune cells comprise one or more of naive T cells, memory T cells, CD8+ T cells, NK cells, or Natural Killer T cells.

In some embodiments, the undesirable effect caused by IL-2 comprises one or more of activation of regulatory T cells, apoptosis of CD25+ T effector cells, IL-2 induced pulmonary edema, pneumonia, or IL-2-induced vascular leakage.

In some embodiments, an anti-IL-2 antibody disclosed herein inhibit IL-2 binding to CD25.

A method of immunizing of a subject, wherein said immunization comprises administration of a vaccine comprising an adjuvant, said adjuvant comprising an IL-2 antibody adjuvant.

In some embodiments, the IL-2 antibody adjuvant comprises the anti-IL-2 antibody and IL-2, or comprises an anti-IL-2 antibody complexed with IL-2.

In some embodiments, a subject is an animal or a human. In some embodiments, the subject has a weakened immune system.

In some embodiments of a method disclosed herein, the immune cells are CD8+ cells or NK cells.

In some embodiments of a method disclosed herein, said anti-IL-2 antibody comprise a heavy chain variable region having the sequence of one of SEQ ID NOs: 10, 12, 14, 16, 18, 20, 22, 24, 26, or 36.

In some embodiments of a method disclosed herein, the anti-IL-2 antibody comprise a light chain variable region having the sequence of one of SEQ ID NOs: 11, 13, 15, 17, 19, 21, 23, 25, 27, or 37.

In some embodiments of a method disclosed herein, the anti-IL-2 antibody comprise a heavy chain variable region and a light chain variable region having the sequences of one of: SEQ ID NOs:10 and 11: SEQ ID NOs:12 and 13; SEQ ID NOs:14 and 15; SEQ ID NOs:16 and 17. SEQ ID NOs:18 and 19; SEQ ID NOs:20 and 21; SEQ ID NOs:22 and 23, SEQ ID NOs:24 and 25; SEQ ID NOs:26 and 27; or SEQ ID NOs:36 and 37.

In some embodiments of a method disclosed herein, the anti-IL-2 antibody comprise a heavy chain variable region comprising complementarity determining region (CDR) 1, CDR2 and CDR3, said CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively.

In some embodiments of a method disclosed herein, the anti-IL-2 antibody comprise a light chain variable region comprising complementarity determining region (CDR) 1, CDR2 and CDR3, said CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively.

In some embodiments of a method disclosed herein, the anti-IL-2 antibody comprise a heavy chain variable region and a light chain variable region, each of said heavy chain variable region and light chain variable region comprises complementarity determining region (CDR) 1, CDR2 and CDR3, wherein said heavy chain CDR1, CDR2 and CDR3 comprise amino acid sequences of SEQ ID NOs:38-40 respectively; SEQ ID NOs:44-46 respectively; SEQ ID NOs:50-52 respectively; SEQ ID NOs:56-58 respectively; or SEQ ID NOs:62-64 respectively, wherein said light chain CDR1, CDR2 and CDR3 comprise amino acid sequences of SEQ ID NOs:41-43 respectively; SEQ ID NOs:47-49 respectively; SEQ ID NOs:53-55 respectively; SEQ ID NOs:59-61 respectively; or SEQ ID NOs:65-67 respectively.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

A skilled artisan would appreciate that the term "about", may encompass a deviance of between 0.0001-5% from the indicated number or range of numbers. In some instances, the term "about", may encompass a deviance of between 1-10% from the indicated number or range of numbers. In some instances, the term "about", encompasses a deviance of up to 25% from the indicated number or range of numbers.

EXAMPLES

Example 1

This example describes generation of modified anti-IL-2 antibodies based on embodiments of the antibodies generated. The exemplification of generating modified anti-IL-2 antibodies is based on a sub-set of the antibodies disclosed herein. The description and results presented in Example 1 are exemplary and do not limit the generation of modified anti-IL-2 antibodies disclosed throughout this application.

Library Design

A library was designed to introduce variation into the sequence of JES6.1. Amino acid sequences for the heavy chain variable region and light chain variable region of JES6.1 are shown in SEQ ID NO:6 and SEQ ID NO:7 respectively. Briefly, three positions were varied with a codon encoding all amino acids (codon NNS). The design of the library allowed for one mutation in both CDRs L3 and H3, as well as a one mutation in one of the following CDRs: H1, H2, or L2. CDRs were defined by meeting either the IMGT or ABR (Kunik et al., 2012) definitions. CDR residues that are conserved (based on Blast search against the PDB database) or don't form specific interactions with mouse IL-2 (mIL-2) in the crystal structure of the mIL2-JES6.1 complex (PDB 4YQX), were excluded from variation. The theoretical size of the library was of 1.38E+7 variants.

Library Selection

Screening and Selection Using Yeast Surface Display

Yeast-displayed scFv libraries were grown in a SDCAA selective medium and induced for expression with 2% w/v galactose at 30° C. overnight according to established protocols. The library was incubated with 100 nM of recombinant human IL-2 with a 6×his tag (hIL-2-His) (Reprokine, Israel) in PBS 0.1% BSA for 1 hour, then washed three times with PBS 0.1% BSA and labeled with fluorescent labeled antibodies mouse anti Myc-FITC (Santa Cruze, USA) and mouse monoclonal anti-His APC (Miltenyi Biotec, Germany. cat 0020130-119-782). Post labeling the library was sorted on BioRad S3e Fluorescence Activated Cell Sorter for high affinity binders to recombinant human IL-2. Isolated clones from the final sort were sequenced by extraction of plasmid DNA from the yeast clones using a Zymoprep kit (Zymo Research, USA) and the DNA was sequenced.

Koff Selection

To select for binders with improved off rate the clones of round 2 of selection were incubated for 15 min with 10 nM 6×his tag (hIL-2), then the yeast were washed 3× with 1 ml PBS 0.1% BSA and incubated for 5 minutes, 4 h, 6 h, and 24 h with 100 nM unlabeled IL-2. At the indicated time points the yeast were washed and labeled with Myc-FITC (Santa Cruze, USA) and monoclonal anti-His APC (Miltenyi Biotec, Germany. cat 0020130-119-782) and sorted on a Se3 as described above.

IgG Production

JES6.1w.t. was bought from Thermo Fisher (cat: 16-7022-81). JES6.1.RMC was cloned as a rat Fv with a mouse IgG2a constant region, and produced by GeneScript antibody production services (Genscript NJ, USA). BDG17.0014 was cloned into human IgG1 constant region and produced by GeneScript antibody production services. Amino acid sequences for the heavy chain variable region and light chain variable region of JES6.1.RMC are shown in SEQ ID NO:8 and SEQ ID NO:9 respectively. All other antibodies were generated as described below.

Reformatting

Selected scFv clone was reformatted to human IgG1 format. The sequences of the light chain (LC) and heavy chain (HC) variable regions were optimized to mammalian codon usage and ordered as genblocks (GB) from IDT (Integrated DNA Technologies. Coralville, Iowa USA). The GB were cloned using standard cloning techniques into pSF-CMV-HuIgG1_HC (HC plasmid) and pSF-CMV-Hu-Lambda_LC (LC plasmid) (Oxford genetics, Oxford UK). When indicated, the variable Heavy chain was cloned into pSF-CMV-HuIgG1_HC_LALA (HC plasmid) in which the DNA coding for L234 and L235 of the heavy chain was mutated to alanine codons (L234A, L235A)

IgG Expression

Expi-CHO cells (Thermo Fisher Scientific, USA) were transfected with LC and HC plasmids at a ratio of 2:1 and expression was done according to the manufacturer's instructions. Briefly: 50 ml Expi-CHO cells were cultured at 37° C., 120 rpm, 8% $CO_2$ to a density of $6 \times 10^6$ cells/ml. Then, 50 μg of heavy chain and light chain expression plasmids at a ratio of 1:2 were transfected into the CHO cells. Post transfections, a booster enhancer and feed were added to the culture, and growth conditions were changed to 32° C., 120 rpm, 5% $CO_2$. The cells were harvested 10 days after transfection. The IgGs were purified from the supernatant using proteinA beads (Tosoh Bioscience GmbH, Germany), followed by size exclusion chromatography (SEC) purification on superdex 200 10/300 increase column, with PBS as mobile phase (GE healthcare, USA).

Sequences

DNA sequences encoding scFv of clone 1 (17.021) is shown in SEQ ID NO:1. DNA sequences encoding scFv of clone 2 (17.022) is shown in SEQ ID NO:2. DNA sequences encoding scFv of clone 4 (17.023) is shown in SEQ ID NO:3. DNA sequences encoding scFv of clone 5 (17.030) is shown in SEQ ID NO:4. DNA sequences encoding scFv of clone 6 (17.035) is shown in SEQ ID NO:5.

Amino acid sequences for the heavy chain variable region and light chain variable region of original JES6_1 starting sequence and the various anti-IL-2 clones are shown in the table below and in FIGS. 11 and 12.

TABLE 2

VH and VL Amino Acid Sequences of a Sub-Set of Anti-IL-2 Clones.

| BDG Clone | Heavy Chain Variable Region | Light Chain Variable Region |
| --- | --- | --- |
| 17.021 | SEQ ID NO: 10 | SEQ ID NO: 11 |
| 17.022 | SEQ ID NO: 12 | SEQ ID NO: 13 |
| 17.023 | SEQ ID NO: 14 | SEQ ID NO: 15 |
| 17.030 | SEQ ID NO: 16 | SEQ ID NO: 17 |
| 17.035 | SEQ ID NO: 18 | SEQ ID NO: 19 |

Measurements of IgG Binding to Human IL-2

The SPR analysis was done on Biacore 200 (GE healthcare, USA) on CM5 chips (cat: br10005-30, GE healthcare, USA). The chip was crosslinked with primary capture Ab against human IgG (Cat: br-1008-39, GE healthcare, USA) or primary capture antibody against mouse IgG (Cat: BR-1008-38, GE healthcare, USA) to a target of 8000 RU. After cross-linking of the primary Ab, the mouse and human tested antibodies were immobilized on the primary Ab to a target of approximately additional 500 RU. JES6.1 was cross-linked directly to the CM5 chip. Human IL-2 (Cat: 60568, Reprokine, Israel) analyte was streamed in HEB-EP or PBS 0.05% tween-20 (PBS-T) buffer at concentrations ranging from 128 nM to 0.03 nM in a series of two-fold or three-fold dilutions, one concentration for each cycle. Mouse IL-2 (Cat: RKPO4351, Reprokine, Israel) was streamed in HEB-EP or PBS-T buffer at concentrations ranging from 0.5 nM to 40 nM. At the end of each cycle the analyte and tested antibody were stripped from the chip using 3M $MgCl_2$ and new tested Ab was loaded on the chip as described above. When indicated, instead of stripping the antibodies, kinetics was determined by injecting series of analyte concentrations in one cycle by the Single-cycle kinetics method. Binding kinetics were determined by the 1:1 Binding model using the Biacore T200 evaluation software.

Binding of IgGs to Cynomolgus Monkey IL-2

The SPR analysis was done on Biacore 200 (GE healthcare, USA) on CM5 chips (cat:br10005-30, GE healthcare, USA). The chip was crosslinked with primary capture Ab against human IgG (Cat: br-1008-39, GE healthcare, USA) to a target of 5000 RU and cynomolgus monkey IL-2 (cIL-2) was tested by the multi-cycle method in the same conditions described above.

SEC Analysis

To analyze the IgGs, 100 μg samples were loaded on a Superdex 200 10/300 increase column (GE healthcare, USA) at a flow rate of 0.8 ml/min on a GE AKTA Explorer chromatography system (GE healthcare, USA). Monitoring of antibody retention time was done at 280 nm.

Testing for Specific Binding to CD25 and CD122

To test specific binding to CD25, BDG17.023 was immobilized to the CM5 chip to a target RU of approximately 300 RU as described above. Subsequently, 50 nM IL-2 was injected till the BDG17.023 or control antibody were saturated. Then the Ab-IL-2 complex was washed with PBS-T buffer for 10 sec and 1000 nM of CD25 was injected and monitored for response.

To test specific binding to CD122, BDG17.023 was immobilized to the CM5 chip to a target RU of approximately 300 RU-500 RU as described above. Subsequently, 50 nM hIL-2 was injected till the BDG17.023 antibody was saturated with hIL-2. Next the Ab-IL-2 complex was washed with PBS-T buffer for 10 sec and 1000 nM of CD122 was injected and response was monitored.

To test specific binding of the humanized antibodies IL-2 complex to CD122 and CD25, antibodies BDG17.038, BDG17.043, BDG17.053, BDG17.054, BDG17.067, BDG17.069 (See, Tables 6 and 7 of Example 2 for sequence information for these clones) were immobilized to an a capture antibody attached to CM5 chip channel to a target RU of approximately 300 RU as described above. Subsequently, 50 nM IL-2 was injected till the respective antibody was saturated with hIL-2. Then the Ab-IL-2 complex was washed with PBS-T buffer for 60 sec and 1000 nM of CD25 was injected and monitored for response. Subsequently, running buffer was injected for 60 seconds to reach a steady baseline, and then 1000 nM of CD122 was injected for 30 seconds in a flow rate of 30 ul/min. To test CD122 binding, the same experiment was repeated in reverse order, with CD122 injected first flowed by injection of CD25.

DSF Analysis of IgG Tm

To determine the T-onset and Tm of the humanized anti-hIL-2 antibodies, antibodies were diluted to 0.5 mg/ml in PBS and analyzed using NanoDSF Prometheus NT.48 (Nanotemper, Germany) in a temperature elevation rate of 1° C./min.

In Vivo Experiments

Treatment of Mice with the IL-2/Ab Complex

Groups of six male C57BL/6 mice, 7-8 weeks old, were injected intraperitoneally (i.p.) with BDG17.023/hIL-2 or JES6.1/mIL-2 immune complex daily, for four consecutive days. PBS and free hIL-2 or mIL-2 served as controls. At the end of the fourth day the mice were sacrificed, spleens were harvested and homogenized to a single cell suspension. The cells were filtered, centrifuged (400 g for 5 minutes) resuspended in 5 ml PBS to a final concentration of $5 \times 10^6$ lymphocytes/ml. The experiment was done in accordance with the guidelines of the national council for Institutional Animal Care and Use Committee (IACUC) in Israel.

Groups of six male C57BL/6 mice, 7-8 weeks old, were injected intraperitoneally (I.P.) with BDG17.038/hIL-2, BDG17.043/hIL-2, BDG17.054/hIL-2, BDG17.038/hIL-2 or Isotype control/hIL-2 immune complex daily, for four consecutive days. To form the complex, 10 μg of the antibody was pre-incubated with 0.5 μg of hIL-2 for 30 minutes at 37° C. before the injection. At the end of the fourth day the mice were sacrificed, spleens were harvested and homogenized to a single cell suspension. The cells were filtered, centrifuged (400 g for 5 minutes) resuspended in 5 ml PBS to a final concentration of $5 \times 10^6$ lymphocytes/ml. The experiment was done in accordance with the guidelines of the national council for Institutional Animal Care and Use Committee (IACUC) in Israel.

B16F10 Murine Melanoma Tumor Xenograft Model

Female C57BL/6 mice were inoculated subcutaneously in the right rear flank region with (2×10) B16-F10 tumor cells. Five days post inoculation when the tumor volume reached ~30-50 $mm^3$, the mice were randomized into experimental groups (n=10 per group) and injected intraperitoneally daily with single doses of 10 μg anti-IL-2 antibody/1 μg hIL-2 complex of the indicated antibodies or with PBS control for four consecutive days. The mice were monitored for tumor volume growth, body weight loss and for non-specific clinical signs throughout the experiments.

Determination of Immune Cell Population by FACS

In order to identify immune cell populations, spleen lymphocytes were labeled with the antibodies described below according to the manufacturer's instructions. Regulatory T cells (Tregs) were designated as cells labeled as $CD45^+/CD3^+/CD4+/CD25^+/FoxP3^+$. Memory phenotype effector T cells (MP $CD8^+$): $CD45^+/CD3^+/CD8^+/CD44^+/IL-2RB(CD122)^+$. Natural killer cells (NK): $CD45^+/CD3^-/CD49b^+/NK1.1$ (CD161). Natural killer T cells (NKT): $CD45^+/CD3^-/CD49b^-/NK1.1$ (CD161). Positive cells frequency and number were calculated from the raw data acquired on the flow cytometer.

TABLE 3

| | Marker/Labeled Antibodies | | | | | |
|---|---|---|---|---|---|---|
| Reagent | Catalog No. Thermo Fisher Scientific | Channel | Excitation Filter | Emission Filter | Concentration (mg/ml) | Dilution (µg)/test |
| Anti-MO/RT FOXP3 FJK-16S FITC 100 UG | 11-5773-82 | FL1 | 488 | 525/50 | 0.5 | 1 |
| CD25 Monoclonal Antibody (CD25-4E3), PE 100 T | 12-0251-82 | FL2 | 488 | 575/30 | 0.2 | 0.125 |
| CD49b (Integrin alpha 2) Monoclonal Antibody (DX5), PE-eFluor 610/100 µg | 61-5971-82 | FL3 | 488 | 620/30 | 0.2 | 0.5 |
| CD4 anti mouse, PerCP/Cyanine5.5 100 µg | BLG 100540 | FL4 | 488 | 695/30 | 0.2 | 0.25 |
| CD122 (IL-2Rβ) anti mouse, PE-Cyanine7/100 µg | BLG 123216 | FL5 | 488 | 755LP | 0.2 | 0.25 |
| NK1.1 Monoclonal Antibody (PK136), APC/100 ug | 17-5941-82 | FL6 | 638 | 660/20 | 0.2 | 0.125 |
| CD3 Monoclonal Antibody (17A2), Alexa Fluor 700, eBioscience ™/ 100 µg | 56-0032-82 | FL7 | 638 | 725/20 | 0.2 | 0.25 |
| CD44 Monoclonal Antibody (IM7), APC-eFluor 780/ 100 µg | 47-0441-82 | FL8 | 638 | 755LP | 0.2 | 0.25 |
| CD8a Monoclonal Antibody (53-6.7), Super Bright 436, eBioscience ™/ 100 µg | 62-0081-82 | FL9 | 405 | 450/50 | 0.2 | 0.25 |
| CD45 Monoclonal Antibody (30-F11), eFluor 506, eBioscience ™/ 100 µg | 69-0451-82 | FL10 | 405 | 525/50 | 0.2 | 0.5 |

Results

JES6.1 Binds Mouse Strongly but does not Bind the Human IL-2

JES6.1 has been reported to bind mouse IL-2 (mIL-2) at a $K_D$ of 5.6 nM. To test if JES6.1 could bind human IL-2 (hIL-2), JES6.1 antibody was tested by SPR on BiacoreT200. JES6.1 was cross-linked directly to the CM5 chip, then human IL-2 or mouse IL-2 analytes were streamed at concentrations ranging from 0.5 nM to 128 nM or 0.5 to 16 nM respectively. As can be seen in FIG. 4A, when tested with human IL-2, the JES6.1 showed no apparent change in response unit (RU). On the other hand, when mouse IL-2 served as analyte, a robust response was apparent (FIG. 4B), indicating that JES6.1 binds mouse IL-2 strongly but does not bind human IL-2. The experiment was repeated with the JES6.1RMC antibody chimera which was expressed as a JES6.1 rat FV with a mouse constant region as described herein. The JES6.1RMC was immobilized on the CM5 chip using the GE antibody capture kit. Streaming hIL-2 at a concentration of up to 100 nM resulted in no change in RU, indicating no binding to the human IL-2 (FIG. 4C). To test whether the JES6.1RMC chimera retained its mIL-2 binding properties like the JES6.1 above, it was tested for binding to mouse IL-2. Streaming of mIL-2 at a concentration of 0.5 nM to 320 nM resulted in large change in RU, indicating robust binding (FIG. 4D). These results indicate that JES6.1 and JES6.1RMC bind mouse IL-2 strongly but show no apparent binding to human IL-2. Analysis of the JES6.1RMC binding kinetics to both hIL-2 and mIL-2 are shown below.

TABLE 4

Binding Kinetics of JES6.1RMC.

| | Mouse IL-2 | | | Human IL-2 | | |
|---|---|---|---|---|---|---|
| Antibody | $K_{D\,(M)}$ | ka (1/Ms) | kd (1/s) | $K_{D\,(M)}$ | ka (1/Ms) | kd (1/s) |
| BDG JES6.1RMC (17.006) | $1.3*10\char`\^-10$ | $4.8*10\char`\^5$ | $6.3*10-5$ | N.D. | N.D | N.D. |

Changing Binding Specificity from Mouse IL-2 to Human IL-2

To change binding specificity from mouse IL-2 to human IL-2, JES6.1 was cloned as a scFv into a yeast display vector. The scFv format of JES6.1 expressed well on the yeast surface as indicated from the carboxy terminal myc tag labeling (FIGS. 5A-5C). Incubating 100 nM JES6.1 in IgG format with YSD clones expressing mouse IL-2 resulted in strong binding (FIGS. 5A-5C). However, in correlation with the SPR results shown above, incubation of JES6.1 YSD clones with up to 1 uM labeled human IL-2 showed no increase in fluorescence, indicating that the JES6.1 scFv does not bind hIL-2.

Based on the JES6.1 scFv, a mutagenesis library was generated as described above. Briefly, the YSD library was selected against recombinant human IL-2 as described above. The mutant library went through one round of MACS selection against 1 uM of human IL-2 and additional round of FACS selection against 1 uM of human IL-2. The top 0.2% clones were selected. Subsequently, the library underwent two additional rounds of selection specifically aimed at improving the koff properties of the selected clones as described above. For $3^{rd}$ round of selection the yeast were incubated with 10 nM His-tagged hIL-2 for 15 minutes at room temperature, then the yeast were washed of the hIL-2 and incubated for 5 minutes with 100 nM unlabeled IL-2 at room temperature. The $4^{th}$ round was done in a similar fashion but post labeling and wash, the yeast were incubated in fold of initial volume in PBS for 24 hours. In the $5^{th}$ round, the yeast were labeled and washed, and then incubated with 100 nM unlabeled IL-2 at room temperature for six hours. After five rounds of selection the clones were isolated. Five YSD clones that gained binding to hIL-2 (FIGS. 6A-6B) were sequenced. In addition, these clones were tested for specificity by labeling with a mixture of 500 nM soluble TNFR2, and 500 nM OX40 and 500 nM PD1. As can be seen in FIGS. 6A-6B, these clones are specific to hIL-2 and do not bind any of the other proteins.

Expression of BDG17.023

Subsequent to YSD characterization, clone #4, which showed significant binding to hIL-2, was reformatted to human chimeric IgG1 (BDG17.023) with rat FV and human Fc chimera. The rat variable domain was subcloned into two separate expression vectors, pSF-CMV-HuIgG1_HC and pSF-CMV-HuLambda_LC as described above. The IgG was expressed in ExpiCHO cells as described above. The purified IgGs were >95% pure as evident from a SDS PAGE analysis. Size exclusion chromatography of BDG17.023 on superdex200 10/300 showed two main peaks: the first peak with a retention time of ~9.2 ml (0.36 CV) was typical of large aggregate and the second peak with retention of approximately ~12.6 ml (0.528 CV) was typical of an ordinary human hIgG1. Peak integration of these SEC runs showed 11% and 89% respectively (FIG. 7).

Binding Kinetics of BDG17.023

To determine BDG17.023 binding kinetics and affinity to mIL-2 and hIL-2, the IgG was analyzed by SPR on a BIAcore T200 using the GE capture antibody kit as described above. As shown in FIGS. 8A-8B, BDG17.023 binds hIL-2 with an affinity of approximately $8\times10^{-11}$, with a on rate of $1.3*10^7$ and off rate of $1*10^{-3}$. BDG17.023 also showed binding to mIL-2 with a much lower affinity of approximately $2.5\times10^{-6}$.

TABLE 5

Kinetic parameters of BDG17.023.

| | Mouse IL-12 | | | Human IL-12 | | |
|---|---|---|---|---|---|---|
| Antibody | $K_{D\,(M)}$ | ka (1/Ms) | kd (1/s) | $K_{D\,(M)}$ | ka (1/Ms) | kd (1/s) |
| BDG17.023 | 2.46E−06 | 3.98E+04 | 0.09795 | 8.18E−11 | 1.31E+07 | 0.00107 |

Receptor Discrimination of the BDG17.023-hIL-2 Complex

JES61-mIL-2 complex was reported to bind specifically to CD25 but not CD122. It was shown that the JES6.1-mIL-2 complex bound to a SPR chip could bind CD25 but not CD122. To test whether BDG17.023-hIL-2 complex can discriminate between binding to CD25 and CD122, a similar experiment was performed as described above. As shown in FIG. 9, a control antibody complexed with hIL-2 binds human CD25 but could not bind CD122. In contrast, the BDG17.023-hIL-2 complex was found to bind CD122 but not CD25. This result indicates that although BDG17.023 is derived from JES6.1, the JES6.1-mIL-2 complex and the BDG17.023-hIL-2 complex show a very different IL-2 receptor preference, possibly through binding of different epitope of the mIL-2 and the hIL-2 respectively. Alternatively, different allosteric effects may be induced on the mIL-2 and hIL-2 that affects binding preference to the IL-2 receptors.

In Vivo Characterization of BDG17.023

In vivo administration of JES6.1 complexed with mIL-2 resulted in robust proliferation of regulatory T cells and much smaller proliferation of effector T cells, thereby shifting the MP CD8+/Tregs ratio towards immune suppression. Since the BDG17.023-hIL-2 complex showed preference to binding CD122 and excluded CD25 from binding in an SPR biochemical assay, it is predicted that the BDG17.023-hIL-2 complex would enhance proliferation of CD8+ effector cells and NK cells in vivo. Human IL-2 can cross react with the mouse IL-2 receptors, thus the BDG17.023-hIL-2 complex was administered to C57BL/6 mice to test its effect in vivo as described above. Briefly, the 17.023 antibody-hIL-2 complex was incubated with hIL-2 at a 1:1 molar ratio and injected intraperitoneally to C57BL/6 mice daily, for four consecutive days. As a control. JES6.1-mIL-2 complex, hIL-2 alone, or mIL-2 alone was also administered in a similar fashion. On the fifth day the mouse spleens were harvested, cells were labeled and analyzed by FACS as described above.

As can be seen in FIGS. 10A-10D, BDG17.023 shows pronounced effect in inducing proliferation of MP CD8+ cells and NK cells, while there was much smaller effect on CD4+ Tregs. On the other hand, JES6.1 showed a much different effect in accordance with its reported anti-inflammatory effect. These results demonstrate that in agreement with the binding data and in contrast to JES6.1, BDG17.023-IL-2 complex has a strong stimulatory effect on the immune system in vivo, as opposed to an anti-stimulatory or pro-regulatory effect.

Example 2

This example presents results on further selection of human IL-2 binder and generation of humanized antibodies.

Additional selection strategy was used to select human IL-2 binder under alternative selection pressure. Briefly: the library went through one round of MACS selection against 1 uM of human IL-2 and additional four rounds of FACS selection against 100 nM of human IL-2. After the first round of FACS selection, all binders were selected, followed by selection of the top 0.5%, top 0.5% and top 0.1% of the binders. After five rounds of selection, clone C #7 (173R5C1-17.002) (SEQ ID NO:28) was isolated, verified for binding and sequenced.

Antibody Humanization

Clone C #7 (173R5C1-17.002) was selected as template for humanization. A human template was chosen using the Schrodinger BioLuminate 'Antibody Humanization: CDR Grafting' CDR tool (Kai Zhu, Tyler Day et al., Antibody structure determination using a combination of homology modeling, energy-based refinement, and loop prediction. Proteins: Structure, Function and Bioinformatics, 82, 8, 8 2014), and the PDB entry of JES6-1 was used as a query (4YQX; Jamie B. Spangler, Jakub Tomala et al., Antibodies to Interleukin-2 Elicit Selective T Cell Subset Potentiation through Distinct Conformational Mechanisms. Immunity, 42, 5, 5 2015). PDB entry 5I18 (Alexey Teplyakov, Galina Obmolova et al., Structural diversity in a human antibody germline library. mAbs, 8, 6, 8 2016) was chosen as it had the best score with regard to a combination of framework identity of the L and H chains and stem geometry. Mutations were introduced to positions that either interact (within 5A radius) with the CDR regions (according to IMGT numbering scheme), or the antigen in 4YQX. The variability on these positions was selected to include amino acids of the human template (5I18) as well as the mouse query (4YQX). In addition, due to significant structural changes between H1 of the query and the template, the option of complete transition between Hi of 4YQX and 5I18 was introduced. This library had approximately 1300 different variants.

The library underwent selection by FACS for two rounds. In the first round, the library was labeled with 5 nM hIL-2 and the top 5% binding clones were sorted. In the second round, the library was labeled with 1 nM hIL-2 and the top 5% of the clones were sorted. The clones were sequenced after selection and clone C #8 (173.2A.C6-17.014)(SEQ ID NO:31) was used as a template for affinity maturation.

Humanized Antibodies Affinity Maturation

CDR positions (IMGT/ABR definition) that were predicted to have a high rate of somatic hypermutation were selected for variation. Additional positions in L3 that are presumed to interact with the antigen based on JES6-1, as well as all of H3, were also targeted for variation. The variation was based on sequence conservation of all positions except for H3 which was the DHY codon. The theoretical diversity of this library was $3.21 \times 10^{12}$.

Based on the clone C #8 (173.2A.C6-17.014) another library was constructed, in which all CDR positions were explored using the NNS degenerate codon that encodes all amino acids. Variants of 2-3 mutations, up to one on each CDR were screened. The theoretical size of such a library is $2 \times 10^6$ double mutants and $1 \times 10^9$ triple mutants.

The humanization affinity maturation libraries generated above were pooled together for selection. Briefly, in the first round the pooled YSD libraries were labeled with 10 nM hIL-2 and selected on MACS. In the second round the yeast were labeled with 0.1 nM hIL-2 and selected using MACS. In the third round of selection, the yeast were labeled with 0.1 nM hIL-2 and all binders were selected on FACS. For the fourth and fifth round of selections, the yeast were labeled with 10 nM hIL-2 and competed with 100 nM unlabeled hIL-2 for 24 hours and 48 hours respectively. Subsequently, the yeast were sorted on FACS to select all the binders. The final round of selection was done in a similar fashion to the fourth and fifth rounds, but post labeling and wash, the yeast were incubated in 1000 fold of initial volume in PBS at room temperature for a week.

After selection, the clones were isolated, verified for binding and sequenced. Amino acid sequences for several clones are shown below. Alignment of Heavy Chain and Light Chain variable regions, and CDR regions of a subset of clones is presented in FIGS. 13A and 13B.

TABLE 6

VH and VL Amino Acid Sequences of a Sub-Set of Anti-IL-2 Clones.

| Clone | Heavy Chain Variable Region | Light Chain Variable Region |
|---|---|---|
| 17.038 | SEQ ID NO: 20 | SEQ ID NO: 21 |
| 17.043 | SEQ ID NO: 22 | SEQ ID NO: 23 |
| 17.053 | SEQ ID NO: 24 | SEQ ID NO: 25 |
| 17.054 | SEQ ID NO: 26 | SEQ ID NO: 27 |
| 17.014 | SEQ ID NO: 36 | SEQ ID NO: 37 |
| 17.066 | SEQ ID NO: 20 | SEQ ID NO: 21 |
| 17.067 | SEQ ID NO: 22 | SEQ ID NO: 23 |
| 17.069 | SEQ ID NO: 26 | SEQ ID NO: 27 |

It should be noted that clones 17.066, 17.067, and 17.069 comprise the LALA mutation (L234A, L235A mutations).

CDR sequences for certain selected clones are shown below.

TABLE 7

CDR Amino Acid Sequences of Anti-IL-2 Clones.

| Clones | Heavy Chain CDR1 | CDR2 | CDR3 | Light Chain CDR1 | CDR2 | CDR3 |
|---|---|---|---|---|---|---|
| 17.014 | SEQ ID NO: 38 | SEQ ID NO: 39 | SEQ ID NO: 40 | SEQ ID NO: 41 | YAS | SEQ ID NO: 43 |
| 17.038 | SEQ ID NO: 44 | SEQ ID NO: 45 | SEQ ID NO: 46 | SEQ ID NO: 47 | YAS | SEQ ID NO: 49 |
| 17.043 | SEQ ID NO: 50 | SEQ ID NO: 51 | SEQ ID NO: 52 | SEQ ID NO: 53 | YAS | SEQ ID NO: 55 |
| 17.053 | SEQ ID NO: 56 | SEQ ID NO: 57 | SEQ ID NO: 58 | SEQ ID NO: 59 | YAS | SEQ ID NO: 61 |
| 17.054 | SEQ ID NO: 62 | SEQ ID NO: 63 | SEQ ID NO: 64 | SEQ ID NO: 65 | DAS | SEQ ID NO: 67 |
| 17.066 | SEQ ID NO: 44 | SEQ ID NO: 45 | SEQ ID NO: 46 | SEQ ID NO: 47 | YAS | SEQ ID NO: 49 |
| 17.067 | SEQ ID NO: 50 | SEQ ID NO: 51 | SEQ ID NO: 52 | SEQ ID NO: 53 | YAS | SEQ ID NO: 55 |
| 17.069 | SEQ ID NO: 62 | SEQ ID NO: 63 | SEQ ID NO: 64 | SEQ ID NO: 65 | DAS | SEQ ID NO: 67 |

TABLE 8

Full-length Amino Acid Sequences of a Subset of Anti-IL-2 Clones.

| BGD-Clone | Heavy Chain (LALA) | Light Chain |
|---|---|---|
| BDG17.066 | SEQ ID NO: 68 | SEQ ID NO: 69 |
| BDG17.067 | SEQ ID NO: 70 | SEQ ID NO: 71 |
| BDG17.069 | SEQ ID NO: 72 | SEQ ID NO: 73 |

Binding Kinetics of Humanized Antibodies

To determine BDG17.038, BDG17.043, BDG17.053, BDG17.054, BDG17.067, BDG17.066 and BDG 17.069 binding kinetics and affinity to hIL-2 and cynomolgus monkey IL-2 (cIL-2), the clones were reformatted to IgG expressed and purified; Subsequently the antibodies were analyzed by SPR on a BIAcore T200 using the GE capture antibody kit as described herein. As shown in Table 9 and FIGS. 14A-14G and FIGS. 15A-15B the antibodies bind tightly both human and cynomolgus monkey IL-2 an the low double digit pM range.

Size Exclusion Chromatography Profile and Thermal Stability of the Humanized Antibodies.

To test if the humanized IgGs BDG17.038, BDG17.043, BDG17.053, BDG17.054, BDG17.066, BDG17.067 and BDG 17.069 are folded correctly and stable, the antibodies were subjected to size exclusion chromatography and Differential Scanning Fluorimetry (DSF) analysis as described above. The results summarized in FIGS. 16A-16G and Table 8 suggesting that these IgGs are produced as >95% non-aggregated species, have a SEC retention profile typical of a human IgG1 and thermal denaturation profile with Tonset of >=54.4° C. and Tm1>=69° C. An illustration of the receptor discrimination assay is presented in FIG. 17A, and the SPR results for the different clones is presented in FIGS. 17B-17G. To conclude the SPR, SEC and DSF experiments indicate that the humanized antibodies bind human and cynomolgus money IL-2 tightly, are folded correctly and are highly stable.

TABLE 9

Biophysical Properties of Select Improved Humanized Clones

| IgG ID | IgG information | DSF T onset | DSF Tm1 | DSF Tm2 | Size exclusion chromatography GE superdex200 increase 10/300 Peak volume | Size exclusion chromatography GE superdex200 increase 10/300 % aggregation | SPR Kinetics of binding human IL-2 Ka ($Ms^{-1}$) | SPR Kinetics of binding human IL-2 Kd ($s^{-1}$) | SPR Kinetics of binding human IL-2 KD (M) |
|---|---|---|---|---|---|---|---|---|---|
| 17.038 | Humanized IgG1 | 62.6° C. | 71.4° C. | N/A | 13.33 ml | 0.38 | 1.41E+07 | 2.00E−04 | 2.02E−11 |
| 17.043 | Humanized IgG1 | 54.4° C. | 76.0° C. | N/A | 13.04 ml | 0 | N/A | 2.22E−04 | 4.82E−11 |

TABLE 9-continued

Biophysical Properties of Select Improved Humanized Clones

| | | | | | | | | | |
|---|---|---|---|---|---|---|---|---|---|
| 17.053 | Humanized IgG1 | 55.1° C. | 76.1° C. | N/A | 13.01 ml | 4.13 | 3.96E+07 | 2.54E−03 | 6.43E−11 |
| 17.054 | Humanized IgG1 | 61.8° C. | 69.0° C. | 74.6° C. | 13.04 ml | 4.16 | 5.50E+07 | 7.00E−04 | 1.27E−11 |
| 17.066 | Humanized IgG1 with reduced Fc-gamma binding (LALA mutation) | 63.9° C. | 71.5° C. | N/A | 12.96 ml | 3.8 | 1.52E+07 | 7.85E−04 | 5.15E−11 |
| 17.067 | Humanized IgG1 with reduced Fc-gamma binding (LALA mutation) | 60.0° C. | 75.7° C. | N/A | 13.02 | 4.7 | 3.37E+07 | 3.72E−04 | 1.10E−11 |
| 17.069 | Humanized IgG1 with reduced Fc-gamma binding (LALA mutation) | 62.8° C. | 69.3° C. | N/A | 13.07 ml | 0.8 | 4.50E+07 | 4.87E−04 | 1.08E−11 |

| IgG ID | IgG information | SPR Kinetics of binding Cynomolgus monkey IL-2 | | |
|---|---|---|---|---|
| | | Ka (Ms$^{-1}$) | Kd (s$^{-1}$) | KD (M) |
| 17.038 | Humanized IgG1 | Not tested | Not tested | Not tested |
| 17.043 | Humanized IgG1 | Not tested | Not tested | Not tested |
| 17.053 | Humanized IgG1 | Not tested | Not tested | Not tested |
| 17.054 | Humanized IgG1 | Not tested | Not tested | Not tested |
| 17.066 | Humanized IgG1 with reduced Fc-gamma binding (LALA mutation) | Not Tested | Not Tested | Not Tested |
| 17.067 | Humanized IgG1 with reduced Fc-gamma binding (LALA mutation) | 2.83E+07 | 3.98E−04 | 1.40E−11 |
| 17.069 | Humanized IgG1 with reduced Fc-gamma binding (LALA mutation) | 4.98E+07 | 5.84E−04 | 1.17E−11 |

Example 3

This example provides disclosure on anti-IL-2 antibodies that specifically block the binding of human EL-2 to IL-2 receptor CD25 and modulate the immune system in vivo.

Anti-IL-2 antibodies that bind human EL-2 at an epitope that specifically block interaction between IL-2 and human CD25, have several implications. This allows for the binding of IL-2 antibody complex to effector T cells and NK cells but prevents the binding of human IL-2 to non-immune cells expressing high levels of CD25 (e.g., lung endothelium and vascular endothelium) or to immune cells expressing the high affinity trimeric complex (e.g., Treg cells and CD25+ short lived cytotoxic effector T cells). As a result, these anti-IL-2 antibodies are able to expand effector T cells and NK cells without significantly expanding regulatory T cells (See, FIG. 1 and FIG. 2). Additionally, it has been previously shown that lung endothelial cells express CD25 and high levels of IL-2 in their presence would lead to pulmonary edema. Similar effect was observed for IL-2 induction of vascular leaking through IL-2's interaction with CD25 expressed on vascular endothelial cells. Thus, by targeting IL-2 away from CD325, the anti-L-2 antibodies disclosed herein are also expected to reduce any IL-2 related pulmonary and vascular toxicity (FIGS. 3A-3B).

Receptor Discrimination of the Humanized IgG-hIL-2 Complex

BDG17.023-hIL-2 complex (anti-IL-2 antibody-human IL-2 complex) showed receptor binding discrimination, the BDG17.023-hIL-2 complex was found to bind CD122 but not CD25 which resulted in a specific immune system modulation outcome. To test if the humanized antibodies have a similar effect, they were complexed with hIL-2 and tested for binding to CD122 and CD25 by SPR. The analysis was done in a similar fashion to BDG17.023 as described herein. As can be seen by the SPR traces in FIGS. 17B-17G when the humanized antibodies BDG17.038, BDG17.043, BDG17.053, BDG17.054, BDG17.066, BDG17.0067 or BDG17.069 are complexed with hIL-2, the complex bind CD122 but cannot bind CD25, indicating that these antibodies retained the binding discrimination properties of human rat chimera BDG17.023.

In Vivo Characterization of the Humanized Antibodies

It has been hypothesized that blocking the CD25 binding epitope on IL-2 by high affinity antibodies allows for the binding of human IL-2 to effector T cells and NK cells but prevents the binding of human IL-2 to non-immune cells expressing CD25 (e.g., lung endothelium and vascular endothelium) or cells expressing the trimeric complex (e.g., Treg cells, CD25+ effector T cells). To test this hypothesis in vivo, anti-IL-2 antibodies were pre-complexed with human IL-2 and administered to healthy C57BL/6 male mice as described herein (FIGS. 18A-B). As can be seen in FIGS. 18A and 18B the anti-IL-2 antibodies BDG17.043 and BDG17.054, were able to expand effector T cells, NKT cells and NK cell populations without significantly expanding regulatory T cells (FIG. 18A-18B), likely due to their epitope specific properties. Additionally, the proliferation of MP CD8+ T cells and NKT is dependent on the administered dose of IgG-hIL-2 complex and is much more robust than the administered isotype control with hIL2, suggesting that BDG17.043/IL-2 and BDG17.054/IL-2 are actively promoting the CD122/CD132 dimer activation pathway while sparing the CD25/CD122/CD132 trimeric pathway (FIGS. 19A-19B).

BDG17.043 and BDG17.054 complexed with IL-2 induced proliferation of MP CD8+ effector T cells and NK cells but do not promote significant expansion of regulatory T cells, suggesting that these antibody-IL2 complexes have strong stimulatory effect on the immune system as opposed to other antibodies IL-2 complexes like JES 6.1-IL-2 (Spangler J B, Tomala J, Luca V C, Jude K M, Dong S, Ring A M, Votavova P, Pepper M, Kovar M, Garcia K C. Antibodies to Interleukin-2 Elicit Selective T Cell Subset Potentiation through Distinct Conformational Mechanisms. Immunity. 2015 May 19; 42(5):815-25.) and Pfizer's F5111.2-IL2 (Trotta E, Bessette P H, Silveria S L, et al. A human anti-IL-2 antibody that potentiates regulatory T cells by a structure-based mechanism. Nat Med. 2018; 24(7):1005-1014.) that induce immune system anti-stimulatory effect by promoting proliferation of Tregs.)

In the mouse study described above, the animals were monitored daily for body weight loss and for non-specific clinical signs. When evaluating drug compounds in mice, a 20% percent body weight loss is considered to be an actionable item that requires ethical intervention. As shown in FIGS. 20A-B, mice administered with and 17.043/IL-2 complex or 17.054/IL-2 complex showed no or less than 10% percent of body weight loss at the end of the experiments. This effect was observed in all dose cohorts including mice treated with the highest dose of 25 µg IgG/1.25 µg IL-2 complex, indicating that the administered complexes are well tolerated.

Activity of the Humanized Antibodies in B16F10 Syngeneic Cancer Model

Both viral clearance and cancer therapy share the common need to expand the acquired T cell immune response for efficacy. The ability of anti-IL-2 antibodies to effectively activate immune response was tested in a B16F10 syngeneic melanoma model. C57BL/6 mice were inoculated with B16F10 melanoma and treated with 10 µg anti-IL-2 antibody/1 µg hIL-2 complex or PBS control as described herein. As shown in FIG. 21A, all mice treated with BDG17.043 or BDR17.054 complexed with IL-2 showed significant tumor growth inhibition 8 days post treatment that is much larger then treating the mice with Isotype control and hIL-2 (study day 17), likely due to robust and specific immune stimulation. Additionally, as can be seen in FIG. 21B the average transient weight loss in mice treated with the two anti-IL-2 antibodies is of 6.84%+/−3.9% and 3.6%+/−5.2%, indicating that in a setting of syngeneic B16F10 tumor model the administered antibody/IL-2 complexes were well tolerated.

In summary, these studies show that anti-IL-2 antibodies (17.043 & 17.054) bind human IL-2 with high affinity on a pre-defined epitope such that the antibodies completely prevent the interaction of IL-2 with its receptor CD25. Consequently, the antibody/IL-2 complex is directed to bind and activate the dimeric form of the IL-2R (CD122/CD132).

The dimeric receptor complex is found on effector cells. Analysis of the immune stimulating effect in vivo demonstrated that IL-2 in the presence of anti-IL-2 clones 17.043 and 17.054, increases T-effector cell populations (IL-2 Rβγ binding and signaling) with no observed effect on regulatory T cells (IL-2 Rαβγ binding and signaling). This demonstrated that the interaction of IL-2 with the dimeric IL-2 receptor resulted in non-toxic immune stimulation. Taken together, these data support the hypothesis that an anti-human IL-2 antibody that interferes with the ability of the cytokine to bind CD25 positive cells could be used to treat oncologic patients to enhance immune responses that lead to immune response against cancer or in the case of COVID-19 infection can increased clearance of viral load. Additionally, these antibodies properties may prevent IL-2-induced pulmonary edema and possibly prevents lung tissue damage in SARS-CoV-2 infected lungs.

Example 4

This example provides a description of studies performed examining formulations of anti-IL-2 antibodies.

Methods: Formulation analysis was done by incubating 30 mg/ml of anti-IL-2 clone BDG17.069 in four different formulations:

F1) 20 mM Histidine, 8% sucrose, 0.04% PS80, pH5.5;
F2) 20 mM Histidine, 8% sucrose, 0.04% PS80, pH6.0;
F3) 20 mM Citrate, 8% sucrose, 0.04% PS80, pH5.5; and
F4) 20 mM Histidine, 8% sucrose, 10 mM Methionine, 0.04% PS80, pH5.5.

The antibody was subjected to (1) incubation for one and two weeks at 40° C., (2) agitation of 300 rpm at 25° C. for three days, and (3) 3-5 cycles of Freeze/Thaw (F/T). At T=0 and post treatment the antibody was analyzed for appearance, size-exclusion chromatography-ultraperformance liquid chromatography (SEC-UPLC), pH, protein concentration, PI (Capillary isoelectric focusing—cIEF), subvisible particles (Micro flow imaging—MFI) and Tm (DSC).

Results: The tables presented as FIGS. 22A-22G, show the results of analyzing the different antibody formulations.

As can be seen in tables provided in FIGS. 22A-22G BDG17.069 formulated in F2, F3, F4 showed no apparent change in concentration, nor change in appearance is detected after one and two weeks of incubation at 40° C. Analysis of sub-visual particles by MFI demonstrate that in BDG17.069 formulated in F1, F2, or F4 shows no formation of particles >=25 uM and only minor change in formation of particles >=10 uM (FIG. 22B). SEC-UPLC analysis revealed only minor increase in small MW species for all four formulation conditions. Additionally, caliper-SDS analysis demonstrated minimal changes for BDG 17.069 formulated in F2 and F4, and analysis by cIEF displayed relatively small changes for BDG17.069 formulated in F4. However, BDG17.069 formulated in F3 presented substantial increase in acidic percentage at 40° C. after 2 weeks of incubation (FIG. 22C).

While BDG17.069 formulated in F2 and in F3 exhibited slight particle formation post agitation (FIG. 22D), and after 5 cycles of Freeze/Thaw, BDG17.069 formulated in F4 and F1 did not show significant changes to its appearance, pH, concentration or any >5 uM sub visible particles formation (FIG. 22F).

Taken together these experiments demonstrate that in formulations F1, F2, F3 and F4, BDG17.069 has good stability performance after agitation, freeze-thaw stresses and a very moderate aggregate percentage after incubation at 40° C. for 2 weeks; taking all stress conditions into account it is apparent that BDG 17.069 is most stable when formulated in 20 mM Histidine, 8% sucrose, 10 mM Methionine, 0.04% PS80, pH5.5 (F4).

Example 5

This example provides a description of studies demonstrating the safety and efficacy of epitope specific anti-hIL-2 antibodies that are designed to enhance the immune response to infectious agents such as SARS-CoV-2 by specifically activating effector T and NK cells while reducing the binding of IL-2 to regulatory T cells and lung endothelium.

Pre-Clinical Studies

The following pre-clinical studies can be done in 2 phases: phase 1 is to demonstrate the safety of the compound as a single intravenous dose in healthy volunteers; phase 2 is to demonstrate safety of multidoses in a virally infected animal model.

As disclosed herein, the anti-IL-2 antibodies specifically bind to human IL-2 and do not bind to mouse IL-2. Although mouse IL-2 receptors can bind human IL-2, allowing one to load hIL-2 into a complex and use a mouse model, normal mice are not desirable as they would subsequently begin to produce high levels of mouse IL-2. Secreted mIL-2 would therefore be available to bind receptors in the lung to induce edema, thereby confounding the safety interpretation. Therefore, animal models that allow either use of human IL-2 or for which antibody cross reactivity with endogenous IL-2 does occur are preferred models. For mouse models, several options are available. First, to investigate whether the antibody or Ab/IL2 complex has any detrimental effect directly on CD25 expressing lung tissue, an IL-2 knock-out mouse is available. The primary limitation of this model is the lack of any subsequent amplification of the immune response and any additional immune elicited cytokines. A second option is to use healthy C57BL/6 or BalbC mice which have been depleted of mouse IL-2 using a neutralizing antibody. However, optimization of this model will still be needed. A third option is to use CD34+ human cord blood cells transferred into the NOD-EXL mouse to generate a mouse expressing a human immune system. The advantage is that a near full human immune system (albeit with some limitations) is expressed, particularly with all T cell and NK cell populations. This model is also conducive for use as an acute viral infection model as well as a model system in oncology research.

Based data presented herein, since 17.067 and 17.069 demonstrated robust affinity towards cynomolgus monkey IL-2 and based on the high homology between hIL-2 and cIL-2 are likely to presented Ab-IL2 complex receptor discrimination for both, primate safety models can be completed. Healthy cynomolgus monkeys can be tested in a single ascending dose test. It has been demonstrated that cynomolgus monkeys can be infected by SARS-CoV-1 and rhesus monkeys have been shown to be infected by SARS-CoV-2. In both situations, a mild case of lung edema was observed, similar to what is observed in mild human infection. As such, these monkey models would allow for examination of both the safety and efficacy of the anti-IL-2 antibodies/IL-2 complexes.

Dose escalation experiments can be done in healthy animals (e.g., humanized mice, cynomolgus monkey etc) as follows:

Supporting First in Man (FIM) Healthy
a. IL-2 KO mouse dose escalation; and/or
b. mIL2 antibody depleted hIL2+antibody; and/or
c. CD34+ SCT humanized mouse (+/−IL2);
d. Healthy cynomolgus or rhesus single dose escalation;
e. Healthy cynomolgus or rhesus multi dose (done concurrently with FIM single ascending dose).

Supporting Patient Dosing (Phase 1b or 2)
a. Mouse (b or c above and/or hACE2 transgenic) viral loaded (acute flu infection model or coronavirus respectively).
b. If available, cynomolgus (SARS-CoV) or rhesus (SARS-CoV-2) coronavirus acute infection model.

Clinical Trials

Part 1) A dose escalation trial in healthy volunteers can be done to identify the maximum tolerated dose. Up to eight cohorts of 10 individuals (8 test, 2 placebo) can be done using an appropriate interval between doses to all for safety determinations.

Part 2) Using the doses determined in Part 1, recently symptomatic SARS-CoV-2 positive patients with mild symptoms can be treated and monitored for safety and efficacy. Efficacy can be determined by decrease in time to viral clearance and a decrease in the signs and symptoms of respiratory infection. Exploratory endpoints can include changes in peripheral blood immune cell populations and activation states.

CHEMISTRY, MANUFACTURING AND CONTROLS

Cell line, drug substance (DS), and drug product (DP) can be done in a GMP qualified manufacturer under GMP guidance (e.g., Wuxi Biologics). An accelerated material production can be done to have material in 6 months ready for an IND. All, bioburden, viral clearance, viral load and host cell proteins can be examined and reduced to specifications as determined by current manufacturing guidelines to ensure product safety. DP can be formulated for intravenous administration. Stability testing can be done concurrently to ensure product quality over time.

What is claimed is:

1. An isolated anti-IL-2 antibody comprising a heavy chain variable region (VH) and a light chain variable region (VL), wherein said VH comprises heavy chain complementarity determining regions (HCDRs) HCDR1, HCDR2 and HCDR3, said VL comprises light chain complementarity determining regions (LCDRs) LCDR1, LCDR2 and LCDR3, wherein said CDRs have the amino acid sequences of (a) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67;

(b) the HCDR1 comprises the amino acid sequence of SEQ ID NO:38, the HCDR2 comprises the amino acid sequence of SEQ ID NO:39, the HCDR3 comprises the amino acid sequence of SEQ ID NO:40, the LCDR1 comprises the amino acid sequence of SEQ ID NO:41, the LCDR2 comprises the amino acid sequence YAS, the LCDR3 comprises the amino acid sequence of SEQ ID NO:43;

(c) the HCDR1 comprises the amino acid sequence of SEQ ID NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49;

(d) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55; or (e) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61.

2. The antibody of claim 1, wherein the VH and VL have the amino acid sequences of (a) the VH comprises the amino acid sequence of SEQ ID NO:26, the VL comprises the amino acid sequence of SEQ ID NO:27;

(b) the VH comprises the amino acid sequence of SEQ ID NO:20, the VL comprises the amino acid sequence of SEQ ID NO:21;

(c) the VH comprises the amino acid sequence of SEQ ID NO:22, the VL comprises the amino acid sequence of SEQ ID NO:23;

(d) the VH comprises the amino acid sequence of SEQ ID NO:24, the VL comprises the amino acid sequence of SEQ ID NO:25; or (e) the VH comprises the amino acid sequence of SEQ ID NO:36, the VL comprises the amino acid sequence of SEQ ID NO:37.

3. The antibody of claim 1, wherein the antibody comprises an IgG, IgA, IgM, IgE, IgD, a Fv, a scFv, a Fab, a F(ab')$_2$, a minibody, a diabody, or a triabody, or wherein said antibody comprises a heavy chain comprising a mutation that reduces binding to Fcγ receptor, or a combination thereof.

4. The antibody of claim 3, wherein when said heavy chain comprises a mutation, said antibody comprises the heavy chain sequence and the light chain sequence as set forth,
- (a) said heavy chain sequence set forth in SEQ ID NO: 72 and said light chain sequence set forth in SEQ ID NO: 73;
- (b) said heavy chain sequence set forth in SEQ ID NO: 68 and said light chain sequence set forth in SEQ ID NO: 69; or
- (c) said heavy chain sequence set forth in SEQ ID NO: 70 and said light chain sequence set forth in SEQ ID NO: 71.

5. A composition comprising an anti-IL-2 antibody and a pharmaceutically acceptable carrier, said anti-IL-2 antibody comprising a heavy chain variable region (VH) and a light chain variable region (VL), wherein said VH comprises heavy chain complementarity determining regions (HCDRs) HCDR1, HCDR2 and HCDR3, said VL comprises light chain complementarity determining regions (LCDRs) LCDR1, LCDR2 and LCDR3, wherein said CDRs have the amino acid sequences of
- (a) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67;
- (b) the HCDR1 comprises the amino acid sequence of SEQ ID NO:38, the HCDR2 comprises the amino acid sequence of SEQ ID NO:39, the HCDR3 comprises the amino acid sequence of SEQ 1D NO:40, the LCDR1 comprises the amino acid sequence of SEQ ID NO:41, the LCDR2 comprises the amino acid sequence YAS, the LCDR3 comprises the amino acid sequence of SEQ ID NO:43;
- (c) the HCDR1 comprises the amino acid sequence of SEQ 1D NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49;
- (d) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55; or
- (e) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61.

6. The composition of claim 5, wherein the composition is formulated to be at a pH between about pH 5.0-6.0 and comprises a buffer selected from a histidine buffer and a citrate buffer.

7. The composition of claim 6, said composition further comprising (a) at least one of sucrose, methionine, or PS80, or any combination thereof; or (b) IL-2; or (c) any combination thereof.

8. The composition of claim 5, wherein the VH and VL have the amino acid sequences of
- (a) the VH comprises the amino acid sequence of SEQ ID NO:26, the VL comprises the amino acid sequence of SEQ ID NO:27;
- (b) the VH comprises the amino acid sequence of SEQ ID NO:20, the VL comprises the amino acid sequence of SEQ ID NO:21;
- (c) the VH comprises the amino acid sequence of SEQ ID NO:22, the VL comprises the amino acid sequence of SEQ ID NO:23;
- (d) the VH comprises the amino acid sequence of SEQ ID NO:24, the VL comprises the amino acid sequence of SEQ ID NO:25; or
- (e) the VH comprises the amino acid sequence of SEQ ID NO:36, the VL comprises the amino acid sequence of SEQ ID NO:37.

9. The composition of claim 5, wherein the antibody comprises an IgG, IgA, IgM, IgE, IgD, a Fv, a scFv, a Fab, a F(ab')$_2$, a minibody, a diabody, or a triabody; or wherein said antibody comprises a heavy chain comprising a mutation that reduces binding to Fcγ receptor; or any combination thereof.

10. The composition of claim 9, said antibody comprising a heavy chain sequence and a light chain sequence,
- (a) said heavy chain sequence set forth in SEQ ID NO: 72 and said light chain sequence set forth in SEQ ID NO: 73;
- (b) said heavy chain sequence set forth in SEQ ID NO: 68 and said light chain sequence set forth in SEQ ID NO: 69; or
- (c) said heavy chain sequence set forth in SEQ ID NO: 70 and said light chain sequence set forth in SEQ ID NO: 71.

11. A method of treating a disease or a condition in a subject comprising the step of administering to the subject a composition comprising an anti-IL-2 antibody, said anti-TL-2 antibody comprising a heavy chain variable region (VH) and a light chain variable region (VL), wherein said VH comprises heavy chain complementarity determining regions (HCDRs) HCDR1, HCDR2 and HCDR3, said VL comprises light chain complementarity determining regions (LCDRs) LCDR1, LCDR2 and LCDR3, wherein said CDRs have the amino acid sequences of
- (a) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67;
- (b) the HCDR1 comprises the amino acid sequence of SEQ ID NO:38, the HCDR2 comprises the amino acid sequence of SEQ ID NO:39, the HCDR3 comprises the amino acid sequence of SEQ ID NO:40, the LCDR1 comprises the amino acid sequence of SEQ ID NO:41, the LCDR2 comprises the amino acid sequence YAS, the LCDR3 comprises the amino acid sequence of SEQ ID NO:43;
(c) the HCDR1 comprises the amino acid sequence of SEQ ID NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49;
(d) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55; or
(e) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61, and
wherein said antibody promotes differential growth of subsets of immune cells and decreases undesirable effects caused by IL-2, wherein said disease is cancer and said cancer is selected from melanoma and metastatic renal cell carcinoma, or wherein said disease is a viral infection and said virus is a SARS-CoV-2 virus, and wherein said condition is selected from pulmonary edema or vascular leak syndrome, thereby treating said disease or condition in said subject.

12. The method of claim 11, wherein the VH and VL have the amino acid sequences of
    (a) the VH comprises the amino acid sequence of SEQ ID NO:26, the VL comprises the amino acid sequence of SEQ ID NO:27;
    (b) the VH comprises the amino acid sequence of SEQ ID NO:20, the VL comprises the amino acid sequence of SEQ ID NO:21;
    (c) the VH comprises the amino acid sequence of SEQ ID NO:22, the VL comprises the amino acid sequence of SEQ ID NO:23;
    (d) the VH comprises the amino acid sequence of SEQ ID NO:24, the VL comprises the amino acid sequence of SEQ ID NO:25; or
    (e) the VH comprises the amino acid sequence of SEQ ID NO:36, the VL comprises the amino acid sequence of SEQ ID NO:37.

13. The method of claim 11, wherein the antibody comprises an IgG, IgA, IgM, IgE, IgD, a Fv, a scFv, a Fab, a F(ab')$_2$, a minibody, a diabody, or a triabody; or wherein said antibody comprises a heavy chain comprising a mutation that reduces binding to Fcγ receptor; or any combination thereof.

14. The method of claim 13, wherein when said heavy chain comprises a mutation said antibody comprising the heavy chain sequence and the light chain sequence as set forth,
    (a) said heavy chain sequence set forth in SEQ ID NO: 72 and said light chain sequence set forth in SEQ ID NO: 73;
    (b) said heavy chain sequence set forth in SEQ ID NO: 68 and said light chain sequence set forth in SEQ ID NO: 69; or
    (c) said heavy chain sequence set forth in SEQ ID NO: 70 and said light chain sequence set forth in SEQ ID NO: 71.

15. The method of claim 11, wherein said composition comprises the anti-IL-2 antibody and IL-2, or the anti-IL-2 antibody complexed with IL-2.

16. The method of claim 11, wherein the immune cells comprise one or more of naive T cells, memory T cells, CD8$^+$ T cells, NK cells, or Natural Killer T cells.

17. The method of claim 11, wherein said undesirable effect caused by IL-2 comprises one or more of activation of regulatory T cells, apoptosis of CD25$^+$ T effector cells, IL-2 induced pulmonary edema, IL-2 induced pneumonia, or IL-2-induced vascular leakage.

18. The method of claim 11, wherein said anti-IL-2 antibody inhibits IL-2 binding to CD25.

19. The method of claim 11, wherein said subject is further treated with one or more immune checkpoint inhibitors targeting one or more immune checkpoints, wherein said treatment with said immune checkpoint inhibitors occurs concurrently, before, or after treatment with said anti-IL-2 antibody.

20. The method of claim 19, wherein said immune checkpoint comprises PD-1, PD-L1, CTLA-4, TIGIT, TIM-3, B7-H3, CD73, LAG3, CD27, CD70, 4-1BB, GITR, OX40, SIRP-alpha (CD47), CD39, ILDR2, VISTA, BTLA, or VTCN-1, or a combination thereof.

21. A method of protecting a subject against pulmonary edema and lung tissue damage caused by SARS-CoV-2 or IL-2, wherein said method comprises administration of a pharmaceutical composition comprising an IL-2 antibody, said anti-IL-2 antibody comprising a heavy chain variable region (VH) and a light chain variable region (VL), wherein said VH comprises heavy chain complementarity determining regions (HCDRs) HCDR1, HCDR2 and HCDR3, and said VL comprises light chain complementarity determining regions (LCDRs) LCDR1, LCDR2 and LCDR3, wherein said CDRs have the amino acid sequences of
    (a) the HCDR1 comprises the amino acid sequence of SEQ ID NO:62, the HCDR2 comprises the amino acid sequence of SEQ ID NO:63, the HCDR3 comprises the amino acid sequence of SEQ ID NO:64, the LCDR1 comprises the amino acid sequence of SEQ ID NO:65, the LCDR2 comprises the amino acid sequence DAS, the LCDR3 comprises the amino acid sequence of SEQ ID NO:67;
    (b) the HCDR1 comprises the amino acid sequence of SEQ ID NO:38, the HCDR2 comprises the amino acid sequence of SEQ ID NO:39, the HCDR3 comprises the amino acid sequence of SEQ ID NO:40, the LCDR1 comprises the amino acid sequence of SEQ ID NO:41, the LCDR2 comprises the amino acid sequence YAS, the LCDR3 comprises the amino acid sequence of SEQ ID NO:43;
    (c) the HCDR1 comprises the amino acid sequence of SEQ ID NO:44, the HCDR2 comprises the amino acid sequence of SEQ ID NO:45, the HCDR3 comprises the amino acid sequence of SEQ ID NO:46, the LCDR1 comprises the amino acid sequence of SEQ ID NO:47, the LCDR2 comprises the amino acid sequence YAS, the LCDR3 comprises the amino acid sequence of SEQ ID NO:49;
    (d) the HCDR1 comprises the amino acid sequence of SEQ ID NO:50, the HCDR2 comprises the amino acid sequence of SEQ ID NO:51, the HCDR3 comprises the amino acid sequence of SEQ ID NO:52, the LCDR1 comprises the amino acid sequence of SEQ ID NO:53, the LCDR2 comprises the amino acid sequence YAS, the LCDR3 comprises the amino acid sequence of SEQ ID NO:55; or (e) the HCDR1 comprises the amino acid sequence of SEQ ID NO:56, the HCDR2 comprises the amino acid sequence of SEQ ID NO:57, the HCDR3 comprises the amino acid sequence of SEQ ID NO:58, the LCDR1 comprises the amino acid sequence of SEQ ID NO:59, the LCDR2 comprises the amino acid sequence YAS, the LCDR3 comprises the amino acid sequence of SEQ ID NO:61;

wherein said administration protects the subject against pulmonary edema and lung tissue damage caused by SARS-CoV-2 or IL-2.

22. The method of claim 21, wherein said pharmaceutical composition comprises the anti-IL-2 antibody and IL-2, or comprises an anti-IL-2 antibody complexed with IL-2.

23. The method of claim 21, wherein said subject has (a) a weakened immune system; or (b) a genetic predisposition that increases likelihood of cancer in said subject; or (c) a combination of (a) and (b).

24. The method of claim 17, wherein said genetic predisposition comprises (a) a change in expression or activity of a gene product, said gene comprising a tumor suppressor gene or a mismatch repair (MMR) gene, or a combination thereof; or (a) a change in expression or activity of a gene product, said gene comprising BRCA1, BRAC2, MLH1, MSH2, MSH6, PMS1, PMS2, TP53, or CHEK2, or a combination thereof; or (c) a combination of (a) and (b).

25. The method of claim 21, wherein the VH and VL have the amino acid sequences of (a) the VH comprises the amino acid sequence of SEQ ID NO:26, the VL comprises the amino acid sequence of SEQ ID NO:27;

(b) the VH comprises the amino acid sequence of SEQ ID NO:20, the VL comprises the amino a id sequence of SEQ ID NO:21;

(c) the VH comprises the amino acid sequence of SEQ ID NO:22, the VL comprises the amino acid sequence of SEQ ID NO:23;

(d) the VH comprises the amino acid sequence of SEQ ID NO:24, the VL comprises the amino acid sequence of SEQ ID NO:2;

(e) the VH comprises the amino acid sequence of SEQ ID NO:36, the VL comprises the amino acid sequence of SEQ ID NO:37.

26. The method of claim 21, wherein the antibody comprises an IgG, IgA, IgM, IgE, IgD, a Fv, a scFv, a Fab, a $F(ab')_2$, a minibody, a diabody, or a triabody; or wherein said antibody comprises a heavy chain comprising a mutation that reduces binding to Fcγ receptor; or any combination thereof.

27. The method of claim 26, said antibody comprising the heavy chain sequence and the light chain sequence set forth, (a) said heavy chain sequence set forth in SEQ ID NO: 72 and said light chain sequence set forth in SEQ ID NO: 73;

(b) said heavy chain sequence set forth in SEQ ID NO: 68 and said light chain sequence set forth in SEQ ID NO: 69; or (c) said heavy chain sequence set forth in SEQ ID NO: 70 and said light chain sequence set forth in SEQ ID NO: 71.

* * * * *

SEQUENCE LISTING

```
Sequence total quantity: 73
SEQ ID NO: 1           moltype = DNA  length = 747
FEATURE                Location/Qualifiers
misc_feature           1..747
                       note = scFv clone 17.021
source                 1..747
                       mol_type = other DNA
                       organism = synthetic construct
```

```
SEQUENCE: 1
gagattcagc tgcagcagag cggtccagaa ctgcgtcgtc caggctcctc cgttaaactg    60
agctgcaaag cctctggtta taacatcacc gataacctga ttcattgggt tcgtcaccgt   120
ccagaacacg gtctggaatg gatcggctgg attgatccag aggacggtga aacccgttac   180
gcccaaaaat tccagtctaa agcaaccctg actgccgaca ctagctccaa cgccgcttac   240
atgcagctga gcagcctgac ccctgaggat accgccacct atttctgcgc acgttctctg   300
gattccacct atatttaccc attcgcatac tggggccaag gcaccttgt  caccgtttcc   360
tccggcggtg gtggtagcgg aggcggagga tcaggtggag gcggcagtga cattgttatg   420
actcagtccc cattctccct ggccgtttct gagggtgaaa tggtaaccat taactgcaaa   480
tcatcccagt ccctgctgcg gtctggcaac cagaaaaaact atctggcctg gtaccagcag   540
aaaccaggtc agtccccaaa actgctgatc tactacgcat ctactggcca gtctggtgtc   600
ccagaccgtt tcattggctc tggctctggt accgatttca ccctgaccat cagcgatgtt   660
caagctgaag acctggccga ttactattgt ctgcagcact accagagccc accaactttc   720
ggtgcaggca ccaaactgga actgaaa                                       747

SEQ ID NO: 2            moltype = DNA    length = 747
FEATURE                 Location/Qualifiers
misc_feature            1..747
                        note = scFv clone 17.022
source                  1..747
                        mol_type = other DNA
                        organism = synthetic construct
SEQUENCE: 2
gagattcagc tgcagcagag cggtccagaa ctgcgtcgtc caggctcctc cgttaaactg    60
agctgcaaag cctctggtta taacatcacc gattacctga ttcattgggt tcgtcaccgt   120
ccagaacacg gtctggaatg gatcggctgg attgatccag aggacggtga aacccgttac   180
gcccaaaaat tccagtctaa agcaaccctg actgccgaca ctagctccaa cgccgcttac   240
atgcagctga gcagcctgac ccctgaggat accgccacct atttctgcgc acgttctctg   300
gattccacct ggatttaccc attcgcatac tggggccaag gcaccttgt  caccgtttcc   360
tccggcggtg gtggtagcgg aggcggagga tcaggtggag gcggcagtga cattgttatg   420
actcagtccc cattctccct ggccgtttct gagggtgaaa tggtaaccat taactgcaaa   480
tcatcccagt ccctgctgcg gtctggcaac cagaaaaaact atctggcctg gtaccagcag   540
aaaccaggtc agtccccaaa actgctgatc tactacgcat ctactggcca gtctggtgtc   600
ccagaccgtt tcattggctc tggctctggt accgatttca ccctgaccat cagcgatgtt   660
caagctgaag acctggccga ttactattgt ctgcagcact acattacccc accaactttc   720
ggtgcaggca ccaaactgga actgaaa                                       747

SEQ ID NO: 3            moltype = DNA    length = 747
FEATURE                 Location/Qualifiers
misc_feature            1..747
                        note = scFv clone 17.023
source                  1..747
                        mol_type = other DNA
                        organism = synthetic construct
SEQUENCE: 3
gagattcagc tgcagcagag cggtccagaa ctgcgtcgtc caggctcctc cgttaaactg    60
agctgcaaag cctctggtta taacatcacc gattacctga ttcattgggt tcgtcaccgt   120
ccagaacacg gtctggaatg gatcggctgg attgatccag aggacggtga aacccgttac   180
gcccaaaaat tccagtctaa agcaaccctg actgccgaca ctagctccaa cgccgcttac   240
atgcagctga gcagcctgac ccctgaggat accgccacct atttctgcgc acgttcagtg   300
gattccacct atatttaccc attcgcatac tggggccaag gcaccttgt  caccgtttcc   360
tccggcggtg gtggtagcgg aggcggagga tcaggtggag gcggcagtga cattgttatg   420
actcagtccc cattctccct ggccgtttct gagggtgaaa tggtaaccat taactgcaaa   480
tcatcccagt ccctgctgcg gtctggcaac cagaaaaaact atctggcctg gtaccagcag   540
aaaccaggtc agtccccaaa actgctgatc tactacgcat ctactggcca gtctggtgtc   600
ccagaccgtt tcattggctc tggctctggt accgatttca ccctgaccat cagcgatgtt   660
caagctgaag acctggccga ttactattgt ctgcagcact acattacccc accaactttc   720
ggtgcaggca ccaaactgga actgaaa                                       747

SEQ ID NO: 4            moltype = DNA    length = 747
FEATURE                 Location/Qualifiers
misc_feature            1..747
                        note = scFv clone 17.030
source                  1..747
                        mol_type = other DNA
                        organism = synthetic construct
SEQUENCE: 4
gagattcagc tgcagcagag cggtccagaa ctgcgtcgtc caggctcctc cgttaaactg    60
agctgcaaag cctctggtta taacatcacc gattacctga ttcattgggt tcgtcaccgt   120
ccagaacacg gtctggaatg gatcggctgg attgatccag aggacggtga aacccgttac   180
gcccaaaaat tccagtctaa agcaaccctg actgccgaca ctagctccaa cgccgcttac   240
atgcagctga gcagcctgac ccctgaggat accgccacct atttctgcgc acgttctctg   300
gattccacct atgactaccc attcgcatac tggggccaag gcaccttgt  caccgtttcc   360
tccggcggtg gtggtagcgg aggcggagga tcaggtggag gcggcagtga cattgttatg   420
actcagtccc cattctccct ggccgtttct gagggtgaaa tggtaaccat taactgcaaa   480
tcatcccagt ccctgctgcg gtctggcaac cagaaaaaact atctggcctg gtaccagcag   540
aaaccaggtc agtccccaaa actgctgatc tactacgcat ctactggcca gtctggtgtc   600
```

```
ccagaccgtt tcattggctc tggctctggt accgatttca ccctgaccat cagcgatgtt    660
caagctgaag acctggccga ttactattgt ctgcagcact acatttcgcc accaactttc    720
ggtgcaggca ccaaactgga actgaaa                                        747
```

```
SEQ ID NO: 5              moltype = DNA  length = 747
FEATURE                   Location/Qualifiers
misc_feature              1..747
                          note = scFv clone 17.035
source                    1..747
                          mol_type = other DNA
                          organism = synthetic construct
SEQUENCE: 5
gagattcagc tgcagcagag cggtccagaa ctgcgtcgtc caggctcctc cgttaaactg     60
agctgcaaag cctctggtta taacatcacc gattacctga ttcattgggt tcgtcaccgt    120
ccagaacacg gtctggaatg gatcggctgg attgatccag aggacggtga aacccgttac    180
gcccaaaaat tccagtctaa agcaaccctg actgccgaca ctagctccaa cgccgcttac    240
atgcagctga gcagcctgac ccctgaggat accgccacct atttctgcgc acgttctctg    300
gattccacct ataactaccc attcgcatac tgggggcaag gcaccgttgt caccgtttcc    360
tccggcggtg gtggtagcgg aggcggagga tcaggtggag gcggcagtga cattgttatg    420
actcagtccc cattctccct ggccgtttct gagggtgaaa tggtaaccat taactgcaaa    480
tcatcccagt ccctgctgcg gtctggcaac cagaaaaact atctggcctg gtaccagcag    540
aaaccaggtc agtccccaaa actgctgatc tactacgcat ctactggcca gtctggtgtc    600
ccagaccgtt tcattggctc tggctctggt accgatttca ccctgaccat cagcgatgtt    660
caagctgaag acctggccga ttactattgt ctgcagcact ggattagccc accaactttc    720
ggtgcaggca ccaaactgga actgaaa                                        747
```

```
SEQ ID NO: 6              moltype = AA  length = 121
FEATURE                   Location/Qualifiers
REGION                    1..121
                          note = Heavy chain variable region of JES6.1
source                    1..121
                          mol_type = protein
                          organism = synthetic construct
SEQUENCE: 6
EIQLQQSGPE LRRPGSSVKL SCKASGYNIT DYLIHWVRHR PEHGLEWIGW IDPEDGETRY     60
AQKFQSKATL TADTSSNAAY MQLSSLTPED TATYFCARSL DSTYIYPFAY WGQGTLVTVS    120
S                                                                   121
```

```
SEQ ID NO: 7              moltype = AA  length = 113
FEATURE                   Location/Qualifiers
REGION                    1..113
                          note = Light chain variable region of JES6.1
source                    1..113
                          mol_type = protein
                          organism = synthetic construct
SEQUENCE: 7
DIVMTQSPFS LAVSEGEMVT INCKSSQSLL SSGNQKNYLA WYQQKPGQSP KLLIYYASTG     60
QSGVPDRFIG SGSGTDFTLT ISDVQAEDLA DYYCLQHYIS PPTFGAGTKL ELK           113
```

```
SEQ ID NO: 8              moltype = AA  length = 121
FEATURE                   Location/Qualifiers
REGION                    1..121
                          note = Heavy chain variable region of JES6.1RMC
source                    1..121
                          mol_type = protein
                          organism = synthetic construct
SEQUENCE: 8
EIQLQQSGPE LRRPGSSVKL SCKASGYNIT DYLIHWVRHR PEHGLEWIGW IDPEDGETRY     60
AQKFQSKATL TADTSSNAAY MQLSSLTPED TATYFCARSL DSTYIYPFAY WGQGTLVTVS    120
S                                                                   121
```

```
SEQ ID NO: 9              moltype = AA  length = 113
FEATURE                   Location/Qualifiers
REGION                    1..113
                          note = Light chain variable region of JES6.1RMC
source                    1..113
                          mol_type = protein
                          organism = synthetic construct
SEQUENCE: 9
DIVMTQSPFS LAVSEGEMVT INCKSSQSLL SSGNQKNYLA WYQQKPGQSP KLLIYYASTG     60
QSGVPDRFIG SGSGTDFTLT ISDVQAEDLA DYYCLQHYIS PPTFGAGTKL ELK           113
```

```
SEQ ID NO: 10             moltype = AA  length = 121
FEATURE                   Location/Qualifiers
REGION                    1..121
                          note = Heavy chain variable region of clone 17.021
source                    1..121
                          mol_type = protein
                          organism = synthetic construct
```

```
SEQUENCE: 10
EIQLQQSGPE LRRPGSSVKL SCKASGYNIT DNLIHWVRHR PEHGLEWIGW IDPEDGETRY     60
AQKFQSKATL TADTSSNAAY MQLSSLTPED TATYFCARSL DSTYIYPFAY WGQGTLVTVS    120
S                                                                   121

SEQ ID NO: 11           moltype = AA   length = 113
FEATURE                 Location/Qualifiers
REGION                  1..113
                        note = Light chain variable region of clone 17.021
source                  1..113
                        mol_type = protein
                        organism = synthetic construct
SEQUENCE: 11
DIVMTQSPFS LAVSEGEMVT INCKSSQSLL RSGNQKNYLA WYQQKPGQSP KLLIYYASTG     60
QSGVPDRFIG SGSGTDFTLT ISDVQAEDLA DYYCLQHYQS PPTFGAGTKL ELK           113

SEQ ID NO: 12           moltype = AA   length = 121
FEATURE                 Location/Qualifiers
REGION                  1..121
                        note = Heavy chain variable region of clone 17.022
source                  1..121
                        mol_type = protein
                        organism = synthetic construct
SEQUENCE: 12
EIQLQQSGPE LRRPGSSVKL SCKASGYNIT DYLIHWVRHR PEHGLEWIGW IDPEDGETRY     60
AQKFQSKATL TADTSSNAAY MQLSSLTPED TATYFCARSL DSTWIYPFAY WGQGTLVTVS    120
S                                                                   121

SEQ ID NO: 13           moltype = AA   length = 113
FEATURE                 Location/Qualifiers
REGION                  1..113
                        note = Light chain variable region of clone 17.022
source                  1..113
                        mol_type = protein
                        organism = synthetic construct
SEQUENCE: 13
DIVMTQSPFS LAVSEGEMVT INCKSSQSLL RSGNQKNYLA WYQQKPGQSP KLLIYYASTG     60
QSGVPDRFIG SGSGTDFTLT ISDVQAEDLA DYYCLQHYIT PPTFGAGTKL ELK           113

SEQ ID NO: 14           moltype = AA   length = 121
FEATURE                 Location/Qualifiers
REGION                  1..121
                        note = Heavy chain variable region of clone 17.023
source                  1..121
                        mol_type = protein
                        organism = synthetic construct
SEQUENCE: 14
EIQLQQSGPE LRRPGSSVKL SCKASGYNIT DYLIHWVRHR PEHGLEWIGW IDPEDGETRY     60
AQKFQSKATL TADTSSNAAY MQLSSLTPED TATYFCARQL DSTYIYPFAY WGQGTLVTVS    120
S                                                                   121

SEQ ID NO: 15           moltype = AA   length = 113
FEATURE                 Location/Qualifiers
REGION                  1..113
                        note = Light chain variable region of clone 17.023
source                  1..113
                        mol_type = protein
                        organism = synthetic construct
SEQUENCE: 15
DIVMTQSPFS LAVSEGEMVT INCKSSQSLL RSGNQKNYLA WYQQKPGQSP KLLIYYASTG     60
QSGVPDRFIG SGSGTDFTLT ISDVQAEDLA DYYCLQHYIT PPTFGAGTKL ELK           113

SEQ ID NO: 16           moltype = AA   length = 121
FEATURE                 Location/Qualifiers
REGION                  1..121
                        note = Heavy chain variable region of clone 17.030
source                  1..121
                        mol_type = protein
                        organism = synthetic construct
SEQUENCE: 16
EIQLQQSGPE LRRPGSSVKL SCKASGYNIT DYLIHWVRHR PEHGLEWIGW IDPEDGETRY     60
AQKFQSKATL TADTSSNAAY MQLSSLTPED TATYFCARSL DSTYDYPFAY WGQGTLVTVS    120
S                                                                   121

SEQ ID NO: 17           moltype = AA   length = 113
FEATURE                 Location/Qualifiers
REGION                  1..113
                        note = Light chain variable region of clone 17.030
source                  1..113
```

```
                              mol_type = protein
                              organism = synthetic construct
SEQUENCE: 17
DIVMTQSPFS LAVSEGEMVT INCKSSQSLL RSGNQKNYLA WYQQKPGQSP KLLIYYASTG    60
QSGVPDRFIG SGSGTDFTLT ISDVQAEDLA DYYCLQHYIS PPTFGAGTKL ELK           113

SEQ ID NO: 18           moltype = AA   length = 121
FEATURE                 Location/Qualifiers
REGION                  1..121
                        note = Heavy chain variable region of clone 17.035
source                  1..121
                        mol_type = protein
                        organism = synthetic construct
SEQUENCE: 18
EIQLQQSGPE LRRPGSSVKL SCKASGYNIT DYLIHWVRHR PEHGLEWIGW IDPEDGETRY    60
AQKFQSKATL TADTSSNAAY MQLSSLTPED TATYFCARSL DSTYNYPFAY WGQGTLVTVS    120
S                                                                   121

SEQ ID NO: 19           moltype = AA   length = 113
FEATURE                 Location/Qualifiers
REGION                  1..113
                        note = Light chain variable region of clone 17.035
source                  1..113
                        mol_type = protein
                        organism = synthetic construct
SEQUENCE: 19
DIVMTQSPFS LAVSEGEMVT INCKSSQSLL RSGNQKNYLA WYQQKPGQSP KLLIYYASTG    60
QSGVPDRFIG SGSGTDFTLT ISDVQAEDLA DYYCLQHWIS PPTFGAGTKL ELK           113

SEQ ID NO: 20           moltype = AA   length = 121
FEATURE                 Location/Qualifiers
REGION                  1..121
                        note = Heavy chain variable region of clone 17.038
source                  1..121
                        mol_type = protein
                        organism = synthetic construct
SEQUENCE: 20
QVQLVQSGAE VKKPGSSVKV SCKASGYSIT DSLIHWVRQA PGQGLEWMGW IDPEDGEINY    60
AQKFQGRVTL TADTSTSTAY MELSSLRSED TAVYYCARSL DSYPIDPFAY WGQGTLVTVS    120
S                                                                   121

SEQ ID NO: 21           moltype = AA   length = 113
FEATURE                 Location/Qualifiers
REGION                  1..113
                        note = Light chain variable region of clone 17.038
source                  1..113
                        mol_type = protein
                        organism = synthetic construct
SEQUENCE: 21
DIVMTQSPDS LAVSLGERAT INCKSSQSLL RNGNQQNYLA WYQQKPGQPP KLLIYYASTG    60
QSGVPDRFSG SGSGTDFTLT ISSLQAEDVA VYYCQQHYVT PPTFGAGTKV EIK           113

SEQ ID NO: 22           moltype = AA   length = 121
FEATURE                 Location/Qualifiers
REGION                  1..121
                        note = Heavy chain variable region of clone 17.043
source                  1..121
                        mol_type = protein
                        organism = synthetic construct
SEQUENCE: 22
QVQLVQSGAE VKKPGSSVKV SCKASGYSIT DYLIHWVRQA PGQGLEWMGW IDPEDGVTAY    60
AQKFQGRVTL TADTSTSTAY MELSSLRSED TAVYYCARSL DYDPIYPFAY WGQGTLVTVS    120
S                                                                   121

SEQ ID NO: 23           moltype = AA   length = 113
FEATURE                 Location/Qualifiers
REGION                  1..113
                        note = Light chain variable region of clone 17.043
source                  1..113
                        mol_type = protein
                        organism = synthetic construct
SEQUENCE: 23
DIVMTQSPDS LAVSLGERAT INCKSSQSLL RNGNQKNYLA WYQQKPGQPP KLLIYYASTG    60
QSGVPDRFSG SGSGTDFTLT ISSLQAEDVA VYYCQQHYVT PPTFGAGTKV EIK           113

SEQ ID NO: 24           moltype = AA   length = 121
FEATURE                 Location/Qualifiers
REGION                  1..121
                        note = Heavy chain variable region of clone 17.053
```

```
source                   1..121
                         mol_type = protein
                         organism = synthetic construct
SEQUENCE: 24
QVQLVQSGAE VKKPGSSVKV SCKASGYSIT DYLIHWVRQA PGQGLEWMGW IDPEDGETNY    60
AQKFQGRVTL TADTSTSTAY MELSSLRSED TAVYYCARSL DYDPIYPFAY WGQGTLVTVS   120
S                                                                  121

SEQ ID NO: 25            moltype = AA   length = 113
FEATURE                  Location/Qualifiers
REGION                   1..113
                         note = Light chain variable region of clone 17.053
source                   1..113
                         mol_type = protein
                         organism = synthetic construct
SEQUENCE: 25
DIVMTQSPDS LAVSLGERAT INCKSSQSLL RNGNQKNYLA WYQQKPGQPP KLLIYYASTG    60
QSGVPDRFSG SGSGTDFTLT ISSLQAEDVA VYYCQQHYIT PPTFGAGTKV EIK          113

SEQ ID NO: 26            moltype = AA   length = 121
FEATURE                  Location/Qualifiers
REGION                   1..121
                         note = Heavy chain variable region of clone 17.054
source                   1..121
                         mol_type = protein
                         organism = synthetic construct
SEQUENCE: 26
QVQLVQSGAE VKKPGSSVKV SCKASGYSIT DDLIHWVRQA PGQGLEWMGW IDPEDGETNY    60
AQKFQGRVTL TADTSTSTAY MELSSLRSED TAVYYCARSL DSTWIYPFAY WGQGTLVTVS   120
S                                                                  121

SEQ ID NO: 27            moltype = AA   length = 113
FEATURE                  Location/Qualifiers
REGION                   1..113
                         note = Light chain variable region of clone 17.054
source                   1..113
                         mol_type = protein
                         organism = synthetic construct
SEQUENCE: 27
DIVMTQSPDS LAVSLGERAT INCKSSQSLL RRGNQKNHLA WYQQKPGQPP KLLIYDASTG    60
QSGVPDRFSG SGSGTDFTLT ISSLQAEDVA VYYCLQSYIT PPTFGAGTKV EIK          113

SEQ ID NO: 28            moltype = DNA   length = 747
FEATURE                  Location/Qualifiers
misc_feature             1..747
                         note = scFv clone 17.002
source                   1..747
                         mol_type = other DNA
                         organism = synthetic construct
SEQUENCE: 28
gagattcagc tgcagcagag cggtccagaa ctgcgtcgtc caggctcctc cgttaaactg    60
agctgcaaaa cctctggtta taacatcacc gattacctga ttcattgggt tcgtcaccgt   120
ccagaacacg gtctgaatg gatcggctgg attgatccag aggacggtga aacccgttac   180
gcccaaaaat tccagtctaa agcaaaccctg actgccgaca ctagctccaa cgccgcttac   240
atgcagctga gcagcctgac ccctgaggat accgccacct atttctgcgc acgttctctg   300
gattccaccc cgatttaccc attcgcatac tggggccaag gcaccttgt caccgtttcc    360
tccggcggtg gtggtagcgg aggcggagga tcaggtggag gcggcagtga cattgttatg   420
actcagtccc cattctccct ggccgtttct gagggtgaaa tggtaaccat taactgcaaa   480
tcatcccagt ccctgctgcg gtctggcaac cagaaaaact atctggcctg gtaccagcag   540
aaaccaggtc agtccccaaa actgctgatc tactacgcat ctactggcca gtctggtgtc   600
ccagaccgtt tcattggctc tggctctggt accgatttca ccctgaccat cagcgatgtt   660
caagctgaag acctggccga ttactattgt ctgcagcact acattacgcc accaactttc   720
ggtgcaggca ccaaactgga actgaaa                                      747

SEQ ID NO: 29            moltype = AA   length = 121
FEATURE                  Location/Qualifiers
REGION                   1..121
                         note = Heavy chain variable region of clone 17.002
source                   1..121
                         mol_type = protein
                         organism = synthetic construct
SEQUENCE: 29
EIQLQQSGPE LRRPGSSVKL SCKASGYNIT DYLIHWVRHR PEHGLEWIGW IDPEDGETRY    60
AQKFQSKATL TADTSSNAAY MQLSSLTPED TATYFCARSL DSTPIYPFAY WGQGTLVTVS   120
S                                                                  121
```

```
SEQ ID NO: 30            moltype = AA  length = 113
FEATURE                  Location/Qualifiers
REGION                   1..113
                         note = Light chain variable region of clone 17.002
source                   1..113
                         mol_type = protein
                         organism = synthetic construct
SEQUENCE: 30
DIVMTQSPFS LAVSEGEMVT INCKSSQSLL RSGNQKNYLA WYQQKPGQSP KLLIYYASTG    60
QSGVPDRFIG SGSGTDFTLT ISDVQAEDLA DYYCLQHYIT PPTFGAGTKL ELK          113

SEQ ID NO: 31            moltype = DNA  length = 747
FEATURE                  Location/Qualifiers
misc_feature             1..747
                         note = scFv clone 17.014
source                   1..747
                         mol_type = other DNA
                         organism = synthetic construct
SEQUENCE: 31
caggtccaac tggtgcagtc cggtgccgaa gttaaaaaac ctgggtcttc cgttaaagtt    60
tcttgcaaag cctctggcta cagcatcacc gattatctga ttcactgggt ccgtcaggct   120
ccaggtcaag gtctggaatg gatgggttgg atcgatccag aagacggtga aaccaactat   180
gcccagaaat tccagggtcg tgtaaccctg accgccgaca cctccacctc taccgcctac   240
atggagttaa gtagcctgcg ttcagaggat accgcagtgt actactgcgc tcgttcactg   300
gactccaccc caatctaccc attcgcatac tgggtcctgg caccctggt aaccgttagt   360
agcggcggtg gtggtagcgg aggcggagga tcaggtggag gcggcagtga catcgtgatg   420
acccagtctc ctgactcctt ggccgtctct ctgggcgaac gtgcaactat caactgcaaa   480
tccagccaga gcttactgcg ttctggtaat cagaaaaact accttgcatg gtatcagcag   540
aaaccaggtc agccaccaaa attactgatc tattatgcat ctaccggtca aagcggtgtc   600
ccagatcgtt tcagcggttc cggctccggt actgacttca ccctgaccat ctcttccctt   660
caggccgaag atgtggccgt gtattactgc ctgcagcact acatcacccc acctactttc   720
ggtgctggta ctaaagttga aatcaaa                                       747

SEQ ID NO: 32            moltype = DNA  length = 747
FEATURE                  Location/Qualifiers
misc_feature             1..747
                         note = scFv clone 17.038
source                   1..747
                         mol_type = other DNA
                         organism = synthetic construct
SEQUENCE: 32
caggtccaac tggtgcagtc cggtgccgaa gttaaaaaac ctgggtcttc cgttaaagtt    60
tcttgcaaag cctctggcta cagcatcacc gattctctga ttcactgggt ccgtcaggct   120
ccaggtcaag gtctggaatg gatgggttgg atcgatccag aagacggtga aattaactat   180
gcccagaaat tccagggtcg tgtaaccctg accgccgaca cctccacctc taccgcctac   240
atggagttaa gtagcctgcg ttcagaggat accgcagtgt actactgcgc tcgttcactg   300
gactcctacc caatcgatcc attcgcatac tgggtcaggg caccctggt aaccgttagt   360
agcggcggtg gtggtagcgg aggcggagga tcaggtggag gcggcagtga catcgtgatg   420
acccagtctc ctgactcctt ggccgtctct ctgggcgaac gtgcaactat caactgcaaa   480
tccagccaga gcttactgcg taatggtaat cagcaaaact accttgcatg gtatcagcag   540
aaaccaggtc agccaccaaa attactgatc tattatgcat ctaccggtca aagcggtgtc   600
ccagatcgtt tcagcggttc cggctccggt actgacttca ccctgaccat ctcttccctt   660
caggccgaag atgtggccgt gtattactgc cagcagcact acgtcacccc acctactttc   720
ggtgctggta ctaaagttga aatcaaa                                       747

SEQ ID NO: 33            moltype = DNA  length = 747
FEATURE                  Location/Qualifiers
misc_feature             1..747
                         note = scFv clone 17.043
source                   1..747
                         mol_type = other DNA
                         organism = synthetic construct
SEQUENCE: 33
caggtccaac tggtgcagtc cggtgccgaa gttaaaaaac ctgggtcttc cgttaaagtt    60
tcttgcaaag cctctggcta cagcatcacc gattatctga ttcactgggt ccgtcaggct   120
ccaggtcaag gtctggaatg gatgggttgg atcgatccag aagacggtga gaccaactat   180
gcccagaaat tccagggtcg tgtaaccctg accgccgaca cctccacctc taccgcctac   240
atggagttaa gtagcctgcg ttcagaggat accgcagtgt actactgcgc tcgttcactg   300
gactacgacc caatctaccc attcgcatac tgggtcaggg caccctggt aaccgttagt   360
agcggcggtg gtggtagcgg aggcggagga tcaggtggag gcggcagtga catcgtgatg   420
acccagtctc ctgactcctt ggccgtctct ctgggcgaac gtgcaactat caactgcaaa   480
tccagccaga gcttactgcg taacggtaat cagaaaaact atcttgcatg gtatcagcag   540
aaaccaggtc agccaccaaa attactgatc tattatgcat ctaccggtca aagcggtgtc   600
ccagatcgtt tcagcggttc cggctccggt actgacttca ccctgaccat ctcttccctt   660
caggccgaag atgtggccgt gtattactgc cagcagcact acgtcacccc acctactttc   720
ggtgctggta ctaaagttga aatcaaa                                       747
```

```
SEQ ID NO: 34           moltype = DNA  length = 747
FEATURE                 Location/Qualifiers
misc_feature            1..747
                        note = scFv clone 17.053
misc_feature            726
                        note = n is a, c, g, or t
source                  1..747
                        mol_type = other DNA
                        organism = synthetic construct
SEQUENCE: 34
caggtccaac tggtgcagtc cggtgccgaa gttaaaaaac ctgggtcttc cgttaaagtt    60
tcttgcaaag cctctggcta cagcatcacc gattatctga ttcactgggt ccgtcaggct   120
ccaggtcaag gtctggaatg gatggttgg atcgatccag aagacggtga aactaactac    180
gcccagaaat ccagggtcg tgtaaccctg accgccgaca cctccacctc taccgcctac    240
atggagttaa gtagcctgcg ttcagaggat accgcagtgt actactgcgc tcgttcactg    300
gactacgacc caatctaccc attcgcatac tgggtcagg gcaccctggt aaccgttagt    360
agcggcggtg gtggtagcgg aggcggagga tcaggtggga gcggcagtga catcgtgatg   420
acccagtctc ctgactcctt ggccgtctct ctgggcgaac gtgcaactat caactgcaaa    480
tccagccaga gcttactgcg taacggtaat cagaaaaact accttgcatg gtatcagcag    540
aaaccaggtc agccaccaaa attactgatc tattatgcat ctaccggtca aagcggtgtc    600
ccagatcgtt tcagcggttc cggctccggt actgacttca ccctgaccat ctcttccctt    660
caggccgaag atgtggccgt gtattactgc cagcagcact acattacccc acctactttc    720
ggtgcnggta ctaaagttga aatcaaa                                         747

SEQ ID NO: 35           moltype = DNA  length = 747
FEATURE                 Location/Qualifiers
misc_feature            1..747
                        note = scFv clone 17.054
source                  1..747
                        mol_type = other DNA
                        organism = synthetic construct
SEQUENCE: 35
caggtccaac tggtgcagtc cggtgccgaa gttaaaaaac ctgggtcttc cgttaaagtt    60
tcttgcaaag cctctggcta cagcatcacc gatgacctga ttcactgggt ccgtcaggct   120
ccaggtcaag gtctggaatg gatggggtgg atcgatccag aagacggtga aaccaactat    180
gcccagaaat ccagggtcg tgtaaccctg accgccgaca cctccacctc taccgcctac    240
atggagttaa gtagcctgcg ttcagaggat accgcagtgt actactgcgc tcgttcactg    300
gactccacct ggatctaccc attcgcatac tgggtcagg gcaccctggt aaccgttagt    360
agcggcggtg gtggtagcgg aggcggagga tcaggtggga gcggcagtga catcgtgatg   420
acccagtctc ctgactcctt ggccgtctct ctgggcgaac gtgcaactat caactgcaaa    480
tccagccaga gcttactgcg tcgcggtaat cagaaaaacc accttgcatg gtatcagcag    540
aaaccaggtc agccaccaaa attactgatc tatgacgcat ctaccggtca aagcggttgc    600
ccagatcgtt tcagcggttc cggctccggt actgacttca ccctgaccat ctcttccctt    660
caggccgaag atgtggccgt gtattactgc ctgcagagct acatcacccc acctactttc    720
ggtgctggta ctaaagttga aatcaaa                                         747

SEQ ID NO: 36           moltype = AA  length = 121
FEATURE                 Location/Qualifiers
REGION                  1..121
                        note = Heavy chain variable region of clone 17.014
source                  1..121
                        mol_type = protein
                        organism = synthetic construct
SEQUENCE: 36
QVQLVQSGAE VKKPGSSVKV SCKASGYSIT DYLIHWVRQA PGQGLEWMGW IDPEDGETNY     60
AQKFQGRVTL TADTSTSTAY MELSSLRSED TAVYYCARSL DSTPIYPFAY WGQGTLVTVS   120
S                                                                   121

SEQ ID NO: 37           moltype = AA  length = 113
FEATURE                 Location/Qualifiers
REGION                  1..113
                        note = Light chain variable region of clone 17.014
source                  1..113
                        mol_type = protein
                        organism = synthetic construct
SEQUENCE: 37
DIVMTQSPDS LAVSLGERAT INCKSSQSLL RSGNQKNYLA WYQQKPGQPP KLLIYYASTG     60
QSGVPDRFSG SGSGTDFTLT ISSLQAEDVA VYYCLQHYIT PPTFGAGTKV EIK          113

SEQ ID NO: 38           moltype = AA  length = 8
FEATURE                 Location/Qualifiers
REGION                  1..8
                        note = 17.014 H- CDR1
source                  1..8
                        mol_type = protein
                        organism = synthetic construct
SEQUENCE: 38
GYSITDYL                                                               8
```

```
SEQ ID NO: 39           moltype = AA  length = 8
FEATURE                 Location/Qualifiers
REGION                  1..8
                        note = 17.014 H- CDR2
source                  1..8
                        mol_type = protein
                        organism = synthetic construct
SEQUENCE: 39
IDPEDGET                                                                      8

SEQ ID NO: 40           moltype = AA  length = 14
FEATURE                 Location/Qualifiers
REGION                  1..14
                        note = 17.014 H- CDR3
source                  1..14
                        mol_type = protein
                        organism = synthetic construct
SEQUENCE: 40
ARSLDSTPIY PFAY                                                              14

SEQ ID NO: 41           moltype = AA  length = 12
FEATURE                 Location/Qualifiers
REGION                  1..12
                        note = 17.014 L- CDR1
source                  1..12
                        mol_type = protein
                        organism = synthetic construct
SEQUENCE: 41
QSLLRSGNQK NY                                                                12

SEQ ID NO: 42           moltype =     length =
SEQUENCE: 42
000

SEQ ID NO: 43           moltype = AA  length = 9
FEATURE                 Location/Qualifiers
REGION                  1..9
                        note = 17.014 L- CDR3
source                  1..9
                        mol_type = protein
                        organism = synthetic construct
SEQUENCE: 43
LQHYITPPT                                                                     9

SEQ ID NO: 44           moltype = AA  length = 8
FEATURE                 Location/Qualifiers
REGION                  1..8
                        note = 17.038 H- CDR1
source                  1..8
                        mol_type = protein
                        organism = synthetic construct
SEQUENCE: 44
GYSITDSL                                                                      8

SEQ ID NO: 45           moltype = AA  length = 8
FEATURE                 Location/Qualifiers
REGION                  1..8
                        note = 17.038 H- CDR2
source                  1..8
                        mol_type = protein
                        organism = synthetic construct
SEQUENCE: 45
IDPEDGEI                                                                      8

SEQ ID NO: 46           moltype = AA  length = 14
FEATURE                 Location/Qualifiers
REGION                  1..14
                        note = 17.038 H- CDR3
source                  1..14
                        mol_type = protein
                        organism = synthetic construct
SEQUENCE: 46
ARSLDSYPID PFAY                                                              14

SEQ ID NO: 47           moltype = AA  length = 12
FEATURE                 Location/Qualifiers
REGION                  1..12
                        note = 17.038 L- CDR1
```

```
source                  1..12
                        mol_type = protein
                        organism = synthetic construct
SEQUENCE: 47
QSLLRNGNQQ NY                                                                    12

SEQ ID NO: 48           moltype =   length =
SEQUENCE: 48
000

SEQ ID NO: 49           moltype = AA   length = 9
FEATURE                 Location/Qualifiers
REGION                  1..9
                        note = 17.038 L- CDR3
source                  1..9
                        mol_type = protein
                        organism = synthetic construct
SEQUENCE: 49
QQHYVTPPT                                                                         9

SEQ ID NO: 50           moltype = AA   length = 8
FEATURE                 Location/Qualifiers
REGION                  1..8
                        note = 17.043 H- CDR1
source                  1..8
                        mol_type = protein
                        organism = synthetic construct
SEQUENCE: 50
GYSITDYL                                                                          8

SEQ ID NO: 51           moltype = AA   length = 8
FEATURE                 Location/Qualifiers
REGION                  1..8
                        note = 17.043 H- CDR2
source                  1..8
                        mol_type = protein
                        organism = synthetic construct
SEQUENCE: 51
IDPEDGVT                                                                          8

SEQ ID NO: 52           moltype = AA   length = 14
FEATURE                 Location/Qualifiers
REGION                  1..14
                        note = 17.043 H- CDR3
source                  1..14
                        mol_type = protein
                        organism = synthetic construct
SEQUENCE: 52
ARSLDYDPIY PFAY                                                                  14

SEQ ID NO: 53           moltype = AA   length = 12
FEATURE                 Location/Qualifiers
REGION                  1..12
                        note = 17.043 L- CDR1
source                  1..12
                        mol_type = protein
                        organism = synthetic construct
SEQUENCE: 53
QSLLRNGNQK NY                                                                    12

SEQ ID NO: 54           moltype =   length =
SEQUENCE: 54
000

SEQ ID NO: 55           moltype = AA   length = 9
FEATURE                 Location/Qualifiers
REGION                  1..9
                        note = 17.043 L- CDR3
source                  1..9
                        mol_type = protein
                        organism = synthetic construct
SEQUENCE: 55
QQHYVTPPT                                                                         9

SEQ ID NO: 56           moltype = AA   length = 8
FEATURE                 Location/Qualifiers
REGION                  1..8
                        note = 17.053 H- CDR1
source                  1..8
```

```
                            mol_type = protein
                            organism = synthetic construct
SEQUENCE: 56
GYSITDYL                                                              8

SEQ ID NO: 57               moltype = AA   length = 8
FEATURE                     Location/Qualifiers
REGION                      1..8
                            note = 17.053 H- CDR2
source                      1..8
                            mol_type = protein
                            organism = synthetic construct
SEQUENCE: 57
IDPEDGET                                                              8

SEQ ID NO: 58               moltype = AA   length = 14
FEATURE                     Location/Qualifiers
REGION                      1..14
                            note = 17.053 H- CDR3
source                      1..14
                            mol_type = protein
                            organism = synthetic construct
SEQUENCE: 58
ARSLDYDPIY PFAY                                                      14

SEQ ID NO: 59               moltype = AA   length = 12
FEATURE                     Location/Qualifiers
REGION                      1..12
                            note = 17.053 L- CDR1
source                      1..12
                            mol_type = protein
                            organism = synthetic construct
SEQUENCE: 59
QSLLRNGNQK NY                                                        12

SEQ ID NO: 60               moltype =   length =
SEQUENCE: 60
000

SEQ ID NO: 61               moltype = AA   length = 9
FEATURE                     Location/Qualifiers
REGION                      1..9
                            note = 17.053 L- CDR3
source                      1..9
                            mol_type = protein
                            organism = synthetic construct
SEQUENCE: 61
QQHYITPPT                                                             9

SEQ ID NO: 62               moltype = AA   length = 8
FEATURE                     Location/Qualifiers
REGION                      1..8
                            note = 17.054 H- CDR1
source                      1..8
                            mol_type = protein
                            organism = synthetic construct
SEQUENCE: 62
GYSITDDL                                                              8

SEQ ID NO: 63               moltype = AA   length = 8
FEATURE                     Location/Qualifiers
REGION                      1..8
                            note = 17.054 H- CDR2
source                      1..8
                            mol_type = protein
                            organism = synthetic construct
SEQUENCE: 63
IDPEDGET                                                              8

SEQ ID NO: 64               moltype = AA   length = 14
FEATURE                     Location/Qualifiers
REGION                      1..14
                            note = 17.054 H- CDR3
source                      1..14
                            mol_type = protein
                            organism = synthetic construct
SEQUENCE: 64
ARSLDSTWIY PFAY                                                      14
```

```
SEQ ID NO: 65              moltype = AA  length = 12
FEATURE                    Location/Qualifiers
REGION                     1..12
                           note = 17.054 L- CDR1
source                     1..12
                           mol_type = protein
                           organism = synthetic construct
SEQUENCE: 65
QSLLRRGNQK NH                                                          12

SEQ ID NO: 66              moltype =     length =
SEQUENCE: 66
000

SEQ ID NO: 67              moltype = AA  length = 9
FEATURE                    Location/Qualifiers
REGION                     1..9
                           note = 17.054 L- CDR3
source                     1..9
                           mol_type = protein
                           organism = synthetic construct
SEQUENCE: 67
LQSYITPPT                                                               9

SEQ ID NO: 68              moltype = AA  length = 451
FEATURE                    Location/Qualifiers
REGION                     1..451
                           note = BDG17.066 heavy Chain LALA
source                     1..451
                           mol_type = protein
                           organism = synthetic construct
SEQUENCE: 68
QVQLVQSGAE VKKPGSSVKV SCKASGYSIT DSLIHWVRQA PGQGLEWMGW IDPEDGEINY        60
AQKFQGRVTL TADTSTSTAY MELSSLRSED TAVYYCARSL DSYPIDPPAY WGQGTLVTVS       120
SASTKGPSVF PLAPSSKSTS GGTAALGCLV KDYFPEPVTV SWNSGALTSG VHTFPAVLQS       180
SGLYSLSSVV TVPSSSLGTQ TYICNVNHKP SNTKVDKKVE PKSCDKTHTC PPCPAPEAAG       240
GPSVFLFPPK PKDTLMISRT PEVTCVVVDV SHEDPEVKFN WYVDGVEVHN AKTKPREEQY       300
NSTYRVVSVL TVLHQDWLNG KEYKCKVSNK ALPAPIEKTI SKAKGQPREP QVYTLPPSRD       360
ELTKNQVSLT CLVKGFYPSD IAVEWESNGQ PENNYKTTPP VLDSDGSFFL YSKLTVDKSR       420
WQQGNVFSCS VMHEALHNHY TQKSLSLSPG K                                     451

SEQ ID NO: 69              moltype = AA  length = 220
FEATURE                    Location/Qualifiers
REGION                     1..220
                           note = BDG17.066 Light Chain
source                     1..220
                           mol_type = protein
                           organism = synthetic construct
SEQUENCE: 69
DIVMTQSPDS LAVSLGERAT INCKSSQSLL RNGNQQNYLA WYQQKPGQPP KLLIYYASTG        60
QSGVPDRFSG SGSGTDFTLT ISSLQAEDVA VYYCQQHYVT PPTFGAGTKV EIKRTVAAPS       120
VFIFPPSDEQ LKSGTASVVC LLNNFYPREA KVQWKVDNAL QSGNSQESVT EQDSKDSTYS       180
LSSTLTLSKA DYEKHKVYAC EVTHQGLSSP VTKSFNRGEC                            220

SEQ ID NO: 70              moltype = AA  length = 451
FEATURE                    Location/Qualifiers
REGION                     1..451
                           note = BDG17.067 heavy Chain LALA
source                     1..451
                           mol_type = protein
                           organism = synthetic construct
SEQUENCE: 70
QVQLVQSGAE VKKPGSSVKV SCKASGYSIT DYLIHWVRQA PGQGLEWMGW IDPEDGVTAY        60
AQKFQGRVTL TADTSTSTAY MELSSLRSED TAVYYCARSL DYDPIYPFAY WGQGTLVTVS       120
SASTKGPSVF PLAPSSKSTS GGTAALGCLV KDYFPEPVTV SWNSGALTSG VHTFPAVLQS       180
SGLYSLSSVV TVPSSSLGTQ TYICNVNHKP SNTKVDKKVE PKSCDKTHTC PPCPAPEAAG       240
GPSVFLFPPK PKDTLMISRT PEVTCVVVDV SHEDPEVKFN WYVDGVEVHN AKTKPREEQY       300
NSTYRVVSVL TVLHQDWLNG KEYKCKVSNK ALPAPIEKTI SKAKGQPREP QVYTLPPSRD       360
ELTKNQVSLT CLVKGFYPSD IAVEWESNGQ PENNYKTTPP VLDSDGSFFL YSKLTVDKSR       420
WQQGNVFSCS VMHEALHNHY TQKSLSLSPG K                                     451

SEQ ID NO: 71              moltype = AA  length = 220
FEATURE                    Location/Qualifiers
REGION                     1..220
                           note = BDG17.067 Light Chain
source                     1..220
                           mol_type = protein
                           organism = synthetic construct
```

```
SEQUENCE: 71
DIVMTQSPDS LAVSLGERAT INCKSSQSLL RNGNQKNYLA WYQQKPGQPP KLLIYYASTG    60
QSGVPDRFSG SGSGTDFTLT ISSLQAEDVA VYYCQQHYVT PPTFGAGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 72          moltype = AA  length = 451
FEATURE                Location/Qualifiers
REGION                 1..451
                       note = BDG17.069 heavy Chain LALA
source                 1..451
                       mol_type = protein
                       organism = synthetic construct
SEQUENCE: 72
QVQLVQSGAE VKKPGSSVKV SCKASGYSIT DDLIHWVRQA PGQGLEWMGW IDPEDGETNY    60
AQKFQGRVTL TADTSTSTAY MELSSLRSED TAVYYCARSL DSTWIYPFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 73          moltype = AA  length = 220
FEATURE                Location/Qualifiers
REGION                 1..220
                       note = BDG17.069 Light Chain
source                 1..220
                       mol_type = protein
                       organism = synthetic construct
SEQUENCE: 73
DIVMTQSPDS LAVSLGERAT INCKSSQSLL RRGNQKNHLA WYQQKPGQPP KLLIYDASTG    60
QSGVPDRFSG SGSGTDFTLT ISSLQAEDVA VYYCLQSYIT PPTFGAGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220
```